(12) United States Patent
Li et al.

(10) Patent No.: US 12,378,535 B2
(45) Date of Patent: *Aug. 5, 2025

(54) ENGINEERED GLUCOSYLTRANSFERASES

(71) Applicant: NUTRITION & BIOSCIENCES USA 4, INC., Rochester, NY (US)

(72) Inventors: Yougen Li, Pennington, NJ (US); Mark S. Payne, Wilmington, DE (US); Jared B. Parker, Elkton, MD (US); Slavko Kralj, Copenhagen K (DK); Veli Alkan, Palo Alto, CA (US); Richard R. Bott, Palo Alto, CA (US); Robert Dicosimo, Chadds Ford, PA (US); Qiong Cheng, Wilmington, DE (US); Ellen D. Semke, Newark, DE (US); Susan Marie Hennessey, Avondale, PA (US)

(73) Assignee: Nutrition & Biosciences USA 4, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,140

(22) Filed: Apr. 5, 2024

(65) Prior Publication Data
US 2024/0417702 A1    Dec. 19, 2024

Related U.S. Application Data

(63) Continuation of application No. 17/338,842, filed on Jun. 4, 2021, now Pat. No. 11,952,598, which is a continuation of application No. 16/381,010, filed on Apr. 11, 2019, now Pat. No. 11,028,373, which is a continuation of application No. 15/702,893, filed on Sep. 13, 2017, now Pat. No. 10,301,604.

(60) Provisional application No. 62/394,354, filed on Sep. 14, 2016.

(51) Int. Cl.
| | | |
|---|---|---|
| C12N 9/10 | (2006.01) | |
| C08B 37/00 | (2006.01) | |
| C12P 19/04 | (2006.01) | |
| C12P 19/18 | (2006.01) | |

(52) U.S. Cl.
CPC ........ *C12N 9/1051* (2013.01); *C08B 37/0009* (2013.01); *C12P 19/04* (2013.01); *C12P 19/18* (2013.01)

(58) Field of Classification Search
None
See application file for complete search history.

*Primary Examiner* — Richard G Hutson

(57) ABSTRACT

Disclosed herein are glucosyltransferases with modified amino acid sequences. Such engineered enzymes exhibit improved alpha-glucan product yields and/or lower leucrose yields, for example. Further disclosed are reactions and methods in which engineered glucosyltransferases are used to produce alpha-glucan.

22 Claims, No Drawings

Specification includes a Sequence Listing.

ENGINEERED GLUCOSYLTRANSFERASES

This application is a continuation of application Ser. No. 17/338,842 (filed Jun. 4, 2021) (now U.S. Pat. No. 11,952,598), which is a continuation of application Ser. No. 16/381,010 (filed Apr. 11, 2019) (now U.S. Pat. No. 11,028,373), which is a continuation of application Ser. No. 15/702,893 (filed Sep. 13, 2017) (now U.S. Pat. No. 10,301,604), which claims the benefit of U.S. Provisional Application No. 62/394,354 (filed Sep. 14, 2016). All of these prior applications are incorporated herein by reference in their entirety.

FIELD

The present disclosure is in the field of enzyme catalysis. For example, the disclosure pertains to glucosyltransferase enzymes with modified amino acid sequences. Such modified enzymes have improved product yield properties.

REFERENCE TO SEQUENCE LISTING SUBMITTED ELECTRONICALLY

The official copy of the sequence listing is submitted electronically via EFS-Web or Patent Center as a file named CL6395USCNT3_SequenceListing.xml created on Sep. 5, 2024, and having a size of about 235 kilobytes. The sequence listing contained in this file is part of the specification and herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., *Microbiology* 141:1451-1460, 1995). Also for example, U.S. Pat. No. 7,000,000 disclosed the preparation of a spun fiber from enzymatically produced alpha-1,3-glucan.

Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages. Large soluble glucans, such as those having a high percentage of alpha-1,6 linkages, have also been enzymatically synthesized (e.g., U.S. Patent Appl. Publ. No. 2016/0122445). Various enzymatic synthesis routes are disclosed in International Patent Appl. Publ. Nos. WO2015/183721, WO2015/183724, WO2015/183729, WO2015/183722, WO2015/183726 and WO2015/183714 for producing small soluble glucan materials suitable for use in dietary and other applications.

While these and other advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

SUMMARY

In one embodiment, the present disclosure concerns a non-native glucosyltransferase comprising at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, wherein the non-native glucosyltransferase synthesizes alpha-glucan comprising 1,3-linkages and/or 1,6-linkages, and wherein the non-native glucosyltransferase has:
(i) an alpha-glucan yield that is higher than the alpha-glucan yield of a second glucosyltransferase that only differs from the non-native glucosyltransferase at the substitution position(s), and/or
(ii) a leucrose yield that is lower than the leucrose yield of the second glucosyltransferase.

In another embodiment, the present disclosure concerns a polynucleotide comprising a nucleotide sequence encoding a non-native glucosyltransferase as presently disclosed, optionally wherein one or more regulatory sequences are operably linked to the nucleotide sequence, and preferably wherein the one or more regulatory sequences include a promoter sequence.

In another embodiment, the present disclosure concerns a reaction composition comprising water, sucrose, and a non-native glucosyltransferase as presently disclosed.

In another embodiment, the present disclosure concerns a method of producing alpha-glucan comprising: (a) contacting at least water, sucrose, and a non-native glucosyltransferase enzyme as presently disclosed, whereby alpha-glucan is produced; and b) optionally, isolating the alpha-glucan produced in step (a).

In another embodiment, the present disclosure concerns a method of preparing a polynucleotide sequence encoding a non-native glucosyltransferase, the method comprising: (a) identifying a polynucleotide sequence encoding a parent glucosyltransferase that (i) comprises an amino acid sequence that is at least about 30% identical to SEQ ID NO:4 or positions 55-960 of SEQ ID NO:4, and (ii) synthesizes alpha-glucan comprising 1,3-linkages and/or 1,6-linkages; and (b) modifying the polynucleotide sequence identified in step (a) to substitute at least one amino acid of the parent glucosyltransferase at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, thereby providing a polynucleotide sequence encoding a non-native glucosyltransferase that has:
(i) an alpha-glucan yield that is higher than the alpha-glucan yield of the parent glucosyltransferase, and/or
(ii) a leucrose yield that is lower than the leucrose yield of the parent glucosyltransferase.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
| --- | --- | --- |
| GTF 0874, *Streptococcus sobrinus*. The first 156 amino acids of the protein are deleted compared to GENBANK Identification No. 450874; a start methionine is included. | 1 [a] | 2 (1435 aa) |

TABLE 1-continued

Summary of Nucleic Acid and Protein SEQ ID Numbers

| Description | Nucleic acid SEQ ID NO. | Protein SEQ ID NO. |
| --- | --- | --- |
| GTF 6855, *Streptococcus salivarius* SK126. The first 178 amino acids of the protein are deleted compared to GENBANK Identification No. 228476855 (Acc. No. ZP_04061500.1); a start methionine is included. | 3 [a] | 4 (1341 aa) |
| GTF 2379, *Streptococcus salivarius*. The first 203 amino acids of the protein are deleted compared to GENBANK Identification No. 662379; a start methionine is included. | 5 [a] | 6 (1247 aa) |
| GTF 7527 or GTFJ, *Streptococcus salivarius*. The first 42 amino acids of the protein are deleted compared to GENBANK Identification No. 47527; a start methionine is included. | 7 [a] | 8 (1477 aa) |
| GTF 1724, *Streptococcus downei*. The first 162 amino acids of the protein are deleted compared to GENBANK Identification No. 121724; a start methionine is included. | 9 [a] | 10 (1436 aa) |
| GTF 0544, *Streptococcus mutans*. The first 164 amino acids of the protein are deleted compared to GENBANK Identification No. 290580544; a start methionine is included. | 11 [a] | 12 (1313 aa) |
| GTF 5926, *Streptococcus dentirousetti*. The first 144 amino acids of the protein are deleted compared to GENBANK Identification No. 167735926; a start methionine is included. | 13 [a] | 14 (1323 aa) |
| GTF 4297, *Streptococcus oralis*. The first 228 amino acids of the protein are deleted compared to GENBANK Identification No. 7684297; a start methionine is included. | 15 [a] | 16 (1348 aa) |
| GTF 5618, *Streptococcus sanguinis*. The first 223 amino acids of the protein are deleted compared to GENBANK Identification No. 328945618; a start methionine is included. | 17 [a] | 18 (1348 aa) |
| GTF 2765, unknown *Streptococcus* sp. C150. The first 193 amino acids of the protein are deleted compared to GENBANK Identification No. 322372765; a start methionine is included. | 19 [a] | 20 (1340 aa) |
| GTF 4700, *Leuconostoc mesenteroides*. The first 36 amino acids of the protein are deleted compared to GENBANK Identification No. 21654700; a start methionine is included. | 21 [a] | 22 (1492 aa) |
| GTF 1366, *Streptococcus criceti*. The first 139 amino acids of the protein are deleted compared to GENBANK Identification No. 146741366; a start methionine is included. | 23 [a] | 24 (1323 aa) |
| GTF 0427, *Streptococcus sobrinus*. The first 156 amino acids of the protein are deleted compared to GENBANK Identification No. 940427; a start methionine is included. | 25 [a] | 26 (1435 aa) |
| GTF 2919, *Streptococcus salivarius* PS4. The first 92 amino acids of the protein are deleted compared to GENBANK Identification No. 383282919; a start methionine is included. | 27 [a] | 28 (1340 aa) |
| GTF 2678, *Streptococcus salivarius* K12. The first 188 amino acids of the protein are deleted compared to GENBANK Identification No. 400182678; a start methionine is included. | 29 [a] | 30 (1341 aa) |
| GTF 2381, *Streptococcus salivarius*. The first 273 amino acids of the protein are deleted compared to GENBANK Identification No. 662381; a start methionine is included. | 31 [a] | 32 (1305 aa) |
| GTF 3929, *Streptococcus salivarius* JIM8777. The first 178 amino acids of the protein are deleted compared to GENBANK Identification No. 387783929; a start methionine is included. | 33 [a] | 34 (1341 aa) |
| GTF 6907, *Streptococcus salivarius* SK126. The first 161 amino acids of the protein are deleted compared to GENBANK Identification No. 228476907; a start methionine is included. | 35 [a] | 36 (1331 aa) |
| GTF 6661, *Streptococcus salivarius* SK126. The first 265 amino acids of the protein are deleted compared to GENBANK Identification No. 228476661; a start methionine is included. | 37 [a] | 38 (1305 aa) |
| GTF 0339, *Streptococcus gallolyticus* ATCC 43143. The first 213 amino acids of the protein are deleted compared to GENBANK Identification No. 334280339; a start methionine is included. | 39 [a] | 40 (1310 aa) |
| GTF 0088, *Streptococcus mutans*. The first 189 amino acids of the protein are deleted compared to GENBANK Identification No. 3130088; a start methionine is included. | 41 [a] | 42 (1267 aa) |
| GTF 9358, *Streptococcus mutans* UA159. The first 176 amino acids of the protein are deleted compared to GENBANK Identification No. 24379358; a start methionine is included. | 43 [a] | 44 (1287 aa) |
| GTF 8242, *Streptococcus gallolyticus* ATCC BAA-2069. The first 191 amino acids of the protein are deleted compared to GENBANK Identification No. 325978242; a start methionine is included. | 45 [a] | 46 (1355 aa) |

TABLE 1-continued

Summary of Nucleic Acid and Protein SEQ ID Numbers

| Description | Nucleic acid SEQ ID NO. | Protein SEQ ID NO. |
|---|---|---|
| GTF 3442, *Streptococcus sanguinis* SK405. The first 228 amino acids of the protein are deleted compared to GENBANK Identification No. 324993442; a start methionine is included. | 47 [a] | 48 (1348 aa) |
| GTF 7528, *Streptococcus salivarius*. The first 173 amino acids of the protein are deleted compared to GENBANK Identification No. 47528; a start methionine is included. | 49 [a] | 50 (1427 aa) |
| GTF 3279, *Streptococcus* sp. C150. The first 178 amino acids of the protein are deleted compared to GENBANK Identification No. 322373279; a start methionine is included. | 51 [a] | 52 (1393 aa) |
| GTF 6491, *Leuconostoc citreum* KM20. The first 244 amino acids of the protein are deleted compared to GENBANK Identification No. 170016491; a start methionine is included. | 53 [a] | 54 (1262 aa) |
| GTF 6889, *Streptococcus salivarius* SK126. The first 173 amino acids of the protein are deleted compared to GENBANK Identification No. 228476889; a start methionine is included. | 55 [a] | 56 (1427 aa) |
| GTF 4154, *Lactobacillus reuteri*. The first 38 amino acids of the protein are deleted compared to GENBANK Identification No. 51574154. | 57 [a] | 58 (1735 aa) |
| GTF 3298, *Streptococcus* sp. C150. The first 209 amino acids of the protein are deleted compared to GENBANK Identification No. 322373298; a start methionine is included. | | 59 (1242 aa) |
| Wild type GTFJ, *Streptococcus salivarius*. GENBANK Identification No. 47527. | | 60 (1518 aa) |
| Wild type GTF corresponding to GTF 2678, *Streptococcus salivarius* K12. | | 61 (1528 aa) |
| Wild type GTF corresponding to GTF 6855, *Streptococcus salivarius* SK126. | | 62 (1518 aa) |
| Wild type GTF corresponding to GTF 2919, *Streptococcus salivarius* PS4. | | 63 (1431 aa) |
| Wild type GTF corresponding to GTF 2765, unknown *Streptococcus* sp. C150. | | 64 (1532 aa) |
| Shorter version of GTF 7527, *Streptococcus salivarius*, (also referred to as "7527-NT" herein. The first 178 amino acids of the protein are deleted compared to GENBANK Identification No. 47527; a start methionine is included. | | 65 (1341 aa) |
| Catalytic domain (approx.) of GTF 6855 (i.e., positions 55-960 of SEQ ID NO: 4), but having a Glu at position 279, which corresponds to position 510 (Ala) of SEQ ID NO: 62. | | 66 (906 aa) |
| Terminator sequence added to pHY300PLK to derive the pHYT vector. | 67 | |
| Wild type GTF 5604, *Streptococcus criceti*. GENBANK Identification No. 357235604 or 4691428. | | 68 (1338 aa) |
| Wild type GTF 8845, *Streptococcus sobrinus*. GENBANK Identification No. 22138845. | | 69 (1554 aa) |
| N-terminal truncated form of GTF 8845, including a heterologous signal sequence. | | 70 (1414 aa) |
| Catalytic domain (approx.) of GTF 6855 (i.e., positions 55-960 of SEQ ID NO: 4), but having an Asp at position 279, which corresponds to position 510 (Ala) of SEQ ID NO: 62. | | 71 (906 aa) |

[a] This DNA coding sequence is codon-optimized for expression in *E. coli*, and is merely disclosed as an example of a suitable coding sequence.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan and dextran.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, wherein at least about 50% of the glycosidic linkages are alpha-1,3. Alpha-1,3-glucan in certain embodiments comprises at least 90% or 95% alpha-1,3 glycosidic linkages. Most or all of the other linkages in alpha-1,3-glucan herein typically are alpha-1,6, though some linkages may also be alpha-1,2 and/or alpha-1,4.

The term "dextran" herein refers to a water-soluble alpha-glucan comprising at least 50% (up to 100%) alpha-1,6 glycosidic linkages (with up to 49% alpha-1,3 glycosidic linkages, some of which may occur at branching points). Glucosyltransferases capable of synthesizing dextran from sucrose may optionally be described as "dextransucrases" (EC 2.4.1.5).

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" will be referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^1$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as $DP_w$ (weight average degree of polymerization) or $DP_n$ (number average degree of polymerization). The molecular weight of smaller alpha-glucan polymers such as oligosaccharides typically can be provided as "DP" (degree of polymerization), which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "leucrose" and "D-glucopyranosyl-alpha (1-5)-D-fructopyranose" are used interchangeably herein and refer to a disaccharide containing an alpha-1,5 glucosyl-fructose linkage.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37: D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain preferably does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity.

The "yield" of an alpha-glucan product in a glucosyltransferase reaction in some aspects herein represents the molar yield based on the converted sucrose. The molar yield of an alpha-glucan product can be calculated based on the moles of the alpha-glucan product divided by the moles of the sucrose converted. Moles of converted sucrose can be calculated as follows: (mass of initial sucrose−mass of final sucrose)/molecular weight of sucrose [342 g/mol]. This molar yield calculation can be considered as a measure of selectivity of the reaction toward the alpha-glucan. In some aspects, the "yield" of an alpha-glucan product in a glucosyltransferase reaction can be based on the glucosyl component of the reaction. Such a yield (yield based on glucosyl) can be measured using the following formula:

$$\text{Alpha-Glucan Yield} = ((IS/2-(FS/2+LE/2+GL+SO))/(IS/2-FS/2)) \times 100\%.$$

The fructose balance of a glucosyltransferase reaction can be measured to ensure that HPLC data, if applicable, are not out of range (90-110% is considered acceptable). Fructose balance can be measured using the following formula:

$$\text{Fructose Balance} = ((180/342 \times (FS+LE)+FR)/(180/342 \times IS)) \times 100\%.$$

In the above two formulae, IS is [Initial Sucrose], FS is [Final Sucrose], LE is [Leucrose], GL is [Glucose], SO is [Soluble Oligomers] (gluco-oligosaccharides), and FR is [Fructose] (all concentrations in units of grams/L and as measured by HPLC, for example).

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A glucosyltransferase reaction herein is performed under aqueous conditions.

The terms "soluble", "aqueous-soluble", "water-soluble" and the like as used herein characterize a glucan that has the capability of dissolving in water and/or an aqueous solution herein. Examples of soluble glucans herein are certain oligosaccharides, such as alpha-1,3-glucan with a DP less than 8, and certain oligosaccharides disclosed in International Patent Appl. Publ. Nos. WO2015/183721, WO2015/183724, WO2015/183729, WO2015/183722, WO2015/183726 and WO2015/183714, which are incorporated herein by reference. In contrast, a glucan that is "insoluble", "aqueous-insoluble", "water-insoluble" (and like terms) does not dissolve (or does not appreciably dissolve) in water and/or an aqueous solution herein. Optionally, the conditions for determining solubility include a water/solution temperature range of about 1 to 85° C. (e.g., 20-25° C.) and/or a neutral pH range of about 6-8.

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

As used herein, the term "polypeptide" is defined as a chain of amino acid residues, usually having a defined sequence. As used herein the term polypeptide is interchangeable with the terms "peptides" and "proteins". Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual,* 2nd ed., Cold Spring Harbor Laboratory: Cold Spring Harbor, NY (1989), which is incorporated herein by reference, particularly Chapter 11 and Table 11.1.

The term "DNA manipulation technique" refers to any technique in which the sequence of a DNA polynucleotide sequence is modified. Although the DNA polynucleotide sequence being modified can be used as a substrate itself for modification, it does not have to be physically in hand for certain techniques (e.g., a sequence stored in a computer can be used as the basis for the manipulation technique). A DNA manipulation technique can be used to delete and/or mutate one or more DNA sequences in a longer sequence. Examples of a DNA manipulation technique include recombinant DNA techniques (restriction and ligation, molecular cloning), polymerase chain reaction (PCR), and synthetic DNA methods (e.g., oligonucleotide synthesis and ligation). Regarding synthetic DNA techniques, a DNA manipulation technique can entail observing a DNA polynucleotide in silico, determining desired modifications (e.g., one or more deletions) of the DNA polynucleotide, and synthesizing a DNA polynucleotide that contains the desired modifications.

The term "in silico" herein means in or on an information storage and/or processing device such as a computer; done or produced using computer software or simulation, i.e., virtual reality.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, WI), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4.

Additionally, the Clustal W method of alignment can be used (described by Higgins and Sharp, *CABIOS.* 5:151-153 (1989); Higgins, D. G. et al., *Comput. Appl. Biosci.* 8:189-191 (1992); Thompson, J. D. et al, *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a glucosyltransferase comprising at least one amino acid substitution at a position corresponding with at least one particular amino acid residue of SEQ ID NO:62. An amino acid position of a glucosyltransferase or subsequence thereof (e.g., catalytic domain or catalytic domain plus glucan-binding domains) (can refer to such an amino acid position or sequence as a "query" position or sequence) can be characterized to correspond with a particular amino acid residue of SEQ ID NO:62 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:62 or a subsequence of SEQ ID NO:62) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:62 herein (e.g., Leu-373, Leu-428, Ala-472, Ala-510, Leu-513, Met-529, Phe-607, Asn-613, Gln-616, Ser-631, Gly-633, Phe-634, Thr-635, or Phe-951) is with respect to the full-length amino acid sequence of SEQ ID NO:62. The first amino acid (i.e., position 1, Met-1) of SEQ ID NO:62 is at the start of the signal peptide. Unless otherwise disclosed, substitutions herein are with respect to the full-length amino acid sequence of SEQ ID NO:62.

A "non-native glucosyltransferase" herein (alternatively, "mutant", "variant", "modified" and like terms can likewise be used to describe such a glucosyltransferase) has at least one amino acid substitution at a position corresponding with a particular amino acid residue (e.g., Leu-373, Leu-428, Ala-472, Ala-510, Leu-513, Met-529, Phe-607, Asn-613, Gln-616, Ser-631, Gly-633, Phe-634, Thr-635, or Phe-951) of SEQ ID NO:62. In most cases, such at least one amino acid substitution is in place of the amino acid residue(s) that normally (natively) occurs at the same position in the native counterpart (parent) of the non-native glucosyltransferase. The amino acid normally occurring at the relevant site in the native counterpart glucosyltransferase often is the same as (or conserved with) the particular amino acid residue (e.g., Leu-373, Leu-428, Ala-472, Ala-510, Leu-513, Met-529, Phe-607, Asn-613, Gln-616, Ser-631, Gly-633, Phe-634, Thr-635, or Phe-951) of SEQ ID NO:62 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:69 (GENBANK Acc. No. BAC07265.1, GI No. 22138845) is a native glucosyltransferase of *Streptococcus sobrinus*. It is noted that Phe-886 of SEQ ID NO:69 corresponds with Phe-951 of SEQ ID NO:62 (alignment not shown). If SEQ ID NO:69 is mutated at position 886 to substitute the Phe residue with a different residue (e.g., Tyr), then it can be stated that the position 886-mutated version of SEQ ID NO:69 represents a non-native glucosyltransferase having an amino acid substitution at a position corresponding with Phe-951 of SEQ ID NO:62, for example. As another example illustrating a substitution/alignment herein, it is noted that Leu-193 of SEQ ID NO:12 corresponds with Leu-373 of SEQ ID NO:62 (alignment not shown). If SEQ ID NO:12 is mutated at position 193 to substitute the Leu residue with a different residue (e.g., Gln), then it can be stated that the position 193-mutated version of SEQ ID NO:12 represents a non-native glucosyltransferase having an amino acid substitution at a position corresponding with Leu-373 of SEQ ID NO:62, for example.

The term "isolated" means a substance (or process) in a form or environment that does not occur in nature. Non-limiting examples of isolated substances include (1) any non-naturally occurring substance (e.g., a non-native glucosyltransferase herein), (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature (e.g., a non-native glucosyltransferase herein); or (4) any substance modified by increasing the amount of the substance relative to other components with which it is naturally associated. It is believed that the embodiments (e.g., enzymes and reaction compositions) disclosed herein are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

While advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

Certain embodiments of the present disclosure concern a non-native glucosyltransferase comprising at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, wherein the non-native glucosyltransferase synthesizes alpha-glucan comprising 1,3-linkages and/or 1,6-linkages, and wherein the non-native glucosyltransferase has:
  (i) an alpha-glucan yield that is higher than the alpha-glucan yield of a second glucosyltransferase that only differs from the non-native glucosyltransferase at the substitution position(s), and/or
  (ii) a leucrose yield that is lower than the leucrose yield of the second glucosyltransferase.

Thus, in general, mutant glucosyltransferase enzymes are disclosed herein that can synthesize higher amounts of alpha-glucan, and/or lower yields of leucrose, which is a by-product often considered undesirable when the main goal is alpha-glucan synthesis.

A non-native glucosyltransferase herein synthesizes alpha-glucan comprising 1,3-linkages and/or 1,6-linkages. In some aspects, at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the glycosidic linkages of such an alpha-glucan can be alpha-1,3 linkages. The linkage profile of an alpha-glucan can optionally be characterized as having a range between any two of these values. The other linkages in any of these aspects having 1%-99% alpha-1,3 linkages can be alpha-1,6, and/or not include any alpha-1,4 or alpha-1,2 linkages, for example. Still, in other aspects, about 100% of the glycosidic linkages of an alpha-glucan can be alpha-1,6 linkages.

Alpha-glucan in some aspects can have, for example, less than 10%, 9%, 8%, 7%, 6%, 5%, 4%, 3%, 2%, or 1% of alpha-1,2 or alpha-1,4 glycosidic linkages. In another embodiment, an alpha-glucan only has alpha-1,3 and/or alpha-1,6 linkages.

Alpha-glucan in some aspects can be linear/unbranched. Alternatively, there can be branches in an alpha-glucan herein. For example, an alpha-glucan can have less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% branch points as a percent of the linkages in the polymer.

In certain aspects, an alpha-glucan can have a molecular weight in $DP_w$ or $DP_n$ of at least about 100. For example, the $DP_w$ or $DP_n$ can be at least about 100, 150, 200, 250, 300, 350, 400, 450, 500, 550, 600, 650, 700, 750, 800, 850, 900, 950, 1000, 1100, or 1200. The molecular weight of an alpha-glucan can optionally be expressed as a range between any two of these values. These molecular weights particularly apply, for example, to alpha-1,3-glucan herein.

Still, in some aspects, an alpha-glucan can have a DP of at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 100, 150, 200, or 250. The DP of an alpha-glucan can optionally be expressed as a range between any two of these values. Particular examples of such an alpha-glucan include (i) those with a DP of less than 8 or 9 and that have mostly (e.g., >80-90%) or all alpha-1,3 linkages, and (ii) those with mostly (e.g., >80-90%) or all alpha-1,6 linkages.

Further still, in some aspects, an alpha-glucan can have an Mw of at least about 1, 5, 10, 15, 20, 25, 50, 60, 70, 80, 90, 100, 110, 120, 130, 140, 150, 160, 170, 180, 190, or 200 million Daltons. The Mw of an alpha-glucan can optionally be expressed as a range between any two of these values. Particular examples of such an alpha-glucan include dextrans with at least about 85% or 90% alpha-1,6 linkages.

An alpha-glucan produced by a non-native glucosyltransferase herein can be water-insoluble or water-soluble. Alpha-1,3-glucan herein is typically insoluble in most aqueous settings, whereas dextran is typically soluble in most aqueous settings. In general, the solubility of a glucan polymer in an aqueous system herein is related to its linkage type, molecular weight, and/or degree of branching. Alpha-1,3-glucan is generally insoluble at a $DP_w$ of 8 or 9 and above in neutral (e.g., pH 6-8) aqueous conditions.

Any of the foregoing linkage profiles, molecular weight profiles, and/or solubility profiles, for example, can be combined herein to appropriately characterize an alpha-glucan product of a non-native glucosyltransferase of the present disclosure. In some aspects, the linkage, molecular weight, and/or solubility profile of an alpha-glucan product herein can be as disclosed in any of the following publications, all of which are incorporated herein by reference: U.S. Pat. Nos. 7,000,000 and 8,871,474; U.S. Patent Appl. Publ. Nos. 2015/0232819, and 2016/0122445; and International Patent Appl. Publ. Nos. WO2015/183721, WO2015/183724, WO2015/183729, WO2015/183722, WO2015/183726 and WO2015/183714.

A non-native glucosyltransferase, for example, can comprise the amino acid sequence of any glucosyltransferase disclosed in the following publications that is capable of producing alpha-glucan as presently disclosed, but with the exception that the non-native glucosyltransferase has at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62: U.S. Pat. Nos. 7,000,000 and 8,871,474; U.S. Patent Appl. Publ. Nos. 2015/0232819, and 2016/0122445; and International Patent Appl. Publ. Nos. WO2015/183721, WO2015/183724, WO2015/183729, WO2015/183722, WO2015/183726 and WO2015/183714, all of which are incorporated herein by reference. In some aspects, such a non-native glucosyltransferase (i) has at least one of the foregoing substitutions, and (ii) comprises an amino acid sequence that is at least about 90%, 91%, 92%, 93%, 94%, 95%, 96%, 97%, 98%, 99%, or 99.5% identical to the amino acid sequence of the respective counterpart/parent glucosyltransferase not having the at least one substitution.

In some aspects, a non-native glucosyltransferase (i) has at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, and (ii) comprises or consists of an amino acid sequence that is at least about 90%, 91%, 92%, 93%, 94%, 95%, 96%, 97%, 98%, 99%, or 99.5% identical to SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 59, 68 (or positions 37-1338 thereof), 69 (or positions 37-1554 or 170-1554 thereof), or 70. Certain information regarding alpha-glucan products of several glucosyltransferases with some of these amino acid sequences is provided in Table 2.

TABLE 2

GTF Enzymes and Related Alpha-Glucan Products[a]

| GTF ID | SEQ ID NO. | Reducing Sugars | Insoluble Product | % alpha-1,3 | % alpha-1,6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 4700 | 22 | yes | no | | | |
| 1366 | 24 | yes | no | <30 | | |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 2381 | 32 | yes | no | | | |
| 3929 | 34 | yes | yes | 100 | 0 | 280 |
| 6907 | 36 | yes | no | <30 | | |
| 6661 | 38 | yes | no | <30 | | |
| 0339 | 40 | yes | no | <30 | | |
| 0088 | 42 | yes | no | <30 | | |
| 9358 | 44 | yes | no | <30 | | |
| 8242 | 46 | yes | no | <30 | | |
| 3442 | 48 | yes | no | <30 | | |
| 7528 | 50 | yes | no | <30 | | |
| 3279 | 52 | yes | no | <30 | | |
| 6491 | 54 | yes | no | | | |
| 6889 | 56 | yes | no | | | |
| 4154 | 58 | yes | no | | | |

[a]GTF reactions and product analyses were performed as follows. Reactions were prepared comprising sucrose (50 g/L), potassium phosphate buffer (pH 6.5, 20 mM) and a GTF enzyme (2.5% bacterial cell extract by volume; extracts prepared according to U.S. application Ser. No. 62/180,779 or US2017/0002335, in a manner similar to procedure disclosed in U.S. Pat. No. 8,871,474). After 24-30 hours at 22-25° C., insoluble product, if present, was harvested by centrifugation, washed three times with water, washed once with ethanol, and dried at 50° C. for 24-30 hours. Approximate linkages and $DP_n$ are shown for each insoluble product, if present. Linkage measurements (if available) are shown for each soluble product (for reactions not producing any insoluble product). Linkages and $DP_n$ were determined by $^{13}C$ NMR and SEC, respectively.

In some aspects, a non-native glucosyltransferase (i) has at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, and (ii) comprises or consists of a glucosyltransferase catalytic domain that is at least about 90%, 91%, 92%, 93%, 94%, 95%, 96%, 97%, 98%, 99%, or 99.5% identical to amino acid residues 54-957 of SEQ ID NO:65, residues 55-960 of SEQ ID NO:30, residues 55-960 of SEQ ID NO:4, residues 55-960 of SEQ ID NO:28, or residues 55-960 of SEQ ID NO:20. Such a non-native glucosyltransferase, for instance, is believed to be able to produce alpha-glucan that is water-insoluble and comprise at least about 50% (e.g., ≥90% or 95%) alpha-1,3 linkages, and optionally further have a $DP_w$ of at least 100. It is noted that a glucosyltransferase with amino acid positions 54-957 of SEQ ID NO:65 can produce alpha-1,3-glucan with 100% alpha-1,3 linkages and a $DP_w$ of at least 400 (data not shown, refer to Table 6 of U.S. Pat. Appl. No. 62/180,779 or U.S. Pat. Appl. Publ. No. 2017/0002335, which are incorporated herein by reference), for example. It is further noted that SEQ ID NOs: 65 (GTF 7527), 30 (GTF 2678), 4 (GTF 6855), 28 (GTF 2919), and 20 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO:65), 2678 (residues 55-960 of SEQ ID NO:30), 6855 (residues 55-960 of SEQ ID NO:4), 2919 (residues 55-960 of SEQ ID NO:28), 2765 (residues 55-960 of SEQ ID NO:20). The amino acid sequences of the catalytic domains (approx.) of GTFs 2678, 6855, 2919 and 2765 have about 94.9%, 99.0%, 95.5% and 96.4% identity, respectively, with the approximate catalytic domain sequence of GTF 7527 (i.e., amino acids 54-957 of SEQ ID NO:65). Each of these particular glucosyltransferases (GTFs 2678, 6855, 2919 and 2765) can produce alpha-1,3-glucan with 100% alpha-1,3 linkages and a $DP_w$ of at least 400 (data not shown, refer to Table 4 of U.S. Pat. Appl. No. 62/180,779 or US2017/0002335). Based on this activity, and the relatedness (high percent identity) of the foregoing catalytic domains, it is contemplated that a non-native glucosyltransferase herein having one of the foregoing catalytic domains further with at least one of the foregoing amino acid substitutions can produce alpha-glucan comprising at least about 50% (e.g., ≥90% or 95%) alpha-1,3 linkages and a $DP_w$ of at least 100.

In some aspects, a non-native glucosyltransferase (i) has at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, and (ii) comprises or consists of an amino acid sequence that is at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:62 or a subsequence thereof such as SEQ ID NO:4 (without start methionine thereof) or positions 55-960 of SEQ ID NO:4 (approximate catalytic domain).

Although it is believed that a non-native glucosyltransferase in certain aspects need only have a catalytic domain sequence with at least one amino acid substitution herein, the non-native glucosyltransferase can be comprised within a larger amino acid sequence. For example, a catalytic domain may be linked at its C-terminus to a glucan-binding domain, and/or linked at its N-terminus to a variable domain and/or signal peptide.

Although amino acid substitutions in a non-native glucosyltransferase are generally disclosed herein with respect to the corresponding positions in SEQ ID NO:62, such substitutions can alternatively be stated simply with respect to its position number in the sequence of the non-native glucosyltransferase itself, as convenience may dictate.

Still further examples of non-native glucosyltransferases can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A non-native glucosyltransferase herein typically lacks an N-terminal signal peptide; such an enzyme can optionally be characterized as being mature if its signal peptide was removed during a secretion process.

A non-native glucosyltransferase herein can be derived from any microbial source, for example, such as a bacteria or fungus. Examples of bacterial glucosyltransferases are those derived from a *Streptococcus* species, *Leuconostoc* species, or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A non-native glucosyltransferase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, *Biomolecules* 4:117-139, 2014, which is incorporated herein by reference). A nucleotide sequence encoding a non-native glucosyltransferase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and glucosyltransferase amino acid coding sequence, a nucleotide sequence encoding a signal peptide (e.g., heterologous signal peptide) that is designed for direct secretion of the glucosyltransferase enzyme. At the end of fermentation, cells may be ruptured accordingly (generally when a signal peptide for secretion is not employed) and the glucosyltransferase enzyme can be isolated using methods such as precipitation, filtration, and/or concentration. Alternatively, a lysate or extract comprising a glucosyltransferase can be used without further isolation. If the glucosyltransferase was secreted (i.e., it is present in the fermentation broth), it can optionally be used as isolated from, or as comprised in, the fermentation broth. The activity of a glucosyltransferase enzyme can be confirmed by biochemical assay, such as measuring its conversion of sucrose to glucan polymer.

A non-native glucosyltransferase herein can comprise at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62. In some aspects, the amino acid substitution at a position corresponding with amino acid Asn-613 of SEQ ID NO:62 can be with a Val, Ile, Thr, Gly, Met, or Leu residue. In some aspects, the amino acid substitution at a position corresponding with amino acid Phe-951 of SEQ ID NO:62 can be with a Tyr residue. In some aspects, the amino acid substitution at a position corresponding with amino acid Ala-510 of SEQ ID NO:62 can be with a Glu, Ile, Val, or Asp residue. In some aspects, the amino acid substitution at a position corresponding with amino acid Phe-607 of SEQ ID NO:62 can be with a Trp, Tyr, or Asn residue. In some aspects, the amino acid substitution at a position corresponding with amino acid Gln-616 of SEQ ID NO:62 can be with a Glu residue. In some aspects, the amino acid substitution at a position corresponding with amino acid Leu-373 of SEQ ID NO:62 can be with a Gln, Ala, Val, Met, Phe, or Leu residue. In some aspects, the amino acid substitution at a position corresponding with amino acid Ala-472 of SEQ ID NO:62 can be with a Ser or Cys residue. In some aspects, the amino acid substitution at a position corresponding with amino acid Gly-633 of SEQ ID NO:62 can be with a Trp residue. In some aspects, the amino acid substitution at a position corresponding with amino acid Leu-513 of SEQ ID NO:62 can be with a Tyr, Phe, or Trp residue. In some aspects, the amino acid substitution at a position corresponding with amino acid Thr-635 of SEQ ID NO:62 can be with a Trp, His, or Tyr residue. In some aspects, the amino acid substitution at a position corresponding with amino acid Met-529 of SEQ ID NO:62 can be with a Leu or Asn residue. In some aspects, the amino acid substitution at a position corresponding with amino acid Phe-634 of SEQ ID NO:62 can be with an Ala residue. In some aspects, the amino acid substitution at a position corresponding with amino acid Ser-631 of SEQ ID NO:62 can be with a Thr, Asp, Glu, or Arg residue. In some aspects, the amino acid substitution at a position corresponding with amino acid Leu-428 of SEQ ID NO:62 can be with a Val residue. A non-native glucosyltransferase herein can comprise one, two, three, four, or more of the disclosed substitutions, for instance. A non-native glucosyltransferase in some aspects can comprise at least one amino acid substitution at a position corresponding with amino acid residue Val-552 of SEQ ID NO:62 (e.g., substitution with a Gly residue).

Suitable substitution sites, and examples of particular substitutions at these sites, can include those as listed in Table 3 in Example 1 (below) that are associated with (i) a decrease in leucrose production by at least about 5%, 10%, 15%, 20%, 25%, 30%, 35%, 40%, 45%, 50%, 55%, 60%, 65%, 70%, 75%, 80%, 85%, 90%, or 95%, and/or (ii) an increase in glucan yield by at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, or 150%. In some aspects, suitable substitutions include those as listed in Table 3 in Example 1 (below) that are associated with a decrease in glucose production by at least about 5%, 10%, 15%, 20%, 25%, 30%, 35%, 40%, 45%, 50%, 55%, 60%, 65%, 70%, 75%, or 80%. In some aspects, suitable substitutions include those as listed in Table 3 in Example 1 (below) that are associated with a decrease in gluco-oligosaccharide (oligomer) production by at least about 5%, 10%, 15%, 20%, 25%, 30%, 35%, 40%, 45%, 50%, 55%, 60%, or 65%. The foregoing substitutions as listed in Table 3 are as they correspond with the listed residue position number in SEQ ID NO:62. In some aspects, one or more substitutions are conserved or non-conserved substitutions; such conservation (or not) can be, for instance, with respect to the amino acid that occurs in the native glucosyltransferase from which the non-native glucosyltransferase is derived.

As disclosed above, a non-native glucosyltransferase herein can be based on any one of a variety of glucosyltransferase amino acid sequences. Simply for illustration purposes, examples of non-native glucosyltransferases comprising at least one amino acid substitution as presently disclosed include glucosyltransferases that: (i) comprise an amino acid sequence that is at least about 90% identical to residues 55-960 of SEQ ID NO:4, or an amino acid sequence that is at least about 90% identical to SEQ ID NO:4 (optionally without the start methionine of SEQ ID NO:4), and (ii) have at least one amino acid substitution as disclosed herein. For instance, SEQ ID NO:66 represents residues 55-960 of SEQ ID NO:4, but with a Glu residue at the position corresponding with amino acid Ala-510 of SEQ ID NO:62 (i.e., Glu substituting for Ala) (the substituting Glu is at position 279 of SEQ ID NO:66). Thus, a non-native glucosyltransferase in some aspects can comprise or consist of SEQ ID NO:66 or an amino acid sequence that is at least about 90%, 91%, 92%, 93%, 94%, 95%, 96%, 97%, 98%, 99%, or 99.5% identical to SEQ ID NO:66, but that has a Glu at position 279. In other aspects, a non-native glucosyltransferase can comprise or consist of SEQ ID NO:71 or an amino acid sequence that is at least about 90%, 91%, 92%, 93%, 94%, 95%, 96%, 97%, 98%, 99%, or 99.5% identical to SEQ ID NO:71, but that has a Glu at position 279.

Examples of non-native glucosyltransferases of the present disclosure can comprise two or more (multiple) amino acid substitutions, wherein at least one of such two or more substitutions is at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62. For instance, such a non-native glucosyltransferase can comprise two, three, four, five, or more amino acid substitutions, where at least one of the substitutions is from the foregoing list. Also for instance, a non-native glucosyltransferase can comprise two or three amino acid substitutions from the foregoing list, and optionally one or two other amino acid substitutions.

In some aspects, a non-native glucosyltransferase with multiple amino acid substitutions comprises at least one amino acid substitution at a position corresponding with amino acid residue Ala-510 or Phe-607 of SEQ ID NO:62. An example is a non-native glucosyltransferase comprising amino acid substitutions at both of these positions. Additional amino acid substitutions, if present, in these and other non-native glucosyltransferases disclosed herein having multiple substitutions can be at a position(s) corresponding with amino acid residue(s) Arg-741, Asn-743, Leu-784, Asp-820, Phe-929, Asp-948, and/or Arg-1172 of SEQ ID NO:62, for example. Just to illustrate, a non-native glucosyltransferase with multiple substitutions herein can include substitutions at either or both of positions corresponding with amino acid residues Arg-741 and/or Asn-743 of SEQ ID NO:62. Just to further illustrate, a non-native glucosyltransferase with multiple substitutions herein can include substitutions at positions Arg-741, Asp-948, and/or Arg-1172 of SEQ ID NO:62. More examples herein include a non-native glucosyltransferase comprising a combination of amino acid substitutions as follows (i-x), where each substitution corresponds with the respective amino acid residue of SEQ ID NO:62:

(i) Ala-510, Phe-607 and Arg-741;
(ii) Ala-510, Phe-607 and Asn-743;
(iii) Ala-510, Phe-607 and Asp-948;
(iv) Ala-510, Arg-741 and Asp-948;
(v) Ala-510, Phe-607, Arg-741 and Asp-948;
(vi) Ala-510, Phe-607, Arg-741 and Arg-1172;
(vii) Ala-510, Phe-607, Asp-820 and Asp-948;
(viii) Ala-510, Phe-607, Asp-948 and Arg-1172;
(ix) Ala-510, Phe-607, Asn-743, Asp-948 and Arg-1172; or
(x) Ala-510, Phe-607, Arg-741, Leu-784, Phe-929 and Arg-1172.

In some aspects of a non-native glucosyltransferase comprising multiple amino acid substitutions (e.g., embodiments i-x above), the amino acid substitution at a position corresponding with amino acid Ala-510 of SEQ ID NO:62 can be with an Asp, Glu, or other residue as presently disclosed (e.g., Ile or Val); the amino acid substitution at a position corresponding with amino acid Phe-607 of SEQ ID NO:62 can be with a Tyr or other residue as presently disclosed (e.g., Trp or Asn); the amino acid substitution at a position corresponding with amino acid Arg-741 of SEQ ID NO:62 can be with a Ser residue; the amino acid substitution at a position corresponding with amino acid Asn-743 of SEQ ID NO:62 can be with a Ser residue; the amino acid substitution at a position corresponding with amino acid Asp-948 of SEQ ID NO:62 can be with a Gly residue; the amino acid substitution at a position corresponding with amino acid Arg-1172 of SEQ ID NO:62 can be with a Cys residue; the amino acid substitution at a position corresponding with amino acid Asp-820 of SEQ ID NO:62 can be with a Gly residue; the amino acid substitution at a position corresponding with amino acid Leu-784 of SEQ ID NO:62 can be with a Gln residue; and/or the amino acid substitution at a position corresponding with amino acid Phe-929 of SEQ ID NO:62 can be with a Leu residue. Some examples of a non-native glucosyltransferase comprising multiple amino acid substitutions include those comprising the following combinations of substitutions (xi-xx), where each substitution corresponds with the respective amino acid residue of SEQ ID NO:62: (xi) A510D/F607Y/R741S, (xii) A510D/F607Y/N743S, (xiii) A510D/F607Y/D948G, (xiv) A510D/R741S/D948G, (xv) A510D/F607Y/R741S/D948G, (xvi) A510E/F607Y/R741S/R1172C, (xvii) A510D/F607Y/D820G/D948G, (xviii) A510D/F607Y/D948G/R1172C, (xix) A510D/F607Y/N743S/D948G/R1172C, or (xx) A510D/F607Y/R741S/L784Q/F929L/R1172C.

In some alternative aspects, a non-native glucosyltransferase can comprise at least one amino acid substitution at a position corresponding with amino acid residue Asn-743 (e.g., N743S) or Arg-741 (e.g., R741S) of SEQ ID NO:62 (with or without additional substitutions).

A non-native glucosyltransferase herein with multiple amino acid substitutions can be based on any of a variety of glucosyltransferase amino acid sequences as presently disclosed, for example. Simply for illustration purposes, examples of such a non-native glucosyltransferase include those with multiple substitutions as described above (e.g., any one of embodiments i-xx) and comprising or consisting of an amino acid sequence that is at least about 90%, 91%, 92%, 93%, 94%, 95%, 96%, 97%, 98%, 99%, or 99.5% identical to SEQ ID NO:65 (optionally without the start methionine of SEQ ID NO:65) or residues 54-957 of SEQ ID NO:65, SEQ ID NO:30 (optionally without the start methionine of SEQ ID NO:30) or residues 55-960 of SEQ ID NO:30, SEQ ID NO:4 (optionally without the start methionine of SEQ ID NO:4) or residues 55-960 of SEQ ID NO:4, SEQ ID NO:28 (optionally without the start methionine of SEQ ID NO:28) or residues 55-960 of SEQ ID NO:28, or SEQ ID NO:20 (optionally without the start methionine of SEQ ID NO:20) or residues 55-960 of SEQ ID NO:20.

A non-native glucosyltransferase herein can have (i) an alpha-glucan yield that is higher than the alpha-glucan yield of a second glucosyltransferase (e.g., parent glucosyltransferase) that only differs from the non-native glucosyltransferase at the substitution position(s), and/or (ii) a leucrose yield that is lower than the leucrose yield of the second glucosyltransferase. In some embodiments, a second glucosyltransferase to which a non-native glucosyltransferase is compared has a native amino acid residue at the substitution position(s). A second glucosyltransferase herein, for example, can be comprised of all of, or mostly, a native amino acid sequence. Thus, while a second glucosyltransferase herein can be a native glucosyltransferase in some aspects, it can be a prior-modified glucosyltransferase in other aspects (e.g., a glucosyltransferase with one or more other amino acid substitutions differing from the substitution [s] of the present disclosure). In some embodiments, a second glucosyltransferase to which a non-native glucosyltransferase is compared has a native amino acid residue(s) at the substitution position(s). Determining whether an amino acid residue is native can be done by comparing the second glucosyltransferase amino acid sequence to the native/wild type glucosyltransferase amino acid sequence from which the second glucosyltransferase is derived. Optionally, a non-native glucosyltransferase in some embodiments can be characterized as having higher selectivity toward alpha-glucan synthesis (as compared to by-product synthesis).

In some aspects, a non-native glucosyltransferase herein can have an alpha-glucan yield that is at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 220%, 240%, 260%, 280%, 300%, 320%, or 340% higher than the alpha-glucan yield of a second glucosyltransferase as presently disclosed. In some additional or alternative embodiments, a non-native glucosyltransferase can have a decrease in leucrose yield by at least about 5%, 10%, 15%, 20%, 25%, 30%, 35%, 40%, 45%, 50%, 55%, 60%, 65%, 70%, 75%, 80%, 85%, 90%, or 95% compared to the leucrose yield of a second glucosyltransferase. These determinations (alpha-glucan and/or leucrose yield) can be made with respect to any glucan synthesis reaction/process as disclosed herein (e.g., taking into account initial sucrose conc., temperature, pH, and/or reaction time), and using any suitable measurement technique (e.g., HPLC or NIR spectroscopy). Typically, a comparison between non-native and second glucosyltransferases herein can be made under identical or similar reaction conditions. The yield of a glucosyltransferase reaction in some aspects can be measured based on the glucosyl component of the reaction.

In some embodiments, particularly those regarding a non-native glucosyltransferase that produces an insoluble alpha-glucan product such as alpha-1,3-glucan, the glucosyltransferase can exhibit a decrease in the yield of soluble gluco-oligosaccharides by at least about 5%, 10%, 15%, 20%, 25%, 30%, 35%, 40%, 45%, 50%, 55%, 60%, 65%, 70%, or 75% compared to the soluble gluco-oligosaccharide yield of a second glucosyltransferase. A soluble gluco-oligosaccharide in some aspects can be DP2-7 or DP2-8, and have any linkage profile disclosed herein. In some aspects, the DP is ≥7, or up to 10, 15, 20, or 25, but with a linkage profile allowing solubility (e.g., not over 90% or 95% alpha-1,3).

In some embodiments, particularly those regarding a non-native glucosyltransferase that produces an insoluble alpha-glucan product such as alpha-1,3-glucan, a non-native glucosyltransferase can exhibit a decrease in the yield of glucose by at least about 5%, 10%, 15%, 20%, 25%, 30%, 35%, 40%, 45%, 50%, 55%, 60%, 65%, 70%, 75%, or 80% compared to the glucose yield of a second glucosyltransferase.

Some embodiments disclosed herein concern a polynucleotide comprising a nucleotide sequence that encodes a non-native glucosyltransferase as presently disclosed (e.g., a non-native glucosyltransferase comprising at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62). Optionally, one or more regulatory sequences are operably linked to the nucleotide sequence, and preferably a promoter sequence is included as a regulatory sequence.

A polynucleotide comprising a nucleotide sequence encoding a non-native glucosyltransferase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding a non-native glucosyltransferase. For example, a nucleotide sequence encoding a non-native glucosyltransferase may be in operable linkage with a promoter sequence (e.g., a heterologous promoter). A promoter sequence can be suitable for expression in a cell (e.g., bacterial cell such as E. coli or Bacillus; eukaryotic cell such as a fungus, yeast, insect, or mammalian cell) or in an in vitro protein expression system, for example. Examples of other suitable regulatory sequences are disclosed herein (e.g., transcription terminator sequences).

Some aspects herein are drawn to a cell comprising a polynucleotide sequence as presently disclosed; such a cell can be any type disclosed herein (e.g., bacterial cell such as E. coli or Bacillus; eukaryotic cell such as a fungus, yeast, insect, or mammalian cell). A cell can optionally express a non-native glucosyltransferase encoded by the polynucleotide sequence. In some aspects, the polynucleotide sequence exists transiently (i.e., not integrated into the genome) or stably (i.e., integrated into the genome) in the cell.

Some embodiments disclosed herein concern reaction compositions comprising water, sucrose, and one or more non-native glucosyltransferases herein (e.g., a non-native glucosyltransferase comprising at least one amino acid substitution at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62). Such a reaction composition produces, at least, alpha-glucan comprising 1,3-linkages and/or 1,6-linkages as disclosed.

The temperature of a reaction composition herein can be controlled, if desired, and can be about 5-50° C., 20-40° C., 20-30° C., 20-25° C., for example.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a reaction composition just after all the reaction components have been added/combined (e.g., at least water, sucrose, non-native glucosyltransferase enzyme).

The pH of a reaction composition in certain embodiments can be about 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 10 mM, 20 mM, or 50 mM, for example.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. An inert vessel can optionally be equipped with a stirring device.

A reaction composition herein can contain one, two, or more glucosyltransferase enzymes, for example, just as long that at least one of the enzymes is a non-native glucosyltransferase as presently disclosed. In some embodiments, only one or two glucosyltransferase enzymes is/are comprised in a reaction composition. A glucosyltransferase reaction herein can be, and typically is, cell-free (e.g., no whole cells present).

Any of the features disclosed herein (e.g., above and in the below Examples) regarding a reaction composition can characterize appropriate aspects of a glucan production method herein, and vice versa.

The present disclosure also concerns a method for producing alpha-glucan, the method comprising: (a) contacting at least water, sucrose, and at least one non-native glucosyltransferase as disclosed herein that produces an alpha-glucan, whereby alpha-glucan is produced; and b) optionally, isolating the alpha-glucan produced in step (a). Conducting such a method, which can optionally be characterized as a glucan synthesis method, is typically also performed when conducting a reaction composition herein.

A glucan synthesis method as presently disclosed comprises contacting at least water, sucrose, and a non-native glucosyltransferase herein that produces an alpha-glucan. These and optionally other reagents can be added altogether or in any order as discussed below. This step can optionally be characterized as providing a reaction composition comprising water, sucrose and a non-native glucosyltransferase enzyme that synthesizes alpha-glucan. The contacting step herein can be performed in any number of ways. For example, the desired amount of sucrose can first be dissolved in water (optionally, other components may also be added at this stage of preparation, such as buffer components), followed by addition of glucosyltransferase enzyme. The solution may be kept still, or agitated via stirring or orbital shaking, for example. A glucan synthesis method can be performed by batch, fed-batch, continuous mode, or by any variation of these modes.

Completion of a reaction in certain embodiments can be determined visually (e.g., no more accumulation of insoluble glucan in certain embodiments), and/or by measuring the amount of sucrose left in the solution (residual sucrose), where a percent sucrose consumption of at least about 90%, 95%, or 99% can indicate reaction completion. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example.

The yield of an alpha-glucan produced in some aspects of a glucan synthesis method herein can be at least about 40%, 45%, 50%, 55%, 60%, 65%, 70%, 75%, 80%, or 85%. This yield in some aspects can be measured based on the glucosyl component of the reaction. In some additional or alternative embodiments, the yield of leucrose can be less than about 18%, 17%, 16%, 15%, 14%, 13%, 12%, 11%, 10%, 9%, 8%, 7%, 6%, 5%, 4%, 3%, 2%, or 1%. Such a yield in alpha-glucan and/or leucrose in some aspects is achieved in a reaction conducted for about 16-24 hours (e.g., ~20 hours), and/or is as measured using HPLC or NIR spectroscopy.

Alpha-glucan produced in a glucan synthesis method herein optionally can be isolated. In certain embodiments, isolating an alpha-glucan product includes at least conducting a step of centrifugation, filtration, fractionation, chromatographic separation, dialysis, evaporation, or dilution. Simply as examples, insoluble alpha-glucan can be separated by centrifugation or filtration, whereas soluble alpha-glucan can be separated by chromatographic separation or dialysis. Isolation can optionally further comprise washing an alpha-glucan product one, two, or more times with water or other aqueous liquid, and/or drying the alpha-glucan product.

Any of the disclosed conditions for synthesizing an alpha-glucan, such as the foregoing or those described in the below Examples, can be applied to practicing a reaction composition as presently disclosed (and vice versa), and/or used to characterize features/activity of a non-native glucosyltransferase, accordingly.

The present disclosure also concerns a method of preparing a polynucleotide sequence encoding a non-native glucosyltransferase herein. This method comprises:

(a) identifying a polynucleotide sequence encoding a parent glucosyltransferase that (i) comprises an amino acid sequence that is at least about 30% identical to SEQ ID NO:4 or positions 55-960 of SEQ ID NO:4, and (ii) synthesizes alpha-glucan comprising 1,3-linkages and/or 1,6-linkages; and (b) modifying the polynucleotide sequence identified in step (a) to substitute at least one amino acid (in the parent glucosyltransferase encoded thereby) at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62, thereby providing a polynucleotide sequence encoding a non-native glucosyltransferase that has:
  (i) an alpha-glucan yield that is higher than the alpha-glucan yield of the parent glucosyltransferase, and/or
  (ii) a leucrose yield that is lower than the leucrose yield of the parent glucosyltransferase.

Such a method can optionally further comprise using a polynucleotide prepared in this manner in a method of expressing the non-native glucosyltransferase encoded by the polynucleotide. Such an expression method can follow any heterologous protein expression method as known in the art, for example. The present method of preparing a polynucleotide can optionally alternatively be characterized as a method of increasing the product yield of a glucosyltransferase.

Identification step (a) herein can, in some instances, comprise identifying an amino acid sequence of a parent glucosyltransferase enzyme. A polynucleotide sequence could be determined from this amino acid sequence according to the genetic code (codons), such as the genetic code used in the species from which the parent glucosyltransferase was identified.

Identifying a polynucleotide encoding a parent glucosyltransferase herein can be performed (a) in silico, (b) with a method comprising a nucleic acid hybridization step, (c) with a method comprising a protein sequencing step, and/or (d) with a method comprising a protein binding step, for example.

Regarding in silico detection, the amino acid sequences of candidate parent glucosyltransferase enzymes (and/or nucleotide sequences encoding such glucosyltransferase enzymes) stored in a computer or database (e.g., public databases such as GENBANK, EMBL, REFSEQ, GENE-PEPT, SWISS-PROT, PIR, PDB) can be reviewed in silico to identify a glucosyltransferase enzyme comprising an amino acid sequence that is at least about 30% 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:4 (optionally without start methionine thereof) or positions 55-960 of SEQ ID NO:4 (approximate catalytic domain), for example. Such review could comprise using any means known in the art such as through use of an alignment algorithm or software as described above (e.g., BLASTN, BLASTP, ClustalW, ClustalV, Clustal-Omega, EMBOSS). It is noted simply for reference purposes that SEQ ID NO:4 without its start methionine is a subsequence of SEQ ID NO:62.

Identifying a parent glucosyltransferase as disclosed above can optionally be performed via a method comprising a nucleic acid hybridization step. Such a method can comprise using DNA hybridization (e.g., Southern blot, dot blot), RNA hybridization (e.g., northern blot), or any other method that has a nucleic acid hybridization step (e.g., DNA sequencing, PCR, RT-PCR, all of which may comprise hybridization of an oligonucleotide), for example. A polynucleotide sequence encoding SEQ ID NO:4 or a subsequence thereof (e.g., positions 55-960 of SEQ ID NO:4) can be used as a probe, for example, in such a hybridization. Conditions and parameters for carrying out hybridization methods in general are well known and disclosed, for example, in Sambrook J, Fritsch E F and Maniatis T, *Molecular Cloning: A Laboratory Manual*, Cold Spring Harbor Laboratory: Cold Spring Harbor, NY (1989); Silhavy T J, Bennan M L and Enquist L W, *Experiments with Gene Fusions*, Cold Spring Harbor Laboratory: Cold Spring Harbor, NY (1984); Ausubel F M et al., *Current Protocols in Molecular Biology*, published by Greene Publishing Assoc. and Wiley-Interscience, Hoboken, NJ (1987); and Innis M A, Gelfand D H, Sninsky J J and White T J (Editors), *PCR Protocols: A Guide to Methods and Applications*, Academic Press, Inc., San Diego, CA (1990).

Identifying a parent glucosyltransferase as disclosed above can optionally be performed via a method comprising a protein sequencing step. Such a protein sequencing step can comprise one or more procedures such as N-terminal amino acid analysis, C-terminal amino acid analysis, Edman degradation, or mass spectrometry, for example.

Identifying a parent glucosyltransferase as disclosed above can optionally be performed via a method comprising a protein binding step. Such a protein binding step can be performed using an antibody that binds to a motif or epitope within SEQ ID NO:4 (e.g., within positions 55-960 of SEQ ID NO:4), for example.

A polynucleotide identified in step (a) (i.e., before its modification in step [b]) can, in some aspects, encode a glucosyltransferase comprising an amino acid sequence that is identical to, or at least 90%, 91%, 92%, 93%, 94%, 95%, 96%, 97%, 98%, or 99% identical to, the amino acid sequence of any glucosyltransferase disclosed in Table 1. An alpha-glucan as produced by such a glucosyltransferase can be as disclosed herein, for example.

A method of preparing a polynucleotide sequence encoding a non-native glucosyltransferase herein comprises step (b) of modifying the polynucleotide sequence (encoding a parent glucosyltransferase) identified in step (a). Such modification substitutes at least one amino acid of the parent glucosyltransferase at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62. The non-native glucosyltransferase (encoded by the modified polynucleotide sequence) resulting from such one or more substitutions can be optionally characterized as a "child glucosyltransferase" herein.

A suitable modification of a polynucleotide in step (b) can be made following any DNA manipulation technique known in the art. Modifying step (b) can optionally be performed in silico, followed by synthesis of the polynucleotide sequence encoding a non-native glucosyltransferase. For example, a polynucleotide sequence identified in step (a) can be manipulated in silico using a suitable sequence manipulation program/software (e.g., VECTOR NTI, Life Technologies, Carlsbad, CA; DNAStrider; DNASTAR, Madison, WI). Following such virtual manipulation, the modified polynucleotide sequence can be artificially synthesized by any suitable technique (e.g., annealing-based connection of oligonucleotides, or any technique disclosed in Hughes et al., *Methods Enzymol.* 498:277-309, which is incorporated herein by reference). It should be appreciated that the foregoing methodology is not believed to necessarily rely on having a pre-existing polynucleotide (encoding a parent glucosyltransferase) in hand.

Modifying step (b) can optionally be performed using a physical copy of a polynucleotide sequence identified in step (a) encoding a parent glucosyltransferase. As an example, such a polynucleotide can serve as a template for amplification using primers designed in a manner such that the amplified product encodes a non-native glucosyltransferase herein (e.g., refer to Innis et al., ibid.).

An amino acid substitution in this method can be any of those substitutions as disclosed herein at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62. Two or more amino acid substitutions as presently disclosed can be applied in some aspects. Essentially any non-native glucosyltransferase as presently disclosed can be encoded by a polynucleotide as prepared by this method, for instance, and consequently can have the higher alpha-glucan yield and/or lower leucrose yield profiles disclosed herein.

Non-limiting examples of compositions and methods disclosed herein include:

1. A non-native glucosyltransferase comprising at least one amino acid substitution at a position corresponding with amino acid residue Leu-373, Leu-428, Ala-472, Ala-510, Leu-513, Met-529, Val-552, Phe-607, Asn-613, Gln-616, Ser-631, Gly-633, Phe-634, Thr-635, or Phe-951 of SEQ ID NO:62, wherein the non-native glucosyltransferase synthesizes alpha-glucan comprising 1,3-linkages and/or 1,6-linkages, and wherein the non-native glucosyltransferase has: (i) an alpha-glucan yield that is higher than the alpha-glucan yield of a second glucosyltransferase that only differs from the non-native glucosyltransferase at the substitution position(s), and/or (ii) a leucrose yield that is lower than the leucrose yield of the second glucosyltransferase.
2. The non-native glucosyltransferase of embodiment 1, wherein: (i) the amino acid substitution at the position corresponding with amino acid residue Leu-373 is with a Gln, Ala, Val, Met, Phe, or Leu residue; (ii) the amino acid substitution at the position corresponding with amino acid residue Leu-428 is with a Val residue; (iii) the amino acid substitution at the position corresponding with amino acid residue Ala-472 is with a Ser or Cys residue; (iv) the amino acid substitution at the position corresponding with amino acid residue Ala-510 is with a Glu, Ile, Val, or Asp residue; (v) the amino acid substitution at the position corresponding with amino acid residue Leu-513 is with a Tyr, Phe, or Trp residue; (vi) the amino acid substitution at the position corresponding with amino acid residue Met-529 is with a Leu or Asn residue; the amino acid substitution at the position corresponding with amino acid residue Val-552 is with a Gly residue; (vii) the amino acid substitution at the position corresponding with amino acid residue Phe-607 is with a Trp, Tyr, or Asn residue; (viii) the amino acid substitution at the position corresponding with amino acid residue Asn-613 is with a Val, Ile, Thr, Gly, Met, or Leu residue; (ix) the amino acid substitution at the position corresponding with amino acid residue Gln-616 is with a Glu residue; (x) the amino acid substitution at the position corresponding with amino acid residue Ser-631 is with a Thr, Asp, Glu, or Arg residue; (xi) the amino acid substitution at the position corresponding with amino acid residue Gly-633 is with a Trp residue; (xii) the amino acid substitution at the position corresponding with amino acid residue Phe-634 is with an Ala residue; (xiii) the amino acid substitution at the position corresponding with amino acid residue Thr-635 is with a Trp, His, or Tyr residue; or (xiv) the amino acid substitution at the position corresponding with amino acid residue Phe-951 is with a Tyr residue.
3. The non-native glucosyltransferase of embodiment 1 or 2, comprising two or more amino acid substitutions, wherein at least one of the substitutions is at a position corresponding with amino acid residue Leu-373, Leu-428, Ala-472, Ala-510, Leu-513, Met-529, Phe-607, Asn-613, Gln-616, Ser-631, Gly-633, Phe-634, Thr-635, or Phe-951 of SEQ ID NO:62.
4. The non-native glucosyltransferase of embodiment 3, comprising at least one amino acid substitution at a position corresponding with amino acid residue Ala-510 or Phe-607 of SEQ ID NO:62.
5. The non-native glucosyltransferase of embodiment 4, comprising amino acid substitutions at positions corresponding with amino acid residues Ala-510 and Phe-607 of SEQ ID NO:62.
6. The non-native glucosyltransferase of embodiment 1, 2, 3, 4, or 5, wherein the alpha-glucan is insoluble and comprises at least about 50% alpha-1,3 linkages, and optionally wherein the alpha-glucan has a weight average degree of polymerization ($DP_w$) of at least 100.
7. The non-native glucosyltransferase of embodiment 6, comprising a catalytic domain that is at least about 90% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.
8. The non-native glucosyltransferase of embodiment 7, comprising an amino acid sequence that is at least about 90% identical to SEQ ID NO:4, SEQ ID NO:65, SEQ ID NO:30, SEQ ID NO:28, or SEQ ID NO:20.
9. The non-native glucosyltransferase of embodiment 7 or 8, wherein the non-native glucosyltransferase synthesizes insoluble alpha-1,3-glucan having at least about 90% (or at least 95%) alpha-1,3-linkages.
10. The non-native glucosyltransferase of embodiment 1, 2, 3, 4, or 5, wherein the alpha-glucan is soluble and comprises at least about 75% alpha-1,6-linkages.
11. The non-native glucosyltransferase of embodiment 10, comprising an amino acid sequence that is at least about 90% identical to SEQ ID NO:68, positions 37-1338 of SEQ ID NO:68, SEQ ID NO:69, positions 37-1554 of SEQ ID NO:69, or positions 170-1554 of SEQ ID NO:69.
12. The non-native glucosyltransferase of embodiment 1, 2, 3, 4, 5, 6, 7, 8, 9, 10, or 11, wherein the alpha-glucan yield is at least about 10% higher than the alpha-glucan yield of the second glucosyltransferase.
13. A polynucleotide comprising a nucleotide sequence encoding a non-native glucosyltransferase according to embodiment 1, 2, 3, 4, 5, 6, 7, 8, 9, 10, 11, or 12, optionally wherein one or more regulatory sequences are operably linked to the nucleotide sequence, and preferably wherein the one or more regulatory sequences include a promoter sequence.
14. A reaction composition comprising water, sucrose, and a non-native glucosyltransferase according to embodiment 1, 2, 3, 4, 5, 6, 7, 8, 9, 10, 11, or 12.
15. A method of producing alpha-glucan comprising: (a) contacting at least water, sucrose, and a non-native glucosyltransferase enzyme according to embodiment 1, 2, 3, 4, 5, 6, 7, 8, 9, 10, 11, or 12, whereby alpha-glucan is produced; and (b) optionally, isolating the alpha-glucan produced in step (a).
16. A method of preparing a polynucleotide sequence encoding a non-native glucosyltransferase (e.g., of any one of embodiments 1-12), the method comprising: (a) identifying a polynucleotide sequence encoding a parent glucosyltransferase that (i) comprises an amino acid sequence that is at least about 30% identical to SEQ ID NO:4 or positions 55-960 of SEQ ID NO:4, and (ii) synthesizes alpha-glucan comprising 1,3-linkages and/or 1,6-linkages; and (b) modifying the polynucleotide sequence identified in step (a) to substitute at least one amino acid of the parent glucosyltransferase at a position corresponding with amino acid residue Leu-373, Leu-428, Ala-472, Ala-510, Leu-513, Met-529, Val-552, Phe-607, Asn-613, Gln-616, Ser-631, Gly-633, Phe-634, Thr-635, or Phe-951 of SEQ ID NO:62, thereby providing a polynucleotide sequence encoding a non-native glucosyltransferase that has: (i) an alpha-glucan yield that is higher than the alpha-glucan yield of the parent glucosyltransferase, and/or (ii) a leucrose yield that is lower than the leucrose yield of the parent glucosyltransferase.

17. The method of embodiment 16, wherein: (i) the amino acid substitution at the position corresponding with amino acid residue Leu-373 is with a Gln, Ala, Val, Met, Phe, or Leu residue; (ii) the amino acid substitution at the position corresponding with amino acid residue Leu-428 is with a Val residue; (iii) the amino acid substitution at the position corresponding with amino acid residue Ala-472 is with a Ser or Cys residue; (iv) the amino acid substitution at the position corresponding with amino acid residue Ala-510 is with a Glu, Ile, Val, or Asp residue; (v) the amino acid substitution at the position corresponding with amino acid residue Leu-513 is with a Tyr, Phe, or Trp residue; (vi) the amino acid substitution at the position corresponding with amino acid residue Met-529 is with a Leu or Asn residue; the amino acid substitution at the position corresponding with amino acid residue Val-552 is with a Gly residue; (vii) the amino acid substitution at the position corresponding with amino acid residue Phe-607 is with a Trp, Tyr, or Asn residue; (viii) the amino acid substitution at the position corresponding with amino acid residue Asn-613 is with a Val, Ile, Thr, Gly, Met, or Leu residue; (ix) the amino acid substitution at the position corresponding with amino acid residue Gln-616 is with a Glu residue; (x) the amino acid substitution at the position corresponding with amino acid residue Ser-631 is with a Thr, Asp, Glu, or Arg residue; (xi) the amino acid substitution at the position corresponding with amino acid residue Gly-633 is with a Trp residue; (xii) the amino acid substitution at the position corresponding with amino acid residue Phe-634 is with an Ala residue; (xiii) the amino acid substitution at the position corresponding with amino acid residue Thr-635 is with a Trp, His, or Tyr residue; or (xiv) the amino acid substitution at the position corresponding with amino acid residue Phe-951 is with a Tyr residue.

18. The method of embodiment 16 or 17, wherein the identifying step is performed: (a) in silico, (b) with a method comprising a nucleic acid hybridization step, (c) with a method comprising a protein sequencing step, and/or (d) with a method comprising a protein binding step; and/or wherein the modifying step is performed: (e) in silico, followed by synthesis of the polynucleotide sequence encoding the non-native glucosyltransferase enzyme, or (f) using a physical copy of the polynucleotide sequence encoding the parent glucosyltransferase.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Analysis of Amino Acid Sites Affecting Glucosyltransferase Selectivity Toward Alpha-Glucan Synthesis This Example describes screening for glucosyltransferase variants with improved selectivity toward alpha-glucan synthesis from sucrose. Another aim of this screening was to identify glucosyltransferase variants that exhibit reduced synthesis of by-products such as leucrose and gluco-oligosaccharides. Variants having either or both of these yield properties were identified.

The amino acid sequence of the glucosyltransferase used to prepare amino acid substitutions in this Example was SEQ ID NO:4 (GTF 6855), which essentially is an N-terminally truncated (signal peptide and variable region removed) version of the full-length wild type glucosyltransferase (represented by SEQ ID NO:62) from *Streptococcus salivarius* SK126 (see Table 1). Substitutions made in SEQ ID NO:4 can be characterized as substituting for native amino acid residues, as each amino acid residue/position of SEQ ID NO:4 (apart from the Met-1 residue of SEQ ID NO:4) corresponds accordingly with an amino acid residue/position within SEQ ID NO:62. In reactions comprising at least sucrose and water, the glucosyltransferase of SEQ ID NO:4 typically produces alpha-glucan having about 100% alpha-1,3 linkages and a $DP_w$ of 400 or greater (e.g., refer to U.S. Pat. Nos. 8,871,474 and 9,169,506, and U.S. Pat. Appl. Publ. No. 2017/0002336, which are incorporated herein by reference). This alpha-glucan product, which is insoluble, can be isolated following enzymatic synthesis via filtration, for example.

To summarize this Example, GTF 6855 variants (each with a single amino acid substitution) from site evaluation libraries (SEL) were each bacterially expressed, purified, and normalized to a concentration of 100 ppm. Each enzyme preparation was then screened (in triplicate) using sucrose as substrate in alpha-1,3 glucan synthesis reactions. In addition to determining the amount of alpha-1,3 glucan polymer produced in each reaction, the soluble sugar products (fructose, glucose, leucrose, gluco-oligosaccharides) and residual sucrose of each reaction were analyzed by HPLC after about a 20-hour incubation.

Plasmids for individually expressing various single amino acid-substituted variants of GTF 6855 (SEQ ID NO:4) in a *Bacillus subtilis* host were prepared. Such plasmids were prepared as follows. A DNA expression cassette having (operably linked in 5'-to-3' order) the *B. subtilis* aprE promoter, a codon-optimized sequence encoding SEQ ID NO:4 (GTF 6855), and a BPN' terminator was synthesized. This expression cassette was cloned into the pHYT replicating shuttle vector (forming pHYT-GTF6855) and transformed into *B. subtilis* CBS12-1. The pHYT vector was derived from pHY300PLK (Takara) by adding a terminator sequence (SEQ ID NO:67) after the tetracycline resistance gene using the BstEII and EcoRI sites. The HindIII site in pHY300PLK had been removed by cloning a linker sequence (not shown) into the BamHI and HindIII sites. The pHYT-GTF6855 plasmid was amplified and used for generating SELs. The resulting plasmids encoding single-amino acid substituted GTFs were sequenced to verify each substitution.

To produce GTF 6855 (SEQ ID NO:4) and single amino acid-substituted variants thereof, *B. subtilis* individually transformed with pHYT-GTF6855 or mutated versions thereof were cultivated in Tryptone Soya Broth (Oxoid Ltd., UK) and Grant's II medium. Heart infusion agar plates (Difco Laboratories, MI) were used to select transformants. Plasmid integrity was maintained by the addition of 25 µg/mL tetracycline. Each GTF targeted for expression was detected in the growth medium after incubation for about 6 hours at 37° C. After centrifugation and filtration, culture supernatants with expressed GTF were obtained. GTF enzyme present in the supernatant was purified to apparent homogeneity by affinity chromatography using washed (2×MILLIQ 1×25 mM NaH$_2$PO$_4$ pH 5.7 with intermediate centrifugation steps 100×g) SUPERDEX 200 resin (GE Healthcare). Each GTF was eluted with a 15% solution of Dextran T1 (Pharmacosmos) in 25 mM NaH$_2$PO$_4$ PH 5.7 by centrifugation 100× g. Each purified GTF was dialyzed against 25 mM NaH$_2$PO$_4$ PH 5.7 buffer (at least 100×) using a Harvard Apparatus 96-well DISPODIALYZER (10000-Dalton MWCO).

After dialysis, GTF enzyme concentration was determined by OD280 using purified GTF 6855 as a standard. Normalization of each purified GTF to 100 ppm was achieved by diluting appropriately with 25 mM NaH$_2$PO$_4$ PH 5.7. Protein concentration for each sample was confirmed using an AGILENT 1200 (Agilent Technologies) HPLC equipped with an AGILENT BIO SEC3 guard-column column (3 µm 100 Å (4.6×50 mm). Five (5) µL of sample was injected onto the column for each determination. Compounds were eluted with isocratic flow of 25 mM KH$_2$PO$_4$ PH 6.8+0.1 M NaCl for 1.3 min at 0.5 mL/min flow rate.

Each GTF (GTF 6855 and each variant thereof) was entered into a reaction with sucrose to determine yield and selectivity. Each reaction was performed as follows: 37.5 µL of 100 ppm enzyme sample (ppm based on a BSA calibration curve) was added to 262.5 µL of 86 g/L sucrose (75 g/L final) in 20 mM Na$_2$HPO$_4$/NaH$_2$PO$_4$ PH 5.7 and incubated overnight (about 20 hours) at 30° C. After this incubation, each reaction was quenched by incubation for 1 hour at 80° C. A 200-µL aliquot of each quenched reaction was filtered in vacuo via a 0.45-µm filter plate (Millipore 0.45-µm Hydrophilic) and each filtrate was diluted 5×(10 µL sample+ 40 µL 20 mM Na$_2$HPO$_4$/NaH$_2$PO$_4$) in preparation for HPLC sugar analysis.

Sucrose, glucose, fructose, leucrose and relative oligosaccharide concentrations in each diluted filtrate were determined using an AGILENT 1200 (Agilent Technologies) HPLC equipped with a 150×7.80 mm PHENOMENEX REZEX RNM carbohydrate Na$^+$ 8% column PHENOMENX KRUDKATCHER 0.5-µm guard column. The column was operated at 80° C. with an isocratic flow-rate of 0.9 mL/min with 10 mM Na$_2$HPO$_4$/NaH$_2$PO$_4$ pH 6.7 (5 min per sample). Five µL of diluted sample was injected. Appropriate sucrose, glucose, fructose, and leucrose calibration curves were used to determine sugar concentrations. A mixture of purified gluco-oligosaccharides was used to determine oligomer concentration.

The profiles of reactions (~20 hours) as measured via the above methodology are provided in Table 3.

TABLE 3

Product Profiles of GTF 6855 (SEQ ID NO: 4) and Single Amino Acid-Substituted Variants thereof

| GTF | Sucrose (g/L)[d] | Leucrose (g/L)[d] | Glucose (g/L)[d] | Fructose (g/L)[d] | Oligomers (g/L)[d,e] | Alpha-1,3 Glucan[f] Yield[i] | Fructose Balance |
|---|---|---|---|---|---|---|---|
| Plate 1[a] | | | | | | | |
| 6855[b] | 1.6 | 21.1 | 6.3 | 28.9 | 9.1 | 31% | 97% |
| 6855[b] | 1.6 | 21.3 | 6.3 | 29.1 | 10.5 | 27% | 98% |
| 6855[b] | 1.6 | 21.2 | 6.3 | 29.3 | 10.0 | 29% | 98% |
| 6855[b] | 1.6 | 21.1 | 6.3 | 28.9 | 10.8 | 27% | 97% |
| V186A[c] | 1.6 | 21.3 | 6.4 | 28.8 | 10.7 | 27% | 97% |
| V186M | 1.6 | 21.4 | 6.4 | 28.7 | 10.6 | 27% | 97% |
| E194C | 1.6 | 21.2 | 6.3 | 29.0 | 9.4 | 30% | 98% |
| L434N | 1.9 | 22.7 | 7.1 | 28.4 | 12.7 | 18% | 99% |
| A472O | 31.0 | 2.6 | 2.5 | 23.8 | 4.6 | 38% | 99% |
| A472S | 5.3 | 2.8 | 13.9 | 36.5 | 9.1 | 31% | 97% |
| A510E | 8.5 | 5.4 | 5.5 | 34.5 | 5.6 | 53% | 100% |
| A510E | 1.9 | 6.5 | 5.6 | 36.7 | 6.1 | 58% | 98% |
| A510I | 4.3 | 6.8 | 5.4 | 35.2 | 5.4 | 57% | 98% |
| A510V | 1.7 | 9.5 | 6.4 | 35.6 | 6.8 | 51% | 99% |
| L513Y | 1.4 | 10.3 | 4.2 | 35.3 | 7.2 | 54% | 99% |
| M529L | 1.9 | 10.4 | 4.2 | 35.2 | 10.9 | 44% | 99% |
| K578M | 1.6 | 21.0 | 6.4 | 28.8 | 10.8 | 27% | 97% |
| Y605W | 6.1 | 8.0 | 2.6 | 33.3 | 5.4 | 59% | 97% |
| F607N | 8.4 | 11.4 | 4.1 | 30.5 | 7.1 | 45% | 98% |
| F607W | 9.1 | 4.6 | 3.8 | 33.9 | 8.6 | 49% | 98% |
| N613I | 4.5 | 7.7 | 6.4 | 35.8 | 14.8 | 29% | 101% |
| N613M | 2.7 | 11.0 | 5.3 | 34.6 | 12.1 | 37% | 100% |
| N613T | 1.7 | 10.3 | 4.6 | 35.0 | 7.1 | 53% | 98% |
| N613V | 2.8 | 0.0 | 6.3 | 37.3 | 12.1 | 48% | 92% |
| Q616E | 3.9 | 2.4 | 5.8 | 37.3 | 8.8 | 53% | 97% |
| K625A | 1.5 | 21.2 | 6.3 | 29.4 | 9.9 | 29% | 99% |
| K625M | 1.5 | 21.3 | 6.3 | 29.3 | 10.6 | 27% | 99% |
| S631T | 5.4 | 11.4 | 4.6 | 32.0 | 7.6 | 46% | 97% |
| T635H | 4.1 | 11.0 | 5.0 | 32.7 | 8.2 | 46% | 97% |
| T635W | 13.1 | 8.5 | 4.5 | 29.6 | 7.0 | 42% | 98% |
| I636H | 7.0 | 11.7 | 5.0 | 31.1 | 8.1 | 42% | 98% |
| D947G | 2.4 | 19.1 | 6.1 | 29.8 | 9.9 | 31% | 98% |
| F951Y | 4.0 | 1.5 | 9.9 | 38.0 | 15.4 | 28% | 97% |

TABLE 3-continued

Product Profiles of GTF 6855 (SEQ ID NO: 4) and Single Amino Acid-Substituted Variants thereof

| GTF | Sucrose (g/L)$^d$ | Leucrose (g/L)$^d$ | Glucose (g/L)$^d$ | Fructose (g/L)$^d$ | Oligomers (g/L)$^{d,e}$ | Alpha-1,3 Glucan$^f$ Yield$^i$ | Fructose Balance |
|---|---|---|---|---|---|---|---|
| E849M | 1.4 | 20.7 | 6.2 | 29.5 | 10.4 | 29% | 98% |
| Q1007A | 1.4 | 19.4 | 6.2 | 30.2 | 10.1 | 31% | 98% |
| D1003G | 13.8 | 10.7 | 4.6 | 28.3 | 5.4 | 42% | 98% |
| A1022M | 1.7 | 20.6 | 6.2 | 29.3 | 12.2 | 24% | 98% |
| D1028L | 1.6 | 22.1 | 6.6 | 28.9 | 11.6 | 23% | 99% |
| D1028Q | 1.6 | 21.7 | 6.5 | 29.4 | 10.9 | 26% | 99% |
| A1057H | 1.5 | 21.4 | 6.4 | 29.2 | 10.6 | 27% | 98% |
| N1096A | 1.6 | 22.4 | 6.6 | 28.6 | 10.7 | 25% | 98% |
| E1132A | 1.5 | 21.4 | 6.4 | 29.2 | 10.6 | 27% | 98% |
| E1132H | 1.5 | 21.3 | 6.4 | 29.2 | 10.5 | 27% | 98% |
| E1132K | 1.5 | 21.4 | 6.4 | 29.2 | 10.4 | 27% | 98% |
| E1132R | 1.5 | 21.6 | 6.4 | 29.1 | 10.8 | 26% | 99% |
| L1212N | 1.5 | 20.9 | 6.3 | 29.5 | 10.4 | 28% | 98% |
| T1431M | 1.5 | 21.4 | 6.3 | 29.4 | 10.5 | 27% | 99% |
| A1442R | 1.5 | 21.3 | 6.4 | 29.1 | 10.6 | 27% | 98% |
| Dead$^g$ | 79.4 | 0.0 | 0.0 | 0.0 | 0.0 | 0% | 100% |
| Blank$^h$ | 79.7 | 0.0 | 0.1 | 0.0 | 0.0 | 0% | 100% |
| Blank$^h$ | 80.1 | 0.0 | 0.0 | 0.0 | 0.0 | 0% | 100% |
| Plate 2$^a$ | | | | | | | |
| 6855$^b$ | 1.4 | 20.1 | 6.4 | 28.2 | 10.0 | 29% | 99% |
| 6855$^b$ | 1.4 | 20.1 | 6.4 | 28.2 | 10.1 | 28% | 99% |
| 6855$^b$ | 1.4 | 20.0 | 6.3 | 28.3 | 10.3 | 28% | 99% |
| 6855$^b$ | 1.5 | 20.2 | 6.3 | 28.2 | 10.0 | 29% | 100% |
| Y219C$^c$ | 1.5 | 20.6 | 6.5 | 27.7 | 10.7 | 25% | 99% |
| E243H | 1.4 | 20.3 | 6.3 | 28.2 | 10.1 | 28% | 100% |
| L373A | 2.4 | 11.3 | 11.2 | 27.4 | 21.6 | −7% | 87% |
| L373Q | 4.0 | 7.5 | 10.7 | 28.4 | 21.5 | −2% | 87% |
| L373V | 2.5 | 11.6 | 11.5 | 27.5 | 21.8 | −9% | 88% |
| A377I | 2.9 | 15.5 | 6.6 | 29.3 | 11.3 | 29% | 98% |
| D425Q | 1.8 | 15.3 | 5.3 | 30.3 | 9.6 | 39% | 99% |
| L428V | 5.3 | 10.5 | 6.2 | 30.8 | 8.2 | 42% | 98% |
| N475F | 6.1 | 26.8 | 20.5 | 24.9 | 7.2 | −16% | 106% |
| N475W | 1.5 | 61.8 | 7.5 | 9.1 | 1.9 | −8% | 106% |
| L513F | 1.0 | 10.9 | 4.6 | 33.3 | 7.1 | 55% | 99% |
| L513W | 1.3 | 11.5 | 4.9 | 32.4 | 8.9 | 48% | 98% |
| M529N | 3.5 | 11.6 | 4.8 | 31.6 | 7.6 | 49% | 99% |
| I608Y | 2.4 | 15.7 | 5.7 | 29.9 | 9.8 | 35% | 99% |
| N613G | 2.2 | 10.5 | 5.0 | 33.5 | 10.6 | 43% | 101% |
| N613L | 2.9 | 13.3 | 5.0 | 32.1 | 11.7 | 35% | 102% |
| D617E | 8.4 | 10.2 | 6.9 | 29.8 | 9.0 | 34% | 99% |
| E621T | 1.5 | 18.6 | 6.0 | 29.1 | 10.4 | 30% | 100% |
| I623H | 69.8 | 0.2 | 1.4 | 3.3 | 0.0 | 4% | 101% |
| I627W | 7.7 | 12.2 | 5.2 | 28.9 | 7.9 | 40% | 99% |
| S631D | 9.8 | 12.3 | 5.7 | 27.5 | 8.0 | 35% | 98% |
| S631E | 10.1 | 12.6 | 5.6 | 27.3 | 8.0 | 35% | 99% |
| S631R | 6.7 | 12.3 | 5.4 | 28.7 | 8.1 | 40% | 97% |
| G633W | 7.0 | 7.2 | 5.5 | 31.9 | 8.5 | 46% | 99% |
| F634A | 7.4 | 8.4 | 5.7 | 30.8 | 8.2 | 43% | 98% |
| T635E | 1.6 | 17.2 | 6.0 | 29.9 | 9.5 | 35% | 100% |
| T635I | 1.5 | 17.4 | 6.2 | 30.5 | 10.1 | 32% | 102% |
| T635Y | 13.8 | 8.0 | 4.6 | 28.0 | 6.7 | 43% | 99% |
| A510E | 2.5 | 5.9 | 5.5 | 34.8 | 4.3 | 66% | 99% |
| N904E | 5.7 | 6.9 | 12.6 | 32.5 | 13.5 | 15% | 98% |
| K930G | 1.4 | 19.8 | 6.2 | 28.4 | 10.0 | 30% | 99% |
| K930V | 1.4 | 19.6 | 6.3 | 28.6 | 10.0 | 30% | 100% |
| D947F | 1.4 | 20.3 | 6.2 | 27.8 | 9.9 | 29% | 99% |
| D947I | 1.4 | 19.9 | 6.3 | 28.6 | 10.7 | 27% | 100% |
| D947K | 1.4 | 19.9 | 6.2 | 28.6 | 9.7 | 30% | 100% |
| D947N | 1.4 | 20.5 | 6.3 | 27.9 | 10.0 | 28% | 99% |
| D947Q | 1.4 | 19.5 | 6.2 | 28.4 | 9.6 | 31% | 99% |
| D947S | 1.3 | 18.9 | 6.1 | 28.8 | 9.4 | 33% | 99% |
| D947V | 1.4 | 19.8 | 6.2 | 28.3 | 9.7 | 30% | 99% |
| D947Y | 1.4 | 20.7 | 6.3 | 28.1 | 10.0 | 28% | 100% |
| Q1007S | 1.3 | 18.3 | 6.1 | 29.1 | 9.6 | 33% | 99% |
| D1003N | 3.6 | 13.1 | 5.7 | 30.5 | 9.8 | 38% | 99% |
| I1026H | 1.4 | 19.4 | 6.2 | 28.7 | 9.7 | 31% | 100% |
| D1028A | 1.5 | 20.1 | 6.5 | 28.4 | 10.8 | 26% | 100% |
| D1028M | 1.5 | 20.4 | 6.6 | 28.1 | 11.1 | 24% | 100% |
| V1037A | 1.5 | 20.2 | 6.4 | 28.4 | 10.3 | 28% | 100% |
| K1041A | 4.3 | 19.6 | 6.5 | 27.0 | 10.7 | 23% | 99% |
| K1041M | 1.5 | 20.5 | 6.4 | 28.0 | 10.5 | 26% | 100% |
| D1080M | 1.4 | 20.0 | 6.4 | 28.3 | 10.1 | 29% | 99% |

TABLE 3-continued

Product Profiles of GTF 6855 (SEQ ID NO: 4) and Single Amino Acid-Substituted Variants thereof

| GTF | Sucrose (g/L)$^d$ | Leucrose (g/L)$^d$ | Glucose (g/L)$^d$ | Fructose (g/L)$^d$ | Oligomers (g/L)$^{d,e}$ | Alpha-1,3 Glucan$^f$ Yield$^i$ | Fructose Balance |
|---|---|---|---|---|---|---|---|
| F1244P | 1.4 | 19.6 | 6.3 | 28.6 | 9.9 | 30% | 100% |
| F1244Q | 1.4 | 19.7 | 6.4 | 28.6 | 9.9 | 30% | 100% |
| T1431Q | 1.4 | 20.0 | 6.2 | 28.5 | 8.9 | 33% | 100% |
| G1484P | 1.5 | 20.1 | 6.3 | 28.5 | 9.2 | 31% | 100% |
| W1437N | 1.4 | 19.5 | 6.0 | 28.9 | 8.4 | 35% | 100% |
| Dead$^g$ | 75.5 | 0.0 | 0.0 | 0.0 | 0.0 | 0% | 100% |
| Blank$^h$ | 75.5 | 0.0 | 0.0 | 0.0 | 0.0 | 0% | 100% |
| Blank$^h$ | 76.0 | 0.0 | 0.0 | 0.0 | 0.5 | −2% | 100% |

$^a$Glucan synthesis reactions were run in microtiter plate format (two plates).
$^b$GTF 6855, SEQ ID NO: 4. Reactions with this GTF were run in quadruplicate per plate.
$^c$Each listed GTF with a substitution is a version of GTF 6855 comprising a substitution at a respective position, where the position number is in correspondence with the residue numbering of SEQ ID NO: 62. The wild type residue is listed first (before residue position number) and the substituting residue is listed second (after the residue position number) (this "wild type residue-position number-variant residue" annotation format applies throughout the present disclosure).
$^d$Sucrose, leucrose, glucose, fructose and oligomers were measured as present in filtrate prepared post reaction.
$^e$"Oligomers", gluco-oligosaccharides (believed to all or mostly be of DP ≤ 7 or 8).
$^f$Insoluble alpha-1,3 glucan product.
$^g$GTF with destroyed activity was entered into the reaction.
$^h$No GTF was added to the reaction.
$^i$Alpha-glucan yield based on glucosyl.

Based on the data in Table 3, it is apparent that certain single amino acid substitutions in GTF 6855 (SEQ ID NO:4) can increase this enzyme's yield of alpha-1,3-glucan and/or decrease its leucrose yield in glucan synthesis reactions, for example.

Example 2

Analysis of the Effects of Single Amino Acid Substitutions on Other Glucosyltransferases This Example describes the effects of certain single amino acid substitutions on the activities of glucosyltransferases other than GTF 6855 (SEQ ID NO:4). In general, it appears that substitutions corresponding to (or similar to) those observed in Example 1 having a significant effect on alpha-glucan and/or leucrose yields may be useful for imparting similar effects to different glucosyltransferases.

Phe-607-Tyr

Example 1 demonstrated, for example, that substitutions in GTF 6855 (SEQ ID NO:4) at the position corresponding to position 607 of SEQ ID NO:62 affected enzyme activity (Table 3). In particular, substitutions of the Phe residue with an Asn or Trp residue both had significant effects on alpha-1,3 glucan yield (increased) and leucrose yield (decreased) compared to the respective yields of the non-substituted enzyme.

To test whether a similar substitution could similarly affect yields in a different GTF, a substitution was made at a position in GTF 7527 (GTFJ, SEQ ID NO:65) corresponding to position 607 of SEQ ID NO:62, exchanging a Phe for a Tyr residue. GTF 7527 (SEQ ID NO:65) essentially is an N-terminally truncated (signal peptide and variable region removed) version of the full-length wild type glucosyltransferase (represented by SEQ ID NO:60) from *Streptococcus salivarius* (see Table 1). Substitutions made in SEQ ID NO:65 can be characterized as substituting for native amino acid residues, as each amino acid residue/position of SEQ ID NO:65 (apart from the Met-1 residue of SEQ ID NO:65) corresponds accordingly with an amino acid residue/position within SEQ ID NO:60. In reactions comprising at least sucrose and water, the glucosyltransferase of SEQ ID NO:65 typically produces alpha-glucan having about 100% alpha-1,3 linkages and a DP$_n$ of 400 or greater (e.g., refer to U.S. Patent Appl. Publ. No. 2017/0002335 [application Ser. No. 15/182,747], which is incorporated herein by reference). Glucan synthesis reactions were prepared as follows using GTF 7527 (SEQ ID NO:65) or a version thereof comprising a Phe-to-Tyr substitution at the position corresponding to position 607 of SEQ ID NO:62: vessel, 250-mL indented shake flask agitated at 100 rpm; initial pH, 5.5; reaction volume, 50 mL; sucrose, 100.1 g/L; GTF, 100 U/L; KH$_2$PO$_4$, 25 mM; temperature, 25° C.; time, 20 hours. The profiles of each reaction (as measured via methodology similar to that disclosed in Example 1), which were run in duplicate, are provided in Table 4.

TABLE 4

Product Profiles of GTF 7527 (SEQ ID NO: 65) and a Single Amino Acid-Substituted Variant thereof

| GTF | Sucrose Conv. | Yield Alpha-Glucan$^d$ based on Glucosyl | Leucrose Yield | Glucose Yield | Oligomer$^c$ Yield | Fructose balance |
|---|---|---|---|---|---|---|
| 7527$^a$ | 99.7% | 29.24% | 42% | 4.20% | 28% | 105.62% |
| 7527 | 99.8% | 22.21% | 43% | 6.26% | 29% | 109.02% |
| F607Y$^b$ | 99.8% | 64.92% | 16% | 3.33% | 15% | 102.73% |
| F607Y | 99.8% | 62.97% | 17% | 3.35% | 17% | 109.17% |

$^a$GTF 7527, SEQ ID NO: 65.
$^b$F607Y, version of GTF 7527 (SEQ ID NO: 65) comprising a Phe-to-Tyr substitution at the position corresponding to position 607 of SEQ ID NO: 62.
$^c$"Oligomer", gluco-oligosaccharides (believed to all or mostly be of DP ≤ 7 or 8).
$^d$"Alpha-Glucan", insoluble alpha-1,3 glucan.

Based on the data in Table 4, it is apparent that the F607Y substitution in GTF 7527 (SEQ ID NO:65) can increase this enzyme's yield of alpha-1,3-glucan and/or decrease its leucrose yield in glucan synthesis reactions, for example.

Ala-510-Glu, Ala-510-Val, or Ala-510-Cys

Example 1 demonstrated, for example, that substitutions in GTF 6855 (SEQ ID NO:4) at the position corresponding to position 510 of SEQ ID NO:62 affected enzyme activity (Table 3). In particular, substitutions of the Ala residue with a Glu, Ile, or Val residue all had significant effects on alpha-1,3 glucan yield (increased) and leucrose yield (decreased) compared to the respective yields of the non-substituted enzyme.

To test whether these or similar substitutions could similarly affect yields in different GTFs, substitutions were made at positions in GTFs 2919 (SEQ ID NO:28), 0427 (SEQ ID NO:26), 5926 (SEQ ID NO:14), 0874 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), and 6907 (SEQ ID NO:36) corresponding to position 510 of SEQ ID NO:62, exchanging an Ala for a Glu, Val, or Cys residue. Each of these GTFs essentially is an N-terminally truncated (signal peptide and variable region removed) version of a full-length wild type glucosyltransferase (e.g., refer to respective GENBANK annotation information, such as that listed in Table 1). Substitutions made in each of SEQ ID NOs: 28, 26, 14, 2, 12, 6, 18, 16, 24 and 36 can be characterized as substituting for native amino acid residues, as each amino acid residue/position of these sequences (apart from the Met-1 residues of each) corresponds accordingly with an amino acid residue/position within each respective full-length wild type glucosyltransferase counterpart. Table 2 lists the alpha-glucan typically produced by each of SEQ ID NOs: 28, 26, 14, 2, 12, 6, 18, 16, 24 and 36 in reactions comprising at least sucrose and water.

Preparation of GTF 2919 (SEQ ID NO:28), 0427 (SEQ ID NO:26), 5926 (SEQ ID NO:14), 0874 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), or 6907 (SEQ ID NO:36), or versions thereof comprising a substitution at the position corresponding to position 510 of SEQ ID NO:62 was performed as follows. Codon-optimized (for *E. coli*) sequences encoding each of these GTFs were individually cloned into a suitable plasmid for bacterial expression. Each construct was then transformed into *E. coli* BL21-AI (Invitrogen, Carlsbad, CA). Transformed strains were grown in 10 mL auto-induction medium (10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose, 0.05% arabinose) containing 100 mg/L ampicillin at 37° C. for 20 hours under 200 rpm agitation. The cells were harvested by centrifugation at 8000 rpm at 4° C. and resuspended in 1 mL of 20 mM sodium phosphate buffer pH 6.0 with CelLytic™ Express (Sigma, St. Louise, MO) according to the manufacturer's instructions. In addition, resuspended cells were subjected to no less than one freeze-thaw cycle to ensure cell lysis. Lysed cells were centrifuged for 10 minutes at 12,000 g at room temperature. Each resulting supernatant was analyzed by SDS-PAGE to confirm expression of the particular GTF enzyme being expressed. Each supernatant was kept on ice at 4° C. until enzyme activity could be determined (within 1 hour), and/or stored at −20° C.

Glucan synthesis reactions were prepared, and the products thereof analyzed, largely according to the disclosure of U.S. Pat. Appl. Publ. No. 2014/0087431, which is incorporated herein by reference. Each reaction was run for 24-30 hours. The profiles of each reaction are provided in Table 5.

TABLE 5

Product Profiles of Various GTFs and Single Amino Acid-Substituted Variants thereof

| GTF | Sucrose Conv. | Yield Alpha-Glucan based on Glucosyl | Leucrose Yield | Glucose Yield | Oligomer Yield | Fructose balance |
|---|---|---|---|---|---|---|
| 2919[a] | 92% | 20% | 28% | 15% | 37% | 90% |
| A510E[b] | 98% | 40% | 13% | 15% | 31% | 93% |
| A510V[b] | 97% | 45% | 15% | 15% | 26% | 84% |
| A510C[b] | 95% | 35% | 19% | 15% | 32% | 87% |
| 0427[a] | 96% | 15% | 33% | 11% | 41% | 97% |
| A510E[b] | 96% | 1.0% | 40% | 16% | 43% | 104% |
| A510V[b] | | | poor conversion | | | |
| A510C[b] | 96% | 9% | 30% | 12% | 50% | 97% |
| 5926[a] | 97% | 12% | 37% | 11% | 41% | 93% |
| A510E[b] | 96% | 12% | 40% | 14% | 34% | 94% |
| A510V[b] | 97% | 25% | 31% | 14% | 31% | 81% |
| A510C[b] | 97% | −1% | 35% | 14% | 52% | 97% |
| 0847[a] | 97% | 18% | 33% | 11% | 38% | 92% |
| A510E[b] | 98% | 11% | 35% | 14% | 40% | 95% |
| A510V[b] | 80% | 32% | 21% | 16% | 31% | 80% |
| A510C[b] | 97% | 10% | 33% | 13% | 44% | 97% |
| 0544[a] | 99% | 37% | 22% | 8% | 33% | 86% |
| A510E[b] | 93% | 46% | 21% | 8% | 25% | 85% |
| A510V[b] | | | poor conversion | | | |
| A510C[b] | 92% | 39% | 16% | 9% | 37% | 90% |
| 2379[a] | 95% | 4% | 30% | 18% | 48% | 92% |
| A510E[b] | 97% | −2% | 23% | 23% | 56% | 93% |
| A510V[b] | 94% | 5% | 20% | 23% | 52% | 82% |
| A510C[b] | 93% | −10% | 37% | 21% | 53% | 101% |
| 5618[a] | 99% | 80% | 10% | 5% | 5% | 89% |
| A510E[b] | 94% | 82% | 5% | 4% | 9% | 93% |
| A510V[b] | 99% | 83% | 7% | 5% | 5% | 78% |
| A510C[b] | 98% | 83% | 9% | 4% | 4% | 96% |
| 4297[a] | 97% | 78% | 12% | 6% | 4% | 86% |
| A510E[b] | 99% | 84% | 7% | 4% | 5% | 83% |
| A510V[b] | 99% | 78% | 8% | 8% | 6% | 77% |
| A510C[b] | 80% | 71% | 8% | 9% | 7% | 84% |
| 1366[a] | 97% | 12% | 39% | 7% | 43% | 91% |
| A510E[b] | 99% | 9% | 39% | 16% | 36% | 89% |
| A510V[b] | 78% | 17% | 28% | 16% | 39% | 80% |
| A510C[b] | 97% | 1% | 39% | 12% | 48% | 96% |
| 6907[a] | 85% | 7% | 42% | 17% | 34% | 91% |
| A510E[b] | 89% | 14% | 35% | 25% | 26% | 94% |
| A510V[b] | | | poor conversion | | | |
| A510C[b] | | | poor conversion | | | |

[a]GTF 2919 (SEQ ID NO: 28), 0427 (SEQ ID NO: 26), 5926 (SEQ ID NO: 14), 0847 (SEQ ID NO: 2), 0544 (SEQ ID NO: 12), 2379 (SEQ ID NO: 6), 5618 (SEQ ID NO: 18), 4297 (SEQ ID NO: 16), 1366 (SEQ ID NO: 24), or 6907 (SEQ ID NO: 36).
[b]A510E/V/C, version of listed GTF (footnote [a]) comprising a substitution with Glu, Val, or Cys at the position corresponding to position 510 of SEQ ID NO: 62.
[c]"Oligomer", gluco-oligosaccharides.

Based on the data in Table 5, it is apparent that some substitutions in various GTFs at the position corresponding to position 510 of SEQ ID NO:62 can increase a GTF's yield of alpha glucan and/or decrease its leucrose yield in glucan synthesis reactions, for example.

Phe-951-Tyr, Leu-373-Phe, or Leu-373-Met

Example 1 demonstrated, for example, that substitutions in GTF 6855 (SEQ ID NO:4) at the positions corresponding to positions 373 and 951 of SEQ ID NO:62 affected enzyme activity (Table 3). In particular, substitution of the Phe-951 residue with a Tyr residue had a significant effect on leucrose yield (decreased) compared to the respective yield of the non-substituted enzyme. Substitution of the Leu-373 residue with an Ala, Gln, or Val residue also had a significant lowering effect on leucrose yield.

To test whether similar substitutions could affect yields in different GTFs, a substitution was made at position 839 (exchanging a Phe for a Tyr) in GTF 5604 (SEQ ID NO:68) and at position 886 (exchanging a Phe for a Tyr) in GTF 8845 (SEQ ID NO:69, refer to proxy GTF below), each of which positions correspond to position 951 of SEQ ID NO:62. In other analyses, a substitution was made at position 316 (exchanging a Leu for a Phe or Met) in GTF 5604 (SEQ ID NO:68) and at position 363 (exchanging a Leu for a Phe or Met) in GTF 8845 (SEQ ID NO:69, refer to proxy GTF below), each of which positions correspond to position 373 of SEQ ID NO:62.

GTF 5604 (SEQ ID NO:68) is a full-length wild type glucosyltransferase (including a signal peptide at residues 1-36) from Streptococcus criceti (see Table 1); it was thus expected that the expressed enzyme in mature form had residues 37-1338 of SEQ ID NO:68. GTF 8845 (SEQ ID NO:69) is full-length wild type glucosyltransferase (including a signal peptide at residues 1-36) from Streptococcus sobrinus (see Table 1). A proxy for GTF 8845 was expressed herein in the form of SEQ ID NO:70, which represents an N-terminally truncated version of the full-length wild type glucosyltransferase fused to a B. subtilis AprE signal peptide (the above substitutions listed for GTF 8845 were actually tested in the context of the proxy GTF). In particular, residues 30-1414 of SEQ ID NO:70 represent residues 170-1554 of GTF 8845 (SEQ ID NO:69), whereas residues 1-29 of SEQ ID NO:70 represent heterologous amino acids including a signal peptide. The expressed proxy GTF in mature form was therefore expected to have residues 170-1554 of GTF 8845 (SEQ ID NO:69). In reactions comprising at least sucrose and water, the mature form of GTF 5604 (SEQ ID NO:68) is believed to produce oligosaccharides of DP8 and above (i.e., DP8+) (e.g., DP 18 or 19) having about 100% alpha-1,6 linkages (see Table 4 [sample SG1018] of WO2015/183714 or U.S. Patent Appl. Publ. No. 2017/0218093, which are incorporated herein by reference). In reactions comprising at least sucrose and water, a mature GTF having residues 170-1554 of GTF 8845 (SEQ ID NO:69) is believed to produce DP8+ oligosaccharides (e.g., DP 116 or 117) having about 80% alpha-1,6 linkages, 3% alpha-1,3 linkages and 17% alpha-1,3,6 linkages (see Table 4 [sample SG1051] of WO2015/183714).

Plasmids for expressing the foregoing GTFs and single amino acid-substituted variants thereof in Bacillus (protein secretion) were prepared accordingly. These plasmids were then individually transformed into Bacillus subtilis strain BG6006, and transformed clones were selected on tetracycline (12.5 µg/mL) plates. BG6006 is a nine protease deletion strain derived from the well-known B. subtilis type strain 168, and has the genotype: amyE::xylRPxylAcomK-ermC, degUHy32, oppA, DspoIIE3501, ΔaprE, ΔnprE, Δepr, ΔispA, Δbpr, Δvpr, ΔwprA, Δmpr-ybfJ, ΔnprB. Each transformed strain was grown up in LB medium containing 10 µg/mL tetracycline first, and then subcultured into Grants II medium containing 12.5 µg/mL tetracycline and grown at 37° C. for 2 days. The cultures were spun at 15,000 g for 30 min at 4° C. and the supernatants were filtered through 0.22-µm filters. The filtered supernatants from each culture were run on SDS-PAGE to confirm GTF expression. No obvious differences in expression levels were observed between the GTF variants and their respective non-variant parents.

Glucan synthesis reactions were prepared, and the products thereof analyzed, as follows. The B. subtilis supernatants prepared above containing an expressed GTF were used to set up reactions comprising sucrose as the substrate. Each reaction comprised 100 g/L sucrose, 10% (v/v) GTF supernatant, 10 mM sodium citrate buffer pH 5.0 and 1 mM $CaCl_2$, and was held at 37° C. for one or two days. Besides forming alpha-glucan product(s) (e.g., soluble gluco-oligosaccharides of DP3-8 or DP8+), each reaction also generated fructose co-product and leucrose by-product, for example. The reactions were filtered and analyzed by HPLC. BioRad AMINEX HPX-87C columns were used to analyze small sugars (mono- and di-saccharides). Two BioRad AMINEX HPX-87C columns (300 cm×7.8 mm) in series were placed in an external heater at 85° C. The standard cartridge holder (BioRad cat #125-0131) contained a MICROGUARD CARBO-C cartridge (BioRad cat #125-0128). The mobile phase was d.d. $H_2O$ at a 0.6 mL/min flow rate. The injection volume was 10 µL. The RI detector was set at 410 at 40° C. The analysis time was 35 min for each sample. The BioRad AMINEX HPX-42A column was used to analyze oligosaccharides. The BioRad AMINEX HPX-42A column (300 cm×7.8 mm) was placed in an external heater at 85° C. The de-ashing cartridge holder (BioRad cat #125-0139) contained de-ashing refill cartridges (BioRad cat #125-0118). The mobile phase and detection was similar as for the HPX-87C columns. Table 6 below summarizes the HPLC analysis of the sugars and oligosaccharides in each GTF reaction. The data are the averages of four replicates of each reaction; each standard deviation was below 7%.

TABLE 6

Product Profiles of GTFs 5604, 8845, and Single Amino Acid-Substituted Variants thereof

| GTF | Sucrose (g/L) | Leucrose (g/L) | Glucose (g/L) | Fructose (g/L) | DP2 (g/L) | DP3-8 (g/L) | DP8+ est. (g/L) | Total Sugars (g/L) |
|---|---|---|---|---|---|---|---|---|
| 5604[a] | 0.2 | 10.6 | 4.7 | 36.6 | 3.3 | 1.0 | 39.8 | 96.2 |
| L373F[b] | 0.2 | 3.4 | 4.6 | 39.8 | 2.4 | 2.0 | 45.2 | 97.6 |
| L373M[b] | 0.3 | 7.1 | 4.9 | 38.2 | 2.7 | 1.4 | 43.3 | 97.8 |
| F951Y[b] | 0.5 | 1.1 | 4.9 | 40.7 | 3.4 | 2.7 | 45.1 | 98.2 |
| 8845[a] | 1.3 | 16.6 | 10.8 | 35.7 | 1.1 | 0.0 | 31.2 | 96.5 |
| L373F[b] | 1.5 | 16.6 | 13.3 | 35.3 | 1.9 | 1.5 | 28.4 | 87.9 |
| L373M[b] | 0.5 | 11.4 | 10.8 | 38.1 | 0.9 | 0.2 | 36.1 | 97.9 |
| F951Y[b] | 1.0 | 1.8 | 10.9 | 42.6 | 0.7 | 0.0 | 41.4 | 92.2 |

[a]GTF 5604 (secreted form having residues 37-1338 of SEQ ID NO: 68), GTF 8845 (secreted form having residues 170-1554 of SEQ ID NO: 69).
[b]Version of listed GTF (footnote [a]) comprising a single amino acid substitution, where the listed position number is in correspondence with the residue numbering of SEQ ID NO: 62.

As shown in Table 6, parent GTF 5604 produced about 10.6 g/L leucrose. In reactions using the L373F, L373M and F951Y variants of GTF 5604, leucrose was reduced to 3.4 g/L, 7.1 g/L, and 1.1 g/L respectively. Consistent with this decrease of leucrose by-product, each variant GTF reaction had an increase in both fructose co-product levels and estimated levels of DP8+ oligomers. These reaction profiles were generally mirrored by GTF 8845 and its variants, except for the L373F variant.

The linkage profiles of the reaction products listed in Table 6 were analyzed by GC/MS. No significant differences in linkages were observed between the products of the non-variant GTF parents and the products of their respective single amino acid-substituted variants.

In summary, based on the data in Table 6, it is apparent that some substitutions in various GTFs at positions corresponding to positions 373 or 951 of SEQ ID NO:62 can increase a GTF's yield of alpha glucan and/or decrease its leucrose yield in glucan synthesis reactions, for example.

Example 3

Analysis of the Effects of Two or More Amino Acid Substitutions on Glucosyltransferase Selectivity toward Alpha-Glucan Synthesis This Example describes the effects of introducing multiple amino acid substitutions to a glucosyltransferase and determining their effect on enzyme selectivity toward alpha-glucan synthesis.

Briefly, certain amino acid substitutions were made to SEQ ID NO:4 (GTF 6855, see Table 1 and Example 1 for description of this glucosyltransferase). These substitutions are listed in Table 7 below. Each variant enzyme was entered into a glucan synthesis reaction with parameters that were the same as, or similar to, the following: vessel, 250-mL indented shake flask agitated at 120 rpm; initial pH, 5.7; reaction volume, 50 mL; sucrose, 75 g/L; GTF, 1.5 mL lysate of E. coli cells heterologously expressing enzyme; KH$_2$PO$_4$, 20 mM; temperature, 30° C.; time, about 20-24 hours. The alpha-1,3 glucan yield of each reaction (as measured via methodology similar to that disclosed in Example 1) is provided in Table 7.

TABLE 7

Alpha-1,3 Glucan Yields of GTF 6855 (SEQ ID NO: 4) Variants with Multiple Amino Acid-Substitutions

| GTF[a] | Alpha-1,3 Glucan[b] Yield[c] |
|---|---|
| A510D/F607Y/R741S | 72.6% |
| A510D/F607Y/N743S | 79.2% |
| A510D/F607Y/D948G | 88.2% |
| A510D/R741S/D948G | 74.5% |
| A510D/F607Y/R741S/D948G | 82.8% |
| A510E/F607Y/R741S/R1172C | 78.2% |
| A510D/F607Y/D820G/D948G | 87.8% |
| A510D/F607Y/D948G/R1172C | 88.6% |
| A510D/F607Y/N743S/D948G/R1172C | 89.4% |
| A510D/F607Y/R741S/L784Q/F929L/R1172C | 79.3% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Based on the data in Table 7, it is apparent that introduction of multiple amino acid substitutions to GTF 6855 (SEQ ID NO:4) can increase this enzyme's yield of alpha-1,3-glucan; for example, compare these yields to those of GTF 6855 (SEQ ID NO:4) without substitutions shown in Table 3. Each of the variant GTF enzymes listed in Table 7 also exhibited significant reductions in yields of leucrose, glucose and gluco-oligomers (data not shown).

It is apparent, for example, that a GTF with multiple substitutions such as at positions corresponding to positions 510 and/or 607 of SEQ ID NO:62 can increase a GTF's yield of alpha glucan.

SEQUENCE LISTING

```
Sequence total quantity: 71
SEQ ID NO: 1            moltype = DNA   length = 4308
FEATURE                 Location/Qualifiers
source                  1..4308
                        mol_type = unassigned DNA
                        organism = Streptococcus sobrinus
SEQUENCE: 1
atggttgacg gcaaatacta ctattatgat caggacggta acgtaaagaa gaatttcgcg   60
gtgagcgttg gtgacaaaat ctactacttc gatgaaactg gtgcatataa ggataccagc  120
aaagtggacg ccgacaagag cagcagcgcg gttagccaaa acgcgaccat ctttgcggcg  180
aataaccgtg cgtacagcac ctctgcaaag aattttgaag cggtggataa ctacctgacc  240
gcagacagct ggtatcgtcc gaaatccatc ctgaaggacg gcaaaacctg gaccgagagc  300
ggtaaggatg atttccgtcc actgctgatg gcatggtggc ctgacaccga aactaagcgc  360
aactacgtga actatatgaa taaagtggtc ggtattgaca agacgtacac tgcggaaacg  420
tcgcaagcgg atttgaccgc agcggcgag ctggttcaag cgcgtatcga gcagaagatt   480
accagcgaaa acaacaccaa atggctgcgc gaagcaatct ccgcgttcgt taagacgcag  540
cctcagtgga acggcgagtc cgaaaagccg tatgacgatc acttgcagaa cggtgcgctg  600
ctgtttgata accaaaccga cctgacgcca gacacccaaa gcaattaccg tttgctgaac  660
cgtaccccga ccaatcagac tggtagcctg gatagccgtt ttacgtataa tccgaatgac  720
ccgttgggcg gctacgattt cttgctgcg aacgacgttg acaatagcaa tccggtcgtc  780
caggctgaac agttgaactg gctgcattat ctgctgaact ttggctctat ttacgctaac  840
gatgccgacg ccaattttga cagcattcgc gttgatgccg tcgataatgt cgatgctgat  900
ctgctgcaaa tcagcagcga ttacctgaaa gcagcgtatg gcatcgacaa gaataacaag  960
aatgcgaaca accatgttag catcgtcgaa gcgtggagcg acaatgatac cccgtatttg 1020
cacgacgatg gcgataaatct gatgaacatg gacaacaaat ttcgcctgtc catgctgtgg 1080
agcctggcaa agccgctgga caaacgtagc ggtttgaacc cgctgattca caatagcctg 1140
gtggaccgcg aggtggacga tcgtgaagtg gaaaccgtgc cgtcctacag ctttgctcgt 1200
gcacatgata gcgaggtgca ggacatcatc cgtgacatta tcaaggctga gattaaccca 1260
aatagctttg gttatagctt cactcaagaa gagatcgagc aagcctttaa gatttacaac 1320
gaggatttga gaaaacgga caagaaatac acccactaca atgtgccgct gagctacacc 1380
ctgctgctga ccaacaaggg cagcatcccg cgtgtgtact atggtgatat gttcaccgat 1440
gatggccaat acatggcaaa caagaccgtc aactacgacg caatcgagag cctgctgaaa 1500
gcccgtatga aatatgtcag cggtggccaa gcaatgcaga actatcaaat tggtaatggc 1560
gagatttga ccagcgtgcg ctatggtaaa ggtgccctga agcagagcga taagggtgac 1620
gcgacgacgc gcactagcgg tgttggcgtg gttatgggta atcagccgaa cttctccctg 1680
```

```
gacggtaaag ttgtggccct gaatatgggt gcggcccatg cgaatcaaga ataccgtgca 1740
ctgatggtca gcactaaaga cggtgtggca acttacgcaa ccgatgctga cgcatccaaa 1800
gcgggcctgg tcaagcgtac cgacgagaac ggctacctgt acttcctgaa tgatgatctg 1860
aagggcgtcg cgaaccctca ggtttccggc ttcttgcaag tgtgggttcc agttggtgcc 1920
gccgatgacc aggacattcg cgtcgccgcc agcgacacgg tgtaaaagc 1980
ctgcatcaag atgcggcgat ggacagccgc gtcatgtttg agggtttcag caattttcaa 2040
tccttcgcga ccaaagaaga gaatacacg aatgttgtta tcgcgaacaa tgtcgataag 2100
ttcgttagct ggggtatcac cgattttgaa atggctccgc agtatgttag cagcaccgac 2160
ggtcagttct tggacacgt catccagaat ggctcgtcgt ttactgatcg ctatgatctg 2220
ggtatgtcca aggcgaacaa gtatgcgcac gcagaccaac tggttaagcc aatcaaagcc 2280
ctgcacgcta aaggcctgaa agttatggcg gactgggtcc cggatcaaat gtacaccttt 2340
ccaaaacagg aagttgtgac cgttacccgc accgacaaat cggtaaaacc gatcgccggc 2400
tctcaaatca atcacagctt gtatgtgacc gacaccaaat ccagcggcga cgactaccaa 2460
gcgaagtacg gcggtgcctt cctgatgaa agtaccggca actgttcacg 2520
aaaaagcaaa ttagcacggg ccaagcgatt gatccgagcg tgaaaatcaa cagtggagc 2580
gcaaaatact tcaatggttc gaatatcctg ggtcgcggtg cggactatgt gctgagcgac 2640
caggtcagca ataagtattt caacgtgcg agcgacacct tgttcctgcc gtccagcctg 2700
ctgggcaagg tcgtggagag cggcattcgt tacgacggca agggttacat ctacaacagc 2760
tccgcgaccg gcgatcaggt caaagcgtct tcattacgg aagccggtaa cctgtattac 2820
ttcggcaaag acgttacat ggttactggt gcccagacga ttaatggcgc caactactc 2880
ttcctggaaa acggtacggc actgcgtaat acgatttaca ccgatgctca aggtaatagc 2940
cactattacg cgaatgatgg caaacgctat gaaaatggct atcaacagtt cggtaacgat 3000
tggcgctact ttaaagatgg taacatggca gtcggcctga ccacggttga tggcaacgtg 3060
caatactttg acaaagacgg cgtccaggca aaggataaga ttatcgtcac ccgtgatggc 3120
aaggtccgtt acttcgatca gcacaacggt aacgcggcga ccaacacgtt cattgctgat 3180
aaaactggcc attggtatta cctgggtaaa gatggcgtcg cggtgactgg cgcccagacc 3240
gtcggcaaac aaaaactgta cttcgaggcc aacggtcaac aagttaaagg tgactttgtt 3300
acgtccgatg agggcaaact gtatttctat gacgttgatt ctggtgacat gtggacggac 3360
accttcatcg aggataaggc gggcaactgg ttctatttgg gcaaggatgg tgcggcagtt 3420
acgggtgccc aaacgattcg cggtcagaag ctgtacttca aggccagtg tcaacaggtc 3480
aagggtgaca ttgttaaggg caccgacggt aaaatccgct actatgatgc aaaatccggt 3540
gaacaggtgt tcaacaaaac ggtgaaagct gcggatggca aaacgtatgt tatcggtaat 3600
gatggtgtcg cggtggaccc tagcgtggtt aaaggtcaaa ccttaaggga cgcttcgggc 3660
gctctgcgtt tctacaactt gaagggtcaa ctggtcactg gcagcggctg gtatgaaacc 3720
gcgaaccatg actgggttta cattcagtcc ggcaaggcac tgaccggcga acagaccatt 3780
aacggtcaac acctgtattt caagaagat ggtcaccaag tcaagggtca gttggtcacg 3840
ggcaccgatg gtaaagtgcg ttactatgac gccaacagcg tgaccaagc attcaacaag 3900
agcgtcactg tgaatggtaa aacctattac tttggcaacg atggtacggc gcagactgct 3960
ggcaacccga agggtcagac gttcaaggat ggctccgaca tccgttttta ctctatgaa 4020
ggccaactgg tgaccggctc gggttgttac gagaacgcgc aaggccagtg gctgtatgtg 4080
aaaaacggta aggtgctgac tggtctgcaa accgttggca gccagcgtgt ttacttcgac 4140
gagaatggta ttcaggccaa gggcaaagca gtgcgtacca cgcgatggcaa aattcgttat 4200
ttcgacgaaa acagcggcag catgatcacg aatcaatgga agttcgtcta tggtcagtat 4260
tactactttg gtaacgacgg tgcacgtatt accgtggtt ggaactaa 4308
```

SEQ ID NO: 2         moltype = AA  length = 1435
FEATURE          Location/Qualifiers
source           1..1435
                mol_type = protein
                organism = Streptococcus sobrinus

```
SEQUENCE: 2
MVDGKYYYYD QDGNVKKNFA VSVGDKIYYF DETGAYKDTS KVDADKSSSA VSQNATIFAA  60
NNRAYSTSAK NFEAVDNYLT ADSWYRPKSI LKDGKTWTES GKDDFRPLLM AWWPDTETKR 120
NYVNYMNKVV GIDKTYTAET SQADLTAAAE LVQARIEQKI TSENNTKWLR EAISAFVKTQ 180
PQWNGESEKP YDDHLQNGAL LFDNQTDLTP DTQSNYRLLN RTPTNQTGSL DSRFTYNPND 240
PLGGYDFLLA NDVDNSNPVV QAEQLNWLHY LLNFGSIYAN DADANFDSIR VDAVDNVDAD 300
LLQISSDYLK AAYGIDKNNK NANNHVSIVE AWSDNDTPYL HDDGDNLMNM DNKFRLSMLW 360
SLAKPLDKRS GLNPLIHNSL VDREVDDREV ETVPSYSFAR AHDSEVQDII RDIIKAEINP 420
NSFGYSFTQE EIEQAFKIYN EDLKKTDKKY THYNVPLSYT LLLTNKGSIP RVYYGDMFTD 480
DGQYMANKTV NYDAIESLLK ARMKYVSGGQ AMQNYQIGNG EILTSVRYGK GALKQSDKGD 540
ATTRTSGVGV VMGNQPNFSL DGKVVALNMG AAHANQEYRA LMVSTKDGVA TYATDADASK 600
AGLVKRTDEN GYLYFLNDDL KGVANPQVSG FLQVWVPVGA ADDQDIRVAA SDTASTDGKS 660
LHQDAAMDSR VMFEGFSNFQ SFATKEEEYT NVVIANNVDK FVSWGITDFE MAPQYVSSTD 720
GQFLDSVIQN GYAFTDRYDL GMSKANKYGT ADQLVKAIKA LHAKGLKVMA DWVPDQMYTF 780
PKQEVVTVTR TDKFGKPIAG SQINHSLYVT DTKSSGDDYQ AKYGGAFLDE LKEKYPELFT 840
KKQISTGQAI DPSVKIKQWS AKYFNGSNIL GRGADYVLSD QVSNKYFNVA SDTLFLPSSL 900
LGKVVESGIR YDGKGYIYNS SATGDQVKAS FITEAGNLYY FGKDGYMVTG AQTINGANYF 960
FLENGTALRN TIYTDAQGNS HYYANDGKRY ENGYQQFGND WRYKDGNMA VGLTTVDGNV 1020
QYFDKDGVQA KDKIIVTRDG KVRYFDQHNG NAATNTFIAD KTGHWYYLGK DGVAVTGAQT 1080
VGKQKLYFEA NGQQVKGDFV TSDEGKLYFY DVDSGDMWTD TFIEDKAGNW FYLGKDGAAV 1140
TGAQTIRGQK LYFKANGQQV KGDIVKGTDG KIRYYDAKSG EQVFNKTVKA ADGKTYVIGN 1200
DGVAVDPSVV KGQTFKDASG ALRFYNLKGQ LVTGSGWYET ANHDWVYIQS GKALTGEQTI 1260
NGQHLYFKED GHQVKGQLVT GTDGKVRYYD ANSGDQAFNK SVTVNGKTYY FGNDGTAQTA 1320
GNPKGQTFKD GSDIRFYSME GQLVTGSGWY ENAQGQWLYV KNGKVLTGLQ TVGSQRVYFD 1380
ENGIQAKGKA VRTSDGKIRY FDENSGSMIT NQWKFVYGQY YYFGNDGARI YRGWN 1435
```

SEQ ID NO: 3         moltype = DNA  length = 4026
FEATURE          Location/Qualifiers
source           1..4026

```
                    mol_type = unassigned DNA
                    organism = Streptococcus salivarius
SEQUENCE: 3
atgatcgacg gcaaatacta ttatgttaat gaggacggta gccacaaaga aaactttgcg    60
attacggtta atggtcaact gctgtatttc ggtaaggacg gcgcactgac ctctagcagc   120
acttacagct ttaccccagg tacgacgaac atcgtggatg gcttttctat caacaaccgc   180
gcgtatgact ccagcgaagc gtcctttgaa ctgattgatg gctacttgac tgccgactcc   240
tggtatcgtc cggcttccat catcaaggac ggtgtcacgt ggcaggccag caccgcagag   300
gactttcgcc cgctgctgat ggcgtggtgg ccaaacgtgg ataccaggt gaactatctg    360
aactacatgt ctaaagtgtt taacctggac gcaaagtata gcagcaccga taaacaagag   420
actctgaagg ttgcagctaa ggatattcag attaagatcg agcagaaaat tcaggcggag   480
aaaagcaccc aatggctgcg cgaaacgatc agcgcttttg tgaaaaccca accacagtgg   540
aacaaagaga ctgagaatta ctcgaaaggt ggtggtgagg atcatctgca aggcggtgca   600
ctgctgtacg tgaatgatag ccgtaccccg tgggcaaata gcgattatcg ccgcctgaac   660
cgcaccgcta ccaatcaaac gggtacgatt gacaagtcca ttctggacga gcagagcgac   720
ccaaatcaca tgggcggttt cgactcctg ctggcgaatg atgttgacct gtccaacccg    780
gttgtgcagg cagagcagct gaaccagatt cactacttga tgaattgggg ctctatcgtg   840
atgggtgaca aagacgcaaa cttgatggt atccgtgcg atgcagttga caacgtcgat     900
gccgacatgc tgcaactgta taccaactac ttccgtgaat actacggtgt taacaaaagc   960
gaagcgaacg cactggcgca cattagcgtt ttggaagcgt ggagcttgaa tgataatcac  1020
tacaacgaca aaaccgatgg tgcagcattg gcgatggaga taagcagcg tctggcgctg   1080
ctgtttagcc tggctaaacc gattaaagag cgcaccccgg cagtgaccg gctgtataac   1140
aacaccttca atacgaccca acgcgatgag aaaaccgact ggatcaataa agacggttct  1200
aaggcctata cgaggatgg tactgtgaag cagagcacca ttggtaagta caatgaaaaa   1260
tatggtgatg catcgggcaa ttatgtgttc atccgtgcc atgataacaa tgtccaagac   1320
atcattgcgg agatcattaa gaaagaaatc aaccegaaaa gcgatggttt caccatcact  1380
gacgccgaaa tgaaacaagc gttcgagatt tacaataagg acatgctgag cagcgacaag  1440
aagtacaccc tgaataacat cccggcagct tatgccgtga tgttcagaa catggaaacg   1500
attcccgtg tctattatgg tgacctgtac accgacgacg ccactacat ggaaaccaag    1560
tccccgtatt acgacaccat cgttaacctg atgaaaagcc gtatcaagta cgtcagcggt  1620
ggccaggcc aacgtagcta ctggctgccg accgacggca agatggacaa tagcgacgtt   1680
gagctgtatc gcaccaacga agtgtatacc agctccgtt acggtaaaga cattatgacc   1740
gcgaacgata ccgagggtag caagtacagc cgcaccagcg gccaggtcac cctggttgca  1800
aacaacccga agctgaccct ggaccagagc gcaaagctga atgtggaaat gggtaagatt  1860
cacgcgaatc agaaataccg tgccctgatt gtgggcacgg ctgacggtat caagaatttc  1920
accagcgacg cagatgctat cgcggcaggc tacgtgaaag aaaccgactc caatggcgtt  1980
ctgactttg gcgctaatga catcaaaggt tatgaaacct cgacatgtc cggctttgtt    2040
gctgtttggg tgccggtcgg cgcgagcgat gatcaggaca ttcgtgtcgc tcctagcact  2100
gaggccaaga aagagggtga attgaccctg aaagcgaccg aagcataca ttcccagctg    2160
atctatgaag gttttagcaa ttttcaaacc atccggatg gtagcgaccc gagcgtgtac    2220
accaatcgca agatcgcaga gaacgtggac ctgttcaagt cctggggtgt tacctcgttt   2280
gaaatggcac cgcagttcgt ttccgcagat gatggcactt tctgactc tgtgatccaa    2340
aacggctgcg cgtttgccga tcgttacgat ttggcgatga gcaagaacaa caatacggcg  2400
agcaaagagg acttgcgtga cgcgctgaaa gccctgcata agcaggcat ccaggcgatt    2460
gcagactggg tcccggacca gatttatcag ttgccgggca agaagtggt cacggcgact    2520
cgcaccgacg gcgcaggccg taaaatcgcg gacgcgatca ttgatcatag cctgtacgtt   2580
gcgaacacta agagcagcgg caaagattac caggcgaagt acggtggtga gttcttggcg   2640
gagctgaagg ccaagtaccc ggagatgttc aaagtgaaca tgatttctac cggcaaaccg   2700
attgatgaca gcgtcaaact gaaacagtgg aaagcagaat actttaacgg caccaacgtc   2760
ttggagcgcg gtgtgggtta tgtcctgagc gatgaagcca cggtaaata ctttaccgtc    2820
acgaaggtga gcaacttcat tccgttgcag ctgacgggta atgagaaagt cgtgaccgc   2880
tttagcaatg atggcaaagg tatcacctac ttcggtacga gcggcactca agcgaaatct  2940
gcgttcgtta cgttcaatgg taatactac tattttgacg ctcgtggtca catggttacg   3000
aacggcgagt attcgccgaa cggtaaggat gtttaccgtt tcctgccgaa tggtattatg   3060
ctgtctaacg cttttacgt tgatgcaaat ggtaacacgt acctgtacaa cagcaagggc   3120
caaatgtaca aaggcggtta caccaaattt gacgttaccg aaacggacaa agatggtaag   3180
gaaagcaagg tggtgaagtt tcgttacttt acgaacgaag gtgtcatggc aaaaggcgtt   3240
accgtgattg acggcttcac gcaatacttt ggtgaagatg gtttccaagc gaaagacaag   3300
ctggtcacgt tcaagggcaa gacgtactac ttcgatgcac acaccggcaa tgcgatcaag   3360
gacacctggc gtaatatcaa tggcaagtgg tatcatttcg acgcaacgg cgttgcagcg   3420
accggcgctc aggtcatcaa tggccaaaaa ctgtatttca acgaggacgg cagccaagtg   3480
aaaggcggtg ttgtcaaaaa cgcggacggt acgtattcta aatacaaaga gggttctggt   3540
gaactggtta ccaacgagtt cttcacgacg gatggcaatg tttggtacta cgcaggcgcg   3600
aatggcaaga ccgttacggg tgcccagtg attaactgcc aacacctgta cttcaatggc    3660
gacggttcgc aagtgaaggg cggtgtggtc aagaacgcgg atggcaccta tagcaaatat   3720
gatgcgtcta ccggcgaacg cctgaccaat gagtttttca ccacgggtga taacaactgg   3780
tactacattg gcgcaaacgg caagagcgtg acgggcgagg tcaagatcgg tgacgatacc   3840
tatttctttg ccaaagatgg caagcaagtt aagggtcaaa ctgtcagcgc gggtaacggt   3900
cgtattagct actactatgg tgatagcggt aagcgtgcgg tgagcacttg gatcgaaatc   3960
caaccgggtg tttatgtcta cttcgacaag aacggcattg cctatccgcc tcgtgtgctg   4020
aattaa                                                              4026

SEQ ID NO: 4          moltype = AA  length = 1341
FEATURE               Location/Qualifiers
source                1..1341
                      mol_type = protein
                      organism = Streptococcus salivarius
SEQUENCE: 4
MIDGKYYVN EDGSHKENFA ITVNGQLLYF GKDGALTSSS TYSFTPGTTN IVDGFSINNR    60
```

```
AYDSSEASFE LIDGYLTADS WYRPASIIKD GVTWQASTAE DFRPLLMAWW PNVDTQVNYL    120
NYMSKVFNLD AKYSSTDKQE TLKVAAKDIQ IKIEQKIQAE KSTQWLRETI SAFVKTQPQW    180
NKETENYSKG GGEDHLQGGA LLYVNDSRTP WANSDYRRLN RTATNQTGTI DKSILDEQSD    240
PNHMGGFDFL LANDVDLSNP VVQAEQLNQI HYLMNWGSIV MGDKDANFDG IRVDAVDNVD    300
ADMLQLYTNY FREYYGVNKS EANALAHISV LEAWSLNDNH YNDKTDGAAL AMENKQRLAL    360
LFSLAKPIKE RTPAVSPLYN NTFNTTQRDE KTDWINKDGS KAYNEDGTVK QSTIGKYNEK    420
YGDASGNYVF IRAHDNNVQD IIAEIIKKEI NPKSDGFTIT DAEMKQAFEI YNKDMLSSDK    480
KYTLNNIPAA YAVMLQNMET ITRVYYGDLY TDDGHYMETK SPYYDTIVNL MKSRIKYVSG    540
GQAQRSYWLP TDGKMDNSDV ELYRTNEVYT SVRYGKDIMT ANDTEGSKYS RTSGQVTLVA    600
NNPKLTLDQS AKLNVEMGKI HANQKYRALI VGTADGIKNF TSDADAIAAG YVKETDSNGV    660
LTFGANDIKG YETFDMSGFV AVWVPVGASD DQDIRVAPST EAKKEGELTL KATEAYDSQL    720
IYEGFSNFQT IPDGSDPSVY TNRKIAENVD LFKSWGVTSF EMAPQFVSAD DGTFLDSVIQ    780
NGYAFADRYD LAMSKNNKYG SKEDLRDALK ALHKAGIQAI ADWVPDQIYQ LPGKEVVTAT    840
RTDGAGRKIA DAIIDHSLYV ANTKSSGKDY QAKYGGEFLA ELKAKYPEMF KVNMISTGKP    900
IDDSVKLKQW KAEYFNGTNV LERGVGYVLS DEATGKYFTV TKDGNFIPLQ LTGNEKVVTG    960
FSNDGKGITY FGTSGTQAKS AFVTFNGNTY YFDARGHMVT NGEYSPNGKD VYRFLPNGIM   1020
LSNAFYVDAN GNTYLYNSKG QMYKGGYTKF DVTETDKDGK ESKVVKFRYF TNEGVMAKGV   1080
TVIDGFTQYF GEDGFQAKDK LVTFKGKTYY FDAHTGNAIK DTWRNINGKW YHFDANGVAA   1140
TGAQVINGQK LYFNEDGSQV KGGVVKNADG TYSKYKEGSG ELVTNEFFTT DGNVWYYAGA   1200
NGKTVTGAQV INGQHLYFNA DGSQVKGGVV KNADGTYSKY DASTGERLTN EFFTTGDNNW   1260
YYIGANGKSV TGEVKIGDDT YFFAKDGKQV KGQTVSAGNG RISYYYGDSG KRAVSTWIEI   1320
QPGVYVYFDK NGIAYPPRVL N                                            1341

SEQ ID NO: 5              moltype = DNA   length = 3744
FEATURE                   Location/Qualifiers
source                    1..3744
                          mol_type = unassigned DNA
                          organism = Streptococcus salivarius
SEQUENCE: 5
atgccaagcc acattaagac catcaacggc aaacaatact acgtggagga tgacggtacg     60
attcgcaaga attacgtcct ggagcgtatc ggtggcagcc aatactttaa tgcagaaacc    120
ggtgaactgt ctaatcagaa agagtatcgt ttcgacaaaa atggtggtac tggtagcagc    180
gcggacagca cgaacaccaa cgtgactgtg aacggtgaca aaaacgcatt ttacggtacc    240
acggacaaag acattgagct ggtcgacggc tatttcaccg cgaacacctg gtatcgcccg    300
aaagaaatcc tgaaagacgg caaagaatgg accgccagca cggagaacga taaacgcccg    360
ctgctgaccg tctggtggcc tagcaaagca atccaggcgt cttatctgaa ctacatgaaa    420
gagcaaggcc tgggtaccaa ccaaacgtac acgagcttct ccagccaaac ccaaatggat    480
caagcagccc tggaagtgca aaagcgtatt gaagagcgca tcgacgcga gggcaatacc    540
gactggctgc gcacgaccat caagaacttc gtgaaaacgc aaccgggttg gaacagcacc    600
tctgaaaatc tggacaataa tgatcatctg caaggtggcg ccctgctgta caataacgac    660
tcccgcacga gccacgcgaa cagcgactat cgcctgctga atcgtacgcc gaccagccag    720
accggcaaac acaatccgaa atacaccaaa gataccagca atggtggttt cgaatttctg    780
ctggcgaacg acatcgataa ctctaatccg gcggttcaag cagagcaact gaactggctg    840
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa aatacggtgc tgatcaaagc caagatcagg cgatcaaaca cttgagcatc   1020
ctggaagcgt ggtcccataa cgacgcctac tataacgaag ataccaaagg cgcagttg    1080
ccgatggatg atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatgcgaaa ctacgcgttc gtacgcgcgc atgatagcga ggtgcaatcg   1260
attattggcc agatcatcaa aaacgagatc aatccgcaca gcaccggtaa tacgttcaca   1320
ctggatgaga tgaagaaagc gtttgagatt tacaacaagg atatgcgtag cgcgaataag   1380
cagtatacgc agtacaacat cccgagcgcg tatgcgttga tgctgaccca aaggataccc   1440
gttccgcgtg tgtattacgg tgatatgtat acggacgacg tcagtacat ggcgcaaaag   1500
agcccatact atgatgcgat cgaaacgctg ctgaaagtc ctatccgctg tgccgcaggt   1560
ggtcaggaca tgaaggtcaa ctatattggt tacggtaaca ctaacgctg ggatgctgcg   1620
ggcgtgctga ccagcgtacg ttatggcacg ggcgcaaata cgccagcga tacgggtacc   1680
gccgaaacgc gtaatcaagg tatggcagtg attgttgcca ccaaccggc gctgcgtctg   1740
actagcaatt tgaccattaa catggtgtcc gcacaccgta atcaggctta ccgtccgctg   1800
ctgctgacga ccaacgatgg cgtcgcgacc tatttgaacg atagcgatgc gaatggtatc   1860
gttaagtaca ccgacggtaa tggtaatctg accttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca gttatctac gaaggcttca gcaactttcca ggacttcgtt   2100
cagaatccga gccagtatac caacaaaaag attgcagaga atgcaaattt gttcaaatcc   2160
tgggggtatta ccagctttga attttcgccg cagtacgtga gctcggatga tggtagcttc   2220
ctggacagcg ttattcagaa cggttatgcg tttacggacc gctacgacat tggtatgagc   2280
aaagcaaaca aatatggttc gctggcggat ttgaaggcag cactgaagag cttgcatgcg   2340
gttggtatta gcgcaatcgc ggattgggtt cctgatcaga tctacaatct gccaggcgac   2400
gaggtcgtca ccgcaacccg cgttaacaac tacggcgaaa ccaaagatgg tgcaatcatt   2460
gatcactctt tgtacgcggc caaaacccgt acttttggta acgactacca gggtaagtat   2520
ggtggtcgct tcctggacga gctgaaacgt ctgtatccgc agatctttga ccgcgttcag   2580
atttctaccg gtaagcgcat gaccacggac gagaagatca cccaatggtc tgcaaagtat   2640
atgaacgatc tggaccggtgc tctgaatacg ttttgaagaa tcgttttgaa   2700
ggttactatg gcaccaatgg tggcaaagtt tcgctgccga agttgtggg tagcaatcaa   2760
agcacgaatg gcgacaatca aaacggcgac ggtagcggca gtttgaaaaa gcgtctgttc   2820
agcgtgcgtt accgttataa caatggccag tacgcgaaaa atgcctttat caaagataac   2880
gacggcaatg tttactattt cgacaatagc ggtcgtatgc ctgtcggtga aaaacgatt   2940
gacggcaagc agtacttctt cctggctaat ggcgttcagc tgcgtgacgg ctaccgtcaa   3000
```

```
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatacga gtgagatgcc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                           3744

SEQ ID NO: 6             moltype = AA   length = 1247
FEATURE                  Location/Qualifiers
source                   1..1247
                         mol_type = protein
                         organism = Streptococcus salivarius
SEQUENCE: 6
MPSHIKTING KQYYVEDDGT IRKNYVLERI GGSQYFNAET GELSNQKEYR FDKNGGTGSS     60
ADSTNTNVTV NGDKNAFYGT TDKDIELVDG YFTANTWYRP KEILKDGKEW TASTENDKRP    120
LLTVWWPSKA IQASYLNYMK EQGLGTNQTY TSFSSQTQMD QAALEVQKRI EERIAREGNT    180
DWLRTTIKNF VKTQPGWNST SENLDNNDHL QGGALLYNND SRTSHANSDY RLLNRTPTSQ    240
TGKHNPKYTK DTSNGGFEFL LANDIDNSNP AVQAEQLNWL HYIMNIGTIT GGSEDENFDG    300
VRVDAVDNVN ADLLQIASDY FKAKYGADQS QDQAIKHLSI LEAWSHNDAY YNEDTKGAQL    360
PMDDPMHLAL VYSLLRPIGN RSGVEPLISN SLNDRSESGK NSKRMANYAF VRAHDSEVQS    420
IIGQIIKNEI NPQSTGNTFT LDEMKKAFEI YNKDMRSANK QYTQYNIPSA YALMLTHKDT    480
VPRVYYGDMY TDDGQYMAQK SPYYDAIETL LKGRIRYAAG GQDMKVNYIG YGNTNGWDAA    540
GVLTSVRYGT GANSASDTGT AETRNQGMAV IVSNQPALRL TSNLTINMGA AHRNQAYRPL    600
LLTTNDGVAT YLNDSDANGI VKYTDGNGNL TFSANEIRGI RNPQVDGYLA VWVPVGASEN    660
QDVRVAPSKE KNSSGLVYES NAALDSQVIY EGFSNFQDFV QNPSQYTNKK IAENANLFKS    720
WGITSFEFAP QYVSSDDGSF LDSVIQNGYA FTDRYDIGMS KDNKYGSLAD LKAALKSLHA    780
VGISAIADWV PDQIYNLPGD EVVTATRVNN YGETKDGAII DHSLYAAKTR TFGNDYQGKY    840
GGAFLDELKR LYPQIFDRVQ ISTGKRMTTD EKITQWSAKY MNGTNILDRG SEYVLKNGLN    900
GYYGTNGGKV SLPKVVGSNQ STNGDNQNGD GSGKFEKRLF SVRYRYNNGQ YAKNAFIKDN    960
DGNVYYFDNS GRMAVGEKTI DGKQYFFLAN GVQLRDGYRQ NRRGQVFYYD QNGVLNANGK   1020
QDPKPDNNNN ASGRNQFVQI GNNVWAYYDG NGKRVTGHQN INGQELFFDN NGVQVKGRTV   1080
NENGAIRYYD ANSGEMARNR FAEIEPGVWA YFNNDGTAVK GSQNINGQDL YFDQNGRQVK   1140
GALANVDGNL RYYDVNSGEL YRNRFHEIDG SWYYFDGNGN AVKGMVNING QNLLFDNNGK   1200
QIKGHLVRVN GVVRYFDPNS GEMAVNRWVE VSPGWWVYFD GEGRGQI                 1247

SEQ ID NO: 7             moltype = DNA   length = 4434
FEATURE                  Location/Qualifiers
source                   1..4434
                         mol_type = unassigned DNA
                         organism = Streptococcus salivarius
SEQUENCE: 7
atggacgaaa cgcaggataa gaccgtgacg cagagcaaca gcggcaccac cgcttccctg      60
gtcactagcc ctgaagccac gaaagaggcg gacaaaacgc cgaacactaa agaggccgac     120
gttctgacgc ctgcaaaaga aacgaacgca gtcgagactg cgaccaccac taacacccag     180
gcgacggcgg aggccgccac gaccgcgacc accgcgacg tcgcggtggc tgcggtgccg      240
aacaaagaag cggtcgttac cacggatgct ccggcggtca cgaccgagaa gcggaagaa      300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatgcg     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc      600
agcgaggcga gctttgagct gatcgacggt tacttgaccg cagacagctg gtatcgtccg     660
gctagcatca tcaaagatgg tgttacgtgg caagcgtcca cgccgagga ttttcgtccg      720
ctgctgatgg catgtggcc gaatgtggat acgcaggtga actatttgaa ttacatgtcc      780
aaagttttca acctggacgc gaaatactct agcaccgaca acaggaaac cctgaaagtg     840
gcagcaaag acattcaaat caagattgaa caaaagattc aagcggagaa gagcacgcag      900
tggctgcgtg aaactatcag cgcctttgt aaaacccgac gcagtggaa caaagaacc       960
gagaattaca gcaagggtgg tggtgaggac cacctgcaag gtggcgcact gctgtatgtt    1020
aacgacagcc gtacccttg ggcgaatagc gattaccgtc gtctgaatcg caccgcaacc     1080
aatcagacgg gcacgatcga taagtctatt ctggacagc agtctgaccc aaaccacatg     1140
ggcggtttcg acttctctgct ggcgaacgac gtcgacctga gcaatccggt cgtgcaggct   1200
gagcagctga atcaaatcca ctatctgatg aattgggtt ccattgtgat gggtgacaag     1260
gatgcgaact tgacggcat tcgtgtcgat gcagttgaca acgttggacgc ggacatgttg    1320
caactgtata ccaattactt ccgtgagtac acggtgtga acaagagcga agctaacgca     1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagacg taccccgaca gtgacccgc tgtataacaa cacctttcaat     1560
accaccagc gtgatgaaaa gaccgattgg attaacaaag acggtagcaa ggcttacaac     1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
```

-continued

```
aataacattc cggcagcgta tgccgtgatg ttgcagaata tggaaacgat tacccgcgtc 1920
tattacggtg atctgtatac ggacgacggt cactacatgg aaaccaaatc tccgtattac 1980
gataccatcg tgaatttgat gaagagccgt atcaagtatg tttcgggtgg ccaggcgcaa 2040
cgtagctatt ggctgccgac cgacggtaag atggacaata gcgacgttga gctgtaccgc 2100
acgaatgagg tttacacgag cgtgcgctat ggtaaggata tcatgaccgc taatgatacc 2160
gaaggctcta agtattcccg caccagcggc caagtcacct tggtcgcgaa caatccgaag 2220
ctgaatctgg accaaagcgc caagttgaat gtggagatgg gcaaaatcca tgcgaatcag 2280
aagtatcgcg cactgattgt cggcactgcg acggcatta agaactttac ttccgacgcg 2340
gacgccattg cagcgggtta tgtgaaagaa accgataaga acggcgtgct gaccttcggt 2400
gctaacgaca ttaagggcta cgaaacgttt gatatgagcg gtttcgtggc ggtgtgggtt 2460
ccggtgggtg catctgacaa tcaggacatt cgtgttgcgc cgagcaccgg ggcaaagaaa 2520
gaaggtgagc tgaccttgaa ggcgacggaa gcgtatgata ccagctgat ttacgaaggc 2580
tttagcaatt tccagacgat cccagatggc agcgatccgt ccgtgtatac gaaccgcaag 2640
attgcggaga acgtggatct gttcaaaagc tgggtgtca ccagctttga gatggcacg 2700
caatttgtct cggcggatga tggcaccttt ctggatagcg ttattcagaa tggctacgcc 2760
ttcgccgacc gttatgacct ggccatgtcc aagaacaaca agtatggtag caaagaggac 2820
ctgcgtgatg cactgaaagc actgcataag gcgggtattc aagctatcgc agactgggtt 2880
ccagacagga tctaccagct gccgggcaaa gaagttgtca ccgccacccg tacggatggt 2940
gctggccgta agatcgcaga cgcgattatc gaccattctc tgtatgttgc aaacagcaaa 3000
agcagcggca agattatca gcaaagtac ggtggcgagt tcctggccga gctgaaagcc 3060
aaatacccgg aaatgttcaa agttaacatg attagcacgg taagccgat tgatgactcc 3120
gtgaaattga agcaatggaa agccgaatac ttcaatgcca ccaacgttt ggaacgtggg 3180
gtcggctatg ttctgagcga cgaggcgacc ggtaagtatt tcacggtgac caaagaaggc 3240
aatttcattc cgctgcaact gacgggtaaa gagaaagtta tcacgggttt ctccagcgat 3300
ggtaaggta tcacctattt cggtacgagc ggtacgcagg cgaagtctgc gtttgttacc 3360
ttcaatggta acacctacta tttcgacgcg cgtggccata tggttaccaa tagcgaatac 3420
agcccgaatg gcaaggacgt ctaccgtttt ctgccgaacg gtatcatgct gagcaatgcg 3480
ttttacattg atgcgaacgg taatacctac ctgtacaact ctaagggtca aatgtacaaa 3540
ggcggttaca cgaaattcga tgtttctgaa acggataagg acggtaaaga gtccaaggtc 3600
gtcaagttcc gctactttac gaacgaaggc gtcatggcca agggtgttac cgtcattgat 3660
ggttttaccc aatacttcgg tgaggacggc tttcaagcga aggataagtc ggtcaccttc 3720
aagggcaaga cgtattactt cgacgcacac actggtaatg gtatcaaaga tacctggcgc 3780
aatatcaatg gtaaatggta ctatttcgac gcgaatggcg ttgctgcgac cggtgcgcag 3840
gtgattaacg gccagaaact gtacttcaac gaggatggct cccaagtcaa aggcggcgtg 3900
gttaagaacg cagacggcac ctatagcaaa tacaaagaag gttttggtga gctggttact 3960
aacgagtttt tcacgactga tggcaatgtt tggtactacg ccggtgcaaa tggtaaaacc 4020
gttaccggtg cacaagtgat caacggccaa catttgtact tcaatgcgga cggttcccag 4080
gtgaagggtg gcgttgtcaa gaacgcggat ggcacctaca gcaagtacaa tgctagcact 4140
ggtgaacgtc tgacgaacga gttctttacg accggtgata acaattggta ttacattggc 4200
gcaaacggta gagcgtgac gggtgaggtc aagattggtg atgatactta ctttttcgcg 4260
aaggatggca aacaagttaa aggtcaaacc gtcagcccg taatggtcg cattagctac 4320
tactacggtg acagcggcaa gcgtgcggtt agcacctgga ttgagattca gccgggtgtt 4380
tatgtgtatt tcgacaaaaa cggtttggcg taccctccgc gtgttctgaa ttaa 4434
```

SEQ ID NO: 8            moltype = AA   length = 1477
FEATURE                 Location/Qualifiers
source                  1..1477
                        mol_type = protein
                        organism = Streptococcus salivarius

SEQUENCE: 8

```
MDETQDKTVT QSNSGTTASL VTSPEATKEA DKRTNTKEAD VLTPAKETNA VETATTTNTQ   60
ATAEAATTAT TADVAVAAVP NKEAVVTTDA PAVTTEKAEE QPATVKAEVV NTEVKAPEAA  120
LKDSEVEAAL SLKNIKNIDG KYYYVNEDGS HKENFAITVN GQLLYFGKDG ALTSSSTYSF  180
TPGTTNIVDG FSINNRAYDS SEASFELIDG YLTADSWYRP ASIIKDGVTW QASTAEDFRP  240
LLMAWWPNVD TQVNYLNYMS KVFNLDAKYS STDKQETLKV AAKDIQIKIE QKIQAEKSTQ  300
WLRETISAFV KTQPQWNKET ENYSKGGGED HLQGGALLYV NDSRTPWANS DYRRLNRTAT  360
NQTGTIDKSI LDEQSDPNHM GGFDFLLAND VDLSNPVVQA EQLNQIHYLM NWGSIVMGDK  420
DANFDGIRVD AVDNVDADML QLYTNYFREY YGVNKSEANA LAHISVLEAW SLNDNHYNDK  480
TDGAALAMEN KQRLALLFSL AKPIKERTPA VSPLYNNTFN TTQRDEKTDW INKDGSKAYN  540
EDGTVKQSTI GKYNEKYGDA SGNYVFIRAH DNNVQDIIAE IIKKEINPKS DGFTITDAEM  600
KQAFEIYNKD MLSSDKKYTL NNIPAAYAVM LQNMETITRV YYGDLYTDDG HYMETKSPYY  660
DTIVNLMKSR IKYVSGGQAQ RSYWLPTDGK MDNSDVELYR TNEVYTSVRY GKDIMTANDT  720
EGSKYSRTSG QVTLVANNPK LNLDQSAKLN VEMGKIHANQ KYRALIVGTA DGIKNFTSDA  780
DAIAAGYVKE TDSNGVLTFG ANDIKGYETF DMSGFVAVWV PVGASDNQDI RVAPSTEAKK  840
EGELTLKATE AYDSQLIYEG FSNFQTIPDG SDPSVYTNRK IAENVDLFKS WGVTSFEMAP  900
QFVSADDGTF LDSVIQNGYA FADRYDLAMS KNNKYGSKED LRDALKALHK AGIQAIADWV  960
PDQIYQLPGK EVVTATRTDG AGRKIADAII DHSLYVANSK SSGKDYQAKY GGEFLAELKA 1020
KYPEMFKVNM ISTGKPIDDS VKLKQWKAEY FNGTNVLERG VGYVLSDEAT GKYFTVTKEG 1080
NFIPLQLTGK EKVITGFSSD GKGITYFGTS GTQAKSAFVT FNGNTYYFDA RGHMVTNSEY 1140
SPNGKDVYRF LPNGIMLSNA FYIDANGNTY LYNSKGQMYK GGYTKFDVSE TDKDGKESKV 1200
VKFRYFTNEG VMAKGVTVID GFTQYFGEDG FQAKDKLVTF KGKTYYFDAH TGNGIKDTWR 1260
NINGKWYYFD ANGVAATGAQ VINGQKLYFN EDGSQVKGGV VKNADGTYSK YKEGFGELVT 1320
NEFFTTDGNV WYYAGANGKT VTGAQVINGQ HLYFNADGSQ VKGGVVKNAD GTYSKYNAST 1380
GERLTNEFFT TGDNNWYYIG ANGKSVTGEV KIGDDTYFFA KDGKQVKGQT VSAGNGRISY 1440
YYGDSGKRAV STWIEIQPGV YVYFDKNGLA YPPRVLN                          1477
```

SEQ ID NO: 9            moltype = DNA   length = 4311
FEATURE                 Location/Qualifiers
source                  1..4311

```
                    mol_type = unassigned DNA
                    organism = Streptococcus downei
SEQUENCE: 9
atggttgacg gcaaatacta ctactacgat caggacggca acgtaaagaa aaacttcgcg    60
gttagcgtgg gcgagaaaat ctattacttt gacgaaactg gcgcctacaa agacaccagc   120
aaagttgagg cggacaaaag cggcagcgac attagcaagg aagagactac cttcgcggca   180
aacaaccgcg cctacagcac cagcgcggag aattttgagg cgatcgacaa ttatctgacc   240
gcggactcct ggtatcgtcc taaatccatc ctgaaggatg caaaacgtg dacggaaagc    300
agcaaagatg actttcgtcc gctgctgatg gcgtggtggc cggatacga aacgaagcgc    360
aattacgtga actacatgaa caaagttgtt ggcatcgaca agacctatac cgcggaaacc   420
agccaggccg acttgaccgc tgcggcggaa ctggtgcaag cacgcattga gcagaagatc   480
acgaccgaac agaacacgaa atggctgcgt gaggcaatct cggcatttgt taaaacgcaa   540
ccgcagtgga acggtgaaag cgagaagccg tacgacgatc acctgcaaaa cggtgctctg   600
aaatttgata atcagagcga cctgaccccg gatacgcaaa gcaactaccg tctgttgaac   660
cgtaccccga ctaatcagac gggtagcctg gacagccgct tcacttataa cgcgaacgac   720
cctttgggcg gttatgagct gctgctggca aatgacgtcg ataacagcaa tccgatcgtg   780
caggcggagc agctgaactg gctgcattac ctgctgaatt ttggtacgat ctacgccaaa   840
gatgccgacg ctaacttcga tagcattcgt gtggacgcgg ttgataacgt cgatgcggat   900
ctgctgcaaa ttagcagcga ttacctgaaa gcagcctacg gcattgataa gaataacaaa   960
aacgcgaaca accacgtgag cattgtcgaa gcctggagcg ataatgatac cccgtacctg  1020
catgacgatg gtgacaacct gatgaatatg gataacaaat ttcgcctgtc catgctgtgg  1080
tcgctggcca aaccgctgga caagcgtagc ggtctgaacc tgattca taacagcttg     1140
gtggatcgtg aagttgatga ccgcgaggtt gaaacggttc cgagctattc ttttgcacgt  1200
gcgcatgata gcgaggtcca ggacttgatc cgtgacatca tcaaggcaga gatcaatccg  1260
aacgcattcg gttatagctt tacccaagac gagattgacc aggcctttaa gatttacaat  1320
gaggatctga agaaaacgga taagaaatac acccactata atgtgccgtt gagctacacc  1380
ctgctgctga cgaataaggg tagcatccca cgtgtctact atggtgatat gtttaccgac  1440
gatggtcagt atatgcgaa caaaaccgtc aactatgacg ccattgaatc tctgctgaaa  1500
gcgcgtatga agtatgtcgc tggcggtcaa gcaatgcaga actaccaaat cggtaatggt  1560
gagatcctga ccagcgttcg ttatgataag ggtgccctga aacagagcga caaggtgat   1620
gcgaccacgc gcaccagcgg tgtcggtgtc gttatgggca atcagccaaa ctttagcttg  1680
gacggcaaag tggtggctct gaacatgggc gcagctcatg cgaatcagga gtatcgtgcg  1740
ctgatggtta gcacgaaaga cggtgttgcc acgtatgcga ccgatgcaga tgcgagcaaa  1800
gccggtctgg tcaaacgtac cgacgaaaac ggctacctgt atttcctgaa tgacgaccgtg 1860
aagggtctgg ccaatcctca ggtgagcggt ttcttgcagg tgtgggttcc ggtgggtgcc  1920
gcggatgatc aagatatccg tgttcagct agcgataccg catccaccga tggcaagagc  1980
ctgcaccaag acgccgcgat ggatagccgt gttatgtttg aaggcttctc taactttcag  2040
tcctttgcca cgaaagaaga ggaatatacc aacgtcgtta tcgccaacaa tgtggataag  2100
ttcgttagct ggggtatcac ggatttcgag atggcccac aatatgtttc cagcaccgac   2160
ggtcaattcc tggactctgt cattcagaac ggttatgctt ttacggaccg ttatgacttg  2220
ggcatgtcta aggcaaacaa atacggcacg gccgatcaac tggttaaggc cattaaggcc  2280
ctgcacgcga agggcctgaa ggttatgca gattgggtgc cggatcagat gtataccttc   2340
ccgaaacagg aagtcgtgac cgttacccgt accgacaaat ttggcaaacc gatcgcaggt  2400
tcccaaatca atcatagcct gtatgttacc gataccaagt ccagcggcga tgactatcag  2460
gccaaatatg tggtgcgtt tctggacgag ctgaaggaga aatatccgga gctgttcacg   2520
aagaaacaaa tcagcacggg tcaagctatt gacccgagcg tgaaaatcaa acagtggtct  2580
gctaagtatt tcaatggctc caacatcctg ggtcgcgtga gggactacgt actgtcggat  2640
caggcgagca acaaatacct gaacgtgtct gacgataaac tgttcctgcc gaaaaccttg  2700
ctgggccaag ttgtcgagag cggtatccgc tttgacggca ctggttatgt gtacaactct  2760
agcactacgg gtgaaaaagt taccgattcc ttcattacgg aggcaggtaa tctgtactac  2820
ttcggtcaag acggctatat ggtgaccggc gcacagaaca ttaagggcag caactattac  2880
ttcctggcca atggtgcggc cctgcgtaac accgtttaca ccgatgcgca aggtcagaat  2940
cactattacg gcaacgacgg caagcgttat gagaatggtt accaacagtt cggcaacgat  3000
tcttggcgtt acttcaaaaa tggcgtgatg gcgctgggtc tgactacggt ggatggtcac  3060
gtgcagtatt tcgataaaga tggtgtccag gccaaggata agatcattgt caccccgcgt  3120
ggcaaagtcc gctatttcga ctcagcacaac ggtaatgcgg ttactaacac gttcgttgcg  3180
gacaagacgg gtcactggta ctatctgggc aagacggcg tcgcggttac cggtgcgcag   3240
actgtgggta acagcatttt gtactttgaa gcgaacggtc aacaagtcaa gggtgacttc  3300
gtgacggcta aagacggtaa actgtacttc tatgatgtgg acagcggcga catgtggacc  3360
aataccttta tcgaggataa agcgggtaat tggttctacc tgggtaagga cggtgcggcc  3420
gtcaccggtg cacagacgat caaaggccag aaattgtatt tcaaagccaa cggtcagcaa  3480
gttaaaggtg acattgtcaa ggacgcggac ggtaagatcc gttattacga cgctcagacc  3540
ggtgaacagg tctttaacaa gtccgttagc gtcaacggta agacctacta tttcggtagc  3600
gacggcaccg cgcaaaccca ggcgaatccg aaaggccaaa cctttaagga ttggtagcgg   3660
gttctgcgtt tctacaattt ggagggccag tatgtctcgg gcagcggctg gtacgaaacg  3720
gccgagcacg agtgggtata tgtgaaatcc ggtaaagttc tgaccggtgc ccagacgatt  3780
ggtaatcaac gtgtttactt caaggacaat ggtcaccagt gaaaggcca gctggtcacg   3840
ggtaatgacg gtaaattgcg ttactacgac gcgaacagcg gtgatcaagc attcaacaaa  3900
tccgtcacgg ttaacggtaa aacctactac tttggcagcg atggtacggc gcagacgcag  3960
gctaatccta agggtcagac cttcaaagat ggtagcggcg tgctgcgttt ttacaacttg  4020
gaaggccaat acgtgtctgg cagcggttgg tacaagaatg cgcagggcca gtggctgtac  4080
gtgaaagatg gcaaggtcct gaccggtctg caaacggtcg gcaatcagaa ggtctacttc  4140
gacaaaaatg gcatccaagc aaagggtaag gccgttcgca cgtccgatgg taaagtgcgc  4200
tactttgatg agaatagcgg tagcatgatt acgaaccaat ggaagttcgt ttacggtcaa  4260
tactattact tcggttctga cggcgcagcg gtttaccgtg gttggaacta a            4311

SEQ ID NO: 10           moltype = AA  length = 1436
FEATURE                 Location/Qualifiers
source                  1..1436
```

|                        | mol_type = protein                          |
|                        | organism = Streptococcus downei             |

SEQUENCE: 10

```
MVDGKYYYD QDGNVKKNFA VSVGEKIYYF DETGAYKDTS KVEADKSGSD ISKEETTFAA    60
NNRAYSTSAE NFEAIDNYLT ADSWYRPKSI LKDGKTWTES SKDDFRPLLM AWWPDTETKR  120
NYVNYMNKVV GIDKTYTAET SQADLTAAAE LVQARIEQKI TTEQNTKWLR EAISAFVKTQ  180
PQWNGESEKP YDDHLQNGAL KFDNQSDLTP DTQSNYRLLN RTPNQTGSL DSRFTYNAND   240
PLGGYELLLA NDVDNSNPIV QAEQLNWLHY LLNFGTIYAK DADANFDSIR VDAVDNVDAD  300
LLQISSDYLK AAYGIDKNNK NANNHVSIVE AWSDNDTPYL HDDGDNLMNM DNKFRLSMLW  360
SLAKPLDKRS GLNPLIHNSL VDREVDDREV ETVPSYSFAR AHDSEVQDLI RDIIKAEINP  420
NAFGYSFTQD EIDQAFKIYN EDLKKTDKKY THYNVPLSYT LLLTNKGSIP RVYYGDMFTD  480
DGQYMANKTV NYDAIESLLK ARMKYVAGGQ AMQNYQIGNG EILTSVRYGK GALKQSDKGD  540
ATTRTSGVGV VMGNQPNFSL DGKVVALNMG AAHANQEYRA LMVSTKDGVA TYATDADASK  600
AGLVKRTDEN GYLYFLNDDL KGVANPQVSG FLQVWVPVGA ADDQDIRVAA SDTASTDGKS  660
LHQDAAMDSR VMFEGFSNFQ SFATKEEEYT NVVIANNVDK FVSWGITDFE MAPQYVSSTD  720
GQFLDSVIQN GYAFTDRYDL GMSKANKYGT ADQLVKAIKA LHAKGLKVMA DWVPDQMYTF  780
PKQEVVTVTR TDKFGKPIAG SQINHSLYVT DTKSSGDDYQ AKYGGAFLDE LKEKYPELFT  840
KKQISTGQAI DPSVKIKQWS AKYFNGSNIL GRGADYVLSD QASNKYLNVS DDKLFLPKTL  900
LGQVVESGIR FDGTGYVYNS STTGEKVTDS FITEAGNLYY FGQDGYMVTG AQNIKGSNYY  960
FLANGAALRN TVYTDAQGQN HYYGNDGKRY ENGYQQFGND SWRYFKNGVM ALGLTTVDGH 1020
VQYFDKDGVQ AKDKIIVTRD GKVRYFDQHN GNAVTNTFVA DKTGHWYYLG KDGVAVTGAQ 1080
TVGKPHLYFE ANGQQVKGDF VTAKDGKLYF YDVDSGDMWT NTFIEDKAGN WFYLGKDGAA 1140
VTGAQTIKGQ KLYFKANGQQ VKGDIVKDAD GKIRYYDAQT GEQVFNKSVS VNGKTYYFGS 1200
DGTAQTQANP KGQTFKDGSG VLRFYNLEGQ YVSGSGWYET AEHEWVYVKS GKVLTGAQTI 1260
GNQRVYFKDN GHQVKGQLVT GNDGKLRYYD ANSGDQAFNK SVTVNGKTYY FGSDGTAQTQ 1320
ANPKGQTFKD GSGVLRFYNL EGQYVSGSGW YKNAQGQWLY VKDGKVLTGL QTVGNQKVYF 1380
DKNGIQAKGK AVRTSDGKVR YFDENSGSMI TNQWKFVYGQ YYYFGSDGAA VYRGWN     1436
```

| SEQ ID NO: 11 | moltype = DNA    length = 3942 |
| FEATURE       | Location/Qualifiers            |
| source        | 1..3942                        |
|               | mol_type = unassigned DNA      |
|               | organism = Streptococcus mutans |

SEQUENCE: 11

```
atgattgacg gcaaatacta ctactatgac aacaacggca agtacgcac caatttcacg    60
ttgatcgcgg acggtaaaat cctgcatttt gatgaaactg gcgcgtacac cgacactagc  120
attgataccg tgaacaagga tattgtcacg acgcgtagca acctgtataa gaaatacaat  180
caagtgtatg atcgcagcgc gcagagcttc gagcatgttg atcactacct gacggcggaa  240
tcttggtacc gtccgaaata cattctgaaa gatggcaaga cctgagccca gagcaccgag  300
aaggacttcc gtcctctgct gatgacctgg tggccgagcc aggaaacgca gcgccagtat  360
gtcaacttca tgaacgccca gttgggtatc aacaaaacgt acgacgacac cagcaatcag  420
ctgcaattga acatcgctgc tgcaacgatc aagcaaaga tcgaagccaa aatcacgacg  480
ctgaagaaca ccgattggct gcgtcaaacg atcagcgcgt tcgtcaaaac ccaaagcgct  540
tggaatagcg acagcgaaaa gccgtttgat gaccatctgc aaaacggtgc ggttctgtat  600
gataacgaag taaattgac gccgtatgcc aatagcaact atcgtattct gaaccgcacg  660
ccgaccaacc agaccggtaa gaaggacccg cgttataccg ccgacaacac gatcggcggc  720
tacgagtttc tgctggccaa cgacgtggat aatgcaacc cggtagttca ggccgagcag  780
ctgaactggc tgcacttcct gatgaacttt ggtaatatct acgcaaacga ccctgacgct  840
aacttcgact ccatccgcgt tgacgctgtc gataatgtgg acgccgatct gttacagatc  900
gcgggtgact atctgaaagc ggcaaagggc atccataaga tgacaaagc ggcgaacgac  960
cacctgtcca ttctgaaagc gtggagcgac aatgcacctc cgtatctgca tgatgatgcc 1020
gacaacatga ttaacatgga taacaaactg cgcctgagcc tgctgttctc cctggcgaaa 1080
ccgctgaatc agcgtagcgg tatgaacccg ttgattacga acagcctggt caaccgtact 1140
gatgataatg ccgaaacggc ggcagtgcca agctactctt ttatccgtgc cacgatagc  1200
gaggtccagg atttgattcg tgatatcatt aaggctgaga ttaacccgaa cgtcgtcggt 1260
tacagcttcc cgatggaaga gattaagaag gcatttgaga tctacaataa ggacctgttg 1320
gccacggaga agaagtatac ccactataac accgcattga gctacgcgtt gctgctgacg 1380
aacaagagca gcgtgccgcg tgtctactat ggtgatatgt ttacggacga tggtcaatac 1440
atggcccaca agaccattaa ctacgaggca atcgaaaacc tgctgaaagc acgtatcaag 1500
tacgtgtccg gtggtcaggc tatgcgcaac cagcaagtgg taattcgga gatcatcacc 1560
agcgtgcgtt acgtaaagg tgcgctgaag gcgatggata cggtgaccg cactacccgt 1620
acctctggtg tggcggtcat tgagggcaac aacccgagct gcgcctgaa ggcttctgat 1680
cgtgtggttg tgaatatggg tgcggccac aaaaatcaag cctatcgccc gctgctgttg 1740
acgaccgata acgtcattaa ggcctatcac gcgaccaag gcggcaagg cctggtgctg 1800
tacaccaacg accgtggcga actgatctt accgcagccg acattaaggg ctacgcaaat 1860
ccgcaagtta gcggctacct gggcgtctgg gtccctgttg gcgcagcagc tgatcaggac 1920
gttcgtgttg cggcgagcac cgcgccaagc acggacggca agagcgttca ccagaacgcg 1980
gctctggaca gccgtgtgat gttcgagggt ttctcgaact tccaggcatt tgctaccaag 2040
aaagaagagt ataccaatgt ggtcatcgct aagaatgtgg ataagttcgc ggagtgggct 2100
gtcaccgatt tcgagatggc tccgcaatac gtttctagca ccgacggtag cttttttggat 2160
agcgtgattc aaaacggtta tgcttttacc gaccgttacg acctgggcat cagcaagccg 2220
aacaaatatg gcaccgcgga cgatctggtt aaagcgatta ggcattgca cagcaaaggc 2280
atcaaagtta tggcggattg ggttccggac cagatgtatg ccctgccgga aaagaggtt 2340
gtgacggcaa cccgtcgttga caaatcggt acgcaggtga ctggcagcca gatcaaaaac 2400
acgctgtacg tggtcgatgg taaatctagc ggtaaggacc agcaggcgaa gtacggtggt 2460
gccttcctgg aagagctgca agcgaagtat ccggaactgt tcgcgcgcaa acagattagc 2520
accggtgttc cgatggaccc gagcgtcaag attaagcaat ggagcgcaaa atacttcaac 2580
ggcacgaata tcctgggtcg tggtgctggt tacgtgctga aagatcaggc aaccaacacc 2640
tactttaaca tcagcgacaa taagagatc aatttcctgc caaagacgtt gctgaaccag 2700
```

```
gattctcaag ttggctttag ctacgacggt aagggctatg tgtactacag cacctcgggc 2760
taccaggcta aaaacacgtt catcagcgag ggtgacaagt ggtattactt cgacaataac 2820
ggttatatgg ttaccggcgc acagagcatt aatggtgtga actattactt cctgccgaat 2880
ggtttacagc tgcgtgatgc gattctgaaa atgaggacgt acgtacgc gtattatggc 2940
aatgatggtc gccgctacga gaatggctat tatcagttta tgagcggtgt ttggcgccat 3000
ttcaataatg gcgagatgtc cgttggtctg accgtcattg acggtcaagt tcaatacttt 3060
gacgagatgg gttaccaggc gaaaggcaaa ttcgttacca ccgcggatgg taagatccgt 3120
tacttcgata gcagagcgg caatatgtat cgtaatcgtt tcattgagaa cgaagagggc 3180
aaatggctgt acctgggtga ggacggcgcg gcagtcaccg gacgcagac gatcaatggt 3240
cagcacctgt attttcgtgc taacggcgtt caggttaagg gtgagttcgt gaccgatcgt 3300
catggccgca tctcttatta cgacggcaac agcggtgatc agatccgcaa ccgtttcgtc 3360
cgcaatgcgc aaggccagtg gttttacttt gacaacaatg gctatgcagt aactggtgct 3420
cgtacgatca acggccagca cctgtatttc cgcgcgaacg gtgttcaggt aaaaggtgag 3480
tttgttacgg accgccacgg ccgcattagc tattatgatg gtaatagcgg tgaccaaatt 3540
cgcaatcgtt tcgtgcgtaa tgcacagggt cagtggttct acttcgacaa taatggttat 3600
gcagtcacgg gtgcacgtac cattaacggc caacacctgt actttcgcgc caatggtgtg 3660
caagtgaaag gcgaatttgt tactgatcgt tatggtcgta tcagctacta tgatggcaat 3720
tctgcggacc aaattcgcaa tcgctttgtt cgtaacgccc aaggtcaatg gttctatttc 3780
gacaacaacg gttacgcggt gaccggtgcc cgcacgatta atggtcaaca cttgtacttc 3840
cgtgccaacg gtgtccaggt gaagggtgaa tttgtgaccg accgctatgg tcgcatttct 3900
tactacgacg caaattccgg tgaacgcgtc cgtatcaatt aa 3942

SEQ ID NO: 12         moltype = AA length = 1313
FEATURE               Location/Qualifiers
source                1..1313
                      mol_type = protein
                      organism = Streptococcus mutans
SEQUENCE: 12
MIDGKYYYYD NNGKVRTNFT LIADGKILHF DETGAYTDTS IDTVNKDIVT TRSNLYKKYN   60
QVYDRSAQSF EHVDHYLTAE SWYRPKYILK DGKTWTQSTE KDFPRPLLMTW WPSQETQRQY  120
VNFMNAQLGI NKTYDDTSNQ LQLNIAAATI QAKIEAKITT LKNTDWLRQT ISAFVKTQSA  180
WNSDSEKPFD DHLQNGAVLY DNEGKLTPYA NSNYRILNRT PTNQTGKKDP RYTADNTIGG  240
YEFLLANDVD NSNPVVQAEQ LNWLHFLMNF GNIYANDPDA NFDSIRVDAV DNVDADLLQI  300
AGDYLKAAKG IHKNDKAAND HLSILEAWSD NDTPYLHDDG DNMINMDNKL RLSLLFSLAK  360
PLNQRSGMNP LITNSLVNRT DDNAETAAVP SYSFIRAHDS EVQDLIRDII KAEINPNVVG  420
YSFTMEEIKK AFEIYNKDLL ATEKKYTHYN TALSYALLLT NKSSVPRVYY GDMFTDDGQY  480
MAHKTINYEA IETLLKARIK YVSGGQAMRN QQVGNSEIIT SVRYGKGALK AMDTGDRTTR  540
TSGVAVIEGN NPSLRLKASD RVVVNMGAAH KNQAYRPLLL TTDNGIKAYH SDQEAAGLVR  600
YTNDRGELIF TAADIKGYAN PQVSGYLGVW VPVGAAADQD VRVAASTAPS TDGKSVHQNA  660
ALDSRVMFEG FSNFQAFATK KEEYTNVVIA KNVDKFAEWG VTDFEMAPQY VSSTDGSFLD  720
SVIQNGYAFT DRYDLGISKP NKYGTADDLV KAIKALHSKG IKVMADWVPD QMYALPEKEV  780
VTATRVDKYG TPVAGSQIKN TLYVVDGKSS GKDQQAKYGG AFLEELQAKY PELFARKQIS  840
TGVPMDPSVK IKQWSAKYFN GTNILGRGAG YVLKDQATNT YFNISDNKEI NFLPKTLLNQ  900
DSQVGFSYDG KGYVYYSTSG YQAKNTFISE GDKWYYFDNN GYMVTGAQSI NGVNYYFLPN  960
GLQLRDAILK NEDGTYAYYG NDGRRYENGY YQFMSGVWRH FNNGEMSVGL TVIDGQVQYF 1020
DEMGYQAKGK FVTTADGKIR YFDKQSGNMY RNRFIENEEG KWLYLGEDGA AVTGSQTING 1080
QHLYFRANGV QVKGEFVTDR HGRISYYDGN SGDQIRNRFV RNAQGQWFYF DNNGYAVTGA 1140
RTINGQHLYF RANGVQVKGE FVTDRHGRIS YYDGNSGDQI RNRFVRNAQG QWFYFDNNGY 1200
AVTGARTING QHLYFRANGV QVKGEFVTDR YGRISYYDGN SGDQIRNRFV RNAQGQWFYF 1260
DNNGYAVTGA RTINGQHLYF RANGVQVKGE FVTDRYGRIS YYDANSGERV RIN         1313

SEQ ID NO: 13         moltype = DNA length = 3972
FEATURE               Location/Qualifiers
source                1..3972
                      mol_type = unassigned DNA
                      organism = Streptococcus dentirousetti
SEQUENCE: 13
atggttgacg gcaaatacta ctactacgat gcagacggca acgtaaagaa aaacttcgcg   60
gttagcgttg gcgatgccat tttctatttt gatgaaacgg gtgcctacaa agataccagc  120
aaagttgatg cggataagac cagctctagc gtcaatcgaa ccacggaaac gttcgcagcg  180
aataaccgtg cgtatagcac cgcagccgag aactttgaag cgattgataa ctacctgact  240
gcggatagct ggtatcgtcc gaagtctatc ttgaaagatg gtacgacgtg accgaaagc   300
accaaggatg attttcgccc gctgctgatg gcgtggtggc cggataccga aaccaaacgt  360
aactacgtga ctatatgaa caaggtggtc ggtatcgaca aaacgtacac ccggaaacg   420
tcccaagctg acctgacggc ggcagccgaa ctggtgcagg cgtatcga gcagaaaatc  480
actagcgaaa agaatacgaa gtggctgcgt gaggcgattt ccgcgttcgt taagactcaa  540
ccgcagtgga atggcgagag cgagaaacct tatgatgacc cctgcaaaa tggtgcgctg  600
aagttcgaca atgaaaccag cctgaccccg cgtagcctg gaccgcgct tcaccttttaa tcagaatgac  660
cgtaccccga cgaatcaaac cggtagcctg gaccgcgct tcaccttttaa tcagaatgac  720
ccgctgggtg ttatgagta tttgctggct aatgatgtgc ataacagcaa cccggtcgtt  780
caggccgaga gcctgaactg gctgcattac ctgctgaatt ttggtagcat ttacgcgaat  840
gatccggagg ccaatttcga cagcatccgt gtggacgcgg tggacaatgt tgacgcagac  900
ctgctgcaaa ttagctcgga ttacctgaaa tcggcgtaca aaattgacaa gaacaacaaa  960
aatgcgaaag accacgttag catcgtcagg cgtggaacg acaatgatac ccgtacctg 1020
aatgatgatg cgacaatctg atgaacatg gataacaagt tcgtctgag catgctgtgg 1080
agcctggcga agcaaccaa tgtccgtagc ggcttgaatc cgctgatcca aacagcgtg  1140
gttgaccgtg aggtggacga ccgtgaagtt gaggctaccc cgaattacag ctttgcacgc  1200
gcacacgaca gcgaagttca agatttgatt cgcgacatca tcaaagctga gatcaaccca  1260
aacagcttcg gttatagctt tacccaagag gaaatcgacc aggccttcaa gatctacaat  1320
```

-continued

```
gaggatttga agaaaaccaa taagaagtat acccactaca acgtcccgct gagctacacc  1380
ctgctgctga cgaacaaggg cagcattcca cgcatttact acggtgacat gtttacggat  1440
gacggtcagt atatggccaa caaaaccgtt aactatgacg ccattgagag cctgctgaaa  1500
gcacgtatga agtatgttag cggtggccaa gcgatgcaga attacaacat cggcaacggc  1560
gagattctga ccagcgtccg ttacggtaag ggtgccctga aacagagcaa caaaggcgat  1620
aagactactc gtaccagcgg tattggcgtt gtgatgggta accagagcaa tttcagcctg  1680
gagggcaagg tggtggccct gaatatgggt gcaacgcata ccaaacagaa gtatcgtgca  1740
ttgatggtgt ctacgaaaac cggcgtggcg atttacaata gcgatgaaga agcagaggca  1800
gcaggcctga tcaaaacgac cgatgagaat ggttatttgt actttctgaa tgacgatctg  1860
aagggcgtgg ctaacccgca ggtcagcggc ttcctgcaag tgtgggttcc ggttggtgca  1920
ccggctgacc aggacattcg tgtggcggcg accgatgcgg cttctaccga cggtaagagc  1980
ctgcatcagg acgcagctct ggattctcgc gtcatgtttg aaggtttcag caacttccag  2040
agcttcgcaa ccaaggaaga ggaatacacc aacgttgtta ttgcaaagaa cgtggataag  2100
ttcgtgagct ggggtatcac cgacttcgag atggcaccgc agtacgttag tctctaccgat  2160
ggcacctttc tggatagcgt gattcaaaat ggctatgcct ttacggaccg ttacgacctg  2220
ggtatgagca agcaaacaa gtatggtact gctgaccaac tggtggccgc gattaaagcg  2280
ctgcatgcga agggtctgcg tgtgatggcg gattgggtcc cagatcaaat gtacacttc  2340
cctaagaagg aagtggttac cgttacccgt acggacaaat ttggcaatcc agtggcaggc  2400
agccaaatca accacacctt gtacgtcact gatactaagg gtagcggtga cgactaccag  2460
gcgaagtacg gtgcgcatt cctggatgaa ctgaaagaaa agtacccgga gctgtttacc  2520
aagaagcaaa tcagcaccgg tcaggcaatc gacccgagcg tgaaaatcaa gcagtggagc  2580
gcgaagtact tcaacggtag caatatcttg gtgcgcggca cgaactacgt gctgtccgac  2640
caggcgtcta acaagtactt taacgtggcc gaaggtaaag tctttctgcc agcggcgatg  2700
ctgggtaagg tcgtcgagag cggtatccgt tcgacggta aggttatat ctataacagc  2760
agcaccactg gcgaacaagt gaaggacagc ttcattaccg aagcgggtaa cttgtactat  2820
tttggcaaag atggttatat ggtcatgggt gcacagaata tccaggggtgc taactactac  2880
ttcttggcga atggtgcggc cctgcgcaat agcatcctga cggatcagga tggcaaagc  2940
cactatatg caaatgacgg caagcgttat gagaacggct actatcaatt cggtaacgac  3000
tcctggcgct attttgaaaa cggcgttatg ccgttggtt tgacgcgcgt tgcgggccac  3060
gaccaatact ttgataagga tggtatccaa gcgaagaata agattcattgt tacgcgtgac  3120
ggtaaggtcc gctacttcga cgaacacaac ggcaatgctg ccacgaatac gtttatcagc  3180
gatcaagccg gccattggta ctacctgggg aaagatggtg tcgccgtgac gggtgcgcag  3240
accgttggca gcaacaccct gtacttgag gctaacggcc aacaagtaaa aggcgatttt  3300
gttaccgcca aggacggtaa gttgtatctt ctggacggtg actctggcga catgtggacc  3360
gataccttcg tccaggataa ggctggtcat tggttctatc tgggcaaaga cggtgcggcg  3420
gtaaccggtg cccagaccgt ccgtggtcag aagctgtact tcaaagcgaa tggccagcag  3480
gttaagggtg acattgtgaa aggcgcggat ggtaaaatcc gttactatga tgcaaattcc  3540
ggtgaccagg tttacaatcg cacggtaaaa ggctccgacg gcaagaccta tcattggt  3600
aatgacggca tcgcaatcac gcaaaccatc gccaaaggcc aaaccatcaa ggatggcagc  3660
gttctgcgct tctatagcat ggagggtcag ctggtgaccg gcagcggctg gtattccaac  3720
gcgaaaggtc aatggttgta tgtcaagaac ggtcaagtcc tgacgggttt gcagacggtg  3780
ggcagccagc gtgtgtactt tgacgcaaat ggtattcaag cgaaaggtaa agcagtgcgt  3840
acctccgatg gcaaactgcg ttacttcgat gcgaacagcg gcagcatgat caccaatcag  3900
tggaaagaag ttaatggtca gtactactat ttcgacaaca acggtgttgc gatctatcgc  3960
ggttggaact aa                                                      3972
```

| | | |
|---|---|---|
| SEQ ID NO: 14 | moltype = AA length = 1323 | |
| FEATURE | Location/Qualifiers | |
| source | 1..1323 | |
| | mol_type = protein | |
| | organism = Streptococcus dentirousetti | |

SEQUENCE: 14

```
MVDGKYYYD ADGNVKKNFA VSVGDAIFYF DETGAYKDTS KVDADKTSSS VNQTTETFAA   60
NNRAYSTAAE NFEAIDNYLT ADSWYRPKSI LKDGTTWTES TKDDFRPLLM AWWPDTETKR  120
NYVNYMNKVV GIDKTYTAET SQADLTAAAE LVQARIEQKI TSEKNTKWLR EAISAFVKTQ  180
PQWNGESEKP YDDHLQNGAL KFDNETSLTP DTQSGYRILN RTPTNQTGSL DPRFTFNQND  240
PLGGYEYLLA NDVDNSNPVV QAESLNWLHY LLNFGSIYAN DPEANFDSIR VDAVDNVDAD  300
LLQISSDYLK SAYKIDKNNK NANDHVSIVE AWSDNDTPYL NDDGDNLMNM DNKFRLSMLW  360
SLAKPTNVRS GLNPLIHNSV VDREVDDREV EATPNYSFAR AHDSEVQDLI RDIIKAEINP  420
NSFGYSFTQE EIDQAFKIYN EDLKKTNKKY THYNVPLSYT LLLLTNKGSIP RIYYGDMFTD  480
DGQYMANKTV NYDAIESLLK ARMKYVSGGQ AMQNYNIGNG EILTSVRYGK GALKQSDKGD  540
KTTRTSGIGV VMGNQSNFSL EGKVVALNMG ATHTKQKYRA LMVSTETGVA IYNSDEEAEA  600
AGLIKTTDEN GYLYFLNDDL KGVANPQVSG FLQVWVPVGA PADQDIRVAA TDAASTDGKS  660
LHQDAALDSR VMFEGFSNFQ SFATKEEEYT NVVIAKNVDK FVSWGITDFE MAPQYVSSTD  720
GTFLDSVIQN GYAFTDRYDL GMSKANKYGT ADQLVAAIKA LHAKGLRVMA DWVPDQMYTF  780
PKKEVVTVTR TDKFGNPVAG SQINHTLYVT DTKGSGDDYQ AKYGGAFLDE LKEKYPELFT  840
KKQISTGQAI DPSVKIKQWS AKYFNGSNIL GRGANYVLSD QASNKYFNVA EGKVFLPAAM  900
LGKVVESGIR FDGKGYIYNS STTGEQVKDS FITEAGNLYY FGKGDGYMVMG AQNIQGANYY  960
FLANGAALRN SILTDQDGKS HYYANDGKRY ENGYYQFGND SWRYFENGVM AVGLTRVAGH 1020
DQYFDKDGIQ AKNKIIVTRD GKVRYFDEHN GNAATNTFIS DQAGHWYYLG KDGVAVTGAQ 1080
TVGKQHLYFE ANGQQVKGDF VTAKDGKLYF LDGDSGDMWT DTFVQDKAGH WFYLGKDGAA 1140
VTGAQTVRGQ KLYFKANGQQ VKGDIVKGAD GKIRYYDANS GDQVYNRTVK GSDGKTYIIG 1200
NDGVAITQTI AKGQTIKDGS VLRFYSMEGQ LVTGSGWYSN AKGQWLYVKN GQVLTGLQTV 1260
GSQRVYFDAN GIQAKGKAVR TSDGKLRYFD ANSGSMITNQ WKEVNGQYYY FDNNGVAIYR 1320
GWN                                                              1323
```

| | | |
|---|---|---|
| SEQ ID NO: 15 | moltype = DNA length = 4047 | |
| FEATURE | Location/Qualifiers | |
| source | 1..4047 | |

```
                mol_type = unassigned DNA
                organism = Streptococcus oralis
SEQUENCE: 15
atgatcgacg gcaaaaacta ctacgtacag gatgatggca cggtaaagaa gaatttcgcg    60
gtagaactga atggtcgtat cctgtatttt gatgcagaaa ccggcgctct ggttgatagc   120
aacgagtatc agttccaaca gggtacgagc agcctgaaca atgaattttc tcagaagaac   180
gcattctatg gtacgaccga taaggatatt gagactgtgg atggctacct gaccgcagat   240
agctggtatc gcccgaaatt catcctgaag gatggcaaga cgtggaccgc gagcacggaa   300
acggatctgc gtccgctgtt gatggcatgg tggccggaca agcgtaccca aatcaactat   360
ctgaactaca tgaaccagca gggtctgggt gcggtgtgcg ttgagaacaa agtggagcag   420
gccctgctga cgggtgcaag ccaacaggta caacgcaaga tcgaagagaa gattggtaaa   480
gagggtgata ccaagtggct gcgcaccctg atgggtgcgt cgtgaaaaac gcaaccaaac   540
tggaatatca aaaccgagtc tgaaacgacc ggcacgaaaa aggaccatct gcaaggcggt   600
gcactgctgt atacgaacaa cgagaaatcc ccgcacgcgg acgcaaattt tcgtctgctg   660
aatcgtaccc cgaccagcca aaccggcacg ccgaagtatt tcatcgacaa gtctaacggt   720
ggctacgaat tctgctggc gaacgatttt gacaatagca atcctgcggt acaagctgag   780
cagctgaatt ggctgcacta catgatgaac tttggcagca ttgttgcgaa tgatccgacc   840
gcgaatttcg acggcgttcg tgtggatgct gttgataacg tcaatgccga cttgttgcaa   900
attgcaagcg attactttaa gagccggttac aaagtcggtg agagcgaaga gaaagcgatc   960
aagcacctgt ccatcctgga agcatggagc gataacgacc cggactacaa caaagatacc  1020
aagggtgcac agttggcgat tgataacaaa ctgcgcctga gcctgctgta ctcttttcatg  1080
cgtaatctga gcatccgtag cggtgttgaa ccgacgatta ccaatagcct gaatgaccgt  1140
tccagcgaaa agaagaacgg cgagcgtatg gcaaattaca tcttcgtgcg tgcccacgat  1200
agcgaggtcc aaacggtgat cgccgacatc attcgcgaaa acatcaatcc gaacaccgac  1260
ggcctgacgt ttacgatgga cgagctgaag caggcattca gatttacaa cgaggacatg  1320
cgcaaggcgg acaaaaagta tacccagttt aacattccta ccgcacacgt gctgatgctg  1380
tctaataagg attctattac ccgcgtgtac tatggtgatc tgtatactga cgatggtcag  1440
tacatggaga agaaaagccc gtatcacgat gcgattgacg ctctgctgcg tgcacgtatt  1500
aaatacgtcg cgggtggcca ggatatgaaa gtgacctata tgggcgtgcc gcgtgaagcg  1560
gataagtgga gctataacgg cattctgacc agcgtgcgct atggcacgag cgctaacgaa  1620
gccacggatg agggcactgc ggaaacgcgc acgcaaggta tggcagtgat tgcgagcaat  1680
aatccaaatc tgaaactgaa tgaatgggac aagttgcaag tcaacatggg tgcggcgcat  1740
aagaatcaat attccgtcc ggttctgctg accactaagg acggtatcag ccgttatctg  1800
accgatgaag aagtgcctca gagcctgtgg aaaaagacgg acgcaaacgg tattctgacc  1860
ttcgacatga atgatattgc tggctacagc aacgtgcaag ttagcggtta cctggccgtc  1920
tgggtccccgg tcggtgcgaa ggcggatcaa gatgcgcgca cgaccgcatc caagaagaaa  1980
aatgcgtcgg gtcaggtgta cgaaagcagc gcggctctgg atagccagct gatttacgaa  2040
ggtttcagca actttcaaga ctttgccact cgcgatgatc agtacacgaa caaggtcatt  2100
gcgaaaaacg tgaatctgtt caaagaatgg ggtgtgacca gcttcgagct gccgccgcag  2160
tacgtgagca gccaagatgg cacctttctg gacagcatta tccaaaacgg ctatgcattt  2220
gaagaccgtt acgatatggc gatgagcaag aataacaagt atggtagcct gaaagacctg  2280
ttgaacgcgc tgcgcgcact gcacagcgtc aacattcaag caatcgccga ttgggtgccg  2340
gaccaaattt acaacttgcc gggcaaagag gtggtgaccg ttcgtgt caacaactac  2400
ggcacctacc gtgagggtgc tgaaatcaaa gaaaagctgt atgtcgccaa tagcaagacc  2460
aacgaaaccg atttccaagg taaatacggt ggtgcgttcc tggatgagct gaaggcgaag  2520
tacccggaga tttttcgagcg tgtccaaatc agcaacggcc aaaagatgac taccgatgaa  2580
aagatcacca aatggagcgc gaaatacttt aatggcacaa atattctggg tcgtggcgcg  2640
tactatgtcc tgaaagattg ggccagcaat gattacctga cgaaccgtaa cggcgagatt  2700
gttttgccga gcaactggt taacaagaat agctataccg gctttgtcag cgacgcgaac  2760
ggcacgaagt tctattctac ctctggctac caggcgaaga acagcttcat tcaagacgaa  2820
aacggtaatt ggtattactt tgacaaacgt ggttatctgg ttacgggcgc acacgagatt  2880
gatggcaagc atgtctactt cctgaaaaac ggtatccaac tgcgtgacag catccgtgag  2940
gatgagaacg gtaatcaata ctattacgac cagaccggcg cacaagtgct gaaccgttac  3000
tacacgacgg acggtcagaa ttggcgctat ttcgatgcga aggtgttat ggcacgcggc  3060
ctggtaaaga ttggtgacgg ccaacagttt ttcgatgaaa acggttacca ggtcaagggc  3120
aagattgtta gcgcaaaaga cggcaagctg cgctactttg ataaagactc tggcaatgtc  3180
gtcattaatc gttcgcgca gggtgacaat ccgagcgact ggtactattt cggtgtggaa  3240
tttgctaaac tgacgggttt gcaaaagatc ggccagcaga cgctgtattt tgaccaagac  3300
ggtaagcaag tcaaaggtaa gatcgtaact ctgtcggaca aaagcattcg ttacttcgat  3360
gccaacagcg gtgaaatggc ggttggtcaa ttcgcgaaga gtgcaaagaa tgagtggtat  3420
tatttcgata aaaccggcaa agcggttact ggtttgcaga aaattggtaa gcagaccctg  3480
tactttgacc aggacggtaa acaggttaaa ggcaaggttg tcacgctggc tgataaaagc  3540
atccgctact tcgacgcaga ctccggcgag atggcggtcg gtaagtttgc agagggtgcg  3600
aagaacgagt ggtactattt tgatcagact gcaaggtcg tgactggttt gcaaaagatt  3660
gacaagcaaa ccttgtactt cgaccaggac ggtaaacaag tcaagggtaa gattgtgacg  3720
ttgagcgaca agtcgatccg ttacttgat gctaatagcg gtgagatggc tactaacaaa  3780
ttcgtcgagg gctcgcagaa tgaatggtac tacttcgatc aagcgggtaa ggctgttacg  3840
ggcttgcaac aggtcggtca gcaaactctg tacttcaccc aggatggtaa gcaagtgaag  3900
ggtaaggtcg tggacggtca cggtgtttct cgttatttcg acgcaaactc cggtgacatg  3960
gctcgttcta aatggattca actgaagat ggcagctgga tgtatttcga ccgtgacggt  4020
cgtggccaga atttttggccg taactaa                                      4047

SEQ ID NO: 16         moltype = AA   length = 1348
FEATURE               Location/Qualifiers
source                1..1348
                      mol_type = protein
                      organism = Streptococcus oralis
SEQUENCE: 16
MIDGKNYYVQ DDGTVKKNFA VELNGRILYF DAETGALVDS NEYQFQQGTS SLNNEFSQKN    60
```

```
AFYGTTDKDI ETVDGYLTAD SWYRPKFILK DGKTWTASTE TDLRPLLMAW WPDKRTQINY    120
LNYMNQQGLG AGAFENKVEQ ALLTGASQQV QRKIEEKIGK EGDTKWLRTL MGAFVKTQPN    180
WNIKTESETT GTKKDHLQGG ALLYTNNEKS PHADSKFRLL NRTPTSQTGT PKYFIDKSNG    240
GYEFLLANDF DNSNPAVQAE QLNWLHYMMN FGSIVANDPT ANFDGVRVDA VDNVNADLLQ    300
IASDYFKSRY KVGESEEEAI KHLSILEAWS DNDPDYNKDT KGAQLAIDNK LRLSLLYSFM    360
RNLSIRSGVE PTITNSLNDR SSEKKNGERM ANYIFVRAHD SEVQTVIADI IRENINPNTD    420
GLTFTMDELK QAFKIYNEDM RKADKKYTQF NIPTAHALML SNKDSITRVY YGDLYTDDGQ    480
YMEKKSPYHD AIDALLRARI KYVAGGQDMK VTYMGVPREA DKWSYNGILT SVRYGTGANE    540
ATDEGTAETR TQGMAVIASN NPNLKLNEWD KLQVNMGAAH KNQYYRPVLL TTKDGISRYL    600
TDEEVPQSLW KKTDANGILT FDMNDIAGYS NVQVSGYLAV WVPVGAKADQ DARTTASKKK    660
NASGQVYESS AALDSQLIYE GFSNFQDFAT RDDQYTNKVI AKNVNLFKEW GVTSFELPPQ    720
YVSSQDGTFL DSIIQNGYAF EDRYDMAMSK NNKYGSLKDL LNALRALHSV NIQAIADWVP    780
DQIYNLPGKE VVTATRVNNY GTYREGAEIK EKLYVANSKT NETDFQGKYG GAFLDELKAK    840
YPEIFERVQI SNGQKMTTDE KITKWSAKYF NGTNILGRGA YYVLKDWASN DYLTNRNGEI    900
VLPKQLVNKN SYTGFVSDAN GTKFYSTSGY QAKNSFIQDE NGNWYYFDKR GYLVTGAHEI    960
DGKHVYFLKN GIQLRDSIRE DENGNQYYYD QTGAQVLNRY YTTDGQNWRY FDAKGVMARG   1020
LVKIGDGQQF FDENGYQVKG KIVSAKDGKL RYFDKDSGNA VINRFAQGDN PSDWYYFGVE   1080
FAKLTGLQKI GQQTLYFDQD GKQVKGKIVT LSDKSIRYFD ANSGEMAVGK FAEGAKNEWY   1140
YFDKTGKAVT GLQKIGKQTL YFDQDGKQVK GKVVTLADKS IRYFDADSGE MAVGKFAEGA   1200
KNEWYYFDQT GKAVTGLQKI DKQTLYFDQD GKQVKGKIVT LSDKSIRYFD ANSGEMATNK   1260
FVEGSQNEWY YFDQAGKAVT GLQQVGQQTL YFTQDGKQVK GKVVDVNGVS RYFDANSGDM   1320
ARSKWIQLED GSWMYFDRDG RGQNFGRN                                     1348

SEQ ID NO: 17             moltype = DNA   length = 4047
FEATURE                   Location/Qualifiers
source                    1..4047
                          mol_type = unassigned DNA
                          organism = Streptococcus sanguinis
SEQUENCE: 17
atgattgatg gtaaaaagta ttacgtacag gacgacgca cggttaagaa gaatttcgcg      60
gttgagctga atggcaagat cctgtacttc gatgcagaga ctggtgcgtt gattgacagc     120
gcggagtatc aattccaaca aggcaccagc agcctgaata tgagttcac tcaaaagaac     180
gccttttacg gtacgaccga taaggatgtg gaaaccattg atggttactt gaccgccgat     240
tcctggtatc gtccgaagtt cattctgaaa gatggcaaga cctggacggc gagcacggaa     300
attgacttgc gtccgttgtt gatggcgtgg tggccggaca aacagaccca ggttagctac     360
ctgaattaca tgaaccagca aggcttgggt gcaggcgcct tcgaaaacaa agtagagcag     420
gcaattctga ccggtgcgtc ccaacaggta aacgtaaaa tcgaagaacg catcggtaaa     480
gagggtgata ccaagtggct gcgtaccctg atgggtgcat ttgtaaagac ccagccgaac     540
tggaacatta agaccgagtc cgaaaccact ggcacgaata aagatcatct ccaaggtggc     600
gcactgctgt atagcaattc cgacaagacg agccatgcca actctaagta ccgtatcctg     660
aaccgcaccc cgaccaacca aacgggcacg ccgaaatact ttattgacaa gagcaatggt     720
ggttatgaat ttctgctggc gaatgacttt gacaatagca atccggcagt gcaagcgaa     780
cagctgaact ggttgcactt tatgatgaat tttggctcca tcgttgcaaa tgatccgacg     840
gccaacttcg acggcgtccg cgttgacgct gtggataacg tgaatgcgga tctgttgcaa     900
attgcgagcg actatttcaa gagccgctat aaagtcggcg aaagcgaaga gaggccatt     960
aagcacctgt ccatcctgga agcgtggagc gacaacgacc cggactacaa caaggatact    1020
aaaggtgccc aactgccgat cgacaacaaa ctgcgtctga gcctgctgta ctccttcatg    1080
cgtaagctga gcatccgtag cggcgtcgag ccgaccatca ccaactctct gaatgatcgc    1140
agcacggaga agaagaatgg tgagcgtatg gcaaactata tcttcgttcg tgcacatgat    1200
agcgaggtgc aaacggtcat cgccgacatt atccgtgaga acatcaatcc gaataccgac    1260
ggcctgacgt tcacgatgga tgaactgaag caggcctta aaatttacaa tgaggatatg    1320
cgtaaagccg acaaaagta cacgcagttc aatatcccga ccgcgcacg gctgatgctg    1380
agcaacaaag attctatcac ccgcgtttac tacggtgacc tgtatacgga tgacggtcag    1440
tatatgaaa agaaaagccc gtatcacgac gccattgacg ctctgctgcg tgcgcgtatc    1500
aaatatgttg cgggtggtca ggacatgaag gtgacctata tgggcgtgcc gcgtgaggca    1560
gataaatgga gctataacgg catcctgacc agcgttcgtt atggtacggg tgccaacgag    1620
gcaaccgacg agggtacggc agaaaccgt acccagggca tggccgtcat tgccagcaac    1680
aatccgaacc tgaaactgaa cgagtgggac aagttgcagg tcaacatggg tgcagctcac    1740
aaaaaccaat actatcgtcc ggtgctgctg accaccaagg acgtcatctc gcgctacctg    1800
accgacgaag aagtccgcga gagcctgtgg aaaaagacg atgcgaacgg catcttgacg    1860
tttgacatga atgatattgc gggttacagc aacgtccaag tgagcggtta tctgccgtc    1920
tgggttcctg tgggtgcgaa ggcggaccag gacgctcgtg ttacggcatc taagaagaaa    1980
aatgcctctg gccaagttta cgaaagcagc gcagccctgg actcccagct gatctatgag    2040
ggcttcagca attttcagga ctttgccacc cgtgacgacc agtacactaa caaggttatc    2100
gcgaaaacg tcaatctgtt taaagagtgg ggcgtcacca gcttcgaatt ccgccacag    2160
tatgtgagca gccaagacgg tacgttcctg gatagcatca tccagaatgg ttatgcattc    2220
gaagatcgct atgatatggc gatgagcaaa acaataagt acggtagctt gaacgacctg    2280
ttgaacgcct tgcgtgcact gcatagcgtg aatatccaag cgattgcgga ttgggtgccg    2340
gaccgatttt acaatctgcc gggtaaagaa gttgtcactg caacccgtgt taacaattat    2400
ggcacgtatc gtgagggtag cgagattaaa gagaacctgt acgttgctaa caccaaaacc    2460
aatggtacgg actaccaagg taagtatggt ggtgcgttct ggacgagct gaaagccaaa    2520
tacccctgaga tttttgagcg cgtccaaatc agcaacggcc agaagatgac caccgacgag    2580
aagattacga aatggtccgc caaacacttt aacggcacga acattctggg tcgtggtgcg    2640
tattgc tgaaagactg ggcagcgcaac gagtacgtga ataacaaaaa tggcgagatg    2700
gttctgccga agcagctggt taataaaaat gcatataccg gcttcgtcag cgacgcgagc    2760
ggcaccaaat actattctac cagcggctat caggctcgta atagctttat tcaagatgaa    2820
aatggtaatt ggtactactt caataaccgt ggttatttgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
```

```
tacactacgg acggccaaaa ttggcgctac ttcgacgtta aaggcgtcat ggcccgtggt   3060
ctggtcacga tgggtggtaa ccaacaattc tttgaccaaa acggttacca ggttaaaggc   3120
aaaattgcgc gtgcaaaaga cggtaaactg cgttacttcg ataaagacag cggtaatgcg   3180
gcagctaacc gtttcgccca aggcgataac cctagcgact ggtactattt cggtgcagat   3240
ggtgttgcgg ttacgggcct gcaaaaggtt ggtcagcaaa ctctgtactt tgatcaggac   3300
ggcaagcagg tgaaaggtaa agttgttacc ttggcggaca aaagcattcg ttatttcgat   3360
gcaaacagcg gcgagatggc ggtgaacaag tttgtggaag tgctaagaa cgtgtggtac   3420
tacttcgatc aagcaggcaa agcggtgacc ggcctgcaaa ccatcaataa acaagtgctg   3480
tatttcgacc aggatgtaa acaagtcaaa ggtaaggtgg tcacgctggc tgataagtct   3540
atccgctact tcgacgcgaa cagcggtgag atggcagtgg gcaaattcgc cgaaggcgca   3600
aagaatgagt ggtattactt tgaccaggcg ggcaaggctg ttaccggtct gcaaaagatc   3660
ggccaacaga cgctgtattt cgaccagaac ggtaaacagg ttaagggtaa agtggtcacc   3720
ctggcggata agagcatccg ctatttcgac gctaactctg gcgaaatggc aagcaataag   3780
ttcgttgagg gtgccaaaaa tgaatggtac tatttcgatc aggctggcaa ggcagtgacg   3840
ggtctgcaac aaattggcca gcagaccctg tattttgacc agaatggcaa acaggtgaag   3900
ggtaagattg tgtatgttaa tggtgcgaat cgctactttg atgccaatag cggtgaaatg   3960
gcgcgtaaca agtggattca gctggaagat ggcagctgga tgtattttga ccgcaatggt   4020
cgtggtcgtc gtttcggttg gaactaa                                       4047

SEQ ID NO: 18        moltype = AA   length = 1348
FEATURE              Location/Qualifiers
source               1..1348
                     mol_type = protein
                     organism = Streptococcus sanguinis
SEQUENCE: 18
MIDGKKYYVQ DDGTVKKNFA VELNGKILYF DAETGALIDS AEYQFQQGTS SLNNEFTQKN    60
AFYGTTDKDV ETIDGYLTAD SWYRPKFILK DGKTWTASTE IDLRPLLMAW WPDKQTQVSY   120
LNYMNQQGLG AGAFENKVEQ AILTGASQQV QRKIEERIGK EGDTKWLRTL MGAFVKTQPN   180
WNIKTESETT GTNKDHLQGG ALLYSNSDKT SHANSKYRIL NRTPTNQTGT PKYFIDKSNG   240
GYEFLLANDF DNSNPAVQAE QLNWLHFMMN FGSIVANDPT ANFDGVRVDA VDNVNADLLQ   300
IASDYFKSRY KVGESEEEAI KHLSILEAWS DNDPDYNKDT KGAQLPIDNK LRLSLLYSFM   360
RKLSIRSGVE PTITNSLNDR STEKKNGERM ANYIFVRAHD SEVQTVIADI IRENINPNTD   420
GLTFTMDELK QAFKIYNEDM RKADKKYTQF NIPTAHALML SNKDSITRVY YGDLYTDDGQ   480
YMEKKSPYHD AIDALLRARI KYVAGGQDMK VTYMGVPREA DKWSYNGILT SVRYGTGANE   540
ATDEGTAETR TQGMAVIASN NPNLKLNEWD KLQVNMGAAH KNQYYRPVLL TTKDGISRYL   600
TDEEVPQSLW KKTDANGILT FDMNDIAGYS NVQVSGYLAV WVPVGAKADQ DARVTASKKK   660
NASGQVYESS AALDSQLIYE GFSNFQDFAT RDDQYTNKVI AKNVNLFKEW GVTSFELPPQ   720
YVSSQDGTFL DSIIQNGYAF EDRYDMAMSK NNKYGSLNDL LNALRALHSV NIQAIADWVP   780
DQIYNLPGKE VVTATRVNNY GTYREGSEIK ENLYVANTKT NGTDYQGKYG GAFLDELKAK   840
YPEIFERVQI SNGQKMTTDE KITKWSAKHF NGTNILGRGA YYVLKDWASN EYLNNKNGEM   900
VLPKQLVNKN AYTGFVSDAS GTKYYSTSGY QARNSFIQDE NGNWYYFNNR GYLVTGAQEI   960
DGKQLYFLKN GIQLRDSLRE DENGNQYYYD KTGAQVLNRY YTTDGQNWRY FDVKGVMARG  1020
LVTMGGNQQF FDQNGYQVKG KIARAKDGKL RYFDKDSGNA AANRFAQGDN PSDWYYFGAD  1080
GVAVTGLQKV GQQTLYFDQD GKQVKGKVVT LADKSIRYFD ANSGEMAVNK FVEGAKNVWY  1140
YFDQAGKAVT GLQTINKQVL YFDQDGKQVK GKVVTLADKS IRYFDANSGE MAVGKFAEGA  1200
KNEWYYFDQA GKAVTGLQKI GQQTLYFDQN GKQVKGKVVT LADKSIRYFD ANSGEMASNK  1260
FVEGAKNEWY YFDQAGKAVT GLQQIGQQTL YFDQNGKQVK GKIVYVNGAN RYFDANSGEM  1320
ARNKWIQLED GSWMYFDRNG RGRRFGWN                                    1348

SEQ ID NO: 19        moltype = DNA   length = 4023
FEATURE              Location/Qualifiers
misc_feature         1..4023
                     note = unknown Streptococcus sp. C150
source               1..4023
                     mol_type = unassigned DNA
                     organism = unidentified
SEQUENCE: 19
atgatcgacg gcaaatacta ctacgtaaac gaggacggca gccacaaaga gaatttcgcg     60
atcacggtta atggtcaact gctgtatttt ggtaaggatg gcgcgctgac cagcagcagc    120
acgtacagct tcacccaagg cactaccaat attgtggcag gttttagcat taacaaccgt    180
gcgtatgact ccagcgaggc ctctttcgag ctgattacg gttatctgac tgcggactct    240
tggtaccgtc cggcgagcat tatcaaagac ggtgtgacgt ggcaagcatc caccgccgag    300
gacttccgcc cgttgctgat ggcgtggtgg ccgaacgttg atactcaggt gaactacctg    360
aactacatgt ccaaagtctt taatctggat gctaaataca gctcgactga taacaggaa    420
accctgaagg tggcggcgaa agatatccag atcaaaattg aacaaaagat tcaggcggaa    480
aagtccacgc aatggctgcg tgaaacgatc agcgcctttg taaaacccca gccgcaatgg    540
aacaaagaga ctgagaacta cagcaaggc ggtggtgagg accatctgca aggtggtgcc    600
ctgctgtatg ttaatgactc tcgtacccg tgggcgaaca gcaactatcg tttgctgaac    660
cgcacggcca ccaaccagac cggtacgatc gacaaagaca tcctggacga gcagagcgat    720
ccgaatcaca tgggtggttt tgatttcttg ctggctaatg acgttgactt gagcaatccg    780
gtcgtccagg cggaacaact gaatcagatc cactacctga tgaattgggg ttctattgtc    840
atgggtgata agacgcgaa ttttgacggt attcgtgtag acgcggtgga taatgttgat    900
gcggacatgc tgcaattgta caccaactat ttccgcgaat actatggtgt caacaaaagc    960
gaggcaaacg cgctcgtgca cattagcgtc tggaagcgt gagcctgaa tgacaaccat   1020
tacaatgata agactgatgt tgcgcgctg caatggaga ataagcagcg cttggcactg   1080
ttgtttagcc tggcgaaacc gattaaagaa cgcacgcctg ccgtgtctcc gctgtacaac   1140
aatacgttta acaccactca gcgtgatgaa agacgcgact ggatcaataa agatggttcg   1200
aaagcctaca tgaggatgg cactgtcaag aaaagcacca tcggcaagta acgagaag    1260
tatggtgatg ctagcggcaa ctacgtttc atccgcgctc acgacaataa cgtgcaagac   1320
```

```
atcatcgcgg agatcattaa gaaagagatt aacgagaaat ctgacggttt taccattacg    1380
gattcggaga tgaagcgtgc atttgagatc tataacaaag acatgctgtc taatgacaaa    1440
aagtacacgc tgaataacat cccggcggcg tacgcggtta tgctgcaaaa catgaaaacg    1500
attcccgcta tgtattacgg cgatctgtac acggacgacg gtaattacat ggaagcgaaa    1560
agcccgtact acgatacgat tgttaacttg atgaagtctc gcatcaaata cgtgagcggt    1620
ggccaggcgc agcgcagcta ctggctgccg accgatggta agatggataa gtcggatgtt    1680
gagctgtacc gtacgaacga agtgtacacg agctccgtt acggcaaaga cattatgacc      1740
gccgatgaca cgcaaggtag caaatacagc cgtaccagcg gtcaggtgac cctggtcgtc    1800
aacaacccaa aactgacctt ggaccaaagc gcaaagctga acgtggttat gggcaagatt    1860
catgctaatc agaagtaccg cgcactgatt gtcggtaccc cgaacggtat taagaatttc    1920
accagcgacg cagaggctat tgccgcaggc tatgtcaaag aaaccgatgg caatggcgtg    1980
ctgaccttcg gtgcaaacga catcaagggt tatgaaactt cgatatgag cggcttcgtc       2040
gctgtttggg ttccggtcgg tgcgagcgac gaccaagata ttcgtgtggc ggcgtctacg    2100
gcagcaaaga aagagggtga gctgacgctg aaagcgaccg aagcctatga ctccaactg      2160
atctatgaag ctttagcaa tttccagacc atcccagatg gcagcgatcc ttctgtttat       2220
accaatcgta agatcgcgga aaatgttgat tgttcaaga gctggggtgt cacgagcttc        2280
gaaatggctc cgcagttcgt ttctgcggac gatggcacgt ttctggacag cgtcattcaa    2340
aacggctatg cgttcgcaga ccgttatgat ctggccatga gcaaaaacaa taagtacggc      2400
agcaaagaag atctgcgtaa cgcgctgaag gcactgcaca aagcaggcat tcaggcgatt    2460
gcagattggg tgccagacca aatctaccag ctgcctggca agaagttgt tactgccacc       2520
cgcacggacg gtgctggtcg caaaatcagc gatgcaatca tcgatcattc cctgtacgtt    2580
gcgaactcca agagctccgg taaggactac caagcgaagt acggtggcga gttcttggcg    2640
gaactgaagg cgaaataccc ggaaatgttc aaagtgaaca tgattagcac cggcaaaccg    2700
attgatgata gcgtgaaaac tgaagcagtg gaaagcagaa tacttcaacg caccaatgtg    2760
ctggatcgcg gtgtcggtta tgttctgagc gatgaggcaa ccggtaagta tttcaccgtt    2820
accaaagagg gtaactttat cccgttgcag ctgaaaggta acaagaaggt gattaccggc    2880
ttttccagcg acggtaaggg cattacctat ttcggtacta gcggtaacca agctaaatcc      2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgctacaa ctccaaagcc  3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac catttgatg ctaacggtgt cgcggctact      3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga ctttgtgaag aatagcgacg gcacctactc caagtatgac    3720
gctgcgagcg gcgaacgtct gaccaacgag ttcttcacta cgggcgacaa tcattggtac    3780
tatattggcc caacggtaa gaccgttacc ggtgaagtta agattggtga cgacacgtat     3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt tgttttcttc gacaaaaac ggcctggctt acccaccgga gaatatgaac       4020
tga                                                                  4023
SEQ ID NO: 20          moltype = AA  length = 1340
FEATURE                Location/Qualifiers
REGION                 1..1340
                       note = unknown Streptococcus sp. C150
source                 1..1340
                       mol_type = protein
                       organism = unidentified
SEQUENCE: 20
MIDGKYYYVN EDGSHKENFA ITVNGQLLYF GKDGALTSSS TYSFTQGTTN IVDGFSINNR     60
AYDSSEASFE LIDGYLTADS WYRPASIIKD GVTWQASTAE DFRPLLMAWW PNVDTQVNYL    120
NYMSKVFNLD AKYSSTDKQE TLKVAAKDIQ IKIEQKIQAE KSTQWLRETI SAFVKTQPQW    180
NKETENYSKG GGEDHLQGGA LLYVNDSRTP WANSNYRLLN RTATNQTGTI DKSILDEQSD    240
PNHMGGFDFL LANDVDLSNP VVQAEQLNQI HYLMNWGSIV MGDKDANFDG IRVDAVDNVD    300
ADMLQLYTNY FREYYGVNKS EANALAHISV LEAWSLNDNH YNDKTDVAAL AMENKQRLAL    360
LFSLAKPIKE RTPAVSPLYN NTFNTTQRDE KTDWINKDGS KAYNEDGTVK KSTIGKYNEK    420
YGDASGNYVF IRAHDNNVQD IIAEIIKKEI NEKSDGFTIT DSEMKRAFEI YNKDMLSNDK    480
KYTLNNIPAA YAVMLQNMET ITRVYYGDLY TDDGNYMEAK SPYYDTIVNL MKSRIKYVSG    540
GQAQRSYWLP TDGKMDKSDV ELYRTNEVYT SVRYGKDIMT ADDTQGSKYS RTSGQVTLVV    600
NNPKLTLDQS AKLNVVMGKI HANQKYRALI VGTPNGIKNF TSDAEAIAAG YVKETDGNGV    660
LTFGANDIKG YETFDMSGFV AVWVPVGASD DQDIRVAAST AAKKEGELTL KATEAYDSQL    720
IYEGFSNFQT IPDGSDPSVY TNRKIAENVD LFKSWGVTSF EMAPQFVSAD DGTFLDSVIQ    780
NGYAFADRYD LAMSKNNKYG SKEDLRNALK ALHKAGIQAI ADWVPDQIYQ LPGKEVVTAT    840
RTDGAGRKIS DAIIDHSLYV ANSKSSGKDY QAKYGGEFLA ELKAKYPEMF KVNMISTGKP    900
IDDSVKLKQW KAEYFNGTNV LDRGVGYVLS DEATGKYFTV TKEGNFIPLQ LKGNKKVITG    960
FSSDGKGITY FGTSGNQAKS AFVTFNGNTY YFDARGHMVT NGEYSPNGKD VYRFLPNGIM   1020
LSNAFYVDGN GNTYLYNSKG QMYKGGYSKF DVTETKDGSK SKVVKFRYFT NEGVMAKGVT   1080
VVDGFTQYFN EDGIQSKDEL VTYNGKTYYF EAHTGNAIKN TWRNIKGKWY HFDANGVAAT   1140
GAQVINGQHL YFNEDGSQVK GSIVKNADGT FSKYKDSSGD LVVNEFFTTG DNVWYYAGAN   1200
GKTVTGAQVI NGQHLFFKED GSQVKGDFVK NSDGTYSKYD AASGERLTNE FFTTGDNHWY   1260
YIGANGKTVT GEVKIGDDTY FFAKDGKQLK GQIVTTRSGR ISYYFGDSGK KAISTWVEIQ   1320
PGVFVFFDKN GLAYPPENMN                                               1340
```

```
SEQ ID NO: 21          moltype = DNA   length = 4479
FEATURE                Location/Qualifiers
source                 1..4479
                       mol_type = unassigned DNA
                       organism = Leuconostoc mesenteroides
SEQUENCE: 21
atgaccccat ccgtattagg tgattcttcc gtcccagatg tatcggctaa caatgtgcaa   60
tccgcgagcg ataatacgac ggacacccag caaaatacca ccatcaccga ggaaaatgat  120
aaggtccaga gcgctgcgac caacgataac gtgaccacgg cagcgtccga cacgacgcag  180
agcgccgata acaacgttac cgagaaacaa tctgatgatc acgcgctgga taatgaaaag  240
gttgacaata agcaggacga ggtcgcccag accaacgtga ctagcaaaaa cgaggagagc  300
gcggtggcct ctaccgacac cgatccggca gagactacca cggacgaaac gcaacaggtt  360
agcggcaagt atgtggaaaa ggatggttct tggtattact actttgacga cggtaagaac  420
gcgaagggtc tgagcacgat tgacaacaat atccaatact ttgatgaaag cggtaagcag  480
gtcaaaggtc agtatgtgac gattgataac cagaccatt actttgataa agatagcggt  540
gatgaactga ccggcctgca atctattgac ggtaacattg ttgccttcaa tgacgagggc  600
cagcagatct ttaatcaata ctaccagagc gagaacggta cgacctacta ttttgatgat  660
aagggccacg ctgccaccgg tattaagaat attgagggca agaactacta ttttgacaat  720
ctgggtcaac tgaaaaaggg cttctccggc gtgatcgacg gtcagattat gacgtttgac  780
caggaaactg tcaagaggt ttccaatacc acgtccgaga tcaaagaggg cctgacgact  840
cagaacactg attactctga acataatgcg gcgcacggta ccgacgccga agattttgag  900
aacatcgatg gctatctgac cgccagctcc tggtaccgtc gacggacat tctgcgcaat  960
ggcactgact gggaaccgag caccgacacg gactttcgtc caatcttgag cgtttggtgg 1020
ccggataaga atacgcaggt caactatctg aactacatgg cggacctggg cttcattagc 1080
aacgcagaca gcttcgaaac gggtgactct cagagcctgc tgaacgaggc gtccaattac 1140
gtccagaaaa gcatcgagat gaaaatctcc gcgcaacaga ccgaagtg gctgaaagac 1200
gccatggccg cgtttattgt tacgcagccg caatgaatg aaacttccga agatatgagc 1260
aacgaccact tgcaaaacgg tgcgctgacc tacgttaaca gcccgctgac cccggacgca 1320
aacagcaact ttcgcctgct gaatcgtacc cctaccaacc agaccggcga acaggcgtac 1380
aacctggata attctaaagg tggctttgag ctgctgctgg caaatgatgt ggataacagc 1440
aacccggtgg ttcaagcgga acaactgaat tggctgtact acctgatgaa tttcggtacg 1500
attaccgcca atgacgcgga tgccaacttt gacggcattc cgtcgatgc agtggataac 1560
gtggatgctg atctgttgca gattgcggca gactacttta actggccta cggtgtggac 1620
cagaatgata gcaccgcaaa ccaacacctg tctatcctgg aagattggag ccacaacgac 1680
ccgctgtatg tcacggatca aggcagcgac cagctgacta tggacgacta cgtgcatacg 1740
caattgattt ggagcctgac caaaagcagc gatatccgtg gtaccatgca acgttttgtg 1800
gattactata tggtggaccg ttccaatgac tccacggaga tgaagcgat cccgaattac 1860
agctttgtcc gcgcacacga tagcgaagtt caaaccgtta tcgcgcaaat cgtgagcgat 1920
ctgtatccag atgttgagaa tagcctggct ccgaccaccg agcagctggc agcagcattc 1980
aaggtgtata tgaagatga gaaattggcc gacaaaaagt atacccaata caacatggcg 2040
agcgcctatg cgatgctgct gaccaataaa gacacggtgc cgcgtgtcta ctatggcgac 2100
ctgtataccg atgacggtca atacatggca acgaagagcc cgtattacga cgcgattaac 2160
accctgctga aagctcgtgt tcaatatgtc gcgggtgccc aaagcatgag cgtgatagc 2220
aacgatgtgc tgaccagcgt tcgctatggc aaagacgcga tgacggcgag cgacacgggc 2280
accagcgaga ctcgtaccga gggcgtcggt gtcattgtgt ccaacaatgc ggagctgcaa 2340
ctggaagatg gtcatacggt taccctgcac atgggtgccg cgcacaaaaa tcaggcatac 2400
cgtcgttgt tgtccaccac ggccgacggt ctggcgtatt atgatacgga cgagaatgcc 2460
ccggtggcat atacggatgc gaacggtgac ttgattttca ccaatgagtc catctacgg 2520
gttcagaatc cgcaagtcag cggttacctg gcggtgtggg tccgttggg tgcacaacag 2580
gaccaggacg cgcgcacggc aagcgatacc accactaaca ccagcgataa agttttccac 2640
agcaacgcgg ctctgacag ccaagtgatc tacgagggct tcagcaactt ccaagcgttt 2700
gcgactgatt ccagcgaata caccaatgtt gttattgctc agaacgctga tcaattcaaa 2760
caatggggcg tgacctcgtt tcagctggct ccgcagtacc gcagcagcac ggacacttcc 2820
ttcctgata gcatcatcca aaatggttac gcgtttacgg accgctatga tctgggttat 2880
ggcacgccga cgaagtacgg taccgcgcgc caactcgtg atgcaatcaa agcactgcat 2940
gcgagcggca tccaagcgat tgcagattgg gttccgacc agattacaa tctgccggaa 3000
caagaactgg cgactgtcac gcgcacgaat agcttcggtg atgatgatac tgacagcgac 3060
attgataatg ctctgtatgt ggttcaaagc cgcggtggtg tcagtacca agagatgtat 3120
ggcggtgcgt ttctggagga gttgcaagcg ctgtacccta gcctgtttaa ggtgaaccag 3180
atttctactg gtgtcccgat cgatggtagc gtgaagatta ccgagtgggc tgcgaaatac 3240
ttcaacggca gcaatatcca gggtaagggt gcggttacg tgttgaaaga catgggtagc 3300
aataagtact tcaaggtcgt gagcaatacc gaggacggcg actatctgcc gaaacagctg 3360
accaacgacc tgagcgaaac cggtttcacc cacgacgaca agggtatcat ctactacacc 3420
ctgagcggct atcgtcaca gaacgccttc attcaagacg atgataacaa ttactattac 3480
tttgacaaga ccggtcacct ggtcacgggt ttgcagaaaa tcaacaacca tacgtacttc 3540
ttcctgccga atggcattga gctggtgaaa tccttcttgc agaacgagga tggcacgatc 3600
gtttacttcg ataagaaagg tcatcaagtc tttgatcaat acattacgga tcaaaatggc 3660
aacgcgtact attcgacga tgccggtgtt atgctgaagt ctggtctggc aacgattgat 3720
ggtcatcagc agtacttcga tcagaatggc gttcaagtta aggacaagtt cgttatcggt 3780
acggatggct acaagtacta cttcgagccg ggttgcggca atttggcaat tttgcgttac 3840
gtgcaaaata gcaagaacca atggttctat ttcgatggca atggccacgc agtcacgggt 3900
ttccaaacca tcaacggcaa gaagcagtat ttctacaacg atggtcacca aagcaagggc 3960
gaatttatca atgcggacgg tgacaccttc taccagagcc caccgacgg tcgtttggtg 4020
acgggtgttc agaagatcaa cggtatcacc tacgcgtttg aaggtcatcg caaccctgga 4080
acgaaccagt attatcagct ggcggacggt aagtacatgc tgctggacga ctctggtcgc 4140
gcaaaaacgg gctttgtcct gcaagacggt gtcctgcgtt atttcgacca gaacggtgaa 4200
caagtgaagg acgccattat cgtcgacccg gacaccaacc tgtcttatta ctttaacgcg 4260
acccagggtg tcgcggtgaa aaacgattac ttcgagtacc aaggcaactg gtacctgacc 4320
gatgcaaaact accagctgat taaaggcttc aaagcagttg acgactcgct gcaacacttc 4380
```

-continued

```
gacgaagtta cgggtgtgca gaccaaggaa agcgctctga ttagcgcaca gggcaaagtt  4440
taccagttcg acaacaatgg taacgcggtg agcgcataa                         4479
```

| SEQ ID NO: 22 | moltype = AA  length = 1492 |
|---|---|
| FEATURE | Location/Qualifiers |
| source | 1..1492 |
| | mol_type = protein |
| | organism = Leuconostoc mesenteroides |

SEQUENCE: 22
```
MTPSVLGDSS VPDVSANNVQ SASDNTTDTQ QNTTITEEND KVQSAATNDN VTTAASDTTQ   60
SADNNVTEKQ SDDHALDNEK VDNKQDEVAQ TNVTSKNEES AVASTDTDPA ETTTDETQQV  120
SGKYVEKDGS WYYYFDDGKN AKGLSTIDNN IQYFDESGKQ VKGQYVTIDN QTYYFDKDSG  180
DELTGLQSID GNIVAFNDEG QQIFNQYYQS ENGTTYYFDD KGHAATGIKN IEGKNYYFDN  240
LGQLKKGFSG VIDGQIMTFD QETGQEVSNT TSEIKEGLTT QNTDYSEHNA AHGTDAEDFE  300
NIDGYLTASS WYRPTDILRN GTDWEPSTDT DFRPILSVWW PDKNTQVNYL NYMADLGFIS  360
NADSFETGDS QSLLNEASNY VQKSIEMKIS AQQSTEWLKD AMAAFIVTQP QWNETSEDMS  420
NDHLQNGALT YVNSPLTPDA NSNFRLLNRT PTNQTGEQAY NLDNSKGGFE LLLANDVDNS  480
NPVVQAEQLN WLYYLMNFGT ITANDADANF DGIRVDAVDN VDADLLQIAA DYFKLAYGVD  540
QNDSTANQHL SILEDWSHND PLYVTDQGSD QLTMDDYVHT QLIWSLTKSS DIRGTMQRFV  600
DYYMVDRSND STENEAIPNY SFVRAHDSEV QTVIAQIVSD LYPDVENSLA PTTEQLAAAF  660
KVYNEDEKLA DKKYTQYNMA SAYAMLLTNK DTVPRVYYGD LYTDDGQYMA TKSPYYDAIN  720
TLLKARVQYV AGGQSMSVDS NDVLTSVRYG KDAMTAGTDG TSETRTEGVG VIVSNNAELQ  780
LEDGHTVTLH MGAAHKNQAY RALLSTTADG LAYYDTDENA PVAYTDANGD LIFTNESIYG  840
VQNPQVSGYL AVWVPVGAQQ DQDARTASDT TTNTSDKVFH SNAALDSQVI YEGFSNFQAF  900
ATDSSEYTNV VIAQNADQFK QWGVTSFQLA PQYRSSDTS FLDSIIQNGY AFTDRYDLGY  960
GTPTKYGTAD QLRDAIKALH ASGIQAIADW VPDQIYNLPE QELATVTRTN SFGDDDTDSD 1020
IDNALYVVQS RGGGQYQEMY GGAFLEELQA LYPSLFKVNQ ISTGVPIDGS VKITEWAAKY 1080
FNGSNIQGKG AGYVLKDMGS NKYFKVVSNT EDGDYLPKQL TNDLSETGFT HDDKGIIYYT 1140
LSGYRAQNAF IQDDDNNYYY FDKTGHLVTG LQKINNHTYF FLPNGIELVK SFLQNEDGTI 1200
VYFDKKGHQV FDQYITDQNG NAYYFDDAGV MLKSGLATID GHQQYFDQNG VQVKDKFVIG 1260
TDGYKYYFEP GCGNLAILRY VQNSKNQWFY FDGNGHAVTG FQTINGKKQY FYNDGHQSKG 1320
EFINADGDTF YTSATDGRLV TGVQKINGIT YAFDNTGNLI TNQYYQLADG KYMLLDDSGR 1380
AKTGFVLQDG VLRYFDQNGE QVKDAIIVDP DTNLSYYFNA TQGVAVKNDY FEYQGNWYLT 1440
DANYQLIKGF KAVDDSLQHF DEVTGVQTKE SALISAQGKV YQFDNNGNAV SA         1492
```

| SEQ ID NO: 23 | moltype = DNA  length = 3972 |
|---|---|
| FEATURE | Location/Qualifiers |
| source | 1..3972 |
| | mol_type = unassigned DNA |
| | organism = Streptococcus criceti |

SEQUENCE: 23
```
atggttgatg gcaaatacta ctactacgac gcagatggca acgttaagaa gaatttcgcg   60
attagcgtcg gtgacgcaat cttctacttt gacgaaaccg gtgcttacaa ggacaccagc  120
aaagttggtg cggataaaac cagcagcagc gcgaatcaaa ccacggccac cttcgcggca  180
aacaaccgtg cctatagcac tgcggcgagc aactttgagg caattgacaa ctatttgacc  240
gcagacagct ggtatcgtcc gaagagcatt ctgaaagatg gtaagacgtg gaccgaatcc  300
accaaagacg acttccgtcc gctgctgatg gcttggtggc cggataccga aactaaacgc  360
aactatgtca actatatgaa taaggtcgtc ggcattgata aaacctatac cgcggagact  420
agccaagccg acctgacggc agctgcggag ctggttcaag cgcgcattga gcaacgcatc  480
acgtctgaga agaacacgaa atggctgcgc gaggctatta gcgcgtttgt caagacccag  540
ccgcaagtga atgcgagtc cgaaaagccg tatgatgagt atttgcagaa cggtgcactg  600
aagttcgaca acgaaccctc tctgaccccg gacacccagt ctggttatcg tatcttgaat  660
cgcacgccga ccaatcaaac gggcagcctg gaccgcgtt tcacctttaa tcaaaatgat  720
ccgctgggtg gctatgaata tctgctggca acgacgtgg ataatagcaa cccggtggtg  780
caagcggaga gcttgaattg gctgcactac ctgctgaatt tcggcagcat tacgcgaat  840
gatccggaag cgaatttcga ttccattcgt gtagacgccg tggataacgt ggatgcggat  900
ctgttcagaa ttagcagcga ctacctgaaa tctgcgtaca aaatcgataa gaacaacaaa  960
aatgcgaatg accacgtgag catcgttgag gcgtggagcg ataacgacac cccgtacctg 1020
cacgatgaag gcgataactt gatgaatatg gacaatagct ttcgcctgag catgttgcgc 1080
tccctggcga agcctctgga caaacgtagc ggcctgaacc ctctgatcca taatagcgtc 1140
gttgatcgcg aggtggatga ccgtgaggtt gagaaaattc cgagctactc tttttgcacgc 1200
gctcacgaca gcgaggttca ggatctgatt cgtgacatca ttaaggcaga aatcaatccg 1260
aacagcttcg gctacagctt tacccaagaa gaaatcgatc aagcgttcaa gatctacaac 1320
gaggacctga agaaaaccaa caagaagtac acccattaca atgtcccgct gtcttacacc 1380
ttgctgctga cgaataaggg tagcattccg cgtatttact acggcgacat gtttaccgac 1440
gatgccagt atatgcgaa caaaacggtg aattacaatg ctattgagag cctgctgaag 1500
gctcgtatga agtatgtgag cggtggtcag gcgatgcaaa actatcaaat tggtaatggt 1560
gaaattctga cgtcggtgcg ctacggtaaa ggtgcgctga agcaatcgga caagggcgac 1620
gcaacgacgc gtacctctgg tattggtatt gtcatgggca accagccgaa tttctcgctg 1680
gaaggtaaag tcgttgccct gaacatgggt gcagcgcatg ccaatcagga gtatcgtgcc 1740
ctgatggtga gcactaaaga cggcgtggcg acctatgcga cggatgcaga cgcgagcaaa 1800
gcgggtatga cgaaacgtac cgacgagaac ggctacttgt atttcctgaa tgacgacttg 1860
aagggtgttg caaatccaca gatctccggt tttctgcaag tatgggtgcc ggtcggtgct 1920
cctgccgacc aggatattcg cgttgccgcg acgaacgtca cagtcgatcc tggtaagtcc 1980
ctgcaccaag atgcggcgat ggatagccgt gttatgttcg agggttttc caactttcag 2040
gcgttcgcaa cgaaagaaga tgagtatgct aatgttgtta ttgcgaaaaa tgtggataag 2100
tttgttagct ggggcatcac tgactttgag atggcaccgc agtataccc tagcgatgac 2160
ggtcagttcc tggatagcgt tattcagaat ggttatgcat tcacgaccg ttatgatctg 2220
ggtatgagca aggcaaacaa atatggtacg gcggaacacc tggtcaaagc tatcaaagcg 2280
```

```
ttgcacaaag caggtctgaa agttatggcg gattgggtcc cggaccagat gtatacctt    2340
ccgaagaaag aggttgtcac cgttacgcgt acggacaagt tcggtaaacc ggttgcgggc    2400
agccaaatca atcatacccc tgtatgtgact gacaccaaag gtagcggtga tgactatcag    2460
gccaaatacg gtggtgcgtt tctggacgag ctgaaagaga atacccgga attgtttacg    2520
aaaaagcaga tttctacggg ccaagcaatc gacccaagtc tcaagattaa gcagtggagc    2580
gcgaaatact ttaacggcag caatatcttg ggtcgtggtg caaattacgt cctgagcgac    2640
caggccagca acaagtattt caatgtggcg gaaggtaagg ttttttctgcc aggcgccatg    2700
ctgggcaagg tggtggaaag cggcatccgt tttgacggca agggctacat ctataacagc    2760
tcgaccaccg gcgaacaagt caaagatagc ttcatcacgg aagcaggtaa tttgtattac    2820
ttcggtaaag acggttacat ggtcatgggt gcgcagaaca ttcaaggcgc caattactac    2880
ttcctggcca acggtgcggc actgcgtaat agcatcctga ccgatcaaga cggcaagtcc    2940
cactactacg cgaacgacgg caaacgttat gaaaacggct attatcagtt tggtaacgat    3000
tcctggcgct acttcgagaa tggtgtaatg gccgtcggcg tgaccgtgt ggctggccat    3060
gaccagtact tcgataagga tggtattcaa gcgaagaaca agtcatcgt taccgcgcat    3120
ggtaaggttc gttacttcga tgagcacaat ggcaatgcag tcaccaacac gttcattagc    3180
gatcaggcag tcactggta ctatctgggt aaggacggtg tggcggtgac gggtgcccaa    3240
acggtgggca acagcacct gtatttcgag gccaacggcc agcaggtcaa aggcgatttt    3300
gtgaccgcga aagacggtaa actgtatttc ttcgatggcg atagcggtga catgtggacc    3360
gacacgttcg tccaagacaa aactggccat tggttttacc tgggtaaaga tggtgcgggc    3420
gtcaccggtg cacagaccgt gcgcggtcag aaattgtact ttaaagccaa cggtcagcaa    3480
gttaaggggcg acattgtcaa aggtgctgat ggtaaaatcc gttactatga tgcaaattcg    3540
ggcgatcagg tctacaaccg tactgtgaag ggttccgacg gtaaaaccta catcatcggt    3600
aaagacggtg ttgccattac gcagaccatc gcgaagggtc aaaccattaa ggacggcagc    3660
gttctgcgtt tctacagcat ggaaggccag ctggttaccg gtagcggctg gtattctaac    3720
gcgaaaggtc agtggctgta cgtgaagaat ggtcaggtc tgaccggtct gcaaaccgtt    3780
ggttcccaac gtgtgtactt cgacgctaac ggtatccaag gagggcaa ggccggtcgc    3840
accagcgacg gtaagctgcg ttactttgat gcgaacagcg gtagcatgat cactaaccag    3900
tggaaagagg tgaacggtca atactattac tttgacaaca atggcgtcgc catctaccgc    3960
ggctggaact aa                                                        3972

SEQ ID NO: 24           moltype = AA  length = 1323
FEATURE                 Location/Qualifiers
source                  1..1323
                        mol_type = protein
                        organism = Streptococcus criceti
SEQUENCE: 24
MVDGKYYYYD ADGNVKKNFA ISVGDAIFYF DETGAYKDTS KVGADKTSSS ANQTTATFAA      60
NNRAYSTAAE NFEAIDNYLT ADSWYRPKSI LKDGKTWTES TKDDFRPLLM AWWPDTETKR     120
NYVNYMNKVV GIDKTYTAET SQADLTAAAE LVQARIEQRI TSEKNTKWLR EAISAFVKTQ     180
PQWNGESEKP YDDHLQNGAL KFDNETSLTP DTQSGYRILN RTPTNQTGSL DPRFTFNQND     240
PLGGYEYLLA NDVDNSNPVV QAESLNWLHY LLNFGSIYAN DPEANFDSIR VDAVDNVDAD     300
LLQISSDYLK SAYKIDKNNK NANDHVSIVE AWSDNDTPYL HDEGDNLMNM DNKFRLSMLR     360
SLAKPLDKRS GLNPLIHNSV VDREVDDREV EKIPSYSFAR AHDSEVQDLI RDIIKAEINP     420
NSFGYSFTQE EIDQAFKIYN EDLKKTNKKY THYNVPLSYT LLLLTNKGSIP RIYYGDMFTD     480
DGQYMANKTV NYNAIESLLK ARMKYVSGGQ AMQNYQIGNG EILTSVRYGK GALKQSDKGD     540
ATTRTSGIGI VMGNQPNFSL EGKVVALNMG AAHANQEYRA LMVSTKDGVA TYATDADASK     600
AGMTKRTDEN GYLYFLNDDL KGVANPQISG FLQVWVPVGA PADQNDIRVAA TNAASTDGKS     660
LHQDAAMDSR VMFEGFSNFQ AFATKEDEYA NVVIAKNVDK FVSWGITDFE MAPQYTSSDD     720
GQFLDSVIQN GYAFTDRYDL GMSKANKYGT AEHLVKAIKA LHKAGLKVMA DWVPDQMYTF     780
PKKEVVTVTR TDKFGKPVAG SQINHTLYVT DTKGSGDDYQ AKYGGAFLDE LKEKYPELFT     840
KKQISTGQAI DPSVKIKQWS AKYFNGSNIL GRGANYVLSD QASNKYFNVA EGKVFLPGAM     900
LGKVVESGIR FDGKGYIYNS STTGEQVKDS FITEAGNLYY FGKDGYMVMG AQNIQGANYY     960
FLANGAALRN SILTDQDGKS HYYANDGKRY ENGYYQFGND SWRYFENGVM AVGVTRVAGH    1020
DQYFDKDGIQ AKNKIIVTRD GKVRYFDEHN GNAVTNFIS DQAGHWYYLG KDGVAVTGAQ    1080
TVGKQHLYFE ANGQQVKGDF VTAKDGKLYF FDGDSGDMWT DTFVQDKTGH WFYLGKDGAA    1140
VTGAQTVRGQ KLYFKANGQQ VKGDIVKGAD GKIRYYDANS GDQVYNRTVK GSDGKTYIIG    1200
KDGVAITQTI AKGQTIKDGS VLRFYSMEGQ LVTGSGWYSN AKGQWLYVKN GQVLTGLQTV    1260
GSQRVYFDAN GIQAKGKAVR TSDGKLRYFD ANSGSMITNQ WKEVNGQYYY FDNNGVAIYR    1320
GWN                                                                 1323

SEQ ID NO: 25           moltype = DNA  length = 4308
FEATURE                 Location/Qualifiers
source                  1..4308
                        mol_type = unassigned DNA
                        organism = Streptococcus sobrinus
SEQUENCE: 25
atggttgacg gcaaatacta ctattatgat caggatggca acgttaagaa gaatttcgcg      60
gttagcgttg gtgacaagat ctactacttt gacgagactg gtgcctacaa agacacctct     120
aaagtggacg cggacaagtc tagcagcgcc gttagccaaa cgaccgctac ctttgcggct     180
aacaatcgtg cgtatagcac ctctgctgag aactttgagg ccgttgataa ctatctgacg     240
gcagatagct ggtatcgtcc taaatctatt ctgaaagatg gcaagacgtg gaccgagtcg     300
ggtaaggacg acttccgtcc gctgctgatg gcgtggtggc cggacacgga gactaaacgc     360
aattacgtga attacatgaa cctggttgtc ggcatcgaca gacgtacac cgcggaaacc     420
tctcaagcga atttgaccgc agcggagcg tcggtcgga tgtactattg acagaaaatc     480
accacgaac agaatacgaa atggctgcgc gaggcgatct ctgctttcgt caagacccag     540
ccgcagtgga atggtgaaag cgagaagccg tatgacgacc acctgcaaaa cggtgctctg     600
aaattcgata tcagagcga cctgacccg gacacccaga gcaactatcg cctgctgaat     660
cgcaccccga ctaaccagac tggcagcctg acagccgtt tcacctataa tgcgaacgat     720
ccgttggggt gctacgaatt tctgctggct aacgacgtgg ataatagcaa ccctgtggtg     780
```

```
caggcagaac aactgaactg gttgcattac ctgttgaatt ttggtagcat ttacgcgaaa    840
gatgcggatg caaacttcga ttccatccgt gtggacgccg tggacaacgt cgatgcagat    900
ctgttgcaga ttagcagcga ttacctgaag gcagcctatg gcattgacaa gaacaataag    960
aacgcgaaca accatgttag cattgttgag gcttggagcg ataacgatac gccgtacctg   1020
cacgatgacg gtgataacct gatgaacatg gacaatgata tccgcttgag catgctgtgg   1080
agcctggcca agccgctgga caagcgcagc ggtctgaatc ctctgattca taacagcctg   1140
gtggaccgtg aggttgatga ccgtgaagtg gaaacggttc cgagctactc ttttgcgcgt   1200
gcgcatgatt ccgaggtcca agacattatc cgcgacatta tcaaggccga aatcaacccg   1260
aatagctttg gttatagctt cacccaagaa gagattgacc aggcgtttaa gatctataat   1320
gaagatctga agaaaaccga caagaaatac acccactata atgtcccgtt gagctatact   1380
ttgctgctga cgaataaagg ttcgattccg cgtgtgtatt acggtgatat gttcaccgat   1440
gatggtcaat acatggcgaa caaaacggtt aactatgatg ccattgagtc gctgctgaaa   1500
gcgcgcatga agtacgttag cggcggtcaa gcgatgcaaa actatcaaat cggcaatggt   1560
gagattctga ccagcgttcg ttatggtaag ggtgcattga agcaatccga caagggtgac   1620
gcgaccacgc gtacgtccgg tgtgggcgtc gtgatgggca accagccgaa ctttagcctg   1680
gacggcaagg tggtggcatt gaacatgggt gccgctcatg caaatcagga gtatcgtgcg   1740
ctgatggtga gcaccaagga tggcgttgcc acgtatgcca ccgacgcgga cgcaagcaag   1800
gcaggtctga tcaaacgcac cgatgaaaat ggttatttgt actttctgaa cgacgatctg   1860
aagggtgtgg caaacccaca agtcagcggt ttcttgcagg tgtgggtccc agtgggtgcg   1920
gctgacgatc aggacattcg tgttgcagcg agcgacacgg ctagcacgga cggtaagtcc   1980
ctgcatcaag atgcggcaat ggatagccgt gttatgtttg agggttttag caacttccag   2040
agctttgcaa ccaaagaaga agagtacacc aacgtagtta tggtcgaaca acgtgggacaaa   2100
ttcgttagct ggggtattac cgactttgag atgcaccgc aatatgtcag ctccaccgat   2160
ggccagtttc tggatagcgt tatccagaat ggttacgcgt tcaccgaccg ttatgatctg   2220
ggtatgagca agccaacaa atacggtacc gcggatcagc tggttaaagc aatcaaagcg   2280
ttgcacgcga agggtctgaa ggtgatggcg gactgggttc cagaccagat gtacacgttt   2340
ccgaagcagg aagttgtcac tgtcacgcgc accgacaaat ttggtaagcc gattgcgggc   2400
agccaaatca atcacagcct gtacgtgacg gacaccaaat ccagcggtga tgattaccag   2460
gccaaatatg gtggtgcgtt cctggatgag ctgaaagaa aatacccgga gctgttcacc   2520
aaaaagcaga tctcgaccgg tcaggcgatc gacccgaacg tgaagattaa gcagtgaagg   2580
gcgaaatact ttaatggtag caacattctg ggtcgtggtg ccgactacgt cctgtccgat   2640
caagttagca acaagtattt caatgtggcc agcacacgc tgtttctgcc gtctagcctg   2700
ttgggtaagg ttgtcgaaag cggtattcgt tacgatggca aaggttatat ctataacagc   2760
agcgcgacta gcgaccaagt caaggcgtct tttatcacgg aagcaggcaa tctgactac   2820
ttcggcaaag acggttacat ggttactggt gcgcagaaca ttaacggtgc gaattcttc   2880
ttcttggaaa atggtacggc cctgcgtaat accatctaca ccgatgcaca gggcaactcc   2940
cactatatg ctaatgatgg caagcgttac gagaacggtt accagcagtt cggcaacgat   3000
tggcgttact tcaaagatgg taacatggcc gtcggtctga ccacggtgga tggtaacgtt   3060
cagtatttcg acaaggacgg tgtccaagct aaagacaaga ttattgtgac ccgcgatgt   3120
aaggtgcgct actttgatca acacaatggc aacgcggtca cgaataccttt atcgccgac   3180
aagaccggtc actggtacta cctgggcaaa gatggcgtcg cggtcaccgg cgctcaaacc   3240
gtcggtaagc aaaaactgta tttgaggcg aacggtgagc aggtgaaagg cgactttgtg   3300
actagccatg aagcaaact gtacttttat gatgttgaca aaacctatgt gatcggcaac   3360
accttcatcg aggataaggc cggcaactgg ttctacctgg gtaaagacgg cgcagcagtt   3420
agcggtgcac agaccattcg cggtcaaaag ctgtacttca aggcgtacgg tcaacaggtc   3480
aaaggtgaca tcgttaaagg caccgacggc aagatccgtt actacgatgc gaaatccggc   3540
gagcaggttt tcaataagac ggtcaaagcc gctgatgcaa aaacctatgt gatcggcaac   3600
aatggtgtgg cggtcgatcc gagcgttgtt aagggtcaga cgttcaaaga cgccagcggc   3660
gcactgcgtt tttacaatct gaaaggtcaa ctggttacgg gctccggttg gtatgaaacg   3720
gccaatcacg attgggtgta tattcagagc ggtaaagcac tgaccggtga gcaaaccatc   3780
aatgctcagc acctgctactt taaagaagat ggccaccaag ttaaaggtca ggtgtcac   3840
cgtacggacg gcaaagtgcg ttactatgac gcaaattctg gcgatcaagc gttcaacaag   3900
tccgtgacgg ttaacggcaa aacgtattac ttcggtaatg atggtaccgc gcaaaccgcg   3960
ggtaacccga aaggccaaat cttcaaggac ggcagcgttc tgcgttttcta tagcatgaa   4020
ggcagctgg taattggcag cggctggtat tccaacgcga aaggccaatg gctgtatgtg   4080
aagaatggta aagtgttgac cggttttcag accgtcggtt cccagcgcgt gtactttgat   4140
gagaatggca ttcaagcaaa aggcaaagcg ttcgcacga gcgacggcaa aattcgctac   4200
ttcgacgaga cagcggtag catgatcacc aatcaatgga gtttgttta cggtcaatac   4260
tattactttg gtaatgacgg tgcggcaatc taccgtggtt ggaattaa             4308
SEQ ID NO: 26        moltype = AA   length = 1435
FEATURE              Location/Qualifiers
source               1..1435
                     mol_type = protein
                     organism = Streptococcus sobrinus
SEQUENCE: 26
MVDGKYYYYD QDGNVKKNFA VSVGDKIYYF DETGAYKDTS KVDADKSSSA VSQNATIFAA     60
NNRAYSTSAE NFEAVDNYLT ADSWYRPKSI LKDGKTWTES GKDDFRPLLM AWWPDTETKR    120
NYVNYMNLVV GIDKTYTAET SQADLTAAAE LVQARIEQKI TTEQNTKWLR EAISAFVKTQ    180
PQWNGESEKP YDDHLQNGAL KFDNQSDLTP DTQSNYRLLN RTPTNQTGSL DSRFTYNAND    240
PLGGYEFLLA NDVDNSNPVV QAEQLNWLHY LLNFGSIYAK DADANFDSIR VDAVDNVDAD    300
LLQISSDYLK AAYGIDKNNK NANNHVSIVE AWSDNDTPYL HDDGDNLMNM DNKFRSLMLW    360
SLAKPLDKRS GLNPLIHNSL VDREVDDREV ETVPSYSFAR AHDSEVQDII RDIIKAEINP    420
NSFGYSFTQE EIDQAFKIYN EDLKKTDKKY THYNVPLSYT LLLTNKGSIP RVYYGDMFTD    480
DGQYMANKTV NYDAIESLLK ARMKVSGGQ AMQNYQIGNG EILTSVRYGK GALKQSDKGD    540
ATTRTSGVGV VMGNQPNFSL DGKVVALNMG AAHANQEYRA LMVSTKDGVA TYATDADASK    600
AGLVKRTDEN GYLYFLNDDL KGVANPQVSG FLQVWVPVGA ADDQDIRVAA SDTASTDGKS    660
LHQDAAMDSR VMFEGFSNFQ SFATKEEEYT NVVIANNVDK FVSWGITDFE MAPQYVSSTD    720
GQFLDSVIQN GYAFTDRYDL GMSKANKYGT ADQLVKAIKA LHAKGLKVMA DWVPDQMYTF    780
```

```
PKQEVVTVTR TDKFGKPIAG SQINHSLYVT DTKSSGDDYQ AKYGGAFLDE LKEKYPELFT  840
KKQISTGQAI DPSVKIKQWS AKYFNGSNIL GRGADYVLSD QVSNKYFNVA SDTLFLPSSL  900
LGKVVESGIR YDGKGYIYNS SATGDQVKAS FITEAGNLYY FGKDGYMVTG AQTINGANYF  960
FLENGTALRN TIYTDAQGNS HYYANDGKRY ENGYQQFGND WRYFKDGNMA VGLTTVDGNV 1020
QYFDKDGVQA KDKIIVTRDG KVRYFDQHNG NAVTNTFIAD KTGHWYYLGK DGVAVTGAQT 1080
VGKQKLYFEA NGEQVKGDFV TSHEGKLYFY DVDSGDMWTD TFIEDKAGNW FYLGKDGAAV 1140
SGAQTIRGQK LYFKAYGQQV KGDIVKGTDG KIRYYDAKSG EQVFNKTVKA ADGKTYVIGN 1200
NGVAVDPSVV KGQTFKDASG ALRFYNLKGQ LVTGSGWYET ANHDWVYIQS GKALTGEQTI 1260
NGQHLYFKED GHQVKGQLVT RTDGKVRYYD ANSGDQAFNK SVTVNGKTYY FGNDGTAQTA 1320
GNPKGQIFKD GSVLRFYSME GQLVIGSGWY SNAQGQWLYV KNGKVLTGLQ TVGSQRVYFD 1380
ENGIQAKGKA VRTSDGKIRY FDENSGSMIT NQWKFVYGQY YYFGNDGAAI YRGWN       1435

SEQ ID NO: 27           moltype = DNA  length = 4023
FEATURE                 Location/Qualifiers
source                  1..4023
                        mol_type = unassigned DNA
                        organism = Streptococcus salivarius
SEQUENCE: 27
atgattgacg gcaaatacta ctacgtaaac aaagatggct cgcacaaaga gaatttcgca   60
attaccgtga atggtcagtt gttgtatttc ggtaaggacg gtgcattgac gtctagcagc  120
acctacagct ttacgcaggg caccaccaac atcgttgatg gctttagcaa aaacaaccgt  180
gcgtacgatt ccagcgaggc gagctttgaa ctgatcgacg gttatctgac cgcggactcc  240
tggtatcgtc cggtgagcat tatcaaggac ggcgttacgg gcaagccag caccaaagag  300
gactttcgcc cgctgctgat ggcctggtgg ccgaatgttg acacccaggt caactacctg  360
aattacatgt cgaaggtgtt taacctggac gcgaagtata cgagcaccga caaacaggtt  420
gacctgaatc gcgcagccaa ggacattcag gttaagattg agcaaaagat tcaggccgag  480
aagagcactc aatggctgcg tgaagcgatt tcggccttcg tcaaaaccca gccgcagtgg  540
aataaagaaa cggagaactt ctccaagggt ggtggtgagg atcatctgca aggtggtgca  600
ctgctgtacg ttaacgaccc gcgtaccccg tgggctaact ccaactaccg cctgctgaat  660
cgtactgcga ccaaccagac cggcacgatc gacaagacg ttctggacga acagagcgat  720
cctaaccaca tgggcggctt cgatttcctg ctggcgaatg acgtcgatac cagcaatccg  780
gtggtgcagg cggaacaact gaatcagatc cactacctga tgaattgggg ttccattgtt  840
atgggcgaca agatgcaaaa cttcgatggt atccgcgtgg acgcggtcga taacgttgac  900
gcagatatgc tgcaactgta caccaactac tttcgtgagt attatggcgt gaacaaaagc  960
gaggcaaacg cttttggcgca catctcggtg ctggaagcgt ggagcttgaa tgataatcac 1020
tataatgaca agactgacgg tgcggccctg cgcgatgaga acaaacagcg tttggccctg 1080
ctgtttagct tggcgaaacc gatcaaagaa cgtaccctg cggtgagccc gctgtacaac 1140
aacactttca cacgacgca gcgtgacgaa aagaccgatt ggattaacaa agacggtagc 1200
aaagcctata atgaggacgg caccgtcaag cagtccacca tcggcaagta caacgagaaa 1260
tacggcgacg cgtccggcaa ttatgtgttc attcgcgccc acgataacaa cgtccaagac 1320
attattgcag agatcattaa gaaagaaatc aatccgaaaa gcgacggttt caccattacc 1380
gacgccgaaa tgaaaaaggc attcgaaatc tacaacaaag atatgctgtc ctctgataag 1440
aaatacaccc tgaacaacat cccagcggcc tacgcggtga tgctgcaaaa catgaaaacct 1500
attactcgtg tgtattacgg cgatctgtat accgacgatg gccattacat ggaaaccaag 1560
agcccgtact acgacaccat tgtgaacctg atgaagaacc gtatcaaata cgtgtccggt 1620
ggtcaagcgc aacgttccta ttggctgccg accgacggta gatggataa aagcgatgtc 1680
gaactgtatc gcaccaacga ggtgtacacc agctccgtt acgttaagga catcatgact 1740
gccgatgaca cccaaggtag caagtacagc cgtaccagcg gtcaggtgac cctggtggtg 1800
aacaacccga gctgtctttt ggataagagc gcgaagctgg acgtcgaaat gggcaagatc 1860
catgcaaacc agaaataccg tgctctgatc gtgggtacgc cgaacggcat caaaaacttc 1920
acgagccacg ccgaggcaat cgcggctggc tacgtgaaaa aaccgacgg caatggtgtg 1980
ctgaccttcg gtgcaaatga catcaaaggt tacgaaacgt ttgacatgag cggtttcgtt 2040
gcagtttggg gttccggtag tgcaagcgat gatcaagaca tccgtgtcgc cgcaagcacc 2100
gcggcaaaga aagaaggtga gctgactttg aaggcaactg aggcgtatga ctctcagctg 2160
atttacgaag gttttcgaa ttttcagacc attccggatg gtagcgatcc gagcgtttac 2220
accaatcgta agatcgcgga aaatgttgat ttgttcaaga gctggggtgt gacctctttc 2280
gaaatggcgc cacagtttgt gagcgcagac gacggtacgt ttctggacag cgttatccag 2340
aacggctatg cgtttgcgga ccgttatgat ctggcgatgt ccaaaaacaa taagtacggt 2400
tcgaaagaag atctgcgtaa cgcgttgaag gctttgcaca aggccggcat ccaagccatt 2460
gcggactggg ttccggatca gatctaccaa ctgccgggca aagaagtagt gaccgccact 2520
cgtaccgatg gtgccggtcg taagattagc gatgcaatta tcgatcacag cctgtacgtc 2580
gcaaacagca agtcgtctgg caaagactat caagctaaat acgtggtgga gttcctggcc 2640
gagctgaaag caaagtaccc ggaaatgttt aaagtcaaca tgattagcac gggtaaaccg 2700
atcgacgact ctgtcaaact gaagcaatgg aaggcggagt actttaacgg tacgaatgtt 2760
ctggaccgtg tgtgttggtta cgtcctgagc gatgaggcga cgggcaagta ctttaccgtt 2820
acgaaagagg gtaactttat cccactgcaa ttgaaaggta cgagaaagt tatcacgggc 2880
ttcagctctg acggcaaggg cattacctat ttcggcacct cgggtaatca agcgaaaagc 2940
gcttttgtca cgttcaatgg taatacctac tattttgacg cgcgtggcca catggttacc 3000
aacggcgaat atagcctaa tggtaaggat gtgtatcgtt cctgccgaa tggtattatg 3060
ttgagcaatg cattctacgt tgacggtaac ggcaatacct acctgtacaa ctccaagggc 3120
caaatgtaca aggtggtta tagcaaatc gacgttacgg aaaccaaaga tggtaaagag 3180
agcaaagtgg tgaaatttcg ctactttacc aatgaaggtg tgatggcaaa aggtgttacc 3240
gtggtggacg gcttcactca atacttcaac gaagatggca ttcagagcaa ggacgaactg 3300
gtgacctaca atggtaaaac ctattacttc gaagcgcata ccggtaactg gatcaaaaac 3360
acgtggcgca atatcaaggg taagtgtat cactttgatg cgaatggcgt ggcggcaacg 3420
ggtcacaggg ttatcaatgg tcagcacctg tactttaatg aggatggttc ccaggtgaag 3480
ggtggcgtcg tgaagaatgc ggatggtacc ttcagcaagt ataaagatgg ttccggtgac 3540
ctggtggtca atgagttctt cactactggt gataacgtgt ggtactacgc tggtgccaac 3600
ggcaaaactg tgacgggtgc ccaggtcatc aatggccaac cctgttttt caaagaggac 3660
```

-continued

```
ggtagccagg ttaagggtga tttcgttaag aacagcgacg gcacctactc taagtatgat 3720
gcggccagcg gcgaacgcct gacgaatgag ttttcacga ccggtgacaa ccactggtac 3780
tatattggtg ccaatggcaa aaccgttacc ggcgaagtca agatcggtga tgatacgtac 3840
ttcttcgcaa aagatggcaa gcagctgaag ggccagatcg tgacgacccg cagcggtcgt 3900
atcagctact acttcggcga ctctggtaag aaggcgatta gcacctgggt ggagattcag 3960
ccgggtgttt tcgtgttttt cgacaaaaat ggcctggcat atccgccgga aaacatgaat 4020
taa                                                                4023

SEQ ID NO: 28          moltype = AA  length = 1340
FEATURE                Location/Qualifiers
source                 1..1340
                       mol_type = protein
                       organism = Streptococcus salivarius
SEQUENCE: 28
MIDGKYYYVN KDGSHKENFA ITVNGQLLYF GKDGALTSSS TYSFTQGTTN IVDGFSKNNR  60
AYDSSEASFE LIDGYLTADS WYRPVSIIKD GVTWQASTKE DFRPLLMAWW PNVDTQVNYL  120
NYMSKVFNLD AKYTSTDKQV DLNRAAKDIQ VKIEQKIQAE KSTQWLREAI SAFVKTQPQW  180
NKETENFSKG GGEDHLQGGA LLYVNDPRTP WANSNYRLLN RTATNQTGTI DKSVLDEQSD  240
PNHMGGFDFL LANDVDTSNP VVQAEQLNQI HYLMNWGSIV MGDKDANFDG IRVDAVDNVD  300
ADMLQLYTNY FREYYGVNKS EANALAHISV LEAWSLNDNH YNDKTDGAAL AMENKQRLAL  360
LFSLAKPIKE RTPAVSPLYN NTFNTTQRDE KTDWINKDGS KAYNEDGTVK QSTIGKYNEK  420
YGDASGNYVF IRAHDNNVQD IIAEIIKKEI NPKSDGFTIT DAEMKKAFEI YNKDMLSSDK  480
KYTLNNIPAA YAVMLQNMET ITRVYYGDLY TDDGHYMETK SPYYDTIVNL MKNRIKYVSG  540
GQAQRSYWLP TDGKMDKSDV ELYRTNEVYT SVRYGKDIMT ADDTQGSKYS RTSGQVTLVV  600
NNPKLSLDKS AKLDVEMGKI HANQKYRALI VGTPNGIKNF TSDAEAIAAG YVKETDNGV  660
LTFGANDIKG YETFDMSGFV AVWVPVGASD DQDIRVAAST AAKKEGELTL KATEAYDSQL  720
IYEGFSNFQT IPDGSDPSVY TNRKIAENVD LFKSWGVTSF EMAPQFVSAD DGTFLDSVIQ  780
NGYAFADRYD LAMSKNNKYG SKEDLRNALK ALHKAGIQAI ADWVPDQIYQ LPGKEVVTAT  840
RTDGAGRKIS DAIIDHSLYV ANSKSSGKDY QAKYGGEFLA ELKAKYPEMF KVNMISTGKP  900
IDDSVKLKQW KAEYFNGTNV LDRGVGYVLS DEATGKYFTV TKEGNFIPLQ LKGNEKVITG  960
FSSDGKGITY FGTSGNQAKS AFVTFNGNTY YFDARGHMVT NGEYSPNGKD VYRFLPNGIM  1020
LSNAFYVDGN GNTYLYNSKG QMYKGGYSKF DVTETKDGKE SKVVKFRYFT NEGVMAKGVT  1080
VVDGFTQYFN EDGIQSKDEL VTYNGKTYYF EAHTGNAIKN TWRNIKGKWY HFDANGVAAT  1140
GAQVINGQHL YFNEDGSQVK GGVVKNADGT FSKYKDGSGD LVVNEFFTTG DNVWYYAGAN  1200
GKTVTGAQVI NGQHLFFKED GSQVKGDFVK NSDGTYSKYD AASGERLTNE FFTTGDNHWY  1260
YIGANGKTVT GEVKIGDDTY FFAKDGKQLK GQIVTTRSGR ISYYFGDSGK KAISTWVEIQ  1320
PGVFVFFDKN GLAYPPENMN                                              1340

SEQ ID NO: 29          moltype = DNA  length = 4026
FEATURE                Location/Qualifiers
source                 1..4026
                       mol_type = unassigned DNA
                       organism = Streptococcus salivarius
SEQUENCE: 29
atgacggacg gtaaatacta ttatgtaaat gaggacggca gccacaaaga gaatttcgca  60
attacggtaa acggtcaact gttgtacttt ggcaaggacg gcgctctgac gagcagcagc  120
acgcacagct tcacgccggg tactacgaat attgtggaca gtttctcgat caacaaccgt  180
gcgtacgata gcagcgaagc gagctttgag ctgatcaacg gttacctgac ggcggattcc  240
tggtatcgcc cggtttctat catcaaggat ggcgtcacgt ggcaggcaag cactgccgag  300
gattttcgtc cgctgttgat ggcctggtgg ccgaacgttg atacccaggt gaactatctg  360
aactatatgt ccaaggtctt taacctggaa gccaagtaca ccgccaccga taaacaggct  420
gatctgaacc gtgctgcaaa ggatatccag gtcaagatcg aacagaagat ccaggcggaa  480
aagagcacgc agtggctgcg tgagactatc tccgcgtttg ttaaaacccc agccgcaatgg 540
aacaaagaga ctgagaatta ctccaagggt ggtggcgaag atcatctgca aggcggtgcg  600
ctgttgtacg tgaacgacag ccgtacccg tgggcgaata gaattaccg cctgctgaat  660
cgcacggcaa cgaaccagac cggtaccatt aacaagtcgg tgttggacga gcatccgat  720
ccaaatcaca tgggtggctt cgacttcctg ctggcaaacg atgtggatct gagcaatcct  780
gttgtgcagg ccgagcagct gaatcaaatc cattatctga tgaactgggg cagcattgtt  840
atgggtgaca aagacgcgaa ttttgatggt atccgtgtgg acgccgttga caacgtgaac  900
gctgacatgt tgcagctgta cacgaactac tttcgtgagt attacggcgt caacaaaagc  960
gaagcgcaag cgctggcgca cattagcgtt ctggaagcgt ggagcttgaa cgataaccac  1020
tataacgaca aaaccgatgg tgcggcactg gcgatggaga ataagcaacg tctgccttg  1080
ctgttctctc tggccaagcc gatcaaagat cgtactccgg cagtgagccc actgtataac  1140
aatactttca ataccaccca acgtgactc aagacgcatt ggattaacaa ggacggtagc  1200
accgcctaca atgaggatgg caccgcgaaa caatctacca tcggtaagta caatgagaaa  1260
tatggtgatg caagcggtaa ctatgtcttt attcgtgccc atgacaataa cgtccaagac  1320
attattgcgg agatcattaa gaaagaaatc aataagaaga gcgatggttt taccatcagc  1380
gatagcgaaa tgaaacaggc gttctacaaa tacaacaaag atatgctgag cagcaataag  1440
aaatacactc tgaataacat tccggcagtc tacgccgtga tgctgcaaaa catggagact  1500
atcacccgtg tgtattatgg tgacctgtac accgacgacg gtcactatat ggaaaccaag  1560
agcccgtatc atgacaccat tgtgaacctg atgaaaaacc gtatcaagta cgtttctggt  1620
ggccaggccc aacgctccta ttggctgccg accgacggta aatggacaa tagcgatgtc  1680
gaactgtacc gtactagcga ggtctatacc agcgttcgct acggtaagga cattatgacg  1740
gcggatgaca ccgaggggtag caagtactcc gacgaggttac ccttggtgtt  1800
aacaaccca agctgactct gcatgaaagc gccaaactga acgtcgagat gggtaagatc  1860
cacgcaaacc agaataccg tgcgctgatt gtgggtaccg ccgatggcat caaaaacttt  1920
acgtctgatg ccgaagcgat cgcggcaggc tacgtaaaag aaacggacag caatggtgtt  1980
ctgaccttcg gcgcaaatga tatcaaaggt tacgagactt cgatatgag cggtttcgtc  2040
gcagtttggg tgccggtggg tgcgagcgat gatcaggaca tccgcgtggc gccgtcgacg  2100
```

```
gaagcgaaga aagaaggtga actgacgctg aaagccacgg aagcgtatga tagccagttg  2160
atttatgaag gcttctccaa tttccagacc attccggatg gcagcgaccc gagcgtttat  2220
accaaccgca aaattgctga gaatgttgat ctgtttaagt cctggggtgt cactagcttc  2280
gaaatggctc cgcagtttgt ttcggcggac gacggcacct tcctggatag cgttatccag  2340
aacggttacg cctttgcgga ccgttatgat ttggccgata gcaagaacaa caagtacggt  2400
tctaaagagg atctgcgcga cgcactgaaa gcgctgcaca aagctggcat tcaggcaatc  2460
gcggactggg tcccagacca aatctaccaa ctgccaggca agaagtggt tacggcgacg  2520
cgcacggacg gtgcgggtcg caagatcgcg gacgccatca ttgatcatag cctgtatgtt  2580
gctaactcca gagctccgg tcgcgattac caagcgcagt atggtggcga gtttctggca  2640
gagctgaaag cgaagtaccc gaaaatgttc acggaaaaca tgattagcac gggtaagccg  2700
atcgatgaca gcgtcaaact gaagcaatgg aaagccaagt atttcaatgg tacgaatgtg  2760
ctggaccgtg gtgtcggtta cgtcctgtcc gacgaggcga ccgcaaata cttcaccgtt  2820
accaaagagg gtaacttcat tccgctgcaa ctgaccggca tgaaaagc ggtgaccggt  2880
ttcagcaacg acggcaaggg tatcacctac tttggtacga gcggtaatca ggccaagagc  2940
gcgttcgtca cctttaacgg caatacgtac tatttcgacg cgcgtggcca catggtcacg  3000
aacggcgagt atagcccgaa cggcaaagat gtctaccgtt ttctgccaaa tggtattatg  3060
ttgtcgaacg cgttttatgt cgacgcaaac ggtaatacgt acttgtacaa ctacaagggc  3120
cagatgtaca aagtggtta tacgaaattt gatgtcaccg aaactgataa agatggtaat  3180
gagagcaagg tggtcaagtt tcgttatttc accaatgagg gcgtcatggc taagggtctg  3240
accgtcattg acgtagcac ccagtacttt ggtgaggatg gtttcaaac gaaggacaag  3300
ctggcgacct ataaaggtaa gacttattac ttcgaggcac acacgggcaa tgcgatcaaa  3360
aacacctggc gtaacatcga cggtaagtgg tatcacttcg acgagaatgg cgttgccgcg  3420
accggtgcac aagtgattaa cggtcaaaaa ctgtatttca acgaggatgg ctcgcaagtg  3480
aagggcggtg ttgttaagaa cgccgacggt acctacagca aatacaaaga gggcagcggt  3540
gagctggtta ccaacgagtt tttcacgacc gacggtaatg tgtggtacta tgctggtgcg  3600
gatgcaaga ctgtgaccgg tgctcaggtc attaatgcg agcacctgta ctttaaagaa  3660
gatggcagcc aggtgaaagg tggtgtggtg aaaaacgcgg acggtacgta cagcaagtat  3720
gacgccgcca ccggtgaacg cttgaccaat gagttctta ccacgggcga taacaattgg  3780
tactatattg gttctaatgg taagaccgta accggtgaag tcaaaatcgg tgcggacacc  3840
tattactttg ccaaagatgg caaacaggtc aagggccaaa ccgtcaccgc aggcaatggc  3900
cgcatctcct attactacgg cgattctggt aagaaagcaa tcagcacgtg gatcgaaatt  3960
caaccgggta tctatgtcta ttttgataag acgggcatcg cgtacccacc gcgtgtgctg  4020
aattaa                                                              4026

SEQ ID NO: 30           moltype = AA  length = 1341
FEATURE                 Location/Qualifiers
source                  1..1341
                        mol_type = protein
                        organism = Streptococcus salivarius
SEQUENCE: 30
MTDGKYYYVN EDGSHKENFA ITVNGQLLYF GKDGALTSSS THSFTPGTTN IVDGFSINNR   60
AYDSSEASFE LINGYLTADS WYRPVSIIKD GVTWQASTAE DFRPLLMAWW PNVDTQVNYL  120
NYMSKVFNLE AKYTSTDKQA DLNRAAKDIQ VKIEQKIQAE KSTQWLRETI SAFVKTQPQW  180
NKETENYSKG GGEDHLQGGA LLYVNDSRTP WANSNYRLLN RTATNQTGTI NKSVLDEQSD  240
PNHMGGFDFL LANDVDLSNP VVQAEQLNQI HYLMNWGSIV MGDKDANFDG IRVDAVDNVN  300
ADMLQLYTNY FREYYGVNKS EAQALAHISV LEAWSLNDNH YNDKTDGAAL AMENKQRLAL  360
LFSLAKPIKD RTPAVSPLYN NTFNTTQRDF KTDWINKDGS TAYNEDGTAK QSTIGKYNEK  420
YGDASGNYVF IRAHDNNVQD IIAEIIKKEI NKKSDGFTIS DSEMKQAFEI YNKDMLSSNK  480
KYTLNNIPAA YAVMLQNMET ITRVYYGDLY TDDGHYMETK SPYHDTIVNL MKNRIKYVSG  540
GQAQRSYWLP TDGKMDNSDV ELYRTSEVYT SVRYGKDIMT ADDTEGSKYS RTSGQVTLVV  600
NNPKLTLHES AKLNVEMGKI HANQKYRALI VGTADGIKNF TSDAEAIAAG YVKETDSNGV  660
LTFGANDIKG YETFDMSGFV AVWVPVGASD DQDIRVAPST EAKKEGELTL KATEAYDSQL  720
IYEGFSNFQT IPDGSDPSVY TNRKIAENVD LFKSWGVTSF EMAPQFVSAD DGTFLDSVIQ  780
NGYAFADRYD LAMSKNNKYG SKEDLRDALK ALHKAGIQAI ADWVPDQIYQ LPGKEVVTAT  840
RTDGAGRKIA DAIIDHSLYV ANSKSSGRDY QAQYGGEFLA ELKAKYPKMF TENMISTGKP  900
IDDSVKLKQW KAKYFNGTNV LDRGVGYVLS DEATGKYFTV TKEGNFIPLQ LTGNEKAVTG  960
FSNDGKITY FGTSGNQAKS AFVTFNGNTY YFDARGHMVT NGEYSPNGKD VYRFLPNGIM 1020
LSNAFYVDAN GNTYLYNYKG QMYKGGYTKF DVTETDKDGN ESKVVKFRYF TNEGVMAKGL 1080
TVIDGSTQYF GEDGFQTKDK LATYKGKTYY FEAHTGNAIK NTWRNIDGKW YHFDENGVAA 1140
TGAQVINGQK LYFNEDGSQV KGGVVKNADG TYSKYKEGSG ELVTNEFFTT DGNVWYYAGA 1200
DGKTVTGAQV INGQLYFKE DGSQVKGGVV KNADGTYSKY DAATGERLTN EFFTTGDNNW 1260
YYIGSNGKTV TGEVKIGADT YYFAKDGKQV KGQTVTAGNG RISYYYGDSG KKAISTWIEI 1320
QPGIYVYFDK TGIAYPPRVL N                                           1341

SEQ ID NO: 31           moltype = DNA  length = 3918
FEATURE                 Location/Qualifiers
source                  1..3918
                        mol_type = unassigned DNA
                        organism = Streptococcus salivarius
SEQUENCE: 31
atgatcgacg gcaaacagta ttatgtagag aacggtgtgg ttaagaaaaa tgcggcaatt   60
gaactggatg gccgcctgta ctactttgat gagactggcg caatggtcga tcagagcaaa  120
ccgttgtatc gtgcggacgc gattccgaac aactctatct acgccgtgta caaccaagcg  180
tatgatacca gcagcaaatc cttcgagcat ttggataact tctgaccgc ggatagctga  240
tatcgcccga aacagattct gaaggacggt aaaaactgga ccgcaagcac tgagaaagac  300
tatcgtcctc tgctgatgac ctggtggccg gacaagtga cccaggtgaa ttacctgaac  360
tatatgtctc aacagggttt tggtaacaaa acgtacacca cggatatgat gagctacgac  420
ctggcggctg cggcagaaac ggtgcagcgt ggcatcgaag agcgtatcgg tcgcgaggct  480
aacaccacgt ggctgcgcca gctgatgagc gatttcatca aaacccagcc gggttggaat  540
```

```
agcgagagcg aggacaatct gctggttggt aaggaccatc tgcaaggtgg tgcgctgacc    600
tttctgaaca atagcgcaac gagccacgcg aatagcgact ttcgtctgat gaaccgtacc    660
ccgaccaatc agaccggtac ccgtaaatac cacatcgatc gtagcaatgg cggctatgag    720
ctgctgctgg ctaacgacat tgataatagc aatccggcag ttcaagcaga gcaactgaat    780
tggctgcact acattatgaa tattggcagc atccttggta atgacccgag cgcgaatttt    840
gacggtgttc gtatcgatgc ggtggataat gtggacgcgg atttgctgca aatcgcgtct    900
gattacttca agagaagta ccgtgtcgcg gacaacgagg caaacgcgat tgcccacctg    960
agcattctgg aagcgtggag ctataatgat catcagtaca acaaggacac gaagggcgca   1020
cagctgtcca tcgataaccc gctgcgcgaa accctgctga ctaccttcct gcgtaaaagc   1080
aattatcgtg gtagcttgga gcgcgttatt accaactccc tgaataaccg tctctagcag   1140
caaaagcaca ctccgcgcga cgcgaactac atctttgtac gtgcgcatga cagcgaagtt   1200
caagacgtgc tggcgaatat cattagcaaa cagatcaacc caaagacgga tggcttcacg   1260
ttcaccatgg atgaactgaa gcaggcgttc gagatctaca atgcggatat tgcgaaggcg   1320
gacaagaagt atacccaata caacattccg gcagcttacg caaccatgct ggacaacaag   1380
gatagcatta cccgcgttta ctacggcgac ctgtttacga tgacggtca gtatatggcc   1440
gagaaatccc cgtactataa cgcaattgac gctctgctgc gtgcgcgcat taagtacgtc   1500
gcgggtggtc aggacatgaa ggtgactaaa ctgaatggtt atgagattat gagcagcgtg   1560
cgttatggta aaggtgcaga agaggctaac cagctgagtca cggcagaaac ccgcaatcaa   1620
ggtatgctgg ttctgacggc taaccgtccg gacatgaaac tgggtgcaaa cgatcgcctg   1680
gtcgtgaata tgggcgctgc ccacaaaaac caggcctacc gcccgttgct gttgtccaaa   1740
tctactggcc tggcgacgta tctgaaagat agcgacgttc cggcaggcct ggtgcgttat   1800
accgataacc agggtaatct gacctttacg gcggacgata ttcaggcca tagcacggtt   1860
gaagtgagcg gttacttggc ggtctgggtt ccggtcggcg cgagcgagaa ccaggacgtg   1920
cgcacgaagg ccagctctac caagaagggc gagcaagttt tcgaatctag cgccgctctg   1980
gacagccagg ttatctacga aggtttctcc aatttccaag attttgtcaa gaccccgagc   2040
cagtacacca accgcgtgat cgcgcaaaat gcgaagctgt ttaaagaatg gggcatcact   2100
agctttgagt tcgcgcctca gtatgttct agccaagacg gcacctttt gaatagcatc   2160
attgaaaacg gctacgcgtt cgaggatcgt tacgatatcg caatgagcaa gaacaataag   2220
tatggcagcc tgaaagattt gatggacgca ctgcgtgcgt tgcatgcgga aggcatcagc   2280
gcaatcgccg attgggtccc ggaccaaatc tataatctgc cgggtaaaga agttgtcacg   2340
gcgagccgta ccaacagcta tggtaccccg cgtccgaatg cggaaatcta caatagcctg   2400
tacgctgcta aaacgcgcac gttcggtaat gacttccagg taagtatgg tggcgcattt   2460
ctggacgaac tgaaagcaaa gtaccggcc atctttgagc gtgttcaaat cagcaacggt   2520
cgtaaattga ccacgaatga aagattacc agtggagcg ccaaatactt taatggtagc   2580
aatattcagg gcacgggtgc gcgttacgtt ttgcaggaca acgctaccaa tcagtacttt   2640
agcgttaagg cgggtcagac tttcctgccg aagcagatga ccgaaattac cggcagcggt   2700
ttccgtcgtg tcggtgacga tgtccaatat ctgagcattg tggttatct ggcgaagaat   2760
accttttatcc aggtcggtgc gaatcagtgg tattattttg acaaaaacgg caatatggtt   2820
acgggtgaac aggtgatcga tggtaaaaag tacttcttct tggataacgg tctgcaactg   2880
cgtcatgttc tgcgccaggg ctccgatggt cacgtctatt actatgaccc taaaggtgtg   2940
caagcgttca atggtttcta cgactttgca ggccctcgcc aagacgttcg ttacttcgat   3000
ggcaatggtc agatgtatcg cggcctgcac gatatgtacg gtacgacctt ttacttcgac   3060
gagaaaaccg gcatccaagc aaaagacaag ttcattcgct tcgcagacgg tcgtacccgt   3120
tacttcattc cggacaccgg taatctggca gtgaatcgtt tcgcccaaaa cccggagaac   3180
aaagcctggt attacctgga tagcaacggt tacgctgtca ccggcttgca gacgattaat   3240
ggcaagcagt tactttga caacgaaggc cgtcaggtta aggccactt tgtgaccatt   3300
aacaaccagc gttacttct ggatggtgac tcgggcgaa tcgcgccatc gcgttttcgtt   3360
accgagaaca acaagtggta ctacgtcgac ggtaatggta agctggtcaa gggtgcacag   3420
gtgattaacg gtaaccacta ctacttcaat aacgactata gccaggtgaa gggtgcatgg   3480
gcgaacggtc gttactacga tggcgacagc ggtcaagcgg tcagcaacca gtttattcaa   3540
attgcggcga accaatgggc atatctgaat caagatgcc acaaggtcac gggtctgcaa   3600
aacatcaaca ataaagtgta ctattttggc tctaatggcg cgcaagttaa gggtaaactg   3660
ctgaccgtgc aaggcaagaa atgctacttt gacgcccaca ccggtgagca agtcgttaat   3720
cgcttcgtgg aagctgcccg tggttgctgg tactatttca attccgctgg ccaggccgtt   3780
accggccaac aagtcatcaa cggtaagcag ttgtattttg atggttctgg tcgtcaagtc   3840
aaaggccgtt atgtgtacgt gggtggtaaa cgtttgttcct gtgatgcgaa aacggcgag   3900
ctgcgtcaac gccgttaa                                                 3918
```

```
SEQ ID NO: 32         moltype = AA   length = 1305
FEATURE               Location/Qualifiers
source                1..1305
                      mol_type = protein
                      organism = Streptococcus salivarius
SEQUENCE: 32
MIDGKQYYVE NGVVKKNAAI ELDGRLYYFD ETGAMVDQSK PLYRADAIPN NSIYAVYNQA     60
YDTSSKSFEH LDNFLTADSW YRPKQILKDG KNWTASTEKD YRPLLMTWWP DKVTQVNYLN    120
YMSQQGFGNK TYTTDMMSYD LAAAAETVQR GIEERIGREG NTTWLRQLMS DFIKTQPGWN    180
SESEDNLLVG KDHLQGGALT FLNNSATSHA NSDFRLMNRT PTNQTGTRKY HIDRSNGGYE    240
LLLANDIDNS NPAVQAEQLN WLHYIMNIGS ILGNDPSANF DGVRIDAVDN VDADLLQIAS    300
DYFKEKYRVA DNEANAIAHL SILEAWSYND HQYNKDTKGA QLSIDNPLRE TLLTTFLRKS    360
NYRGSLERVI TNSLNNRSSE QKHTPRDANY IFVRAHDSEV QDVLANIISK QINPKTDGFT    420
FTMDELKQAF EIYNADIAKA DKKYTQYNIP AAYATMLTNK DSITRVYYGD LFTDDGQYMA    480
EKSPYYNAID ALLRARIKYV AGGQDMKVTK LNGYEIMSSV RYKGAEEAN QLGTAETRNQ    540
GMLVLTANRP DMKLGANDRL VVNMGAAHKN QAYRPLLLSK STGLATYLKD SDVPAGLVRY    600
TDNQGNLTFT ADDIAGHSTV EVSGYLAVWV PVGASENQDA RTKASSTKKG EQVFESSAAL    660
DSQVIYEGFS NFQDFVKTPS QYTNRVIAQN AKLFKEWGIT SFEFAPQYVS SQDGTFLDSI    720
IENGYAFEDR YDIAMSKNNK YGSLKDLMDA LRALHAEGIS AIADWVPDQI YNLPGKEVVT    780
ASRTNSYGTP RPNAEIYNSL YAAKTRTFGN DFQGKYGGAF LDELKAKYPA IFERVQISNG    840
RKLTTNEKIT QWSAKYFNGS NIQGTGARYV LQDNATNQYF SVKAGQTFLP KQMTEITGSG    900
```

```
FRRVGDDVQY LSIGGYLAKN TFIQVGANQW YYFDKNGNMV TGEQVIDGKK YFFLDNGLQL   960
RHVLRQGSDG HVYYYDPKGV QAFNGFYDFA GPRQDVRYFD GNGQMYRGLH DMYGTTFYFD  1020
EKTGIQAKDK FIRFADGRTR YFIPDTGNLA VNRFAQNPEN KAWYYLDSNG YAVTGLQTIN  1080
GKQYYFDNEG RQVKGHFVTI NNQRYFLDGD SGEIAPSRFV TENNKWYYVD GNGKLVKGAQ  1140
VINGNHYYFN NDYSQVKGAW ANGRYYDGDS GQAVSNQFIQ IAANQWAYLN QDGHKVTGLQ  1200
NINNKVYYFG SNGAQVKGKL LTVQGKKCYF DAHTGEQVVN RFVEAARGCW YYFNSAGQAV  1260
TGQQVINGKQ LYFDGSGRQV KGRYVYVGGK RLFCDAKTGE LRQRR               1305

SEQ ID NO: 33           moltype = DNA   length = 4026
FEATURE                 Location/Qualifiers
source                  1..4026
                        mol_type = unassigned DNA
                        organism = Streptococcus salivarius
SEQUENCE: 33
atgatcgacg gcaaatacta ctatgtaaac gaggacggca gccacaaaga gaatttcgcg    60
attacggtaa acggtcagct gctgtacttt ggtaaggacg gtgctctgac gagcagctcc   120
acgtacagct ttaccccggg tacgaccaat attgtcgatg gcttcagcat aacaaccgt   180
gcgtatgaca gcagcgaggc atcctttgag ctgatcgatg gttatttgac cgcggatagc   240
tggtatcgtc cggcgagcat cattaaggac ggcgttacgg gcaggcctc gaccgcagaa   300
gattttcgtc cgctgctgat ggcttggtgg ccgaatgttg acacccaggt gaattatctg   360
aattacatgt ccaaggtttt caacctggat gcaaagtaca ccagcaccga caagcaggaa   420
accctgaacg tggctgcgaa agatatccaa gtcaagattg agcaaaagat tcaggcagag   480
aaatctaccc agtggctgcg tgaaacgatt agccgcgtttg ttaaaactca gccgcaatgg   540
aataaagaaa cggaaaacta ttccaagggt ggtggcgagg accatctgca aggcggtgcc   600
ctgttgtacg ttaacgattc gcgcaccccg tgggcgaact cgaactatcg cttgctgaac   660
catacgccta ccaatcaaaa aggcactatt gacaaatgct tcctgacgca gcagagcgac   720
ccgaaccaca tgggcggttt cgattttctg ctgcgcaacg acgtcgacct gagcaacccg   780
gtggtgcagg ccgaacaact gaccagatt cactacctga tgaattgggg tagcatcgtg   840
atgggtgata aagatgcgaa cttttgacgg cattcgtgtcg atgcggtcga taacgtggac   900
gccgacatgt tgcagctgta cacgaactac tttcgtgagt actacggcgt taacaagagc   960
gaagcaaatg ccctggcgca tatcagcgtt ctggaagcgt ggagcctgaa tgacaatcac  1020
tataacgata gacgacggg tgcggccctg gcaatggaga ataaacaacg tctggcgctg  1080
ctgttcagcc tggcgaaacc gatcaaagag cgtacgccgg ctgtgagccc actgtataac  1140
aacaccttca atactacgca gcgtgtcgag aaaacgactt ggattaacaa agacggtagc  1200
aaagcgtata acgaggatgg taccgtcaag caatcgacca ttggtaagta caatgagaag  1260
tatggcgacg caagcggtaa ttacgtgttc attcgtgccc acgacaacaa tgttcaagac  1320
atcatcgccg aaatcatcaa gaaagagatc aaccctaaga gcgacggttt caccatcacc  1380
gacgcagaga tgaagaaggc ctttgaaatc tacaacaagg acatgttgag cagcgataag  1440
aagtatactc tgaacaacat tccggctgcg tacgcggtga tgttgcagaa tatggaaacc  1500
atcacgcgtg tttactatgg tgatctgtat accgataatg cgaactacat ggaaacgaaa  1560
agcccgtact atgacaccat tgttaatctg atgaagaatc gcatcaagta tgtgtctggc  1620
ggtcaagcgc agcgttctta ctggctgccg accgatggta gatgggacaa tagcgatgtg  1680
gaactgtacc gcaccaacga ggtatacgct tctgtgcgct atggtaaaga cattatgacc  1740
gccgatgata ccgagggttc caagtactcc cgtacgagcg ccaagttac cttggtggca  1800
aacaacccga aattgaccct ggaccaaagc gcgaaactga agtggagat gggtaagatc  1860
cacgcaaatc aaaagtaccg tgcactgatt gtcggtaccg ccgacggtat caagaatttc  1920
accgccgtga cggatgcgat tgcagcaggc tatgttaaag agactgatga caatggtgtg  1980
ctgacgtttg gtgcgaacga cattaaaggc tatgaaacgt ttgacatgag cggtttcgtt  2040
gcggtgtggg tgcctgtggg tgctagcgat gatcaggata tccgtgtcgc gccgagcacc  2100
gaggcaaaga aagaaggtga gctgacgttg aaagcgaccg aggcctatga cagccagttg  2160
atttgcagaa gtttcagcaa tttccaaacc atttcagacg gttccgatcc gagcgtctac  2220
accaatcgca aaatcgcgga aaacgttgat ctgttcaaaa gctggggtgt gaccagcttc  2280
gaaatggcac cgcaattcgt tagcgcggac gatggtacgt tcttgacag cgttatccaa  2340
aatggctatg cgttcgccga tcgttatgac ttggcgatga gcaaaacaa caaatacggc  2400
agcaaagagg atctcgcgga cgccctgaaa gcgctgcata aagcgggtat tcaagccatc  2460
gctgactggg ttccggacca gatctaccag ctgccgggta agaaggtcgt taccgcgacc  2520
cgcaccgatg cgctggccg taagatcgcg gatgcaatta tcgatcatag cttgtatgtg  2580
gccaatacta aaagctccgg taaggattac caggcgaaat atggtggtga atttctggct  2640
gagctgaagg ccaaatacc ggagatgttc aaggtcaaca tgattagcac cggcaaacct  2700
attgatgact ctgtcaaatt gaaacaatgg aaggcagagt atttcaatgg cactaacgtc  2760
ctggaacgtg tgtgttggtta cgtgctgagc gacgaggcga ccgtaaata cttcaccgtt  2820
acgaaggacg gcaatttcat cccgctgcaa ctgaccggta tgagaaggt tgtgacgggt  2880
ttttctaatg acggtaaggg cattacctac ttcggtacct cgggtaccca ggcaaagagc  2940
gcattcgtga cgtttaacgg taacacctac tactttggtc acgcggcca catggcagtc  3000
aacggcgagt acagcccgaa cggcaaggat gtttatcgct tcctgccgaa tggcatcatg  3060
ctgtccaatg cgtttacgt cgatgcaaat ggtaatactt acctgtacaa cagcaagggt  3120
cagatgtata agggcggtta taccaagttc gacgttactg aaacggacaa ggacggtaaa  3180
gagagcaaag tagtgaagtt tcgttatttc acgaacgaag gcgtcatggc gaaaggtgtc  3240
accgttattg atggctttac ccagtatttc ggtgaagatg gctttcaagc gaggacaag  3300
ctggtgaccct taagggcaa aacctactat tttgacgcgc acacgggcaa cgccatcaag  3360
aacacctggc gtaatatcga cggtaagtgg tatcattttg atgcgaacgg tgtggcggcg  3420
accggcgcac aggtcattaa tggtcaaaaa ctgtacttta tgaggacgg tagccaagtc  3480
aaaggtggcg tcgtcaagaa tgcagatggc acctatagca aatacaaaga gggctccggt  3540
gagctggtta acaacgtt cttttaccacg gatgtgacta tgctggtgcg  3600
aatggcaaga ccgttaccgg tgcacaggtt atcaacggcc agcacctgta cttcaatggc  3660
gatggctctc aagtgaaggg cggtgtcgtc aaaaacgcgg acggtacgta ctccaaatac  3720
gatgccgcga ccggtgaacg tctgaccaat gagttttca cgactggtga caacaattgg  3780
tactacatcg gcgccaacgg taagacggtt acgggcgaag tgaaaattgg cgacgatacg  3840
tactacttcg caaaagatgg taaacaggtg aaaggtcaga cggtttccgc tggtaatggc  3900
```

```
cgcatcagct actattacgg tgactctggt aaacgtgcgg ttagcacgtg ggttgaaatt   3960
caaccgggcg tgtatgtcta ttttgataag aatggcctgg catatccacc gcgcgttttg   4020
aattaa                                                               4026

SEQ ID NO: 34           moltype = AA   length = 1341
FEATURE                 Location/Qualifiers
source                  1..1341
                        mol_type = protein
                        organism = Streptococcus salivarius
SEQUENCE: 34
MIDGKYYYVN EDGSHKENFA ITVNGQLLYF GKDGALTSSS TYSFTPGTTN IVDGFSINNR    60
AYDSSEASFE LIDGYLTADS WYRPASIIKD GVTWQASTAE DFRPLLMAWW PNVDTQVNYL   120
NYMSKVFNLD AKYTSTDKQE TLNVAAKDIQ VKIEQKIQAE KSTQWLRETI SAFVKTQPQW   180
NKETENYSKG GGEDHLQGGA LLYVNDSRTP WANSNYRLLN HTATNQKGTI DKSVLDEQSD   240
PNHMGGFDFL LANDVDLSNP VVQAEQLNQI HYLMNWGSIV MGDKDANFDG IRVDAVDNVD   300
ADMLQLYTNY FREYYGVNKS EANALAHISV LEAWSLNDNH YNDKTDGAAL AMENKQRLAL   360
LFSLAKPIKE RTPAVSPLYN NTFNTTQRDE KTDWINKDGS KAYNEDGTVK QSTIGKYNEK   420
YGDASGNYVF IRAHDNNVQD IIAEIIKKEI NPKSDGFTIT DAEMKKAFEI YNKDMLSSDK   480
KYTLNNIPAA YAVMLQNMET ITRVYYGDLY TDNGNYMETK SPYYDTIVNL MKNRIKYVSG   540
GQAQRSYWLP TDGKMDNSDV ELYRTNEVYA SVRYGKDIMT ADDTEGSKYS RTSGQVTLVA   600
NNPKLTLDQS AKLKVEMGKI HANQKYRALI VGTADGIKNF TSDADAIAAG YVKETDSNGV   660
LTFGANDIKG YETFDMSGFV AVWVPVGASD DQDIRVAPST EAKKEGELTL KATEAYDSQL   720
IYEGFSNFQT IPDGSDPSVY TNRKIAENVD LFKSWGVTSF EMAPQFVSAD DGTFLDSVIQ   780
NGYAFADRYD LAMSKNNKYG SKEDLRDALK ALHKAGIQAI ADWVPDQIYQ LPGKEVVTAT   840
RTDGAGRKIA DAIIDHSLYV ANTKSSGKDY QAKYGGEFLA ELKAKYPEMF KVNMISTGKP   900
IDDSVKLKQW KAEYFNGTNV LERGVGYVLS DEATGKYFTV TDGNFIPLQ LTGNEKVVTG   960
FSNDGKGITY FGTSGTQAKS AFVTFNGNTY YFDARGHMVT NGEYSPNGKD VYRFLPNGIM  1020
LSNAFYVDAN GNTYLYNSKG QMYKGGYTKF DVTETDKDGK ESKVVKFRYF TNEGVMAKGV  1080
TVIDGFTQYF GEDGFQAKDK LVTFKGKTYY FDAHTGNAIK NTWRNIDGKW YHFDANGVAA  1140
TGAQVINGQK LYFNEDGSQV KGGVVKNADG TYSKYKEGSG ELVTNEFFTT DGNVWYYAGA  1200
NGKTVTGAQV INGQHLYFNA DGSQVKGGVV KNADGTYSKY DAATGERLTN EFFTTGDNNW  1260
YYIGANGKTV TGEVKIGDDT YYFAKDGKQV KGQTVSAGNG RISYYYGDSG KRAVSTWVEI  1320
QPGVYVYFDK NGLAYPPRVL N                                            1341

SEQ ID NO: 35           moltype = DNA   length = 3996
FEATURE                 Location/Qualifiers
source                  1..3996
                        mol_type = unassigned DNA
                        organism = Streptococcus salivarius
SEQUENCE: 35
atggtcgacg gcaaatacta ctacgtgaaa gaggatggca gctacaaaac gaacttcgca    60
gtttccgtca acgccaact gctgtatttc ggcaaggatg gcgcgctgac gtccaccagc   120
acccatagct ttacgccagg cactaccaat ctggttgatg cgttcagctc ccataaccgc   180
gcctacgact ccaaaaagga gagcttcgaa ctggtcgatg ttatctgac gccgaactct   240
tggtatcgtc cggtcactat cctggaaaat ggtgaaaaat ggcgtgttag caccgagaag   300
gactttcgcc cgttgttgat ggcctggtgg ccggatgtcg acacgcaagt tgcctatctg   360
aacaccttt ctaaacactt caacctgaac gcgacgtact ctacttctca gagccaaagc   420
gagctgaatg cggcagctaa aaccatccaa atcaaaatcg aacaggagat tagcgcgaaa   480
aagagcacgg agtggctgcg ccaggcaatt gagtcctttg tcaaggagca ggatcagtgg   540
aacaccacga ccgagaacta caccctggcg gatcatttgc agggcggtgc gctgctgtat   600
gtgaacaatg acaagacgcc gtgggcgaac agcgactgtc gtctgctgaa ccgtactccg   660
agcaaccagg acggcagcct gaacggtact ggccgttatc tgggtggtta cgagtttctg   720
ctggcgaatg acgtggacaa tagcaatccg tgtgtccagg ctgagcagct gaatcaaatt   780
cactatctgt caactgggg cagcattgtc atgggtgaca aggacgcgaa tttcgacggc   840
attcgtgttg acgccgttga caatgtggac gccgatctgt tgcaggttta cacgaactac   900
ttccgtgcgg cgtttggtgt ggataaaagc gaagcgaacg cactggccca catcagcatt   960
ctggaggcgt gggatctgaa cgacaatgcg tacaaccaga acatgacgg tgcggccttg  1020
gcaatggata caacctgcg ttacgcgatc atgggtgcac tgtatggtag cggtagctcg  1080
ctgaaagatc tgattaccag cagcctgacc gaccgtacga ataactccaa atatggtgat  1140
acccaagcaa actacatctt cgcccgtgct catgataatc tggtccagga cattattcgt  1200
gacatcgtgc agaaagagat caatccgaag agcgacggct acacgatgac cgatgcggag  1260
ctgaagcgtg cgtttgaaat ctacaacgag atatgaaaa aggccgaaaa acgctacact  1320
atcaacaaca tcccggcagc gtatgcactg attttgcaga acatgaaca ggttactcgt  1380
gtgtactacg gtgatctgta taccgacaat ggtcagtaca tggcgaccaa aagccgtac  1440
tacgacgcga ttacgaccct gctgaaaaat cgtatgaagt atgtgagcgg cggtcagagc  1500
atgaaagttg acactttcaa cggtaaagaa atttctgtcg ctgttcgtta cggtaaggac  1560
atcatgaccg cggaccaaac gaccggtgtc gcagaaacca gcaagcacag cggcatgctg  1620
accctgatcg ccaataacca ggatttttct ctgggcgatg gcaccttgaa agtgaacatg  1680
ggcaagctgc acgcgaacca tcgtatcgc ccgctgctgc tgggcacgga taagggcatt  1740
gttacctatg aaaatgacgc ggctgcggca ggcaaaatca agtacacgga cgcagagggt  1800
aatctgacct tcagcggtga cgagatcaag ggctatcgca ccgtggacat gcgcggctac  1860
ctgggtgtgt gggtcccggt cggcgcaccg gacaatcaag acattcgcgt taagggtagc  1920
gataagaaac tggacaagac tttcagcgca accgaagctc tggatagcca ggtgatttac  1980
gaaggtttta caacttca ggacttcgtg gaaaaagaca cggtacac caacaagctg  2040
attgcggaaa acgcggaact gtttaagagc tgggtatta ctagctttga aatggccct  2100
cagtttgtca gcgcagacga tcgtaccttc tggatagcg ttatccaaaa cggttatgcg  2160
tttaccgatc gttacgatct ggccatgtct aagaataaca agtatggcag caaagaagat  2220
ctgcgtgatg cgctgaaggc gctgcacaag cagggcattc aagcaattgc cgactgggtt  2280
ccggatcaac tgtaccaact gccgggtcaa gaggttgtca ccgctacccg tgcaaatagc  2340
```

```
tacggcaccc cgaaggccaa tgcctacatt aacaatacgc tgtatgttgc caatagcaag  2400
agcagcggta aagacttcca ggctcaatac ggtggcgagt tcctggatga attgcagaag  2460
aagtacccgc agttgttcga ggatgtgatg atcagcacgg gtaaaaagat tgacccgagc  2520
gtgaaaatca agcagtggag cgccaaatac atgaatggca ccaacattct gggtcgtggc  2580
aaccgttacg ttctgtcgaa tgacgccacc ggtcgctatt atcaagtgac cgacaacggt  2640
attttcttgc cgaagccgct gacggatcag ggtggtaaga ccggcttcta ttacgatggt  2700
aagggcatgg cctatttcga caattccggc tttcaagcga aaaatgcgtt catcaagtac  2760
gcgggtaact actactactt cgataaagag ggctatatgc tgacgggccg tcaagatatt  2820
gacagcaaga cgtatttctt tctgccgaat ggtatccaac tgcgtgatag catttaccaa  2880
caagatggca agtactacta ttttggtagc ttcggcgaac aatacaaaga cggttatttc  2940
gtctttgacg tgccaaaaga gggcaccagc gaaaccgagg ctaagttccg ctactttttct  3000
ccgacgggtg agatggcagt gggttttgacc tatgcgggtg gtggtctgca atactttgat  3060
gagaacggtt ccaggcgaaa gggtacgaag tatgttacgc cggatggtaa gttgtatttc  3120
ttcgacaaga atagcggcaa cgcgtacacc aatcgttacga gatcga tggtatttgg  3180
tacgagttta atgaccaagg ttacgcgcag gcgaagaaag gtgagtttta caccacggat  3240
ggtagcacgt ggttttaccg cgacgcagca ggtaaaaacg ttaccggtgc cctgaccctg  3300
gacggtcacg agtattactt tcgtgcgaac ggtgcgcagg tgaaaggcga gttcgtcacc  3360
gaaaacggta agattagcta ttacaccgtt gataacggtt acaaggtaaa agacaagttc  3420
ttcgaagtca atggtaagtg gtatcacgct gataaggacg gtaatttggc gacgggtcgt  3480
cagaccatcg accatctgaa ttactactte aacgcggacg gctcccaggt taagtccgat  3540
ttcttcactc tggatggtgg taaaacctgg tattatgcca aagacaacgg tgagattgtg  3600
accggtgcgt actcggtgcg tggcaagaac tattacttca agacgggaca tagccaagtt  3660
aagggcgatt tcgtcaaaaa tgcggacggt tccctgagct attatgacaa ggatagcggc  3720
gaacgtctga caaccgtttc cttgaccacg gtaacaatg tctggtatta ctttaaggat  3780
ggtaaagcgg tcacgggtcg ccagaacatc gacggtaagg agtactactt tgatcacctg  3840
ggtcgtcaag tcaaaggctc ccgattagc actccgaagg gcgttgagta ttatgagtct  3900
gtgctgggtg agcgtgtcac caacacctcc aagacggcaa aaccgtgttc  3960
tttgatgaaa atggctacgc ggactttgat aagtaa  3996
```

SEQ ID NO: 36          moltype = AA  length = 1331  
FEATURE                Location/Qualifiers  
source                 1..1331  
                       mol_type = protein  
                       organism = Streptococcus salivarius  
SEQUENCE: 36
```
MVDGKYYYVK EDGSYKTNFA VSVNGQLLYF GKDGALTSTS THSFTPGTTN LVDAFSSHNR   60
AYDSKKESFE LVDGYLTPNS WYRPVTILEN GEKWRVSTEK DFRPLLMAWW PDVDTQVAYL  120
NTFSKHFNLN ATYSTSQSQS ELNAAAKTIQ IKIEQEISAK KSTEWLRQAI ESFVKEQDQW  180
NTTTENYTLA DHLQGGALLY VNNDKTPWAN SDYRLLNRTP SNQDSLNGT GRYLGGYEFL   240
LANDVDNSNP VVQAEQLNQI HYLVNWGSIV MGDKDANFDG IRVDAVDNVD ADLLQVYTNY  300
FRAAFGVDKS EANALAHISI LEAWDLNDNA YNQKHDGAAL AMDNNLRYAI MGALYGSGSS  360
LKDLITSSLT DRTNNSKYGD TQANYIFARA HDNLVQDIIR DIVQKEINPK SDGYTMTDAE  420
LKRAFEIYNE DMKKAEKRYT INNIPAAYAL ILQNMEQVTR VYYGDLYTDN GQYMATKSPY  480
YDAITTLLKN RMKYVSGGQS MKVDTFNGKE ILSSVRYGKD IMTADQTTGV AETSKHSGML  540
TLIANNQDFS LGDGTLKVNM GKLHANQAYR PLLLGTDKGI VTYENDAAAA GKIKYTDAEG  600
NLTFSGDEIK GYRTVDMRGY LGVWVPVGAP DNQDIRVKGS DKKLDKTFSA TEALDSQVIY  660
EGFSNFQDFV EKDSQYTNKL IAENAELFKS WGITSFEMAP QFVSADDRTF LDSVIQNGYA  720
FTDRYDLAMS KNNKYGSKED LRDALKALHK QGIQIAIADWV PDQLYQLPGQ EVVTATRANS  780
YGTPKANAYI NNTLYVANSK SSGKDFQAQY GGEFLDELQK KYPQLFEDVM ISTGKKIDPS  840
VKIKQWSAKY MNGTNILGRG NRYVLSNDAT GRYYQVTDNG IFLPKPLTDQ GGKTGFYYDG  900
KGMAYFDNSG FQAKNAFIKY AGNYYYFDKE GYMLTGRQDI DSKTYFFLPN GIQLRDSIYQ  960
QDGKYYYFGS FGEQYKDGYF VFDVPKEGTS ETEAKFRYFS PTGEMAVGLT YAGGGLQYFD 1020
ENGFQAKGTK YVTPDGKLYF FDKNSGNAYT NRWAEIDGIW YEFNDQGYAQ AKKGEFYTTD 1080
GSTWFYRDAA GKNVTGALTL DGHEYYFRAN GAQVKGEFVT ENGKISYYTV DNGYKVKDKF 1140
FEVNGKWYHA DKDGNLATGR QTIDHLNYYF NADGSQVKGD FFTLDGGKTW YYAKDNGEIV 1200
TGAYSVRGKN YYFKEDGSQV KGDFVKNADG SLSYYDKDSG ERLNNRFLTT GNNVWYYFKD 1260
GKAVTGRQNI DGKEYYFDHL GRQVKGSPIS TPKGVEYYES VLGERVTNTW ITFQDGKTVF 1320
FDENGYADFD K                                                     1331
```

SEQ ID NO: 37          moltype = DNA  length = 3918  
FEATURE                Location/Qualifiers  
source                 1..3918  
                       mol_type = unassigned DNA  
                       organism = Streptococcus salivarius  
SEQUENCE: 37
```
atgattgacg gcaaacagta ttatgtagag aacggtgtgg ttaagaagaa tacggcgatt   60
gaactggatg gccgtctgta ttactttgac gaaaccggtg caatggttga tcaatctaag  120
ccgctgtatc gcgcggatgc aatcccgaac aactctatct acgcagttta caaccaggct  180
tacgacacca gcagcaagag ctttgaacac ctggacaact ttctgacggc cgatagctgg  240
taccgtccga agcagatttt gaaagacggc aagaattcaa ccgcctcgac ggagaaggac  300
tatcgtcctt tgctgatgac gtggtggccg gataaagtca cgcaagtcaa ctacctgaac  360
tatatgtccc aacagggctt tggtaacaag acctacacca cggatatgat gagctacgac  420
ctggcggcag cggcggaaac ggttcagcgt ggcatcgaag agcgtattgg tcgtgagggt  480
aatacgacgt ggctgcgtca gttgatgagc gacttcatca aacccagcc gggctgagat  540
agcgagagcg aagataatct gctggtcggt aaggatcatc tgcaaggtgg tgcactgacg  600
tttctgaaca atagcaccac gagccatgcg aacagcgatt tccgcctgat gaatcgtacc  660
ccgacgaacc agaccggcac ccgcaaatac acatcgatc gtagcaatgg tggctacgaa  720
ctgctgctgg cgaacgacat cgacaatagc aatccggccg tccaagcgga acagctgaac  780
tggctgcatt acatcatgaa catcggctct atccctgggca atgacccaag cgcgaatttt  840
```

```
gatggcgtcc gtatcgatgc agttgacaat gtggatgcgg acttgttgca aattgcgtct   900
gactacttta aggaaaagta ccgtgttgcc gataacgagg caaacgctat tgcgcacctg   960
tcgattctgg aggcatggtc ctacaatgat catcaataca acaaagacac gaagggcgct  1020
caactgagca ttgataatcc gctgcgtgag actttgctga cgaccttcct gcgcaagtct  1080
aactaccgtg gttccctgga gcgtgtgatc accaactcgt tgaacaaccg tagcagcgaa  1140
cagaagcaca cgccgcgtga cgccaactac attttgtgc gtgctcacga cagcgaagtt   1200
caagcggtgc tggcaaacat catctctaaa cagatcaacc cgaaaccgac cggttttacc  1260
tttacgatgg atgagctgaa gcaggcgttt gagatttaca acgcagacat gcgtaaggcg  1320
gataagaagt acacgcagta caacattccg gcagcttacg ccaccatgct gaccaataag  1380
gatagcatca cccgtgtgta ctatggtgat ttgtttaccg acgacggtca atacatggcg  1440
gagaaaagcc cgtactataa cgcaattgac gccctgctgc gtgctcgcat caaatacgtc  1500
gcgggtggtc aggacatgaa ggtgaccaaa ttgaacggct atgagatcat gtcctccgtt  1560
cgctacggta aggcgcaga ggaagctaat cagctgggca ccgcagaaac ccgcaatcaa   1620
ggcatgctgg tcctgaccgc gaatcgccca gacatgaagc tgggtacgaa tgatcgcctg  1680
gtcgtcaata tgggtgcagc ccacaagaat caggcgtatc gtccgctgct gctgtccaag  1740
tccaccggct tggcaaccta cctgaaagac agcgacgtcc ctgcgggcct ggtgcgttac  1800
acggacaatc aaggtaatct gaccttcacg gcggacgaca tcaccggcca tagcaccgta  1860
gaggtgagcg gttacctggc ggttttggtg ccggtgggtg cgagcgagaa ccaagatgca  1920
cgcacgaaag cgagcacgac gaaaagggc gaacaagttt ttgaaagctc cgcagcgctg  1980
gatagccagg tcatctatga gggtttctcc aacttccagg attttgttaa ccccccttcc  2040
cagtacacga atcgcgttat cgcacagaac gcgaagcgct taaggagtg gggtatcacc  2100
agctttgagt tcgcgcctca atatgttagc agccaagacg gtaccttttct ggatagcatt  2160
attgagaacg gctacgcgtt cgaggaccgt tacgatatcg cgatgagcaa aaacaacaag  2220
tacggcagcc tgaaggatct gatggacgcg ctgcgtgcac tgcacgcgga gggtatcagc  2280
gccattgctg actgggttcc ggaccaaatc tataacctgc cgggtaagga agttgtaacc  2340
gcaagccgca cgaatagcta cggtacgccg cgtccgaacg cgaaatcta taacagcctg  2400
tatgcggcga aaacgcgtac gtttggcaat gattttcagg gtaaatacgg tggcgcgttt  2460
ctggatgaac tgaaagcaaa gtaccggcg atcttcgagc gtgtgcaaat ttcgaatggt  2520
cgtaagctga ctaccaatga gaaaatcacg caatggagcg cgaagtactt taatggcagc  2580
aacattcaag gtaccggtgc gcgttacgtt ctgcaagata atgccacgaa ccagtatttc  2640
aacctgaagg ccggtcaaac ctttctgcca aagcagatga ccgagattac cgcaacgggc  2700
ttccgtcgtg tcggtgacaa agtgcaatac ctgtccacgt ccggctacct ggcgaagaat  2760
acctttatcc agattggtgc gaaccagtgg tattacttcg acaagaatgg caacatggtg  2820
accggtgagc aagtgattga tggtaaaaag tatttcttcc tggataacgg tctgcaactg  2880
cgtcatgtct tgcgtcaagg ttctgacggt cacgtgtatt actacgatcc gaaaggcgtc  2940
caggcgttta atggtttcta tgactttgcg ggtccgcgcc aagatgtccg ttatttcgac  3000
ggtaatggtc agatgtaccg tggtctgcat gatatgtatg gtaccacgtt ctactttgat  3060
gaaaagacg gtatccaggc taaggataag tttatccgtt tcgccgacgg ccgtacccgt  3120
tactttattc cggacaccgg caatttggct gtgaatcgct tcgctcagaa tccggaaaac  3180
aaggcgtggt actacctgga cagcaacggt tatgcagtca cgggtttgca gaccattaat  3240
ggcaaacaat actatttcga caacgagggc cgtcaggtca aggccacttt cgttactatc  3300
aacaatcagc gctacttctt ggacggtgac tcgggtgaga tcgcacgtag ccgcttcgtg  3360
acggagaaca acaaatggta ctatgtggat ggtaaaggta aattggtcaa gggtgcacaa  3420
gtcatcaacg gtaaccacta ttacttcaat aatgattatt ctcaggtgaa aggtgcttgg  3480
gccaatggcc gctactacga cggcgatagc ggccaggcgg tcacgaatcg tttcgtgcag  3540
gtcggtgcaa accagtgggc ctatctgaat cagaacggtc agaaggttgt gggcttgcaa  3600
cacatcaatg gcaagcgta cactttgaa ggcaaggtg tccaagcaaa aggcaagctg   3660
ctgacctata agggtaagaa atactacttc gatgctaaca gcggtgaggc agtcaccaac  3720
cgctttattc aaatctctcg cggtgtttgg tactatttca atgcgagcgg tcaagcagtg  3780
accggcgagc aagttatcaa tggtcaacac ctgtacttcg acgcaagcgg tcgccaggtt  3840
aaaggccgct atgtctggat taaggccag cgccgttatt acgacgcgaa cactggtgcc  3900
tgggtacgta atcgttaa                                                3918
```

SEQ ID NO: 38           moltype = AA   length = 1305
FEATURE                 Location/Qualifiers
source                  1..1305
                        mol_type = protein
                        organism = Streptococcus salivarius
SEQUENCE: 38
MIDGKQYYVE NGVVKKNTAI ELDGRLYYFD ETGAMVDQSK PLYRADAIPN NSIYAVYNQA    60
YDTSSKSFEH LDNFLTADSW YRPKQILKDG KNWTASTEKD YRPLLMTWWP DKVTQVNYLN   120
YMSQQGFGNK TYTTDMMSYD LAAAAETVQR GIEERIGREG NTTWLRQLMS DFIKTQPGWN   180
SESEDNLLVG KDHLQGGALT FLNNSTTSHA NSDFRLMNRT PTNQTGTRKY HIDRSNGGYE   240
LLLANDIDNS NPAVQAEQLN WLHYIMNIGS ILGNDPSANF DGVRIDAVDN VDADLLQIAS   300
DYFKEKYRVA DNEANAIAHL SILEAWSYND HQYNKDTKGA QLSIDNPLRE TLLTTFLRKS   360
NYRGSLERVI TNSLNNRSSE QKHTPRDANY IFVRAHDSEV QAVLANIISK QINPKTDGFT   420
FTMDELKQAF EIYNADMRKA DKKYTQYNIP AAYATMLTNK DSITRVYYGD LFTDDGQYMA   480
EKSPYYNAID ALLRARIKYV AGGQDMKVTK LNGYEIMSSV RYGKGAEEAN QLGTAETRNQ   540
GMLVLTANRP DMKLGTNDRL VVNMGAAHKN QAYRPLLLSK STGLATYLKD SDVPAGLVRY   600
TDNQGNLTFT ADDITGHSTV EVSGYLAVWV PVGASENQDA RTKASTTKKG EQVFESSAAL   660
DSQVIYEGFS NFQDFVKTPS QYTNRVIAQN AKRFKEWGIT SFEFAPQYVS SQDGTFLDSI   720
IENGYAFEDR YDIAMSKNNK YGSLKDLMDA LRALHAEGIS AIADWVPDQI YNLPGKEVVT   780
ASRTNSYGTP RPNAEIYNSL YAAKTRTFGN DFQGKYGGAF LDELKAYPA IFERVQISNG   840
RKLTTNEKIT QWSAKYFNGS NIQGTGARYV LQDNATNQYF NLKAGQTFLP KQMTEITATG   900
FRRVGDKVQY LSTSGYLAKN TFIQIGANQW YYFDKNGNMV TGEQVIDGKK YFFLDNGLQL   960
RHVLRQGSDG HVYYYDPKGV QAFNGFYDFA GPRQDVRYFD GNGQMYRGLH DMYGTTFYFD  1020
EKTGIQAKDK FIRFADGRTR YFIPDTGNLA VNRFAQNPEN KAWYYLDSNG YAVTGLQTIN  1080
GKQYYFDNEG RQVKGHFVTI NNQRYFLDGD SGEIARSRFV TENNKWYYVD GNGKLVKGAQ  1140
VINGNHYYFN NDYSQVKGAW ANGRYYDGDS GQAVTNRFVQ VGANQWAYLN QNGQKVVGLQ  1200

```
HINGKLYYFE GNGVQAKGKL LTYKGKKYYF DANSGEAVTN RFIQISRGVW YYFNASGQAV   1260
TGEQVINGQH LYFDASGRQV KGRYVWIKGQ RRYYDANTGA WVRNR                 1305
```

| SEQ ID NO: 39 | moltype = DNA   length = 3933 |
|---|---|
| FEATURE | Location/Qualifiers |
| source | 1..3933 |
|  | mol_type = unassigned DNA |
|  | organism = Streptococcus gallolyticus |

SEQUENCE: 39
```
atgatcgacg gcaaatacta ctatgttcag gcagatggca gcgttaagaa gaatttcgcg    60
attacggtca acggtcagct gctgtacttt gatgctgaga ctggcgctct gacgagcacg   120
agcacttata gctttaccga aggcctgacc aatctggtgg ataactttag caagaacaat   180
caagcgtatg acagcacgga gaaatccttt gagctggttg atggctacct gacggcgaac   240
agctggtatc gtccgactaa agttttggag aatggcgaaa cctggttga cagcaccgaa   300
gagagcttcc gtccactggt gatggcttgg tggcctgacg tcgataccca gattaactac   360
ctgaacagca tgagcgaata ctttggtttg aataagaagt attctgcatc ggatagccaa   420
gcatctctga atgtggcggc tgaagcgatc caggtgaaaa ttgagcagga gattgcgcgt   480
cgtggttcga ccgagtggtt gcgtgaggtc attagctctt ttgttacgac ccaagataag   540
tggaatatga acagcgaaga tcgcgacact gaccacctgc aaggtggcgc actgctgtat   600
gtcaacagcg atctgactga gtgggccaat agcgattacc gctgctgaa ccgcgctccg   660
acctatcaaa ctggtgaaac taagtaccac aaagccgacc gcacgggtgg ctacgacttc   720
ctgctggaca atgatgttga caatagcaat ccggttgttc aggccgaaca actgaatcag   780
ctgtactacc tgatgaactg ggtaagatt gtgttcggtg acgcagatgc aaacttcgat   840
ggcgtccgtg ttgacgcggt ggacaacgtg gatgctgatc tgttgcaaat ctacacgaat   900
ctgtttgaag cggcctacgg cgtcgataag accgaagcac aagcgctggc gcatattagc   960
atcttggaag cgtggagctt caacgacccg gactataatc acgacaccaa cggtgcagca  1020
ctggccatcg acaacggtct gcgtatggcc ttcctggatg ctctgactcg tcctctggac  1080
tcccgcacta atttggagag cctgattcac aacgatctgg gcatgactga ccgtaccgtc  1140
gatagcgcgt atggtgatgc tatgccgagc tatgccttcg tccgtgccca cgactctgaa  1200
gttcagggca tcattgcatc tatcatcgcc ggtcagatca atccgaaaac ggacggtttt  1260
acctttacct tggatgagct gcaaaaggca ttcgaaatct acaacgccga catgaactcc  1320
gtgcacaaga agtataccca tttcaatatc ccagcagcat acgctttgct gctgaccaac  1380
atggagagcg ttccgcgtgt atactatggc gatttgttca ccgataacgg tcagtacatg  1440
gccgttaaaa gcccgtacta cgaccagatc accgcgctgc tgaagtctcg tatcaagtac  1500
gcggcaggcg gtcaagccat gaatgtgcaa taccggatg gtgcgggtgc gggtatcctg  1560
acttctgtgc gcttcggcta tggcattatg acggcggatc aaaaagcgac cgacgacagc  1620
gttactacca gcggcattgt caccattgtt ccaacaacc cgaacctgaa actgaatagc  1680
agcgacaaaa ttgcggtgca agttggtctg gcacacgcag gccaatacta ccgtccgctg  1740
ctgtctccga cggagaatgg tctgcaagtg ttcctgaata ttccgacac cgacatcgcc  1800
aagctggtcg atgataacgg ttacatctat ttcacgggtg atgagatcaa aggtttcgag  1860
actgtgggaca tgaatggctt cctgaccgtt tgggttccgg tgggtgcggc agccgatcag  1920
gatattcgcg tcaaggcgag cacggaagcg aagaaggatg tgagctgac ctatgaaacc  1980
tctgcggcgc tggattctca ggtcatttt gaaggcttca gcaacttca agactttggt  2040
caggacccaa gccagtacac caataaggtg attgcggaga atgcggatct gttcgcgagc  2100
tggggcatca cgtctttcga gctggcaccg cagtatgtta gcagcacgga cggtacgttc  2160
ctggacagca ttattcagaa cggttatgct tttacggatc gttatgactt ggcgatgtct  2220
aagaacaata agtatggtag cgcagaagat ttgcgcaaga gctgcacgca  2280
cgcggtattc aagtgattgc tgattgggtc cctgaccaga tttatgcgct gcctggtgaa  2340
gagattgtga cggcgacccg tgttaatgac tacggcgaag aacgtgaagg cgcgcaaatc  2400
aagaacaaac cgtatgcggc gaatacgaaa agctccggtg aggattacca agcccaatac  2460
ggtgcgagt tctttggaata tctgcaagag aattacccgg agttgtttga aaaggtcatg  2520
attagcacgg gtaagaccat tgacccatcg acgaagatca aggtctggaa agcggagtat  2580
tcaacggca cgaatattct gggtaagggt gccgattacg tcctgaacga tgcggccacc  2640
ggcacctact tcaccgtaac ggagaacggc gccttcctgc cgaaacaaat gacgagcgat  2700
accgcccaaa cgggttttcta ttatgatggc accggcacga cgtactattc tacctcggg  2760
taccaagcta agtctagctt cgtgctgtac aacggcaacc gttactattt cgatgaaac  2820
ggtcacatgg ttacgggtat gcgcgatatt gatggtcaga cgtactactt tctgccgaat  2880
ggtatcgaac tgcgtgacgc gatctatgag gacgcgaacg gtaatcagta ttactttggc  2940
aaatcgggta accgctcgc gggtcattac tacgcctttg aaaccacgag caccgttgac  3000
ggtgtcacca agaccactac taactgcgc tatttttgatg aaaacggcgt tatgcgacgc  3060
ggcctggtga aaatcggtaa tgattatcaa tactacgacg ataacggcaa tcagatcaag  3120
ggtcaactgg tgacggacaa ggacggcaac accgttact ttaaagctga cagcggtgca  3180
atggttacgg gtgagtttgc actggtgaat ggtggttggt actacttcga tgacaatggt  3240
gttgcagtca aagtgctca gaccattaac ggtcaacagt tgtacttcga cgaaatggt  3300
gtccaagcaa aaggtgtgtt cgtgaccaat gaggatgca cccgtagcta ttacgacgcc  3360
aagtccggtg agaagtttgt tggcgacttc tttacgaccg cgacaaccaa ttggtactat  3420
gccgacgaga acggcaattt ggcaacgggt agccaggtta tccgtggtca gaagttatat  3480
tttgcagccg atggtttgca ggcgaaaggt atctttacca ccgcgccga aggtaaccgc  3540
cacttctacg acccggactc cggcgatctg cggaaataca gtttatcgc ggatggtac  3600
gactggtact atttttgacga aacgggtcat gttgttaccg cgagcaagt gatcaacggc  3660
caacagctgt atttcgacga aaatggcgtt caggcgaagg gtgtttttcgt gaccgatgat  3720
aatggtaata agcgttacta tgatgcacag acgggtgaga tggtggtgaa ccagacgctg  3780
acggtggatg tgtggaata taccttggt gcggatggcc tcgcggtggt taatgcacaa  3840
gatagcgacg aacaaagcga aagcacggat gaaacgcaag tgaccagcga tgacgcgacg  3900
gttgcaaaga cggaaaccag ctctgctgaa taa                              3933
```

| SEQ ID NO: 40 | moltype = AA   length = 1310 |
|---|---|
| FEATURE | Location/Qualifiers |
| source | 1..1310 |

```
                        mol_type = protein
                        organism = Streptococcus gallolyticus
SEQUENCE: 40
MIDGKYYVQ  ADGSVKKNFA  ITVNGQLLYF  DAETGALTST  STYSFTEGLT  NLVDNFSKNN    60
QAYDSTEKSF  ELVDGYLTAN  SWYRPTKVLE  NGETWVDSTE  ESFRPLVMAW  WPDVDTQINY   120
LNSMSEYFGL  NKKYSASDSQ  ASLNVAAEAI  QVKIEQEIAR  RGSTEWLREV  ISSFVTTQDK   180
WNMNSEDRDT  DHLQGGALLY  VNSDLTEWAN  SDYRLLNRAP  TYQTGETKYH  KADRTGGYDF   240
LLANDVDNSN  PVVQAEQLNQ  LYYLMNWGKI  VFGDADANFD  GVRVDAVDNV  DADLLQIYTN   300
LFEAAYGVDK  TEAQALAHIS  ILEAWSFNDP  DYNHDTNGAA  LAIDNGLRMA  FLDALTRPLD   360
SRTNLESLIH  NDLGMTDRTV  DSAYGDAMPS  YAFVRAHDSE  VQGIIASIIA  GQINPKTDGF   420
TFTLDELQKA  FEIYNADMNS  VHKKYTHFNI  PAAYALLLTN  MESVPRVYYG  DLFTDNGQYM   480
AVKSPYYDQI  TALLKSRIKY  AAGGQAMNVQ  YPDGAGAGIL  TSVRFGYGIM  TADQKATDDS   540
VTTSGIVTIV  SNNPNLKLNS  SDKIAVQVGL  AHAGQYYRPL  LSPTENGLQV  FLNDSDTDIT   600
KLVDDNGYIY  FTGDEIKGFE  TVDMNGFLTV  WVPVGAAADQ  DIRVKASTEA  KKDGELTYET   660
SAALDSQVIF  EGFSNFQDFV  QDPSQYTNKV  IAENADLFAS  WGITSFELAP  QYVSSTDGTF   720
LDSIIQNGYA  FTDRYDLAMS  KNNKYGSAED  LRNAIKALHA  RGIQVIADWV  PDQIYALPGE   780
EIVTATRVND  YGEEREGAQI  KNKPYAANTK  SSGEDYQAQY  GGEFLEYLQE  NYPELFEKVM   840
ISTGKTIDPS  TKIKVWKAEY  FNGTNILGKG  ADYVLNDAAT  GTYFTVTENG  AFLPKQMTSD   900
TAQTGFYYDG  TGMTYYSTSG  YQAKSSFVLY  NGNRYYFDEN  GHMVTGMRDI  DGQTYYFLPN   960
GIELRDAIYE  DANGNQYYFG  KSGNRYAGHY  YAFETTSTVD  GVTKTTTNWR  YFDENGVMAR  1020
GLVKIGNDYQ  YYDDNGNQIK  GQLVTDKDGN  TRYFKADSGA  MVTGEFALVN  GGWYYFDDNG  1080
VAVKGAQTIN  GQQLYFDENG  VQAKGVFVTN  EDGTRSYDA   KSGEKFVGDF  FTTGDNHWYY  1140
ADENGNLATG  SQVIRGQKLY  FAADGLQAKG  IFTTDAEGNR  HFYDPDSGDL  AENKFIADGD  1200
DWYYFDETGH  VVTGEQVING  QQLYFDENGV  QAKGVFVTDD  NGNKRYYDAQ  TGEMVVNQTL  1260
TVDGVEYTFG  ADGVAVVNAQ  DSDEQSESTD  ETQVTSDDAT  VAKTETSSAE              1310

SEQ ID NO: 41           moltype = DNA   length = 3804
FEATURE                 Location/Qualifiers
source                  1..3804
                        mol_type = unassigned DNA
                        organism = Streptococcus mutans
SEQUENCE: 41
atggtcaatg  gcaaatacta  ctactacaaa  gaggacggta  cgttgcagaa  gaactacgca    60
ctgaacatta  acggcaagac  cttttttctt  gacgagactg  gcgccctgag  caataacacc   120
ctgccgagca  agaaaggtaa  catcaccaat  aacgacaata  ccaatagctt  cgcgcaaatc   180
aatcaggtgt  attcgacgga  tgcagccgaa  ttcgaacatg  tcgatcacta  cctgacgggc   240
gagtcctgga  tcgcccgaaa  gtatattctg  aaagatggca  agacgtggac  tcagtccacg   300
gagaaagatt  ttcgcccgtt  gttgatgacc  tggtggccgg  atcaggaaac  ccagcgtcag   360
tatgtaaact  atatgaatgc  ccagctgggt  attcaccaga  cctacaacac  ggcgaccagc   420
ccgttgcaac  tgaatctggc  ggacagacg   atccagacca  agattgaaga  agaagatcacg   480
gcggagaaga  cactaattg   gctgcgtcaa  acgatttcgg  cctttgtcaa  acccagagc    540
gcgtggaact  cggacagcga  aaaaccgttt  gacgatcatc  tgcaaaaggg  tgcactgctg   600
tactcctaaca  atagcaagtt  gacctctcaa  gctaatgaca  actaccgtat  tctgaaccgt   660
acccccaacca  accaaaccgg  caagaaagat  ccgcgttata  ccgctgaccg  taccatcggt   720
ggttatgagt  tcttgctggc  gaacgatgtg  gataatagca  atcctgttgt  tcaagcggaa   780
cagctgaact  ggctgcactt  cctgatgaac  tttggcaata  tctatgcaaa  cgaccctgac   840
gccaactttg  acagcatccg  tgtagacgcc  gtggacaacg  tggatgcaga  tttgttgcaa   900
atcgctggtg  actatctgaa  ggctgcaaag  gcatccata   agaacgacaa  agcagccgaac   960
gaccacctgt  cgatcctgga  agcatggagc  tataatgaca  ccccgtatct  gcacgacgac  1020
ggtgacaaca  tgatcaatat  ggacaaccgt  ctgcgtctga  gcctgctgta  tagcctggcg  1080
aagccgttga  accagcgttc  gggcatgaac  ccgctgacca  gcgaacagcct  ggttaaccgt  1140
accgatgaca  acgcagaaac  cgcagcggtc  ccgagctaca  gctttatccg  tgcacacgat  1200
agcgaggttc  aagaccgat   tcgtaacatt  atcgtgctg   agattaatcc  gaacgtcgtc  1260
ggttatagct  tcacgatgga  agagatcaag  aaggcctttg  agatttacaa  caaggatctg  1320
ctggcgacgg  aaaagaaata  cacccactat  aacaccgcgc  tgagctacgc  gctgctgctg  1380
accaataaga  gcagcgttcc  gcgtgtgtat  tacggtgata  tgtttactga  cgacggtcag  1440
tacatggcac  ataaaacgat  caactacgag  gctatcgaaa  cgctgttgaa  ggcgcgcatt  1500
aagtacgtgt  ctggtggcca  agcgatgcgt  aatcaacagg  tgggtaatag  cgaaatcatt  1560
acgagcgtcc  gctatggcaa  gggcgcactg  aaagcgacag  ataccggcga  tcgtaccacg  1620
cgcaccagcg  gcgttgcggt  tattgaaggc  aatacccga   gcctgcgctt  gaaggcgagc  1680
gaccgcgtcg  ttgttaacat  gggtgcagca  cacaagaacc  aggcatatcg  tccgctgttg  1740
ctgaccactg  ataatggcat  caaagcgtat  cacagcgatc  aggaagctgc  gggcctggtg  1800
cgctatacca  atgatcgtgg  tgaattgatc  ttcacgcag   ctgacattaa  aggttatgca  1860
aatccgcaag  tcacggttta  tctgggcgtc  tgggtcgcag  tcggcgcagc  ggctgatcaa  1920
gacgtgcgtg  tggccgcgag  caccgcgcca  tcgaccgacg  gtaaaagcgt  gcaccagaat  1980
gcggcgctgg  acagcgtgt   catgtttgag  ggttttagca  actttcaagc  ctttgcaacg  2040
aagaaagaag  agtacaccaa  cgtcgtcatc  gcgaagaacg  tcgataagtt  cgcggaatgg  2100
ggcgttaccg  atttcgaaat  ggcaccgcag  tatgtgtcta  gcaccgatgg  ctcgttttctg  2160
gattccgtga  tccaaaatgg  ttatgcattt  accgaccgct  atgacctggc  cattagcaag  2220
ccgaataagt  atggtacggc  ggatgatctg  gttaaagcga  tcaaggcgct  gcattctaaa  2280
ggtattaagg  ttatgccga   ctgggttcca  gatcagatgt  atgctttccc  ggaaaagaaa  2340
gtggtgacgg  ccaccgcgt   ggacaaatat  ggtacgccgg  tcgcgggcag  ccagatcaaa  2400
aacactctgt  atgtcgtgga  tggcaaaagc  tccggtaaag  atcagcaagc  gaaatatggc  2460
ggtgcctttc  tggaagagtt  gcaggcgaaa  taccggaaat  gttcgcgcg   taagcagatc  2520
agcactggtg  ttccgatgga  cccgagcgtg  aagattaaac  aatggtccgc  gaaatacttt  2580
aacggcacga  acatcctggg  tcgtggtgcc  ggctacgtgc  tgaaagacca  ggcaacgaat  2640
acgtacttta  gcttggtgtc  cgacaatacg  tttctgccga  agtctctggt  caacccgaac  2700
cacggtacga  gcagctctgt  gaccggcctg  gtgttcgatg  gtaagggcta  cgtgtactac  2760
tctaccagcg  gttaccaggc  caagaatacg  ttcatcagcc  tgggtaacaa  ctggtattac  2820
```

```
ttcgacaata acggttacat ggtcacgggt gcgcagagca tcaacggtgc caactactat  2880
tttctgagca acggcattca gctgcgtaat gcgatttacg acaatggcaa taaggttctg  2940
agctactacg gtaatgacgg tcgtcgttat gagaatggct attacctgtt tggccaacag  3000
tggcgctact tcaaaatgg tattatggcc gtcggtctga cccgtgtcca cggtgcggtg  3060
cagtattttg acgccagcgg cttccaagcc aagggccagt tcatccaccac tgcggacggt  3120
aaactgcgtt actttgaccg tgacagcggc aaccaaatca gcaatcgttt tgttcgtaac  3180
agcaagggtg aatggttttt gttcgatcat aacggcgtgg cggttaccgg caccgttact  3240
ttcaatggtc aacgtctgta ctttaagccg aacggtgttc aggcaaaggg tgagttcatt  3300
cgcgacgcgg atggtcactt gcgttactac gaccctaatt ccggtaatga ggttcgtaac  3360
cgtttcgtcc gcaactctaa gggcgaatgg ttcctgtttg accacaatgg catcgcagtc  3420
accggcgctc gtgtggtcaa cggccaacgc ttgtacttca aaagcaatgg cgtccaagct  3480
aagggtgagc tgattaccga acgtaagggc cgtattaagt attatgatcc taacagcggt  3540
aacgaagtgc gtaaccgcta cgtccgcacc agcagcggta attggtacta ttttggtaac  3600
gatggttacg cgctgatcgg ctggcatgtt gttgaggtgc gtcgtgtgta ctttgatgag  3660
aacggtgtct atcgttacgc gagccacgac cagcgtaatc attggaacta cgactatcgt  3720
cgcgatttcg gtcgtggtag cagctccgct atccgttttc gccatagccg taacggcttt  3780
ttcgacaact tcttccgctt ctaa                                         3804

SEQ ID NO: 42          moltype = AA   length = 1267
FEATURE                Location/Qualifiers
source                 1..1267
                       mol_type = protein
                       organism = Streptococcus mutans
SEQUENCE: 42
MVNGKYYYYK EDGTLQKNYA LNINGKTFFF DETGALSNNT LPSKKGNITN NDNTNSFAQY   60
NQVYSTDAAN FEHVDHYLTA ESWYRPKYIL KDGKTWTQST EKDFRPLLMT WWPDQETQRQ  120
YVNYMNAQLG IHQTYNTATS PLQLNLAAQT IQTKIEEKIT AEKNTNWLRQ TISAFVKTQS  180
AWNSDSEKPF DDHLQKGALL YSNNSKLTSQ ANSNYRILNR TPTNQTGKKD PRYTADRTIG  240
GYEFLLANDV DNSNPVVQAE QLNWLHFLMN FGNIYANDPD ANFDSIRVDA VDNVDADLLQ  300
IAGDYLKAAK GIHKNDKAAN DHLSILEAWS YNDTPYLHDD GDNMINMDNR LRLSLLYSLA  360
KPLNQRSGMN PLITNSLVNR TDDNAETAAV PSYSFIRAHD SEVQDLIRNI IRAEINPNVV  420
GYSFTMEEIK KAFEIYNKDL LATEKKYTHY NTALSYALLL TNKSSVPRVY YGDMFTDDGQ  480
YMAHKTINYE AIETLLKARI KYVSGGQAMR NQQVGNSEII TSVRYGKGAL KATDTGDRTT  540
RTSGVAVIEG NNPSLRLKAS DRVVVNMGAA HKNQAYRPLL LTTDNGIKAY HSDQEAAGLV  600
RYTNDRGELI FTAADIKGYA NPQVSGYLGV WVPVGAAADQ DVRVAASTAP STDGKSVHQN  660
AALDSRVMFE GFSNFQAFAT KKEEYTNVVI AKNVDKFAEW GVTDFEMAPQ YVSSTDGSFL  720
DSVIQNGYAF TDRYDLGISK PNKYGTADDL VKAIKALHSK GIKVMADWVP DQMYAFPEKE  780
VVTATRVDKY GTPVAGSQIK NTLYVVDGKS SGKDQQAKYG GAFLEELQAK YPELFARKQI  840
STGVPMDPSV KIKQWSAKYF NGTNILGRGA GYVLKDQATN TYFSLVSDNT FLPKSLVNPN  900
HGTSSSVTGL VFDGKGYVYY STSGYQAKNT FISLGNNWYY FDNNGYMVTG AQSINGANYY  960
FLSNGIQLRN AIYDNGNKVL SYYGNDGRRY ENGYYLFGQQ WRYFQNGIMA VGLTRVHGAV 1020
QYFDASGFQA KGQFITTADG KLRYFDRDSG NQISNRFVRN SKGEWFLFDH NGVAVTGTVT 1080
FNGQRLYFKP NGVQAKGEFI RDADGHLRYY DPNSGNEVRN RFVRNSKGEW FLFDHNGIAV 1140
TGARVVNGQR LYFKSNGVQA KGELITERKG RIKYYDPNSG NEVRNRYVRT SSGNWYYFGN 1200
DGYALIGWHV VEGRRVYFDE NGVYRYASHD QRNHWNYDYR RDFGRGSSSA IRFRHSRNGF 1260
FDNFFRF                                                          1267

SEQ ID NO: 43          moltype = DNA   length = 3864
FEATURE                Location/Qualifiers
source                 1..3864
                       mol_type = unassigned DNA
                       organism = Streptococcus mutans
SEQUENCE: 43
atgattgacg gcaaatacta ctacatcggc agcgacggtc agccaaagaa gaattttgcg   60
ttgacggtta acaataaagt cctgtatttt gacaagaaca cgggtgcgct gaccgacacc  120
agccaatatc agttcaaaca aggtctgacg aagctgaaca acgactacac ccctcacaat  180
cagattgtca actttgaaaa tactagcctg gaaactattg ataactatgt tactgccgac  240
tcttggtatc gtccgaaaga cattctgaag aacggtaaga cgtggaccgc gtcctctgag  300
agcgatctgc gtccgctgct gatgtcctgg tggcctgata agcagaccca gatcgcatac  360
ctgaactaca tgaaccaaca aggcttgggc actggcagaa actataccgc tgatagctct  420
caagagagcc tgaacctggc ggcacaaacc gttcaagtca aaatcgaaac caagatcagc  480
caaacgcaac agactcagtg gctgcgtgac atcattaact ctttcgttaa gacgcaaccg  540
aactggaata gccaaaccga gtctgacacg agcgctggtg aaaagatca tttgcagggc  600
ggtgccctgc tgtatagcaa ttcggacaaa accgcatacg caaatgcca ctatcgtctg  660
ctgaaccgta ccccgaccag ccagactggt aagccgaaat acttcgagga caatagcagc  720
ggtggttacg acttcctgtt ggcaaacgat attgataatt ccaatccggt ggtgcaggct  780
gagcagctga attggctgca ttacctgatg aattacggta gcattgtcgc aaatgacccg  840
gaagcgaatt tcgatggtgt ccgtgttgac gcggtggata acgtgaacgc agacgttgg  900
cagatcgcaa gcgattatct gaaagcccat atggtggttg ataagcggca gaagaatgcg  960
atcaaccacc tgagcatcct ggaagcgtgg tctgacaacg acccacagta taacaaagac 1020
accaaggtg cccagctgcc gatcgacaac aaactgcgtc tgtcgttgct gtacgcactg 1080
acccgtccgc tggagaagga tgcaagcaac aaaaatgaga ttcgtagcgg tctggagccg 1140
gttattacca attccctgaa taatcgttcc gctgagggca agaactctga acgcatggcg 1200
aattcatcct catccgtgc tcacgattct gaagttcaaa cggtgatcgc aaagatcatc 1260
aaagcgcaga ttaaccccgaa aacgatggc ctgaccttca ccctggatga gctgaaacag 1320
gcgttcaaaa tctataacga ggatatgcgc aggcgaaga gaagtatac ccagagcaat 1380
atcccgacgg catacgccct gatgctgagc aataaggact ccatcacgcg cctgtattac 1440
ggtgatatgt acagcgatga tggccaatac atggcgacca atcccgta ctacgatgcg 1500
attgacaccc tgctgaaggc gcgcattaag tatgccgctg cggtcagga tatgaagatc 1560
```

```
acctacgttg agggtgacaa aagccacatg gactgggact atacgggtgt cctgacgagc   1620
gttcgctacg gcacgggcgc aaacgaagcg accgaccagg gcagcgaagc taccaagacg   1680
caaggtatgg ccgtcatcac ttctaacaac ccgtccctga agctgaatca gaacgacaag   1740
gtcattgtca atatgggcac cgctcacaaa aatcaggaat accgtccgtt gctgctgacc   1800
accaaagacg gtctgaccag ctacaccagc gacgccgtca ccaagagcct gtaccgtaaa   1860
acgaacgata agggcgagtt ggtgttcgat gcaagcgaca ttcagggcta tctgaatccg   1920
caagtgagcg gttacctggc tgtttgggtg cctgtgggtg cgagcgacaa ccaggatgtg   1980
cgtgtcgcgg ccagcaataa agccaatgcg accggccaag tctatgaaag cagcagcgca   2040
ctggatagcc aactgattta tgagggtttt tccaactttc aggacttcgt caccaagagt   2100
tctgattaca ccaataaaaa gatcgcgcaa aatgtccagc tgtttaagag ctggggcgtc   2160
accagctttg agatggctcc gcaatacgtc agcagcgagg acggcagctt tttgacagc    2220
attatccaga acgctatgc gttcgaggat cgttacgacc tggcgatgag caaaaacaac    2280
aaatacggct cccagcagga catgatcaac gcggttaagg cgctgcataa gagcggtatc   2340
caagtgatcg cggactgggt cccggatcaa atctacaatt tgccgggtaa agaggtcgtc   2400
accgcgaccc gtgtgaacga ctacggcgag tatcgcaagg actccgaaat caaaaacacc   2460
ctgtacgccg ccaacaccaa aagcaacggt aaagattatc aagcaaagta cggtggcgcc   2520
tttttgagcg agctggccgc caaatatccg agcatcttta accgcactca gattagcaat   2580
ggcaagaaga tcgacccgtc tgaaaagatc accgcctgga aggccaaata cttcaatggt   2640
acgaacattt tgggtcgcgg cgttggttac gtcttgaaag acaatgccag cgacaagtat   2700
tttgagctga agggcaatca gacttatctg ccgaagcaaa tgacgaataa agaagcctcg   2760
actggtttcg ttaatgacgg caatggtatg accttttaca gcacgagcgg ttatcaagcg   2820
aagaacagct tcgttcagga cgcaaaaggc aactggtact actttgacaa caatggccac   2880
atggtttacg gtctgcaaca tctgaacggc gaggtgcaat acttcctgag caatggcgtg   2940
caactgcgtg aatccttctt ggaaaatgcc gacggcagca aaaactattt cggtcacctg   3000
ggcaaccgtt atagcaatgg ttactacagc ttcgataatg atagcaaatg cgctatttc    3060
gatgcgagcg gtgttatggc agtgggtctg aaaactatta acggtaacac ccagtatttc   3120
gatcaagacg gctaccaagt gaagggtgca tggattaccg gcagcgatgg taagaagcgt   3180
tacttcgacg acggtagcgg caatatggca gttaatcgct ttgctaacga caagaatggc   3240
gattggtatt acctgaatag cgacggtatt gcactggtgg tgttcagac catcaacggc    3300
aaaacgtatt actttggcca agatgtaaa caaatcaatt accgataat                3360
ggtaaactga aatactttct ggcgaacagc ggtgagctgg cgcgtaacat ttttgcgacc   3420
gacagccaga caactggta ttacttcggc tcggatggtg ttgcggttac gggttcgcag    3480
acgattgcgg gtaaaagtt gtactttgcg tccgacggta acaggtgaa gggtagcttt    3540
gttacttaca atggtaaagt gcactattac catgcggaca gcggcgaact gcaagtcaac   3600
cgtttcgagg cggataaaga cggtaattgg tactatctgg acagcaacgg tgaggcactg   3660
acgggtagcc agcgtatcaa tggtcaacgt gtgtttttca cccgcgaggg caaacaggtt   3720
aagggtgatg tcgcgtatga tgaacgcggc ttgctgcgct attacgacaa aaacagcggt   3780
aatatggtgt acaacaaggt ggtcacgctg gcgaacggtc gtcgtattgg tattgaccgc   3840
tggggtattg ctcgctatta ctaa                                          3864

SEQ ID NO: 44            moltype = AA  length = 1287
FEATURE                  Location/Qualifiers
source                   1..1287
                         mol_type = protein
                         organism = Streptococcus sobrinus
SEQUENCE: 44
MIDGKYYYIG SDGQPKKNFA LTVNNKVLYF DKNTGALTDT SQYQFKQGLT KLNNDYTPHN     60
QIVNFENTSL ETIDNYVTAD SWYRPKDILK NGKTWTASSE SDLRPLLMSW WPDKQTQIAY    120
LNYMNQQGLG TGENYTADSS QESLNLAAQT VQVKIETKIS QTQQTQWLRD IINSFVKTQP    180
NWNSQTESDT SAGEKDHLQG GALLYSNSDK TAYANSDYRL LNRTPTSQTG KPKYFEDNSS    240
GGYDFLLAND IDNSNPVVQA EQLNWLHYLM NYGSIVANDP EANFDGVRVD AVDNVNADLL    300
QIASDYLKAH YGVDKSEKNA INHLSILEAW SDNDPQYNKD TKGAQLPIDN KLRLSLLYAL    360
TRPLEKDASN KNEIRSGLEP VITNSLNNRS AEGKNSERMA NYIFIRAHDS EVQTVIAKII    420
KAQINPKTDG LTFTLDELKQ AFKIYNEDMR QAKKKYTQSN IPTAYALMLS NKDSITRLYY    480
GDMYSDDGQY MATKSPYYDA IDTLLKARIK YAAGGQDMKI TYVEGDKSHM DWDYTGVLTS    540
VRYGTGANEA TDQGSEATKT QGMAVITSNN PSLKLNQNDK VIVNMGTAHK NQEYRPLLLT    600
TKDGLTSYTS DAAAKSLYRK TNDKGELVFD ASDIQGYLNP QVSGYLAVWV PVGASDNQDV    660
RVAASNKANA TGQVYESSSA LDSQLIYEGF SNFQDFVTKD SDYTNKKIAQ NVQLFKSWGV    720
TSFEMAPQYV SSEDGSFLDS IIQNGYAFED RYDLAMSKNN KYGSQQDMIN AVKALHKSGI    780
QVIADWVPDQ IYNLPGKEVV TATRVNDYGE YRKDSEIKNT LYAANTKSNG KDYQAKYGGA    840
FLSELAAKYP SIFNRTQISN GKKIDPSEKI TAWKAKYFNG TNILGRGVGY VLKDNASDKY    900
FELKGNQTYL PKQMTNKEAS TGFVNDGNGM TFYSTSGYQA KNSFVQDAKG NWYYFDNNGH    960
MVYGLQHLNG EVQYFLSNGV QLRESFLENA DGSKNYFGHL GNRYSNGYYS FDNDSKWRYF   1020
DASGVMAVGL KTINGNTQYF DQDGYQVKGA WITGSDGKKR YFDDGSGNMA VNRFANDKNG   1080
DWYYLNSDGI ALVGVQTING KTYYFGQDGK QIKGKIITDN GKLKYFLANS GELARNIFAT   1140
DSQNNWYYFG SDGVAVTGSQ TIAGKKLYFA SDGKQVKGSF VTYNGKVHYY HADSGELQVN   1200
RFEADKDGNW YYLDSNGEAL TGSQRINGQR VFFTREGKQV KGDVAYDERG LLRYYDKNSG   1260
NMVYNKVVTL ANGRRIGIDR WGIARYY                                      1287

SEQ ID NO: 45            moltype = DNA  length = 4068
FEATURE                  Location/Qualifiers
source                   1..4068
                         mol_type = unassigned DNA
                         organism = Streptococcus sobrinus
SEQUENCE: 45
atgatcgacg gcaaatacta ctatattgac gaggacggta acgtaaagaa gaatttcgcg     60
attacggtgg atggtcagtt gctgtacttc gacgctgaaa cgggtgctct gaccagcacg    120
tccacctata gcttctccga gggcctgact aatctggtcg ataacttcag cattaacaac    180
cagtcctacg acagcaccga agagtcgttt gagctgatcg acggttacct gaccgtcaat    240
```

-continued

```
acttggtacc gtccgaccaa aattctggaa aacggtgaaa cctgggtcga tagcaccgaa  300
acggatttcc gtccgctgct gatggcctgg tggccggatg ttgacaccca aattgactac  360
ttgaactaca tgagcgatta cttcgatctg ggtacgacct atagcgctga cgattcccaa  420
gcgagcctga atctggcagc tgaggcggtt caggtgaaaa ttgaacaaga aattacccgt  480
caagagaaca ccgcctgctc gcgcgagatc atctctagct ttgttaccac ccaggataaa  540
tggaatatca ataccgagaa tgagggcacc gaccatctgc aaggtggtgc cctgctgtac  600
gttaacagcg acttgactcc gtgggcaaac agcgattatc gcctgctgaa ccgcaccccg  660
acgtaccaga cgggtgagac taattacttt aaagcagatc gtactggtgg ctacgaattt  720
ctgctggcaa atgacgtgga taattctaac ccggtcgttc aagccgaaca gttgaaccag  780
ctgtactact tgatgaattg gggctctatt gtattcggtg atgacgacgc caatttttgat  840
ggcgtgcgtg ttgacgcggt ggacaatgtg aacgctgacc tgttcagatt tacacgaac   900
ctgttcgaag cggcgtatgg tgttaacgag tctgaggcgc aggccctggc tcacattagc  960
atcctggaag cgtggtctta aacgacccg gactacaacc acgacacgaa tggcgctgcc  1020
ctggcaatcg acaatggtct gcgtctgagc tttctgtact ctttgacgcg ccctacggac  1080
gagcgcagcg gtttggagcc actgatcacc tctgagattg gcctgaccga tcgttccgag  1140
gactctgcat acggtgacac catgccgagc tatgttttcg tccgtgcaca tgacagcgag  1200
gttcagacca ttattgcgag cattatcgca gaacagatca acccggaaac cgatggctat  1260
accttccaccc tggacgagct gaaccaggcg tttgagattt caacgcgcga tatgaacagc  1320
gtggataaag agtatacgca ttacaatatc ccggctgcgt atagcctgct gctgaccaac  1380
atggaaagcg tcccgcgtgt ttactacggt gacctgtata cggataacgg tcagtacatg  1440
gcgactaaga gcccgtatta tgaccagatc accaccctgc tgcaagcgcg cattcgttac  1500
gcggcgggtg gccaatctat ggctgttacg tactacaccc ctgcgtcgaa cgtgtctacc  1560
gacaatgcgg atagcgtcct gaatgagact ggtgtgctga cttctgtgcg ttacggctat  1620
ggcatcatga ccgccgacca agaggccacg gacgactccg ttctgacctc tggtattgtt  1680
actattatca gcaacaaccc taatttgcag ctggatgatt ccgaagtgat tgcagtccag  1740
gttggtgtgg cgcacgctgg tcagtattat cgtccgctgt tgtacccgac ggcggatggt  1800
ctgcaaagct acctgaacga tagcgatacc gacattacta agctggtcga tgataatggt  1860
tatatctact ttacggcaga tgagattaaa ggctacgaaa cggttgacat gaatggctac  1920
ctgagcgttt gggtcccggt tggtgcagac gagaatcagg acatccgtgt cagcgcagac  1980
accagcgcgt acaccgaggg tgaattgatc tatcaagcaa ccgcagcgct ggatagccaa  2040
gtgatctacg agggtttcag caacttccaa gatttcgtta cctctaacag cgagtacact  2100
aacaagctga tcgcggagaa cgtcgatctg tttaccagct ggggcattac gagctttgag  2160
atggcgccac agtatgtgag caccgatgac ggtactttttc tggatagcat cattcaaaac  2220
ggttatgcat ttgacgatcg ctacgacctg gcaatgagcc agaataacaa gtatggtagc  2280
gctgaagatt tgcgtaatgc catcaaggcc ctgcacgctg ctggcattca ggtcattgct  2340
gactgggtgc cggatcaaat ctattcgctg ccaggcgaag aagtcgttac ggcgactcgc  2400
gtgaatgact atggcgaaga aaccgaaggc gcgtacatta caatacgtt gtatgtggcg   2460
aacagcaaaa gcagcggcga ggactaccag gcacagtatg gtggtgagtt cctggattac  2520
ttgcaagaaa cctacccgga aatgttcgaa gttgcgatta ttagcacgga tgagccgatt  2580
gatccgagca ccaagatcaa gatttggaaa gcagaatact ttaatggtac gaacattctg  2640
ggtaagggcg ctggttacgt gctgagcgat ccgcgactg gcacgtactt taccgtgact  2700
gagaatggca cgtttctgcc gaagcagctg accaccgact ccgccattac gggtttctat  2760
tacgacggcg cgggtatgtc ttactttagc acctcggtt atcgcgctaa acgagcgttc  2820
attgtttaca acggcactca ctactatttt gatgataacg gctacatggt cactggcacg  2880
gtggaaatca acggtaagac ctactatttc ctgccgaatg gtattcagct gcgtgatgcg  2940
atttacgaag acgagaacgg taatcagtac tatttcggtc cgttgggcaa ccagtattc   3000
aacaactatt acagctttga cgttgaagag gtggtggacg gtgtaacgac tacggtaacg  3060
aagtggcgtc attttgacga aacggcgtg atggcgcgtg gtttggtcga gattgatggt  3120
gtctaccagt attacgatga aaacggctac caggtcaaag gtgagctgat caccgatgct  3180
gatggtaatt tgcgttattt caaagaagat agcggtgaaa tggttgttag cgattttgtg  3240
aagatcggcg ataacaactg gtactacttt gacgaaaacg gtattgcagt cacgggtgcc  3300
caaaccattg ccggccagaa cttgtatttc gatgacaacg gtgtgcaggc gaaaggtgcc  3360
tttgtcacga acgccgatgg cacgcgcagc tattatgacg cggacagcgg tgagaagatc  3420
gtggcagatt tcttcactac gggcgataat gactggtatt atgcagatga aaatggcaat  3480
ctggtgactg gtagccaaac tatcaatggt caaaacctgt actttgctga ggacggtttg  3540
caggccaagg tgtgtgtttgt taccgatacg gctggtaaca ttcactatta tgatgcgaac  3600
tctggcagt tggcggttaa taccttcgtt ggtgatggcg acgactggta ttactttgat  3660
gagaatggca tcgcagttac cggcgcacaa gtcattaacg tcaacacct gtatttcgca  3720
gacaacggca tccaagtgaa aggtgaaatc gtcaccgacg caaacggcac ccgctattac  3780
tacgatgcag attccggcga aatggcagtt aacaccttttg tggagattga cggtgttttgg  3840
tactattttg gtgccgatgg tatcgcggtc acgggtgcac aagtaattga tggtcagaat  3900
ttgtactta acgcagacgg tagccaagtc aagggtacgg ttgtccgtat caacggtttg  3960
cgttactact acgacgctaa tagcggcgaa caggtgcgca atcagtgggt cacgctgccg  4020
gatggtactg ttgttttctt taatgcgcgt ggctatactt ggggctaa              4068
```

SEQ ID NO: 46          moltype = AA  length = 1355
FEATURE                Location/Qualifiers
source                 1..1355
                       mol_type = protein
                       organism = Streptococcus sobrinus
SEQUENCE: 46

```
MIDGKYYYID EDGNVKKNFA ITVDGQLLYF DAETGALTST STYSFSEGLT NLVDNFSINN   60
QSYDSTEESF ELIDGYLTVN TWYRPTKILE NGETWVDSTE TDFRPLLMAW WPDVDTQIDY  120
LNYMSDYFDL GTTYSADDSQ ASLNLAAEAV QVKIEQEITR QENTAWLREI ISSFVTTQDK  180
WNINTENEGT DHLQGGALLY VNSDLTPWAN SDYRLLNRTP TYQTGETNYF KADRTGGYEF  240
LLANDVDNSN PVVQAEQLNQ LYYLMNWGSI VFGDDDANFD GVRVDAVDNV NADLLQIYTN  300
LFEAAYGVNE SEAQALAHIS ILEAWSYNDP DYNHDTNGAA LAIDNGLRLS FLYSLTRPTD  360
ERSGLEPLIT SEIGLTDRSE DSAYGDTMPS YVFVRAHDSE VQTIIASIIA EQINPETDGY  420
TFTLDELNQA FEIYNADMNS VDKEYTHYNI PAAYSLLLTN MESVPRVYYG DLYTDNGQYM  480
```

```
ATKSPYYDQI  TTLLQARIRY  AAGGQSMAVT  YYTPASSMST  DNADSVLNET  GVLTSVRYGY   540
GIMTADQEAT  DDSVLTSGIV  TIISNNPNLQ  LDDSEVIAVQ  VGVAHAGQYY  RPLLYPTADG   600
LQSYLNDSDT  DITKLVDDNG  YIYFTADEIK  GYETVDMNGY  LSVWVPVGAD  ENQDIRVSAD   660
TSAYTEGELI  YQATAALDSQ  VIYEGFSNFQ  DFVTSNSEYT  NKLIAENVDL  FTSWGITSFE   720
MAPQYVSTDD  GTFLDSIIQN  GYAFDDRYDL  AMSQNNKYFA  AEDLRNAIKA  LHAAGIQVIA   780
DWVPDQIYSL  PGEEVVTATR  VNDYGEETEG  AYINNTLYVA  NSKSSGEDYQ  AQYGGEFLDY   840
LQETYPEMFE  VAMISTGEPI  DPSTKIKIWK  AEYFNGTNIL  GKGAGYVLSD  AATGTYFTVT   900
ENGTFLPKQL  TTDSAITGFY  YDGTGMSYFS  TSGYRAKASF  IVYNGYYYYF  DDNGYMVTGT   960
VEINGKTYYF  LPNGIQLRDA  IYEDENGNQY  YFGPLGNQYF  NNYYSFDVEE  VVDGVTTTVT  1020
KWRHFDENGV  MARGLVEIDG  VYQYYDENGY  QVKGELITDA  DGNLRYFKED  SGEMVVSDFV  1080
KIGDNNWYYF  DENGIAVTGA  QTIAGQNLYF  DDNGVQAKGA  FVTNADGTRS  YYDADSGEKI  1140
VADFFTTGDN  DWYYADENGN  LVTGSQTING  QNLYFAEDGL  QAKGVFVTDT  AGNIHYYDAN  1200
SGELAVNTFV  GDGDDWYYFD  ENGIAVTGAQ  VINGQHLYFA  DNGIQVKGEI  VTDANGNRYY  1260
YDADSGEMAV  NTFVEIDGVW  YYFGADGIAV  TGAQVIDGQN  LYFNADGSQV  KGDVVRINGL  1320
RYYYDANSGE  QVRNQWVTLP  DGTVVFFNAR  GYTWG                              1355

SEQ ID NO: 47          moltype = DNA  length = 4047
FEATURE                Location/Qualifiers
source                 1..4047
                       mol_type = unassigned DNA
                       organism = Streptococcus sobrinus
SEQUENCE: 47
atgatcgatg gcaagaaata ctatgttcag gacgacggta cggtaaagaa gaatttcgcg     60
gttgaactga acggcaaggt cctgtatttc gatgcagaaa ccggtgccct ggtcgacagc    120
gcggagtacc agtttcaaca gggtacgagc tccctgaata acgagttcag ccgcatgaat    180
gcgttccatg gcacgacgga gaaagatatt gaaaccgttg atggctatct gaccgcagat    240
acgtggtacc gcccgaaggc catcctgaaa gatggcaaaa cctggactca gagcaccgaa    300
accgatctgc gtccgctgct gatggcatgg tggccggaca acaaacgca ggtaagctac    360
ttgaactata tgaaccagca gggtctgggt gcggtgcgt ttgagaacaa agttgagcag    420
gcaatcttga cgggcgcaag ccagcaggtg cagcgcaaga tcgaagaacg tattggcaag    480
gacggcgata ccaaatggct gcgtaccctg atgggtgcat tgtgaaaac ccagccgaat    540
tggaatatca agacggagag cgaaaccacg gtactaata aggatcatct gcaaggtggt    600
gcgctgctgt acaccaactc tgaaaagacg agccacgcga cagcaaata ccgtattctg    660
aatcgtaccc cgaccaatca gaccggtacg ccgaagtatt tcatcgacaa atcgaattgt    720
ggttacgagt tcttgctggc aaatgattt gataatagca acccagcagt ccaagcggaa    780
cagctgaatt ggctgcactt tatgatgaat tccggcagca ttgttgcaaa tgaccccgacc    840
gcaaacttcg atggcgtgcg tgtggatgcg gtggacaatg ttaatgccga tttgctgcaa    900
attgccagcg actatttcaa atctcgttac aaagtgggcg agagcgaaga acaagcgatt    960
aaacatctga gcatcctgga agcctgggagc cggactataa caaagaccc                1020
aaaggcgccc aactgccgat cgacaataag ctgcgtctga gcctgttgta cagctttatg    1080
cgtaagctga gcattcgcag cggtgtcgaa ccgacgatta ccaacagcct gaacgaccgt    1140
tctgcggaga agaagaacgg tgagcgcatg gcaaactata tctttgttcg tgcgcatgat    1200
tccgaagtgc agacggtcat tgccgacatt attcgcgaga atatcaatcc gaacacgat    1260
ggtctgacct ttaccatgga cgagctgaaa caggcgttca agatctacaa tgaagatatg    1320
cgcaaggcgg ataagaagta cccaattc aatattccga ccgctcacgc gttgatgttg    1380
agcaacaagg attccattac gcgtgtgtac tacggtgacc tgtatacgga tgatggtcag    1440
tatatggaaa agaaaagccc ttattacgac gcgatcgaca cgctgctgcg cgcacgcatt    1500
aagtacgttg cgggtggcca ggacatgaaa gttacctaca tgggtgtgcc gcgtgaaacc    1560
gacaaatgga gctacaacgg catcctgacc agctccgct acggcaccgg cgcaaatgag    1620
gctacggacg agggtactgc cgagactcgc acccagggta tggccgtcat cgcaagcaac    1680
aatccgaatt tgaaactgaa cgagtcggat aagttgcaag tcaacatggg tgcggcacac    1740
aagaaccaat actatcgtcc ggtgctgctg accaccaagg acggtattag ccgttacctg    1800
accgacgaag aagttccgca aagcctgtgg aagaaaaccg atgcaaacgg catcttgacg    1860
ttcgacatga acgatatcgc aggttacagc aatgtccaag tatctggcta cttggctgtg    1920
tgggtgccgg ttggtgccaa agcggatcaa gacgcgcgtg ttactgcgtc gaagaagaaa    1980
aacgccagcg gtcaggtgta tgagtccagc gctgcactgg acagccaact gatttatgaa    2040
ggcttctcta acttccaaga cttcgcgacc cgcgacgatc aatacaccaa caaagttatt    2100
gccaaaaatg ttaatctgtt taagagtgg ggtgtgacca gctttgagct gccacctcag    2160
tatgtttcca gccaggatgg cacgtttttca gatagcatca tccagaatgg ctacgcattt    2220
gaagatcgtt atgacatggc gatgagcaaa aacaataagt acggtagcct ggacgacctg    2280
ctgaacgcgc tgcgtgcctt gcacagcgtc aacatccaag cgatcgcgga ctgggtcccg    2340
gatcagattt acaacctgcc gggcaaagaa gtggttacgg ctacgcgtgt caacaattat    2400
ggtacctatc gtgagggtgc ggaaatcaaa gaaaatctgt acgtggcaaa cacgaaaacc    2460
aacgccaccg actatcaagg caaatacggt ggtgcgttcc tggacgaact gaaagcgaaa    2520
tatcctgaga tcttcgaacg tgttcaaatt tccaatggtc aaaagatgac caccgatgag    2580
aagattacga aatggagcgc gaaacacttc aatggtacca cattctgggg ccgtggtgca    2640
tactacgtgc tgaaagattg ggccagcaat gagtatctga acaataagaa tggtgagatg    2700
gtgttgccga agcaactggt taacaaaaac gcgtacaccg gctttgttaa ggacaccacc    2760
ggttttaagt actatagcac ctcgggctat caagcgcgta atagcttcat ccaagatgag    2820
aacggtaatt ggtactactt tgacaaacgt ggttacctgg cgactggtgc acacgaaatc    2880
gacggcaagc aggtctattt cctgaaaaac ggcattcaac tgcgcgactc tctgcgtgag    2940
gacgagaacg gcaatcagta ctattacgac aagaccggtg cgcaggtgct gaaccgctac    3000
tacaccaccg acggccagaa ctggcgttac ttcgacgcca aggtgttat ggcgcgtggc    3060
ctggttgtaa tgggtggtaa ccaacaattc ttcgaccagg acggttatca ggtgaaaggc    3120
aagatcgcgc gtgccaagga tggtaaactg cgctacttcg acaaagacag cggtaacgca    3180
gcggcgaatc gctttgcaca gggcgataat ccgagcgatt ggtattactt tggtgccgat    3240
ggcgtcgctg ttaccggttt gcaaaaactg ggtcaacaaa ctctgtactt tgatcaagaa    3300
ggtaaacaag tgaagggcaa gattgtcacg ctggctgata agtccatccg ttacttgat    3360
gcgaacagcg gcgagatggc tgtcggtaag tttgctgagg gtagcaagaa cgaatggtac    3420
```

```
tatttcgatc agacgggcaa agcggttacg ggtctgcaaa agattggcca gcagaccctg   3480
tattttgacc aagatggtaa gcaggtaaag ggtaaagtgg taaccctggc agataagtcg   3540
attcgctact ttgatgcaaa ctccggcgaa atggcggtgg gtaagttcgc cgagggtgct   3600
aagaatgagt ggtactactt tgaccaggcg ggcaaggcgg tgaccggctt gcagaaaatt   3660
ggtcagcaaa cgctgtattt tgatcaggac ggcaaacaag tcaaaggccg actggtgacg   3720
ctggcggaca agagcattcg ttatttcgac gcaaacagcg gtgagatggc ctctaacaag   3780
ttcgttgagg gtgccaaaaa cgaatggtac tatttcgacc aagccggtaa agcagtgacc   3840
ggtctgcaac aaatcggtca gcagaccttg tacttcgacc aaaacggtaa acaggtcaaa   3900
ggtaaaatcg tgtatgttaa cggtgccaat cgttactttg acgccaattc gggtgaaatg   3960
gcgcgcaata agtggatcca actgcaagat ggtagctgga tgtacttcga tcgtaacggt   4020
cgtggtcgtc gtttcggctg gaattaa                                      4047

SEQ ID NO: 48          moltype = AA  length = 1348
FEATURE                Location/Qualifiers
source                 1..1348
                       mol_type = protein
                       organism = Streptococcus sobrinus
SEQUENCE: 48
MIDGKKYYVQ DDGTVKKNFA VELNGKVLYF DAETGALVDS AEYQFQQGTS SLNNEFSRMN    60
AFHGTTEKDI ETVDGYLTAD TWYRPKAILK DGKTWTQSTE TDLRPLLMAW WPDKQTQVSY   120
LNYMNQQGLG AGAFENKVEQ AILTGASQQV QRKIEERIGK DGDTKWLRTL MGAFVKTQPN   180
WNIKTESETT GTNKDHLQGG ALLYTNSEKT SHANSKYRIL NRTPTNQTGT PKYFIDKSNG   240
GYEFLLANDF DNSNPAVQAE QLNWHFMMN FGSIVANDPT ANFDGVRVDA VDNVNADLLQ   300
IASDYFKSRY KVGESEEQAI KHLSILEAWS DNDPDYNKDT KGAQLPIDNK LRLSLLYSFM   360
RKLSIRSGVE PTITNSLNDR SAEKKNGERM ANYIFVRAHD SEVQTVIADI IRENINPNTD   420
GLTFTMDELK QAFKIYNEDM RKADKKYTQF NIPTAHALML SNKDSITRVY YGDLYTDDGQ   480
YMEKKSPYYD AIDALLRARI KYVAGGQDMK VTYMGVPRET DKWSYNGILT SVRYGTGANE   540
ATDEGTAETR TQGMAVIASN NPNLKLNEWD KLQVNMGAAH KNQYYRPVLL TTKDGISRYL   600
TDEEVPQSLW KKTDANGILT FDMNDIAGYS NVQVSGYLAV WVPVGAKADQ DARVTASKKK   660
NASGQVYESS AALDSQLIYE GFSNFQDFAT RDDQYTNKVI AKNVNLFKEW GVTSFELPPQ   720
YVSSQDGTFL DSIIQNGYAF ERDYDMAMSK NNKYGSLDDL LNALRALHSV NIQAIADWVP   780
DQIYNLPGKE VVTATRVNNY GTYREGAEIK ENLYVANTKT NGTDYQGKYG GAFLDELKAK   840
YPEIFERVQI SNGQKMTTDE KITKWSAKHF NGTNILGRA YYVLKDWASN EYLNNKNGEM   900
VLPKQLVNKN AYTGFVKDTT GFKYYSTSGY QARNSFIQDE NGNWYYFDKR GYLATGAHEI   960
DGKQVYFLKN GIQLRDSLRE DENGNQYYYD KTGAQVLNRY YTTDGQNWRY FDAKGVMARG  1020
LVTMGGNQQF FDQNGYQVKG KIARAKDGKL RYFDKDSGNA AANRFAQGDN PSDWYYFGAD  1080
GVAVTGLQKL GQQTLYFDQE GKQVKGKIVT LADKSIRYFD ANSGEMAVGK FAEGSKNEWY  1140
YFDQTGKAVT GLQKIGQQTL YFDQDGKQVK GKVVTLADKS IRYFDANSGE MAVGKFAEGA  1200
KNEWYYFDQA GKAVTGLQKI GQQTLYFDQD GKQVKGQLVT LADKSIRYFD ANSGEMASNK  1260
FVEGAKNEWY YFDQAGKAVT GLQQIGQQTL YFDQNGKQVK GKIVYVNGAN RYFDANSGEM  1320
ARNKWIQLED GSWMYFDRNG RGRRFGWN                                    1348

SEQ ID NO: 49          moltype = DNA  length = 4284
FEATURE                Location/Qualifiers
source                 1..4284
                       mol_type = unassigned DNA
                       organism = Streptococcus salivarius
SEQUENCE: 49
atgaaggatg gcaaatacta ctacttgttg gaagatggct cgcacaaaaa gaatttcgca    60
atcaccgtca atggtcaagt gctgtatttt gacgagaacg gtgcgctgag cagcaccagc   120
acgtacagct tcacgcagga aaccaccaat ctggttacga actttacgga gaataatgca   180
gcgtatgact ccacgaaagc gtctttcgaa ttggtggacg gctatctgac cgcagacagc   240
tggtatcgcc cgaaagagat tctggaagcc ggcaccacct ggaaggcgag caccgaaaag   300
gacttccgtc cgctgctgat gtcctggtgg ccggataagg acacgcaagt tgcttatctg   360
aattacatga cgaaagcact gtcgaacggc gaagaaaaca aggatgtctt tacgatcgaa   420
aacagccaag cgagcctgaa tgcggcagcg caaatcctgc aacgtaagat tgaggtcaag   480
attgcggcca acaagagcac cgactggctg cgccaaagca tcgaggcgtt tgtcaaagac   540
caagataagt ggaatatcaa tagcgaaagc cctggcaaag agcatttcca gaagggtgcg   600
ctgctgtttg ttaatagcga cagcaccaag tgggcgaact ccgattatcg taaactgaat   660
cagaccgcga cgtcttacat caagaatcat aagatcgtga acggtagcga tggtggttac   720
gagttcttgc tgagcaacga catcgacaac agcaacccgg tggtccaggc agagatgctg   780
aatcaactgt actactttat gaactggggt cagattgtgt tcggcgataa agataaagac   840
gcacatttcg atggcatccg tgtggacgcg gtggacaatg ttagcgttga catgctgcaa   900
ctggtcagca gctacatgaa ggcggcatac aaggtcaatg aatctgaagc ccgtcgcgta   960
gcgaatatca gcattttgga agcgtggagc cataatgacc cgtattatgt gaacgagcac  1020
aatacggcag cactgagcat ggataacggt ctgcgtctgt ctattgtgca tggtctgacg  1080
cgtccggtga ctaacaaagg cacgggtgct cgtaacgcca gcatgaagga cctgatcaac  1140
ggcggttact ttggcttgag caaccgtgcg gaagttacta gctgaccaca gctgggcttt  1200
gccacttacc tgtttgtgcg tgcgcatgac agcgaggttc agacggttat cgctgatatt  1260
atttctaaaa agattgaccc gaccaccgac ggttttaccttaccctgga ccagctgaag  1320
caggcttttg atatttataa gcggacatg ttgaaggttg ataaagagta tacgcatagc  1380
aacatcccgg ctgcgtatgc gctgatgctg caaacgatgg tgcagcgac cgcgtgtat  1440
tacggcgatc tgtacactga taacggccaa tacatggcga aaaagagccc gtattttgat  1500
cagattacca cgctgttgaa ggcccgtccg aagtacgtga caggtcgca gacgagctac  1560
atccacaacc tggcaggcga tggtgtcagc tcgccaaag ataacaaaga ggttctggtt  1620
agcgtgcgct acggtcagga tctgatgagc aaaaccggata ctgagggcgg taaatacggt  1680
cgtaacagcg gtatgctgac tctgatcgcg aacaacccgg acctgaagct ggccgatggt  1740
gagactatca cggttaacat gggtgctgcc cacaaaaatc aggcgtatcg tccgttgctg  1800
ctgggcacgg aaaaggggtat tgtcagcagc ctgaacgata cgacaccaa atcgtgaag  1860
```

```
tatacggacg cccaaggtaa cctggttttc accgccgacg agatcaaggg cttcaaaacc 1920
gtggacatgt ctggctacct gtctgtttgg gttccggttg gtgccacgga tgaccgaaac 1980
gtcctggcga aaccgagcac caaagcatac aaagaaggtg ataaggttta cagcagcagc 2040
gcggctctgg aagctcaggt tatctatgaa ggttttagca atttccagga tttcgtgaaa 2100
gaagatagcc agtataccaa taagctgatt gcggctaatg cggacctgtt taagagctgg 2160
ggtatcacga gctttgagat cgcaccgcaa tatgtgagca gcaaagatgg tacttttctg 2220
gacagcatca ttgaaaatgg ttacgcgttc accgatcgtt atgacttcgc gatgagcaag 2280
aacaataagt atggtagcaa agaggatctg cgcgacgcgc tgaaggcact gcacaaacaa 2340
ggcatccaag tcatcgcgga ttgggtgccg gatcagctgt ataccctgcc gggcaaagag 2400
gtggttaccg caacccgtac cgatacgcac ggtaaagtgc tggatgacac gagcctggtg 2460
aataaactgt atgtgaccaa tacgaagtct agcggtaacg atttccaggc acagtatggt 2520
ggtgcgttcc tggataaact gcaaaagctg tacccagaga ttttcaaaga gttatggaa 2580
gcgtccggca agaccatcga cccaagcgtc aagattaaac aatgggaagc taaatacttt 2640
aatggcacga atattcaaaa gcgtggttcc gattatgttc tgagcgatgg caaactgtac 2700
tttacggtta acgataaggg caccttcctg cctgctgccc tgacgggtga caccaaggct 2760
aaaacgggtt ttgcctacga tggtacgggg gtcacgtatt acactaccag cggtactcaa 2820
gctaagagcc agtttgtgac gtataatggt aagcaatact acttcaacga caagggttac 2880
ttggttaccg gcgagcagac gattgatggc tccaactatt tcttcctgcc gaatggtgtt 2940
atgtttaccg atggtgtgcg taaaaacgcg aagggtcaga gcctggttta tgcaagtct 3000
ggtaagctga ccacgcaaac gggctggaaa gaagtgaccg ttaaagatga tagcggcaaa 3060
gaagaaaagt tttaccagta tttcttcaag ggtggcatca tggcgaccgg cctgacggaa 3120
gttgaaggta aagagaagta tttctatgac aatggctacc aaagcaaagg cgtctttgtc 3180
ccgaccaaag acgccaccct gatgttcttt tgcggcgaca gcggtgagcg taaatacagc 3240
ggtttctttg aacaagacgg taactggtac tatgcgaatg acaagggcta cgtcgcgacc 3300
ggctttacca aggtgggtaa acaaaatctg tatttcaatg agaaaggcgt ccaggtcaaa 3360
aaccgctttt tccaagtggg tgacgccacc tattacgcga ataacgaggg cgacgtgctg 3420
cgtggtgcgc aaaccatcaa tggtgatgag ctgtacttcg acgaaagcgg caaacaagtt 3480
aagggtgagt tcgtgaataa cccagacggc acgacctctt actatgatgc gatcacgggc 3540
gttaagctga tcgatacctc gctggttgtt gatggtcaga cgttcaacgt ggatgcgaag 3600
ggtgtcgtaa ccaaggcgca cacgccgggt ttctacacca ggcgacaaa caactggttc 3660
tacgcagata gctatggtcg taatgttacc ggtgcgcaag taatcaacgg ccaacacctg 3720
tatttcgatg caaatggtcg tcaagtgaaa ggcggctttg tcacgaacac ggacggtagc 3780
cgtagctttt accactggaa taccggcgac aaactggtgt ccacgttctt tgcgacgggt 3840
cacgatcgct ggtactacgc tgatgatcgt ggcaacgtcg tacgggtgc acaggtcatc 3900
aacggtcaga agctgttctt tgacaccgat ggtaaacaag tcaaaggtgc tttcgccgac 3960
aacgcgaatg gttcccgtag ctattatcat tggaatacgg gcaacaagct ggtgagcacc 4020
ttcttcacct cgggtgacaa taactggtat tacgcggacg ccaaaggtga ggttgtggtc 4080
ggtgaacaga cgattaatgg ccagcacctg tactttgacc agactggcaa gcaagtgaag 4140
ggcgcgactg caacgaaccc ggacggctcg atcagctatt atgatgtgca cacgggtgaa 4200
aaggctatca atcgttgggt gaagattccg agcggtcaat gggtgtactt caatgcgcag 4260
ggcaaaggtt acgtcagcaa ctaa                                        4284

SEQ ID NO: 50           moltype = AA   length = 1427
FEATURE                 Location/Qualifiers
source                  1..1427
                        mol_type = protein
                        organism = Streptococcus salivarius
SEQUENCE: 50
MKDGKYYYLL EDGSHKKNFA ITVNGQVLYF DENGALSSTS TYSFTQETTN LVTDFTKNNA  60
AYDSTKASFE LVDGYLTADS WYRPKEILEA GTTWKASTEK DFRPLLMSWW PDKDTQVAYL 120
NYMTKALSNG EETKDVFTIE NSQASLNAAA QILQRKIEVK IAANKSTDWL RQSIEAFVKD 180
QDKWNINSES PGKEHFQKGA LLFVNSDSTK WANSDYRKLN QTATSYIKNH KIVNGSDGGY 240
EFLLSNDIDN SNPVVQAEML NQLYYFMNWG QIVFGDKDKD AHFDGIRVDA VDNVSVDMLQ 300
LVSSYMKAAY KVNESEARAL ANISILEAWS HNDPYYVNEH NTAALSMDNG LRLSIVHGLT 360
RPVTNKGTGA RNSAMKDLIN GGYFGLSNRA EVTSYDQLGF ATYLFVRAHD SEVQTVIADI 420
ISKKIDPTTD GFTFTLDQLK QAFDIYNADM LKVDKEYTHS NIPAAYALML QTMGAATRVY 480
YGDLYTDNGQ YMAKKSPYFD QITTLLKARP KYVAGGQTSY IHNLAGDVS SAKDNKEVLV 540
SVRYGQDLMS KTDTEGGKYG RNSGMLTLIA NNPDLKLADG ETITVNMGAA HKNQAYRPLL 600
LGTEKGIVSS LNDSDTKIVK YTDAQGNLVF TADEIKGFKT VDMSGYLSVW VPVGATDDQN 660
VLAKPSTKAY KEGDKVYSSS AALEAQVIYE GFSNFQDFVK EDSQYTNKLI AANADLFKSW 720
GITSFEIAPQ YVSSKDGTFL DSIIENGYAF TDRYDFAMSK NNKYGSKEDL RDALKALHKQ 780
GIQVIADWVP DQLYTLPGKE VVTATRTDTH GKVLDDTSLV NKLYVTNTKS SGNDFQAQYG 840
GAFLDKLQKL YPEIFKEVME ASGKTIDPSV KIKQWEAKYF NGTNIQKRGS DYVLSDGKLY 900
FTVNDKGTFL PAALTGDTKA KTGFAYDGTG VTYYTTSGTQ AKSQFVTYNG KQYYFNDKGY 960
LVTGEQTIDG SNYFFLPNGV MFTDGVRKNA KGQSLVYGKS GKLTTQTGWK EVTVKDDSGK 1020
EEKFYQYFFK GGIMATGLTE VEGKEKYFYD NGYAKGVPV PTKDGHLMFF CGDSGERKYS 1080
GFFEQDGNWY YANDKGYVAT GFTKVGKQNL YFNEKGVQVK NRFFQVGDAT YYANNEGDVL 1140
RGAQTINGDE LYFDESGKQV KGEFVNNPDG TTSYYDAITG VKLVDTSLVV DGQTFNVDAK 1200
GVVTKAHTPG FYTTDNNWF YADSYGRNVT GAQVINGQHL YFDANGRQVK GGFVTNTDGS 1260
RSFYHWNTGD KLVSTFFATG HDRWYYADDR GNVVTGAQVI NGQKLFFDTD GKQVKGAFAT 1320
NANGSRSYYH WNTGNKLVST FFTSGDNNWY YADAKGEVVV GEQTINGQHL YFDQTGKQVK 1380
GATATNPDGS ISYYDVHTGE KAINRWVKIP SGQWVYFNAQ GKGYVSN              1427

SEQ ID NO: 51           moltype = DNA   length = 4182
FEATURE                 Location/Qualifiers
source                  1..4182
                        mol_type = unassigned DNA
                        organism = Streptococcus sp.
SEQUENCE: 51
```

```
atgatcaatg gcaaacagta ctatgtaaat tcggacggta gcgtgcgtaa gaatttcgtt    60
tttgaacagg atggtaagag ctactacttt gacgcggaaa ctggcgcgct ggccactaaa   120
agccaagatg aatttagcac ggagccgatt aaagcagcag tggacttctc tagcggcaac   180
cagctgtaca aaaatgacaa caaatcgctg atcagctgg  atacgtttat caccgctgac   240
gcatggtacc gccctaagtc tattctgaag gatggcaaaa cctggaccgc gtctaccgaa   300
gctgataagc gtccgttgct gatggtgtgg tggccggaca agtccaccca agttaactac   360
ctgaactaca tgcagaacca gggtttgggt gcgggtagct tcagcaccaa tagcagccaa   420
gaatccctga atctggctgc gaaagcagtt cagaccaaga tcgaagaacg catcgcacgt   480
gagggtaacca ccaattggct gcgtaccagc attgaccaat tcattaagac gcagccaggc   540
tggaacagca gcactgagaa tagcagctat gatcacttgc agggtggtca actgctgttc   600
aataacagca aaggtgatac gggtaaccgc accagctatg cgaatagcga ctatcgtctg   660
ctgaaccgta cccccaactaa tcaaagcggc acccgtaagt actttaagga taattccatc   720
ggtggtctgg aatttctgct ggcaaacgac atcgacaaca gcaaccctgc cgttcaggcg   780
gagcagctga actggctgca cttcatgatg aacattggtt ctatcatggc gaatgaccgc   840
acggcgaact tgatggtttt gcgtgtggac gcgttggata acgtggatgc ggacctgttg   900
cagatcgcga gcgattactt caaggcagtc tacggtgttg ataaatccga ggcgaatgcg   960
atcaagcacc tgagctatct ggaggcgtgg agcgccaatg accgtattaa caacaaggat  1020
accaaaggcg cgcaactgcc gattgacaac gcgctgccga acgcactgac caacctgttg  1080
atgcgtgaca agaatacgcg catgcagctg ggtgacatga cggcgtttat gaatagctct  1140
ctgaacccac gtggtgcgaa tgacaaaaac ggcgagcgta tggcgaatta cattttcacc  1200
cgcgcacacg ataccgaggc gcagaccatc attcagcgta ttatccgcga tcgtatcaat  1260
ccgaacctgt ttggctacaa tttcacccgc gatgaaatca aaaaggcgtt tgagatctac  1320
aacgcggaca ttaacacggc gcataagacg tacgcgagct acaatctgcc gtccgtctac  1380
gcactgatgc tgacgaataa ggacagcgtg acccgtgtgt attacggtga cctgtatcgt  1440
gaggacggtc actacatggc caagaaaacg ccttatttcg atgcaatcga taccctgctg  1500
cgtgcgcgca tcaaatacgt ggcgggtggt caagacatgg aggtgaagaa agttggtaat  1560
gacggcttgc tgacgagcgt ccgctatggc aagggtgcga acaatagcac cgactggggc  1620
acgactgaaa cccgtaccca aggtatgggc gttatcctga cgaacaacta tgatttccgc  1680
ctgggcagca acgaaaccgt cacgatgaac atgggccgtg cgcatcgcaa tcagctgtat  1740
cgtccgctgc tgctgacgac caaggatggt ctggccgact acctgaatga tagcgacgtg  1800
ccttcgaatt tgctgaaacg cacggactgg aatggtaact tgacctttaa tgccaacgat  1860
gtgtttggtg tagagaacgt ccaggtcagc ggttacctgg tgtgtttggt accggttggt  1920
gctaaagcta accaggatgc gcgtacccaa ccgagcaacc gtgcgaacag cgatggtcag  1980
gtctataagt cgtctgcggc attggacagc caggtcatgt atgagcgtt tagcaatttt  2040
caggcatttg cggacgatca accggaactg tacatgaacc gcgttcgtgg caagaacacc  2100
gatctgctga agcgtggggg cgttactagc gttggcttgc cgccacaata cgttagcagc  2160
aaagacggca ccttcctgga tagcactatt gataacggct atgcgttcga tgatcgttac  2220
gacatggcgc tgagccagaa caacaaatac ggttctctgg aggacttgct gaacgttctg  2280
cgcgctctgc acaaagacgg tattcaggcg attgcggact gggtcccgga tcaaatctac  2340
aatttgccgg gtaaagaggt tgttaatgcg acgcgtgtta acgttacggg ttaccatcag  2400
cagggctacc agattgttga ccaggcgtac gttgcaaaca cccgtacgga tggtaccgat  2460
tatcagggtc gttacggtgg tgcttttctg gacgaactga aggcgaagta cccgagcatt  2520
tcaatcgtga tccagattag caacgataaa cagctgccaa caatgagaa aatcacgaaa  2580
tggtccgcga aatacttcaa tggcacgaac atcctgggcc gtggtattaa ctatgtgctg  2640
cgcgacgaca agaccaatca gtatttcaac accagcgcaa acggccaact gctgccgacg  2700
ccactgcgcg acaccggtgc catcaccagc acgcaagttt ccagcgtcg  tggccaagac  2760
gtctatttc  tgcgtgataa ccaggttatc aaaaacgagt ttgtgcaaga tggtaacgat  2820
aattggtact acttcggtgc cgacggtaaa atgacgaagg gtgcacaaaa catcaatagc  2880
aaggattact atttcttcga taatggcgtc cagctgcgta atgcgctgcg tcgcgcgtcc  2940
aatggttaca cctactatta tggcctggac ggtgccatga tcaagaacgc tttcgtcgat  3000
tttgatgata agcaccaaca ggtgcgtgcg tttactacga agggcacgat ggtggtcggt  3060
aatttgcact ggagcggtca ccacttctat tttgaccgcg aaacgggtat ccaagccaaa  3120
gaccgcattg tgcgtaccga tgatggcaag ctgcactatt atgtcgcaca aaccggcgat  3180
atgggccgca atgtgtttgc gaccgacagc cgcacgggca agcgctatta ctttgatgcg  3240
gacggcaaca ccgttacggg ctcccgtgtc atcgaccgga agacctacta cttcaaccag  3300
gacggttcgg tcggtaccgc gtacagcaat cgtgcggata gcattatctt gagaatggc  3360
aaggctcgct atatcactcc ggctggcgag attggccgtt ccatttttgt ctacaacccg  3420
gcgaccaaaa cgtggaatta cttcgacaag gaaggtaacc gtgtcaccgg tcgtcagtat  3480
attgacggca atctgtacta cttttaaagag gacggctccc aagtgaaagg tgcgattgtt  3540
gaagaaacg gtatcaagta ctactacgaa ccgggcagcg gtatcctgac gagcggtcgt  3600
tatctgcaag tcggtgacga ccaatggatc tacttcaaac acgacggtag cctggcgatc  3660
ggtcaggttc gtgcagacgg tggttacttg aaatactttg ataagaatgg catccaggtc  3720
aagggccaaa ccattgtgga ggatggtcat acctattact acgatgccga ctccggtgct  3780
ctggtgacct ctagcttcgc ggagattgct ccgaaccagt cgtactact  caatacgaa  3840
ggccaagccc tgaagggcaa atggaccatc aatggtaaag agtactattt tgatcagaac  3900
ggcattcagt ataaaggcaa ggcagttaag gtcggcagcc gttacaaata ctatgacgag  3960
aatgacggtc aaccggtcac taaccgtttt gcccagattg agccgaacgt ctgggcgtac  4020
tttggtgccg atggctacgc agttactggc gaacaggtga ttaatggcca gcacctgtac  4080
ttcgatcagt cgggtcgtca ggttaaaggt gcgtacgtca ccgtgaatgg tcaacgtcgt  4140
tactacgacg caaacacggg tgaatacatt ccgggtcgtt aa                     4182
```

SEQ ID NO: 52         moltype = AA   length = 1393
FEATURE                Location/Qualifiers
source                 1..1393
                         mol_type = protein
                         organism = Streptococcus sp.
SEQUENCE: 52
MINGKQYYVN SDGSVRKNFV FEQDGKSYYF DAETGALATK SQDEFSTEPI KAAVDFSSGN   60
QLYKNDNKSL DQLDTFITAD AWYRPKSILK DGKTWTASTE ADKRPLLMVW WPDKSTQVNY   120

```
LNYMQNQGLG AGSFSTNSSQ ESLNLAAKAV QTKIEERIAR EGNTNWLRTS IDQFIKTQPG     180
WNSSTENSSY DHLQGGQLLF NNSKGDTGNR TSYANSDYRL LNRTPTNQSG TRKYFKDNSI     240
GGLEFLLAND IDNSNPAVQA EQLNWLHFMM NIGSIMANDP TANFDGLRVD ALDNVDADLL     300
QIASDYFKAV YGVDKSEANA IKHLSYLEAW SANDPYYNKD TKGAQLPIDN ALRNALTNLL     360
MRDKNTRMQL GDMTAFMNSS LNPRGANDKN GERMANYIFT RAHDTEAQTI IQRIIRDRIN     420
PNLFGYNFTR DEIKKAFEIY NADINTAHKT YASYNLPSVY ALMLTNKDSV TRVYYGDLYR     480
EDGHYMAKKT PYFDAIDTLL RARIKYVAGG QDMEVKKVGN DGLLTSVRYG KGANNSTDWG     540
TTETRTQGMG VILTNNYDFR LGSNETVTMN MGRAHRNQLY RPLLLTTKDG LATYLNDSDV     600
PSNLLKRTDW NGNLTFNAND VFGVENVQVS GYLGVWVPVG AKANQDARTQ PSNRANSDGQ     660
VYKSSAALDS QVMYEAFSNF QAFADDQPEL YMNRVLAKNT DLLKAWGVTS VGLPPQYVSS     720
KDGTFLDSTI DNGYAFDDRY DMALSQNNKY GSLEDLLNVL RALHKDGIQA IADWVPDQIY     780
NLPGKEVVNA TRVNGYGYHQ QGYQIVDQAY VANTRTDGTD YQGRYGGAFL DELKAKYPSI     840
FNRVQISNGK QLPTNEKITK WSAKYFNGTN ILGRGINYVL RDDKTNQYFN TSANGQLLPT     900
PLRDTGAITS TQVFQRRGQD VYFLRDNQVI KNEFVQDGNG NWYYFGADGK MTKGAQNINS     960
KDYYFFDNGV QLRNALRRAS NGYTYYYGLD GAMIKNAFVD FDDKHQQVRA FTTQGTMVVG    1020
NLHWSGHHFY FDRETGIQAK DRIVRTDDGK LHYYVAQTGD MGRNVFATDS RTGKRYYFDA    1080
DGNTVTGSRV IDGKTYYFNQ DGSVGTAYSN RADSIIFENG KARYITPAGE IGRSIFVYNP    1140
ATKAWNYFDK EGNRVTGRQY IDGNLYYFKE DGSQVKGAIV EENGIKYYYE PGSGILASGR    1200
YLQVGDDQWI YFKHDGSLAI GQVRADGGYL KYFDKNGIQV KGQTIVEDGH TYYYDADSGA    1260
LVTSSFAEIA PNQWAYFNTE GQALKGKWTI NGKEYYFDQN GIQYKGKAVK VGSRYKYYDE    1320
NDGQPVTNRF AQIEPNVWAY FGADGYAVTG EQVINGQHLY FDQSGRQVKG AYVTVNGQRR    1380
YYDANTGEYI PGR                                                      1393

SEQ ID NO: 53           moltype = DNA   length = 3789
FEATURE                 Location/Qualifiers
source                  1..3789
                        mol_type = unassigned DNA
                        organism = Streptococcus sobrinus
SEQUENCE: 53
atgattaacg gccacaatta ctatttcgac agcttgggtc aactgaagaa aggtttcacg      60
ggcgtgatcg acggtcaggt ccgttacttc gaccaggagt ccggtcagga agttagcacc     120
accgacagcc aaatcaaaga gggcttgacg agcaaacga ccgactacac cgcccataac     180
gcggtccaca gcacggactc cgcagatttt gacaacttca atggttacct gaccgcgagc     240
agctggtatc gtcctaagga cgttctgcgt aacggccaac attgggaagc caccaccgcg     300
aatgacttcc gtcctatcgt cagcgtgtgg tggccgagca agcaaacgca ggtcaactac     360
ctgaactata tgagccagat gggtttgatc gataaccgtc aaatgttctc gttgaaagat     420
aaccaagcga tgctgaacat cgcgtgcacg accgtgcaac aagcaatcga actaaaatc      480
ggtgtggcga atagcaccgc gtggctgaaa accgcgatcg atgactttat ccgtacccag     540
ccgcagtgga acatgagcag cgaagatccg aagaatgacc atctgcaaaa tggcgccctg     600
acgtttgtta acagcccgct gaccccggat acgaatagca atttccgcct gctgaatcgt     660
accccgacca atcaaaccgg tgttccgaaa tacaccatcg accaaagcaa aggtggtttt     720
gaactgctgc tggcgaatga cgtggataat tcgaacccgg ttgtgcaggc cgagcagttg     780
aactggctgc actacctgat gaactttggt agcattactc gaatgacagc cgcagcaaac     840
ttcgacggta ttcgcgttga cgcagtggat aacgtggatg cggacctgct gcaaattgcg     900
gcagattact tcaaagcagc atacggtgtg gacaagaacg acgcaacggc aaatcagcat     960
ctgtcgatcc tggaagattg gagccacaac gacccggagt acgttaaaga cttcggcaat    1020
aaccaactga ccatggacga ttacatgcac acgcagctga tctggagcct gacgaaagac    1080
atgcgtatgc gtggtacgat gcagcgcttt atggactact atctggttaa ccgcaatcac    1140
gacagcaccg agaatactgc cattccgaat tacagctttg tccgtgccca tgacagcgaa    1200
gttcaaacgg ttattgcgca gatcatttct gagctgcatc cagacgtgaa gaatagcctg    1260
gcgccgaccg cggatcaact ggctgaggcg ttcaaaatct acaacaacga cgagaagcaa    1320
gctgataaga agtataccca atacaatatg ccaagcgcgt acgcaatgct gttgaccaat    1380
aaagatacag ttccgcgtgt ttactacggt gacctgtata ccgatgacgg tcagtatatg    1440
gctaacaaat cccgtatttt tgacgctatc aacggtctgc tgaagagccg tatcaaatat    1500
gtggcaggcg gtcaaagcat gcggtggat cagaatgata tcctgacagc tgtgcgctat    1560
ggcaaaggtg ccatgagcgt gacggatagc ggcaacgcgg atacgcgtac ccagggcatc    1620
ggcgttattg ttagcaacaa agaaaaacctg ctctgaaat ccggcgacac cgttaccctg    1680
cacatgggcg cagcgcacaa gaaccaggcg tttcgcctgc tgttgggtac gacggcggac    1740
aacctgagct actacgacaa tgacaatgcg ccggtgaagt acaccaatga tcaaggtgat    1800
ctgattttcg ataataccga gatttatggt gttcgcaatc cgcaagtctc tggttttctg    1860
gcggtgtggg tcccggttgg tgccgatagc catcaagatg ctcgcacttt gagcgacgat    1920
acggcacacc acgacggcaa gaccttccac tcgaacgcag cactggatag ccaggtgatt    1980
tacgaaggtt ttagcaactt ccaagcattt gcaacgaata cggaagatta cactaacgct    2040
gtgatcgcca aaaacggcca gctgttcaag gattgggcga tcacctcgtt ccagctgacc    2100
ccgcagtatc gcagctccac cgatacgagc ttcctggata gcattattca gaacggctat    2160
gccttcacgg accgttatga cctgggctat ggcacccga cgaagtatgg caccgtggac    2220
cagctgcgcg atgcaatcaa ggctctgcac gccaatggca tccaagcaat tgccgactgg    2280
gttccggacc agatctacaa cctgccgggt caggagctgg ccacggtgac ccgtacgaac    2340
tcctatgtgt ataaagacac caatagcgat attgatcaga gcttgtacgt gatcaatcg    2400
cgcggtggcg gtaagtatca agcccaatac ggtggtgcat tcctgagcga cattcaaaag    2460
aagtatccgc tctgttcga gactaaacag atcagcacgg tctgccgat ggacccgagc    2520
caaaagatta ccgagtggag cggcaagtac ttcaacggta gcaatattca aggtaagggc    2580
gctggttacg tcctgaagga cagcggcacc gaccagtact ataaagtgac gagcaacaat    2640
aacaacgata atttcctgcc gaaacagctg acggatgatc tgtctgaaac cggttttgtg    2700
cgtgacaata ttggcatggt ctattacacc ctgtctggct acctggcacg caataccttc    2760
atccaggacg acaacggtaa ctattactac tttgatagca ccgtcacct ggttacgggt    2820
ttccagaaca ttaacaacca ccactacttt tccttgccga acggcattga actggttcag    2880
agctttctgc aaaacgctga tggtagcacg atctacttcg atcaaagggg tcgtcaagtt    2940
ttcaaccagt atatcactga tcagactggt accgcgtact acttccagaa cgacggcacc    3000
```

-continued

```
atggtcactt ctggctttac tgagatcgat ggccacaagc agtatttcta taagaatggc  3060
actcaggtta agggtcagtt tgtgagcgac accgatggtc acgtcttta cctggaagcg   3120
ggtaatggta atgtcgccac gcaacgtttc gcacagaaca gccagggtca atggttctac   3180
ttgggtaatg atggcattgc gttgacgggt ttgcagacga tcaacggtgt tcagaactac   3240
ttttatgcgg acggtcatca aagcaagggt gacttcatca ccatccagaa tcatgtcctg   3300
tacaccaacc cgctgacggg tgccatcacg accggcatgc aacagatcgg cgacaaaatc   3360
ttcgtgtttg ataatacggg taatatgctg acgaaccagt attatcagac gctggatggt   3420
cagtggctgc acctgagcac ccagggtcca gcagatacgg gtctggtcaa tatcaatggt   3480
aatctgaagt atttcaggc aaatggtcgt caggtgaaag gccaattcgt caccgaccvg   3540
attaccaacg tcagctacta catgaacgcg acggacggta gcgcagtgtt caatgactat   3600
ttcacctatc agggccaatg gtatttgacg gactccaact atcagttggt caaaggcttc   3660
aaagtggtga acaacaaact gcaacatttc gatgaaatca ccggtgtgca aaccaagagc   3720
gctcacatta ttgttaacaa tcgtacctac atttttgacg accagggcta ttttgtcagc   3780
gtggcataa                                                          3789

SEQ ID NO: 54            moltype = AA   length = 1262
FEATURE                  Location/Qualifiers
source                   1..1262
                         mol_type = protein
                         organism = Streptococcus sobrinus
SEQUENCE: 54
MINGHNYYFD SLGQLKKGFT GVIDGQVRYF DQESGQEVST TDSQIKEGLT SQTTDYTAHN   60
AVHSTDSADF DNFNGYLTAS SWYRPKDVLR NGQHWEATTA NDFRPIVSVW WPSKQTQVNY  120
LNYMSQMGLI DNRQMFSLKD NQAMLNIACT TVQQAIETKI GVANSTAWLK TAIDDFIRTQ  180
PQWNMSSEDP KNDHLQNGAL TFVNSPLTPD TNSNFRLLNR TPTNQTGVPK YTIDQSKGGF  240
ELLLANDVDN SNPVVQAEQL NWLHYLMNFG SITANDSAAN FDGIRVDAVD NVDADLLQIA  300
ADYFKAAYGV DKNDATANQH LSILEDWSHN DPEYVKDFGN NQLTMDDYMH TQLIWSLTKD  360
MRMRGTMQRF MDYYLVNRNH DSTENTAIPN YSFVRAHDSE VQTVIAQIIS ELHPDVKNSL  420
APTADQLAEA FKIYNNDEKQ ADKKYTQYNM PSAYAMLLTN KDTVPRVYYG DLYTDDGQYM  480
ANKSPYFDAI NGLLKSRIKY VAGGQSMAVD QNDILTNVRY GKGAMSVTDS GNADTRTQGI  540
GVIVSNKENL ALKSGDTVTL HMGAAHKNQA FRLLLGTTAD NLSYYDNDNA PVKYTNDQGD  600
LIFDNTEIYG VRNPQVSGFL AVWVPVGADS HQDARTLSDD TAHHDGKTFH SNAALDSQVI  660
YEGFSNFQAF ATNTEDYTNA VIAKNGQLFK DWGITSFQLA PQYRSSTDTS FLDSIIQNGY  720
AFTDRYDLGY GTPTKYGTVD QLRDAIKALH ANGIQAIADW HPDQIYNLPG QELATVTRTN  780
SYGDKDTNSD IDQSLYVIQS RGGGKYQAQY GGAFLSDIQK KYPALFETKQ ISTGLPMDPS  840
QKITEWSGKY FNGSNIQGKG AGYVLKDSGT DQYYKVTSNN NNRDFLPKQL TDDLSETGFV  900
RDNIGMVYYT LSGYLARNTF IQDDNGNYYY FDSTGHLVTG FQNINNHHYF FLPNGIELVQ  960
SFLQNADGST IYFDQKGRQV FNQYITDQTG TAYYFQNDST MVTSGFTEID GHKQYFYKNG 1020
TQVKGQFVSD TDGHVFYLEA GNGNVATQRF AQNSQGQWFY LGNDGIALTG LQTINGVQNY 1080
FYADGHQSKG DFITIQNHVL YTNPLTGAIT TGMQQIGDKI FVFDNTGNML TNQYYQTLDG 1140
QWLHLSTQGP ADTGLVNING NLKYFQANGR QVKGQFVTDP ITNVSYYMNA TDGSAVFNDY 1200
FTYQGQWYLT DSNYQLVKGF KVVNNKLQHF DEITGVQTKS AHIIVNNRTY IFDDQGYFVS 1260
VA                                                                1262

SEQ ID NO: 55            moltype = DNA   length = 4284
FEATURE                  Location/Qualifiers
source                   1..4284
                         mol_type = unassigned DNA
                         organism = Streptococcus salivarius
SEQUENCE: 55
atgaaagacg gcaagtacta ttacctgttg gaggacggta gccacaagaa aaactttgcg   60
atcacggtca acggccaagt gctgtatttc gatgagaacg tgcactgag cagcacgtct   120
acctattcgt ttacccagga gactaccaac ctggttaccg atttcactaa gaataatgct   180
gcgtacgaca gcaccaaggc ttccttgag ctggttgatg gctacctgac tgcggacagc   240
tggtatcgtc cgaaggaaat cctggaggct ggcaccaccg gcgaaagcgag caccgagaaa   300
gactttcgtc cgctgctgat gagctggtgg ccggataaag acacccaggt tgcgtacctg   360
aattacatga cgaaggcgct gagcaatggc gaggaaacga aagacgtgtt tacgatcgag   420
aactcccaag catctctgaa cgcagccgct cagatcatcc aacgcaagat cgaggtcaag   480
attgcagcga acaaaagcac ggactggctg cgccagagca tcgaggcgtt cgtgaaagat   540
caagacaagt ggaatatcaa ttcggagagc ccgggtaaag agcatttcca aaaaggtgct   600
ctgctgttcg ttaacagcga cctgaccaaa tgggcgaata gcgactatcg taaactggac   660
caaacggcga ccagccgtct gccgaaagac aagattaaga gcggcagcga tgcgggctac   720
gagtttttgc tgtcctctga cattgataac agcaaccccga ttgttcaggc ggagatgctg   780
aaccaactgt actatttcat gaactggggt cagttgctg ttggcgacaa agataaggat   840
gcccatttcg acggtatccg cgtcgacgcc gtagacaacg ttagcattga tatgctgcaa   900
ctggttagct cttatatgaa ggcggcatac aaagttaatg aaagcgaagc gcgtgcactg   960
gcaaacattt ccattctgga ggcttggagc cagaacgatc cgtactacgt tgatgaacac  1020
aacacggctg cgctgtctct ggacaacggt ctgcgcctga gcatcgttca cggttttgac  1080
cgtccggtta ctaacaaggg taccggtgcc cgtaatgcaa gcatgaaaga cctgatcaac  1140
ggtggtactc tcggcttgtc caatcgtgca gaagttacga gctacgatca ctgggcgttc  1200
gccacctacc tgtttgtgcg tgcccatgac tctgaagtc agaccgttat gcggacatt  1260
atctcgaaga aaatcgatcc aaccacggac ggtttcacgt tcaccctgga ccagttgaaa  1320
caagcctcg acatctacga cgccgatatg ctgaaggttg ataaggagta cacgcacagc  1380
aacatccggg ctgcgtatgc cctgatgctg caaactacg gtgcggctac ggtggtgtat  1440
tatggtgatt tgtatacgga caatggccag tacatggcga aaaagagccc gtactttgat  1500
cagatcacga ccctgctgaa ggcgcgtagc aagtacgttg cggtggcca gaccagctac  1560
atccataacc tggcgggtga tggtgtcagc agcgcgaagg ataacaaaga ggtgttggtc  1620
agcgtccgct acggtcagga tttgatgagc aaaaccgaca ccgagggtgg taagtatggt  1680
cgtaacagcg gtatgctgac cctgatcgcc aacaaccctg atctgaagct ggcagacggt  1740
```

```
gaaaccatca ccgtcaacat gggcgcagcg cacaagaatc aagcatatcg tccgttgttg    1800
ctgggcaccg aaaagggcat tgtgagcagc ctgaatgatt ccgacacgaa aattgttaag    1860
tataccgacg cgcaaggcaa tctggttttt accgctgatg agatcaaagg tttcaaaacc    1920
gtggatatga gcggttacct gtccgtgtgg gtgccggttg gcgcgaccga ggaccaaaac    1980
gtgctggcca agccgagcac gaaggtctac aaagagggta ataaagttta ttcgagcagc    2040
gcggcactgg aagcacaggt gatctacaga ggttttagca attttcaaga cttcgtgaag    2100
gaagatagcc agtataccaa caagctgatt gcggccaatg cggaccgttg caaaagctgg    2160
ggtattacga gctttgaaat cgctccgcag tatgttagct ccaaggatgg caccttcctg    2220
gatagcatca ttgagaatgg ctacgcgttt accgatcgtt acgacttcgc gatgtcgaaa    2280
aacaataagt acggctccaa agaggatctc cgtgacgcgt tgaaagccct gcacaaacaa    2340
ggcattcaag ttattgcaga ttgggtcccg gaccagctgt acaccctgcc gggtaaggaa    2400
gtggtcacgg cgacccgcac ggacacccac ggtaaagtcc tggatgacac ctccctggtc    2460
aataaactgt acgttaccaa taccaaatct agcggtaacg acttccaggc gcaatacggc    2520
ggtgcattcc tggacaaact gcaaaagttg tacccggaga ttttcaagga agtgatggag    2580
gctagcggca aaaccattga tccgtccgtc aaaatcaagc agtgggaggc aaagtatttc    2640
aacggtacga acattcagaa acgcggtagc gactacgttc tgagcgacgg caaactgtat    2700
ttcacggtaa acgacaaagg taccttcttg ccggcagctc tgaccggtga cacgaaggca    2760
aagaccggtt tcgcctatga cggtactggc gtcacttact atacgacctc cggcacgcag    2820
gcaaagagcc aatttgtcac ctacaatggc aagcagtact atttcaatga caaaggttat    2880
ctggtcacgg gtgaacaggc gattgacggt agcaactact tcttcctgcc gaacggcgtt    2940
atgtttacgg acggtgtgat caaaaatgct aaaggtcagt ctctggtcta cggcaaatct    3000
ggtaagctga ccacgcaaac cggttggaag aagttacgg tgaaggatga tagcggcaag    3060
gaagagaaat tctaccaata cttctttaag ggtggcatta tggcgacggg tctgaccgag    3120
gttgaaggta aagagaaata cttttatgat aatggttatc aggctaaagg tattttcatc    3180
cctaccaaaa cggccatctg atgtttttc tgcggtgata cgtgagcg taaatacagc     3240
ggtttcttcg aacaagacgg taactgtat acgcaaacg aaggtta cgtcgcgaag        3300
ggttttacca aagtgggtaa gcagaacttg tactttaacg agaaaggtgt gcaggtcaag    3360
aaccgtttct ttcaggttgg tgatgctact tattacgcga ataacgaggg tgatgtactg    3420
cgtggtgcac agacgatcaa cggcgacgaa ctgtacttcg acgaaagcgg caagcaagtc    3480
aaaggtgaat ttgtgaataa ccccgacggt accacgacgt attatgacgc aattaccggt    3540
gtgaaactgg tggacaccag cttggtcgtt aatggtcaaa cgttcaacat tgacgctaaa    3600
ggcgttgtca ccaaggcgca cacgccgggt ttctatacca ctggcgacaa caattggttt    3660
tatgcagata gccacggtcg caatgtcact ggcgcacaga tcattaacgg ccaacacctg    3720
tatttcgatg cgaatggccg tcaggtgaag ggcggctttg ttatgaacac tgatggttct    3780
cgttcgttct atcattggaa taccggtgat aaactggtga gcacgttctt tacgaccggc    3840
cacgatcgtt ggtactacgc cgacgacaaa ggtaacgtgg tgaccggcgc acaagtcatc    3900
aacggtcaga aattgttctt cgcgaccgac ggtaaacaag ttaagggcga tttcgcgacc    3960
aacgcaaatg gttcccgttc ttactatcac ggtgccacgg taataagct ggtcagcacc    4020
ttctttacca cgggcgataa caactggtac tatgcagacg cgaaaggtga ggttgtcgtt    4080
ggtgaacaaa cgattaacgg tcaaactctg tattttgatc agaccggtaa gcaagtgaaa    4140
ggtgcgaccg cgaccaatcc agatggcagc atttcttatt acgatgttca cacgggcgag    4200
aaggtcatca ccgctgggt caaaattccg agcggtcaat gggtgtactt caacgcgcag    4260
ggtaagggtt acgtcagcaa ttaa                                          4284

SEQ ID NO: 56          moltype = AA   length = 1427
FEATURE                Location/Qualifiers
source                 1..1427
                       mol_type = protein
                       organism = Streptococcus salivarius
SEQUENCE: 56
MKDGKYYYLL EDGSHKKNFA ITVNGQVLYF DENGALSSTS TYSFTQETTN LVTDFTKNNA     60
AYDSTKASFE LVDGYLTADS WYRPKEILEA GTTWKASTEK DFRPLLMSWW PDKDTQVAYL    120
NYMTKALSNG EETKDVFTIE NSQASLNAAA QIIQRKIEVK IAANKSTDWL RQSIEAFVKD    180
QDKWNINSES PGKEHFQKGA LLFVNSDLTK WANSDYRKLD QTATSRLPKD KIKSGSDAGY    240
EFLLSSDIDN SNPIVQAEML NQLYYFMNWG QIVFGDKDLD AHPDGIRVDA VDNVSIDMLQ    300
LVSSYMKAAY KVNESEARAL ANISILEAWS QNDPYYVDEH NTAALSMDNG LRLSIVHGLT    360
RPVTNKGTGA RNASMKDLIN GGYFGLSNRA EVTSYDQLGF ATYLFVRAHD SEVQTVIADI    420
ISKKIDPTTD GFTFTLDQLK QAFDIYNADM LKVDKEYTHS NIPAAYALML QTMGAATRVY    480
YGDLYTDNGQ YMAKKSPYFD QITTLLKARS KYVAGGQTSY IHNLAGDGVS SAKDNKEVLV    540
SVRYGQDLMS KTDTEGGKYG RNSGMLTLIA NNPDLKLADG ETITVNMGAA HKNQAYRPLL    600
LGTEKGIVSS LNDSDTKIVK YTDAQGNLVF TADEIKGPFK TVDMSGYLSVW VPVGATEDQN   660
VLAKPSTKVY KEGDKVYSSS AALEAQVIYE GFSNFQDFVK EDSQYTNKLI AANADLFKSW    720
GITSFEIAPQ YVSSKDGTFL DSIIENGYAF TDRYDFAMSK NNKYGSKEDL RDALKALHKQ    780
GIQVIADWVP DQLYTLPGKE VVTATRTDTH GKVLDDTSLV NKLYVTNTKS SGNDFQAQYG    840
GAFLDKLQKL YPEIFKEVME ASGKTIDPSV KIKQWEAKYF NGTNIQKRGS DYVLSDGKLY    900
FTVNDKGTFL PAALTGDTKA KTGFAYDGTG VTYYTTSGTQ AKSQFVTYNG KQYYFNDKGY    960
LVTGEQAIDG SNYFFLPNGV MFTDVIKNA KGQSLVYGKS GKLTTQTGWK EVTVKDDSGK   1020
EEKFYQYFFK GGIMATGLTE VEGKEKYFYD NGYQAKGIFI PTKDGHLMFF CGDSGERKYS   1080
GFFEQDGNWY YANDKGYVAT GFTKVGKQNL YFNEKGVQVK NRFFQVGDAT YYANNEGDVL   1140
RGAQTINGDE LYFDESGKQV KGEFVNNPDG TTSYYDAITG VKLVDTSLVV NGQTFNIDAK   1200
GVVTKAHTPG FYTTGDNNWF YADSHGRNVT GAQIINGQHL YFDANGRQVK GGFVMNTDGS   1260
RSFYHWNTGD KLVSTFFTTG HDRWYYADDK GNVVTGAQVI NGQKLFFATD GKQVKGDFAT   1320
NANGSRSYYH GATGNKLVST FFTTGDNNWY YADAKGEVVV GEQTINGQNL YFDQTGKQVK   1380
GATATNPDGS ISYYDVHTGE KVINRWVKIP SGQWVYFNAQ GKGYVSN                 1427

SEQ ID NO: 57          moltype = DNA   length = 5208
FEATURE                Location/Qualifiers
source                 1..5208
                       mol_type = unassigned DNA
```

```
organism = Lactobacillus reuteri
SEQUENCE: 57
atggatcagc aagtacaaag cagcaccacc caggagcaga cgagcacggt taacgcggac   60
acgactaaaa ccgtcaatct ggataccaac actgaccagc cggctcagac gaccgataag  120
aatcaggtcg cgaatgatac caccaccaac caaagcaaga cggacagcac cagcacgacg  180
gttaagaatc cgacgtttat tcctgttagc acttttgtcca gctccgataa cgaaaagcag  240
agccagaatt acaataaacc agataacggt aattacggta atgttgatgc ggcctacttc  300
aataacaatc agctgcacat tagcggttgg cacgcaacca acgcgagcca gggtacggat  360
agccgccaag taatcgtacg cgacattacc accaagaccg agctgggtcg tactaatgtg  420
accaacaatg ttctgcgtcc ggacgtgaaa aatgttcaca acgtctacaa cgctgacaac  480
agcggctttg atgtgaatat caatattgat ttcagcaaga tgaaagacta tcgtgacagc  540
atcgagatcg tttctcgtta tagcggcaac ggcaagagcg ttgactggtg gtcgcagccg  600
atcacgtttg acaaaaacaa ttatgcttat ctggacactt tcgaggtgaa gaacggtgaa  660
ctgcatgcaa cgggctggaa tgccaccaac aaggctatca attacaatca ccacttcgtt  720
attctgtttg atcgtacgaa tggcaaagaa gtcacccgcc aagaggtgcg tgatggtcaa  780
agccgtccgg atgtggcgaa ggtatacccg caagtcgttg gcgcgaacaa tagcggtttt  840
gacgttacgt ttaacattgg tgatttggac tacacccatc agtaccagat cctgtctcgt  900
tacagcaacg cagacaacgg tgaaggcgat tatgtgacct attggtttgc gccgcagagc  960
atcgctccgg cgaatcaaag caaccaaggt tacctggaca gcttcgatat ttcgaaaaac 1020
ggtgaggtga ccgtgacggg ttggaatgcg acggatctga gcgagttgca aacgaatcac 1080
tacgtgatcc tgtttgatca gacggcgggt caacaggttg catccgctaa ggtcgacctg 1140
atcagccgtc cagacgtcgc gaaggcgtac cctaccgtta aaacggcaga aacctccggt 1200
ttcaaggtca cgtttaaggt tagcaatctg caaccgggcc accaatacag cgtcgttagc 1260
cgctttagcg ccgatgaaaa cggtaatggc aacgacaaac gccacacgga ctactggtac 1320
tctccggtta ccctgaacca aacggctagc aacattgaca ctatcaccat gacttccaac 1380
ggtctgcaca tcaccggctg gatggcgagc gataataagca ttaacgaagc gaccccgtac 1440
gcgattatcc tgaacaacgg tcgcgaggtg acgcgccaga aactgaccct gatcgcgcgt 1500
ccggatgttg cggcagtgta tccgagcctg tacaatagcg cggttagcgg cttcgacacc 1560
accatcaagc tgactaacgc gcaatatcaa gcattgaacg ccagctgca agtgctgctg 1620
cgcttttagca aggcggtgga cggtaacccg aatggtcaca ataccgtcac ggatcaattt 1680
agcaaaaact acgcaacgac cggtggtaat ttcgattacg tcaaggttaa tggtaaccaa 1740
attgagtttt ctggctggca cgcgacgaat cagagcaatg ataagaacag ccaatggatt 1800
atcgtcttgt taacggtaa agaggtcaaa cgccagctgg tcaatgacac gaaagacggc 1860
gcagccggct tcaatcgtaa tgatgtgtat aaagtgaacc cagcgatcga aaatagcatt 1920
atgtctggct tccagggcat tatcacgttg ccggttacgg tgaaagacga aaacgtgcag 1980
ctggtgcacc gcttctccaa tgacgcaaaa acgggtgagg gcaattatgt cgatttctgg 2040
agcgaggtga tgtctgtgaa ggactctttc caaaagggta atggtccgct gaaccagttt 2100
ggcctgcaaa ccatcaacgg ccaacaatac tatattgacc cgacgaccgg ccagccgcgt 2160
aagaatttcc tgctgcaaaa cggcaacgat tggatttact tcgacaaaga cactggcgca 2220
ggcaccaacg cgctgaaatt gcagtttgat aagggcacga ttagcgctga cgaacaatac 2280
cgtcgcggca acgaggcgta ctcctacgat gataagagca ttgaaaatgt caacggttac 2340
ttgacggcgg acacgtggta ccgccgaag cagatcctga aggatggcac cacttggacc 2400
gattccaaag aaaccgatat gcgtccgatc ttgatggtct ggtggccaaa cacggtgact 2460
caggcgtact atctgaacta catgaaacaa tatggcaatc tgctgccggc gagcctgccg 2520
agctttagca ccgacgccga tagcgcggag ttgaatcatt attccgagct ggtccaacag 2580
aatatcgaga aacgtattag cgagactggt agcactgatt ggctgcgtac cctgatgcac 2640
gagttcgtga cgaagaatag catgtggaac aaagatagcg agaacgttga ctacggtggc 2700
ctgcaactgc aaggtggttt cctgaagtac gttaacagcg acctgacgaa gtacgcaaac 2760
tctgattggc gtctgatgaa ccgtaccgcg acgaacattg acggtaagaa ttacggtggt 2820
gccgagtttg tgctggcgaa tgacatcgac aactctaacc cggtggtgca ggccgaagaa 2880
ttgaattggc tgtattatct gatgaacttc ggtaccatca ccggtaacaa cccagaagct 2940
aacttcgacg gcatccgtgt cgacgcggtc gataatgtgg atgttgatct gctgagcatt 3000
gcccgtgact actttaatgc agcgtataac atggaacaaa gcgatgctag cgcgaataag 3060
cacatcaata ttctgggaaga ttggggctgg acgatccgg cgtacgtgaa caaaatcggc 3120
aatccacagt tgaccatgga tgaccgcctg cgtaatgcaa ttatggacac cctgagcggt 3180
gcgccggata gaaccaagc gctgaacaag ctgattactc agtctctggt gaatcgcgca 3240
aatgataata ctgaaaacgc ggtgatccct tcctacaact ttgtccgcgc tcatgacagc 3300
aatgcccagg accagatccg tcaagcgatc caggcggcaa ccggcaaacc ttatggcgag 3360
ttcaacttgg atgatgagaa aaagggtatg gaggcttaca tcaatgacca aaatagcacc 3420
aataagaaat ggaacctgta caacatgccg agcgcatata ccatcctgct gacgaataag 3480
gactcggtcc cgcgtgtcta ctatggcgac ttgtaccagg atggtggcca gtacatggaa 3540
cacaaaactc gttactttga caccatcacg aatctgctga aaacccgcgt caagtatgtc 3600
gcaggcggcc agaccatgtc tgtggataag aatggcattt tgactaatgt ccgttttcggt 3660
aagggtgcga tgaacgcaac tgaacacgggt accgatgaaa cccgcaccga aggtatcggc 3720
gttgttatca gcaacaatac gaatttgaaa ctgaatgacg cgaaagcgt tgtgctgcac 3780
atgggcgctg cccataagaa tcagaagtat cgtgcagtga tcctgaccac ggaggacggt 3840
gtgaagaatt acaccaacga caccgatgcg ccggtcgcat acaccgacgc gaacggcgat 3900
ttgcatttca ccaatataa cctggacggt cagcaatata ccgccgttcg tggctacgca 3960
aacccggacg ttacgggtta tctgccgtc tgggttcctg ctggtgccgc cgatgaccaa 4020
gacgcacgta ccgctccgag cgacgaggcc cacaccacga aaacggcgta tcgttccaat 4080
gcggcattgg actccaacgt catctacgaa ggcttttcga actttatcta ttggccgacg 4140
accgagagcg agcgcacgaa tgtccgcatc gcgcagaacg cggatctgtt caaatcgtgg 4200
ggtatccaca ccttcgagct ggcgccacag tacaatagca gcaaggacgg tacgtttctg 4260
gattcgatca ttgacaatgg ttacgcgttt accgatcgtt atgacctggg tatgtctacc 4320
ccgaacaagt acggtagcga tgaggatctg cgtaacgccc tgcaagcact gcacaaggcc 4380
ggtctgcaag ccatcgcaga ttgggttccg gaccaaatct acaatctgcc gggcaaagag 4440
gctgtcacgg ttactcgtag cgatgaccac ggcactacct gggaggttag cccgatcaag 4500
aatgtggtgt atatcactaa taccatcggt ggtggcgaat accagaaaaa gtatggtggt 4560
gaatttctgg acaccttgca aaaagaatat ccgcagctgt ttagccaagt ttacccggtg 4620
```

```
acccaaacga cgattgaccc tagcgttaag attaaagagt ggtccgcgaa gtacttcaat    4680
ggtactaata tcctgcatcg cggtgcgggt tacgtcctgc gtagcaatga tggtaagtat    4740
tacaacctgg gtactagcac ccagcagttc ctgccgagcc agctgagcgt tcaagataat    4800
gagggttacg gtttcgttaa agagggtaac aactatcact attatgacga gaacaaacaa    4860
atggttaagg acgcgtttat ccaggatagc gtcggcaatt ggtactattt tgataagaac    4920
ggcaatatgg ttgcaaacca aagcccggtt gaaatcagca gcaacggtgc gagcggcacc    4980
tacttgtttt tgaataatgg taccagcttc cgcagcggcc tggtcaaaac ggatgcaggc    5040
acctattact acgatggtga cggtcgcatg gttcgtaatc aaacggtttc tgacggtgcc    5100
atgacgtacg ttctggacga aaatggtaaa ctggtcagcg aatcttttga tagcagcgcg    5160
accgaggccc atccgctgaa accgggcgat ctgaacggtc aaaagtaa                 5208
```

SEQ ID NO: 58          moltype = AA   length = 1735
FEATURE                Location/Qualifiers
source                 1..1735
                       mol_type = protein
                       organism = Lactobacillus reuteri
SEQUENCE: 58
MDQQVQSSTT QEQTSTVNAD TTKTVNLDTN TDQPAQTTDK NQVANDTTTN QSKTDSTSTT     60
VKNPTFIPVS TLSSSDNEKQ SQNYNKPDNG NYGNVDAAYF NNNQLHISGW HATNASQGTD    120
SRQVIVRDIT TKTELGRTNV TNNVLRPDVK NVHNVYNADN SGFDVNINID FSKMKDYRDS    180
IEIVSRYSGN GKSVDWWSQP ITFDKNNYAY LDTFEVKNGE LHATGWNATN KAINYNHHFV    240
ILFDRTNGKE VTRQEVRDGQ SRPDVAKVYP QVVGANNSGF DVTFNIGDLD YTHQYQILSR    300
YSNADNGEGD YVTYWFAPQS IAPANQSNQG YLDSFDISKN GEVTVTGWNA TDLSELQTNH    360
YVILFDQTAG QQVASAKVDL ISRPDVAKAY PTVKTAETSG FKVTFKVSNL QPGHQYSVVS    420
RFSADENGNG NDKRHTDYWY SPVTLNQTAS NIDTITMTSN GLHITGWMAS DNSINEATPY    480
AIILNNGREV TRQKLTLIAR PDVAAVYPSL YNSAVSGFDT TIKLTNAQYQ ALNGQLQVLL    540
RFSKAVDGNP NGTNTVTDQF SKNYATTGGN FDYVKVNGNQ IEFSGWHATN QSNDKNSQWI    600
IVLVNGKEVK RQLVNDTKDG AAGFNRNDVY KVNPAIENSI MSGFQGIITL PVTVKDENVQ    660
LVHRFSNDAK TGEGNYVDFW SEVMSVKDSF QKGNGPLNQF GLQTINGQQY YIDPTTGQPR    720
KNFLLQNGND WIYFDKDTGA GTNALKLQFD KGTISADEYN RRGNEAYSYD DKSIENVNGY    780
LTADTWYRPK QILKDGTTWT DSKETDMRPI LMVWWPNTVT QAYYLNYMKQ YGNLLPASLP    840
SFSTDADSAE LNHYSELVQQ NIEKRISETG STDWLRTLMH EPVTKNSMWN KDSENVDYGG    900
LQLQGGFLKY VNSDLTKYAN SDWRLMNRTA TNIDGKNYGG AEFLLANDID NSNPVVQAEE    960
LNWLYYLMNF GTITGNNPEA NFDGIRVDAV DNVDVDLLSI ARDYFNAAYN MEQSDASANK   1020
HINILEDWGW DDPAYVNKIG NPQLTMDDRL RNAIMDTLSG APDKNQALNK LITQSLVNRA   1080
NDNTENAVIP SYNFVRAHDS NAQDQIRQAI QAATGKPYGE FNLDDEKKGM EAYINDQNST   1140
NKKWNLYNMP SAYTILLTNK DSVPRVYYGD LYQDGGQYME HKTRYFDTIT NLLKTRVKYV   1200
AGGQTMSVDK NGILTNVRFG KGAMNATDTG TDETRTEGIG VVISNNTNLK LNDGESVVLH   1260
MGAAHKNQKY RAVILTTEDG VKNYTNDTDA PVAYTDANGD LHFTNTNLDG QQYTAVRGYA   1320
NPDVTGYLAV WVPAGAADDQ DARTAPSDEA HTTKTAYRSN AALDSNVIYE GFSNFIYWPT   1380
TESERTNVRI AQNADLFKSW GITTFELAPQ YNSSKDGTFL DSIIDNGYAF TDRYDLGMST   1440
PNKYGSDEDL RNALQALHKA GLQAIADWVP DQIYNLPGKE AVTVTRSDDH GTTWEVSPIK   1500
NVVYITNTIG GGEYQKKYGG EFLDTLQKEY PQLFSQVYPV TQTTIDPSVK IKEWSAKYFN   1560
GTNILHRGAG YVLRSNDGKY YNLGTSTQQF LPSQLSVQDN EGYGFVKEGN NYHYYDENKQ   1620
MVKDAFIQDS VGNWYYFDKN GNMVANQSPV EISSNGASGT YLFLNNGTSF RSGLVKTDAG   1680
TYYYDGDGRM VRNQTVSDGA MTYVLDENGK LVSESFDSSA TEAHPLKPGD LNGQK        1735

SEQ ID NO: 59          moltype = AA   length = 1242
FEATURE                Location/Qualifiers
source                 1..1242
                       mol_type = protein
                       organism = Streptococcus sp.
SEQUENCE: 59
MINGKEYYVE DDGTVRKNYV LERNGGSQYF NAETGELSNQ KDYRFDKNGG TGSAADSTTN     60
TNVTVNGDKN AFYGTTEKDI ELVDGYFTAN TWYRPKEILV DGKEWTASTE NDKRPLLTVN    120
WPSKAIQASY LNYMREEGLG TNQTFTSYSS QTQMDQAALE VQKRIEEERIA REGNTDWLRT    180
TIKNFVKTQP GWNSTSENLD NSDHLQGGAL LYNNSNRTSY ANSDYRLLNR TPTQQDGTRR    240
YFKDNSSGGF EFLLANDIDN SNPAVQAEQL NWLHYIMNIG SLTGGSEDEN FDGVRVDAVD    300
NVNADLLQIA SDYFKAKYGV EKSEEEAIKH LSILEAWSHN DAYYNEDTKG AQLPMDDPLR    360
LAMVFSFLRP IGNRSGLEPL ITNSLNDRSE SKKNTKRMAN YTFVRAHDSE VQSVIGQIIK    420
NEINPQSTGN TFTLDEMKKA FKIYNADMRS ANKRYTQYNI PSAYAFMLTN KDTVPRVYYG    480
DLYTDDGQYM AQKSPYHDAI STLLQARIRY AAGGQDMKMS YVGSGNTNGW DASGVLTSVR    540
YGKGANNASD AGTAETRNQG MAVILSNQPA LRLNSNLTIN MGAAHRNQAY RPLLLTTSNG    600
VASYLNDGDA NGIVKYTDAN GYLTFNPGEI SGVRNAQVDG YLAVWVPLGA SENQDVRVAA    660
SKSKNSSGLV YDSSAALDSQ VIYEGFSNFQ DFVQDPSQYT NKKIAENANL FKSWGITSFE    720
FAPQYVSSDD GTFLDSVIQN GYAFSDRYDI GMSKDNKYGS LADLKAALKS LHAVGISAIA    780
DWVPDQIYNL PGDEVVTATR VNNYGETKDG AIIDHSLYVA KTRTFGNDYQ GKYGGAYLDE    840
LKRLYPQFFD RVQISTGKRL TTDEKITKWS AKYMNGTNIL DRGSEYVLKN GLSGYYGTNG    900
GKVSLPKVVG SNQSTNNNQ NGDGSGRFEK SWGSVYYRYN DGQRARNAFI KDNDGNVYYF    960
DNTGRMAIGE KTIDGKQYFF LANGVQLRDG YRQNRRGQVF YYDENGIMSQ TGKPSPKPEP   1020
KPDNNTFSRN QFIQIGNNVW AYYDGNGKRV IGRQNINGQE LFFDNNGQVQ KGRTAQVDGV   1080
TRYFDANSGE MARNRFAEVE PGVWAYFNND GAAVTGSQNI NGQTLYFDQN GHQVKGALVT   1140
VDGNLRYYDA NSGDLYRNRF QEVNGSWYYF DGNGNAVKGM VNINGQNLLF DNDGKQVKGH   1200
LVRVNGVIRY YDPNSGEMAV NRWVEISSGW WVYFDGEGRG QI                     1242

SEQ ID NO: 60          moltype = AA   length = 1518
FEATURE                Location/Qualifiers
source                 1..1518
                       mol_type = protein

```
                    organism = Streptococcus salivarius
SEQUENCE: 60
MENKIHYKLH KVKKQWVTIA VASVALATVL GGLSVTTSSV SADETQDKTV TQSNSGTTAS    60
LVTSPEATKE ADKRTNTKEA DVLTPAKETN AVETATTTNT QATAEAATTA TTADVAVAAV   120
PNKEAVVTTD APAVTTEKAE EQPATVKAEV VNTEVKAPEA ALKDSEVEAA LSLKNIKNID   180
GKYYYVNEDG SHKENFAITV NGQLLYFGKD GALTSSSTYS FTPGTTNIVD GFSINNRAYD   240
SSEASFELID GYLTADSWYR PASIIKDGVT WQASTAEDFR PLLMAWWPNV DTQVNYLNYM   300
SKVFNLDAKY SSTDKQETLK VAAKDIQIKI EQKIQAEKST QWLRETISAF VKTQPQWNKE   360
TENYSKGGGE DHLQGGALLY VNDSRTPWAN SDYRRLNRTA TNQTGTIDKS ILDEQSDPNH   420
MGGFDFLLAN DVDLSNPVVQ AEQLNQIHYL MNWGSIVMGD KDANFDGIRV DAVDNVDADM   480
LQLYTNYFRE YYGVNKSEAN ALAHISVLEA WSLNDNHYND KTDGAALAME NKQRLALLFS   540
LAKPIKERTP AVSPLYNNTF NTTQRDEKTD WINKDGSKAY NEDGTVKQST IGKYNEKYGD   600
ASGNYVFIRA HDNNVQDIIA EIIKKEINPK SDGFTITDAE MKQAFEIYNK DMLSSDKKYT   660
LNNIPAAYAV MLQNMETITR VYYGDLYTDD GHYMETKSPY YDTIVNLMKS RIKYVSGGQA   720
QRSYWLPTDG KMDNSDVELY RTNEVYTSVR YGKDIMTAND TEGSKYSRTS GQVTLVANNP   780
KLNLDQSAKL NVEMGKIHAN QKYRALIVGT ADGIKNFTSD ADAIAAGYVK ETDSNGVLTF   840
GANDIKGYET FDMSGFVAVW VPVGASDNQD IRVAPSTEAK KEGELTLKAT EAYDSQLIYE   900
GFSNFQTIPD GSDPSVYTNR KIAENVDLFK SWGVTSFEMA PQFVSADDGT FLDSVIQNGY   960
AFADRYDLAM SKNNKYGSKE DLRDALKALH KAGIQAIADW VPDQIYQLPG KEVVTATRTD  1020
GAGRKIADAI IDHSLYVANS KSSGKDYQAK YGGEFLAELK AKYPEMFKVN MISTGKPIDD  1080
SVKLKQWKAE YFNGTNVLER GVGYVLSDEA TGKYFTVTKE GNFIPLQLTG KEKVITGFSS  1140
DGKGITYFGT SGTQAKSAFV TFNGNTYYFD ARGHMVTSPY YSPNGKDVYR FLPNGIMLSN  1200
AFYIDANGNT YLYNSKGQMY KGGYTKFDVS ETDKDGKESK VVKFRYFTNE GVMAKGVTVI  1260
DGFTQYFGED GFQAKDKLVT FKGKTYYFDA HTGNGIKDTW RNINGKWYYF DANGVAATGA  1320
QVINGQKLYF NEDGSQVKGG VVKNADGTYS KYKEGFGELV TNEFFTTDGN VWYYAGANGK  1380
TVTGAQVING QHLYFNADGS QVKGGVVKNA DGTYSKYNAS TGERLTNEFF TTGDNNWYYI  1440
GANGKSVTGE VKIGDDTYFF AKDGKQVKGQ TVSAGNGRIS YYYGDSGKRA VSTWIEIQPG  1500
VYVYFDKNGL AYPPRVLN                                                1518

SEQ ID NO: 61              moltype = AA   length = 1528
FEATURE                    Location/Qualifiers
source                     1..1528
                           mol_type = protein
                           organism = Streptococcus salivarius
SEQUENCE: 61
MTNKITGKII MENKVHYKLH KVKKQWVTIA VASAALATVV GGLSATTSSV SADETQDKIV    60
TQPNLDTTAD LVTSTEATKE VDKRTNTKEA DVLTPAKETN AVETATTTNT QATAEAATTA   120
TTSDVAVAAV PNKEAVVTTD APAVTTEKAE EQPATVKAEV VNTEVKAPQA ALKDSEVEAA   180
LSLKNIKYTD GKYYYVNEDG SHKENFAITV NGQLLYFGKD GALTSSSTHS FTPGTTNIVD   240
GFSINNRAYD SSEASFELIN GYLTADSWYR PVSIIKDGVT WQASTAEDFR PLLMAWWPNV   300
DTQVNYLNYM SKVFNLEAKY TSTDKQADLN RAAKDIQVKI EQKIQAEKST QWLRETISAF   360
VKTQPQWNKE TENYSKGGGE DHLQGGALLY VNDSRTPWAN SNYRLLNRTA TNQTGTINKS   420
VLDEQSDPNH MGGFDFLLAN DVDLSNPVVQ AEQLNQIHYL MNWGSIVMGD KDANFDGIRV   480
DAVDNVNADM LQLYTNYFRE YYGVNKSEAQ ALAHISVLEA WSLNDNHYND KTDGAALAME   540
NKQRLALLFS LAKPIKDRTP AVSPLYNNTF NTTQRDFKTD WINKDGSTAY NEDGTAKQST   600
IGKYNEKYGD ASGNYVFIRA HDNNVQDIIA EIIKKEINKK SDGFTISDSE MKQAFEIYNK   660
DMLSSNKKYT LNNIPAAYAV MLQNMETITR VYYGDLYTDD GHYMETKSPY HDTIVNLMKN   720
RIKYVSGGQA QRSYWLPTDG KMDNSDVELY RTSEVYTSVR YGKDIMTADD TEGSKYSRTS   780
GQVTLVNNP KLTLHESAKL NVEMGKIHAN QKYRALIVGT ADGIKNFTSD AEAIAAGYVK   840
ETDSNGVLTF GANDIKGYET FDMSGFVAVW VPVGASDDQD IRVAPSTEAK KEGELTLKAT   900
EAYDSQLIYE GFSNFQTIPD GSDPSVYTNR KIAENVDLFK SWGVTSFEMA PQFVSADDGT   960
FLDSVIQNGY AFADRYDLAM SKNNKYGSKE DLRDALKALH KAGIQAIADW VPDQIYQLPG  1020
KEVVTATRTD GAGRKIADAI IDHSLYVANS KSSGRDYQAQ YGGEFLAELK AKYPKMFTEN  1080
MISTGKPIDD SVKLKQWKAK YFNGTNVLDR GVGYVLSDEA TGKYFTVTKE GNFIPLQLTG  1140
NEKAVTGFSN DGKGITYFGT SGNQAKSAFV TFNGNTYYFD ARGHMVTGPY YSPNGKDVYR  1200
FLPNGIMLSN AFYVDANGNT YLYNYKGQMY KGGYTKFDVT ETDKDGNESK VVKFRYFTNE  1260
GVMAKGLTVI DGSTQYFGED GFQTKDKLAT YKGKTYYFEA HTGNAIKNTW RNIDGKWYHF  1320
DENGVAATGA QVINGQKLYF NEDGSQVKGG VVKNADGTYS KYKEGSGELV TNEFFTTDGN  1380
VWYYAGADGK TVTGAQVING QHLYFKEDGS QVKGGVVKNA DGTYSKYDAA TGERLTNEFF  1440
TTGDNNWYYI GSNGKTVTGE VKIGADTYYF AKDGKQVKGQ TVTAGNGRIS YYYGDSGKKA  1500
ISTWIEIQPG IYVYFDKTGI AYPPRVLN                                    1528

SEQ ID NO: 62              moltype = AA   length = 1518
FEATURE                    Location/Qualifiers
source                     1..1518
                           mol_type = protein
                           organism = Streptococcus salivarius
SEQUENCE: 62
MENKIHYKLH KVKKQWVTIA VASVALATVL GGLSVTTSSV SADETQDKTV TQSNSGTTAS    60
LVTSPEATKE ADKRTNTKEA DVLTPAKETN AVETATTTNT QATAEAATTA TTADVAVAAV   120
PNKEAVVTTD APAVTTEKAE EQPATVKAEV VNTEVKAPEA ALKDSEVEAA LSLKNIKNID   180
GKYYYVNEDG SHKENFAITV NGQLLYFGKD GALTSSSTYS FTPGTTNIVD GFSINNRAYD   240
SSEASFELID GYLTADSWYR PASIIKDGVT WQASTAEDFR PLLMAWWPNV DTQVNYLNYM   300
SKVFNLDAKY SSTDKQETLK VAAKDIQIKI EQKIQAEKST QWLRETISAF VKTQPQWNKE   360
TENYSKGGGE DHLQGGALLY VNDSRTPWAN SDYRRLNRTA TNQTGTIDKS ILDEQSDPNH   420
MGGFDFLLAN DVDLSNPVVQ AEQLNQIHYL MNWGSIVMGD KDANFDGIRV DAVDNVDADM   480
LQLYTNYFRE YYGVNKSEAN ALAHISVLEA WSLNDNHYND KTDGAALAME NKQRLALLFS   540
LAKPIKERTP AVSPLYNNTF NTTQRDEKTD WINKDGSKAY NEDGTVKQST IGKYNEKYGD   600
ASGNYVFIRA HDNNVQDIIA EIIKKEINPK SDGFTITDAE MKQAFEIYNK DMLSSDKKYT   660
```

```
LNNIPAAYAV MLQNMETITR VYYGDLYTDD GHYMETKSPY YDTIVNLMKS RIKYVSGGQA      720
QRSYWLPTDG KMDNSDVELY RTNEVYTSVR YGKDIMTAND TEGSKYSRTS GQVTLVANNP      780
KLTLDQSAKL NVEMGKIHAN QKYRALIVGT ADGIKNFTSD ADAIAAGYVK ETDSNGVLTF      840
GANDIKGYET FDMSGFVAVW VPVGASDDQD IRVAPSTEAK KEGELTLKAT EAYDSQLIYE      900
GFSNFQTIPD GSDPSVYTNR KIAENVDLFK SWGVTSFEMA PQFVSADDGT FLDSVIQNGY      960
AFADRYDLAM SKNNKYGSKE DLRDALKALH KAGIQAIADW VPDQIYQLPG KEVVTATRTD     1020
GAGRKIADAI IDHSLYVANT KSSGKDYQAK YGGEFLAELK AKYPEMFKVN MISTGKPIDD     1080
SVKLKQWKAE YFNGTNVLER GVGYVLSDEA TGKYFTVTKD GNFIPLQLTG NEKVVTGFSN     1140
DGKGITYFGT SGTQAKSAFV TFNGNTYYFD ARGHMVTNGE YSPNGKDVYR FLPNGIMLSN     1200
AFYVDANGNT YLYNSKGQMY KGGYTKFDVT ETDKDGKESK VVKFRYFTNE GVMAKGVTVI     1260
DGFTQYFGED GFQAKDKLVT FKGKTYYFDA HTGNAIKDTW RNINGKWYHF DANGVAATGA     1320
QVINGQKLYF NEDGSQVKGG VVKNADGTYS KYKEGSGELV TNEFFTTDGN VWYYAGANGK     1380
TVTGAQVING QHLYFNADGS QVKGGVVKNA DGTYSKYDAS TGERLTNEFF TTGDNNWYYI     1440
GANGKSVTGE VKIGDDTYFF AKDGKQVKGQ TVSAGNGRIS YYYGDSGKRA VSTWIEIQPG     1500
VYVYFDKNGI AYPPRVLN                                                  1518

SEQ ID NO: 63           moltype = AA  length = 1431
FEATURE                 Location/Qualifiers
source                  1..1431
                        mol_type = protein
                        organism = Streptococcus salivarius
SEQUENCE: 63
MTKETNTVDA ATTTNTQAAA DAATKTADAA VTALPNKEAV VTTDAPAVTT EKAAEQPATV       60
KSEVVNTEVK APEAALKDSE VEAALSLKNI KNIDGKYYYV NKDGSHKENF AITVNGQLLY      120
FGKDGALTSS STYSFTQGTT NIVDGFSKNN RAYDSSEASF ELIDGYLTAD SWYRPVSIIK      180
DGVTWQASTK EDFRPLLMAW WPNVDTQVNY LNYMSKVFNL DAKYTSTDKQ VDLNRAAKDI      240
QVKIEQKIQA EKSTQWLREA ISAFVKTQPQ WNKETENFSK GGGEDHLQGG ALLYVNDPRT      300
PWANSNYRLL NRTATNQTGT IDKSVLDEQS DPNHMGGFDF LLANDVDTSN PVVQAEQLNQ      360
IHYLMNWGSI VMGDKDANFD GIRVDAVDNV DADMLQLYTN YFREYYGVNK SEANALAHIS      420
VLEAWSLNDN HYNDKTDGAA LAMENKQRLA LLFSLAKPIK ERTPAVSPLY NNTFNTTQRD      480
EKTDWINKDG SKAYNEDGTV KQSTIGKYNE KYGDASGNYV FIRAHDNNVQ DIIAEIIKKE      540
INPKSDGFTI TDAEMKKAFE IYNKDMLSSD KKYTLNNIPA AYAVMLQNME TITRVYYGDL      600
YTDDGHYMET KSPYYDTIVN LMKNRIKYVS GGQAQRSYWL PTDGKMDKSD VELYRTNEVY      660
TSVRYGKDIM TADDTQGSKY SRTSGQVTLV VNNPKLSLDE SAKLDVEMGK IHANQKYRAL      720
IVGTPNGIKN FTSDAEAIAA GYVKETDGNG VLTFGANDIK GYETFDMSGF VAVWVPVGAS      780
DDQDIRVAAS TAAKKEGELT LKATEAYDSQ LIYEGFSNFQ TIPDGSDPSV YTNRKIAENV      840
DLFKSWGVTS FEMAPQFVSA DDGTFLDSVI QNGYAFADRY DLAMSKNNKY GSKEDLRNAL      900
KALHKAGIQA IADWVPDQIY QLPGKEVVTA TRTDGAGRKI SDAIIDHSLY VANSKSSGKD      960
YQAKYGGEFL AELKAKYPEM FKVNMISTGK PIDDSVKLKQ WKAEYFNGTN VLDRGVGYVL     1020
SDEATGKYFT VTKEGNFIPL QLKGNEKVIT GFSSDGKGIT YFGTSGNQAK SAFVTFNGNT     1080
YYFDARGHMV TNGEYSPNGK DVYRFLPNGI MLSNAFYVDG NGNTYLYNSK GQMYKGGYSK     1140
FDVTETKDGK ESKVVKFRYF TNEGVMAKGV TVVDGFTQYF NEDGIQSKDE LVTYNGKTYY     1200
FEAHTGNAIK NTWRNIKGKW YHFDANGVAA TGAQVINGQH LYFNEDGSQV KGGVVKNADG     1260
TFSKYKDGSG DLVVNEFFTT GDNVWYYAGA NGKTVTGAQV INGQHLFFKE DGSQVKGDFV     1320
KNSDGTYSKY DAASGERLTN EFFTTGDNHW YYIGANGKTV TGEVKIGDDT YFFAKDGKQL     1380
KGQIVTTRSG RISYYFGDSG KKAISTWVEI QPGVFVFFDK NGLAYPPENM N              1431

SEQ ID NO: 64           moltype = AA  length = 1532
FEATURE                 Location/Qualifiers
REGION                  1..1532
                        note = unknown Streptococcus sp. C150
source                  1..1532
                        mol_type = protein
                        organism = unidentified
SEQUENCE: 64
MENKVHYKLH KVKKQWVTIA VASAALATVV GGLSATTSSV SADETQDKTV TQPNSDTTAD       60
LVTSTEATKE VDKRTNTKEA DVLTPAKETN TVETAATTNT QATAEAAKTA TTTNTQATAE      120
VAKTATTADV AVAAVPNKEA VVTTDAPAVT TEKAEEQPAT VKAEVVNTEV KAPEAALKDS      180
EVEAALSLKN IKNIDGKYYY VNEDGSHKEN FAITVNGQLL YFGKDGALTS SSTYSFTQGT      240
TNIVDGFSIN NRAYDSSEAS FELIDGYLTA DSWYRPASII KDGVTWQAST AEDFRPLLMA      300
WWPNVDTQVN YLNYMSKVFN LDAKYSSTDK QETLKVAAKD IQIKIEQKIQ AEKSTQWLRE      360
TISAFVKTQP QWNKETENYS KGGGEDHLQG GALLYVNDSR TPWANSNYRL LNRTATNQTG      420
TIDKSILDEQ SDPNHMGGFD FLLANDVDLS NPVVQAEQLN QIHYLMNWGS IVMGDKDANF      480
DGIRVDAVDN VDADMLQLYT NYFREYYGVN KSEANALAHI SVLEAWSLND NHYNDKTDVA      540
ALAMENKQRL ALLFSLAKPI KERTPAVSPL YNNTFNTTQR DEKTDWINKD GSKAYNEDGT      600
VKKSTIGKYN EKYGDASGNY VFIRAHDNNV QDIIAEIIKK EINEKSDGFT ITDSEMKRAF      660
EIYNKDMLSN DKKYTLNNIP AAYAVMLQNM ETITRVYYGD LYTDDGNYME AKSPYYDTIV      720
NLMKSRIKYV SGGQAQRSYW LPTDGKMDKS DVELYRTNEV YTSVRYGKDI MTADDTQGSK      780
YSRTSGQVTL VVNNPKLTLD QSAKLNVVMG KIHANQKYRA LIVGTPNGIK NFTSDAEAIA      840
AGYVKETDGN GVLTFGANDI KGYETFDMSG FVAVWVPVGA SDDQDIRVAA STAAKKEGEL      900
TLKATEAYDS QLIYEGFSNF QTIPDGSDPS VYTNRKIAEN VDLFKSWGVT SFEMAPQFVS      960
ADDGTFLDSV IQNGYAFADR YDLAMSKNNK YGSKEDLRNA LKALHKAGIQ AIADWVPDQI     1020
YQLPGKEVVT ATRTDGAGRK ISDAIIDHSL YVANSKSSGK DYQAKYGGEF LAELKAKYPE     1080
MFKVNMISTG KPIDDSVKLK QWKAEYFNGT NVLDRGVGYV LSDEATGKYF TVTKEGNFIP     1140
LQLKGNKKVI TGFSSDGKGI TYFGTSGNQA KSAFVTFNGN TYYFDARGHM VTNGEYSPNG     1200
KDVYRFLPNG IMLSNAFYVD GNGNTYLYNS KGQMYKGGYS KFDVTETKDG KESKVVKFRY     1260
FTNEGVMAKG TVVDGFTQYF NEDGIQSKDE LVTYNGKTY YFEAHTGNAI KNTWRNIKGK     1320
WYHFDANGVA ATGAQVINGQ HLYFNEDGSQ VKGSIVKNAD GTFSKYKDSS GDLVVNEFFT     1380
TGDNVWYYAG ANGKTVTGAQ VINGQHLFFK EDGSQVKGDF VKNSDGTYSK YDAASGERLT     1440
```

```
NEFFTTGDNH WYYIGANGKT VTGEVKIGDD TYFFAKDGKQ LKGQIVTTRS GRISYYFGDS   1500
GKKAISTWVE IQPGVFVFFD KNGLAYPPEN MN                                1532

SEQ ID NO: 65           moltype = AA   length = 1341
FEATURE                 Location/Qualifiers
source                  1..1341
                        mol_type = protein
                        organism = Streptococcus salivarius
SEQUENCE: 65
MIDGKYYYVN EDGSHKENFA ITVNGQLLYF GKDGALTSSS TYSFTPGTTN IVDGFSINNR    60
AYDSSEASFE LIDGYLTADS WYRPASIIKD GVTWQASTAE DFRPLLMAWW PNVDTQVNYL   120
NYMSKVFNLD AKYSSTDKQE TLKVAAKDIQ IKIEQKIQAE KSTQWLRETI SAFVKTQPQW   180
NKETENYSKG GGEDHLQGGA LLYVNDSRTP WANSDYRRLN RTATNQTGTI DKSILDEQSD   240
PNHMGGFDFL LANDVDLSNP VVQAEQLNQI HYLMNWGSIV MGDKDANFDG IRVDAVDNVD   300
ADMLQLYTNY FREYYGVNKS EANALAHISV LEAWSLNDNH YNDKTDGAAL AMENKQRLAL   360
LFSLAKPIKE RTPAVSPLYN NTFNTTQRDE KTDWINKDGS KAYNEDGTVK QSTIGKYNEK   420
YGDASGNYVF IRAHDNNVQD IIAEIIKKEI NPKSDGFTIT DAEMKQAFEI YNKDMLSSDK   480
KYTLNNIPAA YAVMLQNMET ITRVYYGDLY TDDGHYMETK SPYYDTIVNL MKSRIKYVSG   540
GQAQRSYWLP TDGKMDNSDV ELYRTNEVYT SVRYGKDIMT ANDTEGSKYS RTSGQVTLVA   600
NNPKLNLDQS AKLNVEMGKI HANQKYRALI VGTADGIKNF TSDADAIAAG YVKETDSNGV   660
LTFGANDIKG YETFDMSGFV AVWVPVGASD NQDIRVAPST EAKKEGELTL KATEAYDSQL   720
IYEGFSNFQT IPDGSDPSVY TNRKIAENVD LFKSWGVTSF EMAPQFVSAD DGTFLDSVIQ   780
NGYAFADRYD LAMSKNNKYG SKEDLRDALK ALHKAGIQAI ADWVPDQIYQ LPGKEVVTAT   840
RTDGAGRKIA DAIIDHSLYV ANSKSSGKDY QAKYGGEFLA ELKAKYPEMF KVNMISTGKP   900
IDDSVKLKQW KAEYFNGTNV LERGVGYVLS DEATGKYFTV TKEGNFIPLQ LTGKEKVITG   960
FSSDGKGITY FGTSGTQAKS AFVTFNGNTY YFDARGHMVT NSEYSPNGKD VYRFLPNGIM  1020
LSNAFYIDAN GNTYLYNSKG QMYKGGYTKF DVSETDKDGK ESKVVKFRYF TNEGVMAKGV  1080
TVIDGFTQYF GEDGFQAKDK LVTFKGKTYY FDAHTGNGIK DTWRNINGKW YYFDANGVAA  1140
TGAQVINGQK LYFNEDGSQV KGGVVKNADG TYSKYKEGFG ELVTNEFFTT DGNVWYYAGA  1200
NGKTVTGAQV INGQHLYFNA DGSQVKGGVV KNADGTYSKY NASTGERLTN EFFTTGDNNW  1260
YYIGANGKSV TGEVKIGDDT YFFAKDGKQV KGGQTVSAGNG RISYYYGDSG KRAVSTWIEI  1320
QPGVYVYFDK NGLAYPPRVL N                                            1341

SEQ ID NO: 66           moltype = AA   length = 906
FEATURE                 Location/Qualifiers
REGION                  1..906
                        note = 6855 gtf catalytic domain with corresponding A510E
                         substitution
source                  1..906
                        mol_type = protein
                        organism = synthetic construct
SEQUENCE: 66
FSINNRAYDS SEASFELIDG YLTADSWYRP ASIIKDGVTW QASTAEDFRP LLMAWWPNVD    60
TQVNYLNYMS KVFNLDAKYS STDKQETLKV AAKDIQIKIE QKIQAEKSTQ WLRETISAFV   120
KTQPQWNKET ENYSKGGGED HLQGGALLYV NDSRTPWANS DYRRLNRTAT NQTGTIDKSI   180
LDEQSDPNHM GGFDFLLAND VDLSNPVVQA EQLNQIHYLM NWGSIVMGDK DANFDGIRVD   240
AVDNVDADML QLYTNYFREY YGVNKSEANA LAHISVLEEW SLNDHYNDK TDGAALAMEN   300
KQRLALLFSL AKPIKERTPA VSPLYNNTFN TTQRDEKTDW INKDGSKAYN EDGTVKQSTI   360
GKYNEKYGDA SGNYVFIRAH DNNVQDIIAE IIKKEINPKS DGFTITDAEM KQAFEIYNKD   420
MLSSDKKYTL NNIPAAYAVM LQNMETITRV YYGDLYTDDG HYMETKSPYY DTIVNLMKSR   480
IKYVSGGQAQ RSYWLPTDGK MDNSDVELYR TNEVYTSVRY GKDIMTANDT EGSKYSRTSG   540
QVTLVANNPK LTLDQSAKLN VEMGKIHANQ KYRALIVGTA DGIKNFTSDA DAIAAGYVKE   600
TDSNGVLTFG ANDIKGYETF DMSGFVAVWV PVGASDDQDI RVAPSTEAKK EGELTLKATE   660
AYDSQLIYEG FSNFQTIPDG SDPSVYTNRK IAENVDLFKS WGVTSFEMAP QFVSADDGTF   720
LDSVIQNGYA FADRYDLAMS KNNKYGSKED LRDALKALHK AGIQAIADWV PDQIYQLPGK   780
EVVTATRTDG AGRKIADAII DHSLYVANTK SSGKDYQAKY GGEFLAELKA KYPEMFKVNM   840
ISTGKPIDDS VKLKQWKAEY FNGTNVLERG VGYVLSDEAT GKYFTVTKDG NFIPLQLTGN   900
EKVVTG                                                              906

SEQ ID NO: 67           moltype = DNA   length = 93
FEATURE                 Location/Qualifiers
misc_feature            1..93
                        note = terminator sequence added to pHYT
source                  1..93
                        mol_type = unassigned DNA
                        organism = unidentified
SEQUENCE: 67
ggttaccttg aatgtatata aacattctca aagggatttc taataaaaaa cgctcggttg    60
ccgccgggcg ttttttatgc atcgatggaa ttc                                93

SEQ ID NO: 68           moltype = AA   length = 1338
FEATURE                 Location/Qualifiers
source                  1..1338
                        mol_type = protein
                        organism = Streptococcus criceti
SEQUENCE: 68
MEKNLRYKLH KVKKQWVAIG VTTFAVGFLA GGQVVAADAT DGNGGNTQVA HLIPKEPTDY    60
KFDTPSGILT GLNFANAQTS PAGDNAGANQ PAGGIEPQTA ENAATDGQAV PQTSDQPGHL   120
ENVDGKTYYV DANGQRLKNY STVIDGKTYY FDAQTGQAQA ETPQINQNDN QVAPDTYAAN   180
```

```
NQAFTNDVSS FETVDNYVTA DSWYRPRKIL KNGESWQASA ESDMRPILMT WWPDAATKAA    240
YANYWVKEGL ISGSYSPNSA NLETAVQTIQ AAIEKKIASE GSTAWLRDKM SQFVKSQNQW    300
SLASENPTVY PNQDHLQGGA LLFSNNEATA HANSDWRLLN RNPTFQTGKQ KYFTTNYAGY    360
ELLLANDVDN SNPIVQAEQL NHFHYLMNWG EIVMGDKNAN FDGVRVDAVD NVNADLLQIQ    420
RDYYKAKYGV DQNEKNAIDH LSILEAWSGN DNDYVKDQNN FSLSIDNSQR SYMLAAFAYP    480
ASQRGNDYIS LLPKVGLKDR RYAKNGNPVP NYVFIRAHDS EVQTRIAKII RERLGKTNAD    540
GLTNITLDDL NKAFDIYNQD MKAVDKQYYP NNLPMAYAWM LQNKDTVTRV YYGDMYTDDG    600
QYMETKTPFH DAIETLLKAR IKYVAGGQTA GYVQGWGSGI LTSVRYGKGA DTAIDAGTAE    660
TRTSGMAVLI NNKPNFQSYN GLTLDMGAAH KNQAYRPLLL STKDGIATYL NDSDVSSNQY    720
KYTDGQGRLN FSASELRSVA NVQVSGMIQV WVPVGAADNQ DVRVAPNTNR NNSSNIYTQS    780
DALDSQVIYE GFSNFQAFAK TPEQYTNAVI AKNADLFKSW GITQFEMAPQ YVSSEDGTFL    840
DSVVLNGYAF SDRYDLAMSK NNKYGSKEDL ANAIKGLHNA GIKVLSDWVP DQMYNLPGKE    900
VVTATRVDQY GRPKAGATIN RTPYVVNTKT YGDYQEQYGG KFLDELQKLY PSLFTTKQIS    960
TGKPIDPSVK ITNWSAKYFN GSNILGRGAK YVLSDNNKYL NLGAGQFFLP TNLNNTYGQP   1020
QAPANGFISK NGGIHYIDNN GQEVKNQFKE IAGSWYYFDA NGKMATGQTK IGNTTYLFMP   1080
NGKQLKEGVW YDGKKAYYYD DNGRTWTNKG FVEFKVNGQD KWRYFNGDGS IAVGLVSLDN   1140
RTLYFDAYGY QVKGQTLTIN GKTYSFDANE GDLITGNTPS PEPNNQGAWE ALGDNQWGYR   1200
KDGKLLTGSQ TIAGQKVFFQ PNGVQVKGGT AKDEAGVLRF YDRDQGHLAG KGWYSTADNN   1260
WVYVDDAGRV VTGLQKIGSQ TLYFDDNGIQ AKGKAIWDKD GNLRYFAAGS GDMITNRWYN   1320
IGDNQWYWFN NQGIASRW                                                 1338

SEQ ID NO: 69            moltype = AA  length = 1554
FEATURE                  Location/Qualifiers
source                   1..1554
                         mol_type = protein
                         organism = Streptococcus sobrinus
SEQUENCE: 69
MEKKLHYKLH KVKKHWVTIA VASIGLVSLV GAGTVSAEDK VANDTTAQAT VGVDTGQDQA     60
TTNDANTNTT DTDTADQSAN TNQDQAGSDQ SNNQDQAKQD TANTDRNQAD NSQTDNNQAT    120
DQATSPATDG TSVQRRDAAN VATAADQEGQ TAPSEQEKSA ALSLDNVKLI DGKYYVQAD     180
GSYKKNFAIT VNGQMLYFDS DTGALSSTST YSFSQGTTNL VDDFSSHNKA YDSTAKSFEL    240
VNGYLTANSW YRPAGILRNG QTWEASNEND LRPVLMSWWP DKDTQVAYVN YMNKYLSANE    300
TEVTNETSQV DLNKEAQSIQ TKIEQKITSD NSTQWLRTAM EAFVAAQPKW NMSTENFNKG    360
DHLQGGALLY TNSDLTPWAN SDYRLLNRTP TQQDGTKKYF TEGGEGGYEF LLSNDVDNSN    420
PVVQAEQLNQ LHYLMNWGDI VMGDKDANFD GVRVDAVDNV NADLLQVYSN YFKDNYKVTD    480
SEANALAHIS ILEAWSLNDN QYNEDTNGTA LSIDNSSRLT SLAVLTKQPG QRIDLSNLIS    540
ESVNKERAND TAYGDTIPTY SFVRAHDSEV QTVIAKIVKE KIDTNSDGYT FTLDQLKDAF    600
KIYNEDMAKV NKTYTHYNIP AAYALLLSNM ESVPRVYYGD LYTDDGQYMA KKSPYYDAIA    660
TMLQGRIAYV SGGQSEEVHK VNGNNQILSS VRYGQDLMSA DDTQGTDLSR TSGLVTLVSN    720
DPNLDLGGDS LTVNMGRAHA NQAYRPLILG TKDGVQSYLK DSDTNIVKYT DANGNLTFTA    780
DDIKGYSTVD MSGYLAVWVP VGAKDGQDVR VAADTNQKAD GKSLKTSAAL DSQVIYEGFS    840
NFQDFANNDA DYTNKKIAEN ADFFKKLGIT SFEMAPQYVS ATDGSFLDSI IQNGYAFSDR    900
YDLAMSKNNK YGSKDDLANA LKALHANGIQ AIADWVPDQI YQLPGEEVVT AKRTNSYGNP    960
TFDAYINNAL YATNTKSSGS DYQAQYGGAF LDELKAKYPD MFTVNMISTG KPIDPSTKIK   1020
QWEAKYFNGT NVLGKGAGYV LSDDATGKYF TVNENGDFLP ASFTGDQNAK TGFYYDGTGM   1080
AYYSTSGNKA VNSFIYEGGH YYYFDKDGHM VTGSYKAEDG NDYYFLPNGI QMRDAIYQDA   1140
QGNSYYYGRT GILYKGDNWY PFVDPNNANK TVFRYFDANN VMAIGYRNMY GQTYYFDENG   1200
FQAKGQLLTD DKGTHYFDED NGAMAKNKFV NVGDDWYYMD GNGNAVKGQY PVNNQILYFN   1260
PETGVVKGQ FITDAQGRTS YYDANSGALK SSGFFTPNGS DWYYAENGYV YKGFKQVAEN    1320
QDQWYYFDQT TGKQAKGAAK VDGRDLYFNP DSGVQVKGDF ATDESGNTSF YHGDNGDKVV   1380
GGFFTTGNNA WYYADNNGNL VKGFQEIDGK WYHFDEVTGQ QAKGAALVNG QQLYFDDLSG   1440
IQVKGDFVTD GQGNTSYYDV NSGDKKVNGF FTTGDNAWYY ADGQGNLAKG RKSIDNQDLY   1500
FDPATGKQVK GQLVSIDGRN YYFDSGSGNM AKNRFVRIGD QWIYFGNDGA ATNL         1554

SEQ ID NO: 70            moltype = AA  length = 1414
FEATURE                  Location/Qualifiers
REGION                   1..1414
                         note = N-terminal truncated 8845 gtf protein
source                   1..1414
                         mol_type = protein
                         organism = synthetic construct
SEQUENCE: 70
MRSKKLWISL LFALTLIFTM AFSNMSASAI DGKYYYVQAD GSYKKNFAIT VNGQMLYFDS     60
DTGALSSTST YSFSQGTTNL VDDFSSHNKA YDSTAKSFEL VNGYLTANSW YRPAGILRNG    120
QTWEASNEND LRPVLMSWWP DKDTQVAYVN YMNKYLSANE TEVTNETSQV DLNKEAQSIQ    180
TKIEQKITSD NSTQWLRTAM EAFVAAQPKW NMSTENFNKG DHLQGGALLY TNSDLTPWAN    240
SDYRLLNRTP TQQDGTKKYF TEGGEGGYEF LLSNDVDNSN PVVQAEQLNQ LHYLMNWGDI    300
VMGDKDANFD GVRVDAVDNV NADLLQVYSN YFKDNYKVTD SEANALAHIS ILEAWSLNDN    360
QYNEDTNGTA LSIDNSSRLT SLAVLTKQPG QRIDLSNLIS ESVNKERAND TAYGDTIPTY    420
SFVRAHDSEV QTVIAKIVKE KIDTNSDGYT FTLDQLKDAF KIYNEDMAKV NKTYTHYNIP    480
AAYALLLSNM ESVPRVYYGD LYTDDGQYMA KKSPYYDAIA TMLQGRIAYV SGGQSEEVHK    540
VNGNNQILSS VRYGQDLMSA DDTQGTDLSR TSGLVTLVSN DPNLDLGGDS LTVNMGRAHA    600
NQAYRPLILG TKDGVQSYLK DSDTNIVKYT DANGNLTFTA DDIKGYSTVD MSGYLAVWVP    660
VGAKDGQDVR VAADTNQKAD GKSLKTSAAL DSQVIYEGFS NFQDFANNDA DYTNKKIAEN    720
ADFFKKLGIT SFEMAPQYVS ATDGSFLDSI IQNGYAFSDR YDLAMSKNNK YGSKDDLANA    780
LKALHANGIQ AIADWVPDQI YQLPGEEVVT AKRTNSYGNP TFDAYINNAL YATNTKSSGS    840
DYQAQYGGAF LDELKAKYPD MFTVNMISTG KPIDPSTKIK QWEAKYFNGT NVLGKGAGYV    900
LSDDATGKYF TVNENGDFLP ASFTGDQNAK TGFYYDGTGM AYYSTSGNKA VNSFIYEGGH    960
YYYFDKDGHM VTGSYKAEDG NDYYFLPNGI QMRDAIYQDA QGNSYYYGRT GILYKGDNWY   1020
```

```
PFVDPNNANK TVFRYFDANN VMAIGYRNMY GQTYYFDENG FQAKGQLLTD DKGTHYFDED   1080
NGAMAKNKFV NVGDDWYYMD GNGNAVKGQY PVNNQILYFN PETGVQVKGQ FITDAQGRTS   1140
YYDANSGALK SSGFFTPNGS DWYYAENGYV YKGFKQVAEN QDQWYYFDQT TGKQAKGAAK   1200
VDGRDLYFNP DSGVQVKGDF ATDESGNTSF YHGDNGDKVV GGFFTTGNNA WYYADNNGNL   1260
VKGFQEIDGK WYHFDEVTGQ QAKGAALVNG QQLYFDVDSG IQVKGDFVTD GQGNTSYYDV   1320
NSGDKKVNGF FTTGDNAWYY ADGQGNLAKG RKSIDNQDLY FDPATGKQVK GQLVSIDGRN   1380
YYFDSGSGNM AKNRFVRIGD QWIYFGNDGA ATNL                              1414

SEQ ID NO: 71            moltype = AA  length = 906
FEATURE                  Location/Qualifiers
REGION                   1..906
                         note = 6855 gtf catalytic domain with corresponding A510D
                          substitution
source                   1..906
                         mol_type = protein
                         organism = synthetic construct
SEQUENCE: 71
FSINNRAYDS SEASFELIDG YLTADSWYRP ASIIKDGVTW QASTAEDFRP LLMAWWPNVD    60
TQVNYLNYMS KVFNLDAKYS STDKQETLKV AAKDIQIKIE QKIQAEKSTQ WLRETISAFV   120
KTQPQWNKET ENYSKGGGED HLQGGALLYV NDSRTPWANS DYRRLNRTAT NQTGTIDKSI   180
LDEQSDPNHM GGFDFLLAND VDLSNPVVQA EQLNQIHYLM NWGSIVMGDK DANFDGIRVD   240
AVDNVDADML QLYTNYFREY YGVNKSEANA LAHISVLEDW SLNDNHYNDK TDGAALAMEN   300
KQRLALLFSL AKPIKERTPA VSPLYNNTFN TTQRDEKTDW INKDGSKAYN EDGTVKQSTI   360
GKYNEKYGDA SGNYVFIRAH DNNVQDIIAE IIKKEINPKS DGFTITDAEM KQAFEIYNKD   420
MLSSDKKYTL NNIPAAYAVM LQNMETITRV YYGDLYTDDG HYMETKSPYY DTIVNLMKSR   480
IKYVSGGQAQ RSYWLPTDGK MDNSDVELYR TNEVYTSVRY GKDIMTANDT EGSKYSRTSG   540
QVTLVANNPK LTLDQSAKLN VEMGKIHANQ KYRALIVGTA DGIKNFTSDA DAIAAGYVKE   600
TDSNGVLTFG ANDIKGYETF DMSGFVAVWV PVGASDDQDI RVAPSTEAKK EGELTLKATE   660
AYDSQLIYEG FSNFQTIPDG SDPSVYTNRK IAENVDLFKS WGVTSFEMAP QFVSADDGTF   720
LDSVIQNGYA FADRYDLAMS KNNKYGSKED LRDALKALHK AGIQAIADWV PDQIYQLPGK   780
EVVTATRTDG AGRKIADAII DHSLYVANTK SSGKDYQAKY GGEFLAELKA KYPEMFKVNM   840
ISTGKPIDDS VKLKQWKAEY FNGTNVLERG VGYVLSDEAT GKYFTVTKDG NFIPLQLTGN   900
EKVVTG                                                             906
```

What is claimed is:

1. A polynucleotide comprising a nucleotide sequence encoding a non-native glucosyltransferase, wherein the non-native glucosyltransferase comprises at least one amino acid substitution at a position corresponding with amino acid residue Ala-510, Phe-607, or Asp-948 of SEQ ID NO:62, wherein the non-native glucosyltransferase synthesizes alpha-glucan comprising 1,3-linkages, and wherein the non-native glucosyltransferase has:
(i) an alpha-glucan yield that is higher than the alpha-glucan yield of a second glucosyltransferase that only differs from the non-native glucosyltransferase at the substitution position(s), and/or
(ii) a leucrose yield that is lower than the leucrose yield of the second glucosyltransferase;
wherein the non-native glucosyltransferase comprises a catalytic domain that is at least about 90% identical to residues 55-960 of SEQ ID NO:4, residues 54-957 of SEQ ID NO:65, residues 55-960 of SEQ ID NO:30, residues 55-960 of SEQ ID NO: 28, or residues 55-960 of SEQ ID NO:20.

2. The polynucleotide of claim 1, wherein one or more regulatory sequences are operably linked to the nucleotide sequence.

3. The polynucleotide of claim 2, wherein said one or more regulatory sequences include a promoter sequence.

4. The polynucleotide of claim 1, wherein the amino acid substitution is at the position corresponding with amino acid residue Ala-510.

5. The polynucleotide of claim 4, wherein the amino acid substitution at the position corresponding with amino acid residue Ala-510 is with an Ile or Val residue.

6. The polynucleotide of claim 4, wherein the amino acid substitution at the position corresponding with amino acid residue Ala-510 is with a Glu or Asp residue.

7. The polynucleotide of claim 1, wherein the amino acid substitution is at the position corresponding with amino acid residue Phe-607.

8. The polynucleotide of claim 7, wherein the amino acid substitution at the position corresponding with amino acid residue Phe-607 is with a Trp residue.

9. The polynucleotide of claim 7, wherein the amino acid substitution at the position corresponding with amino acid residue Phe-607 is with a Tyr residue.

10. The polynucleotide of claim 7, wherein the amino acid substitution at the position corresponding with amino acid residue Phe-607 is with an Asn residue.

11. The polynucleotide of claim 1, wherein the amino acid substitution is at the position corresponding with amino acid residue Asp-948.

12. The polynucleotide of claim 11, wherein the amino acid substitution at the position corresponding with amino acid residue Asp-948 is with a Gly residue.

13. The polynucleotide of claim 1, wherein the non-native glucosyltransferase comprises two or more amino acid substitutions.

14. The polynucleotide of claim 13, wherein the two or more amino acid substitutions include substitutions at the positions corresponding with amino acid residues Ala-510 and Phe-607.

15. The polynucleotide of claim 13, wherein the two or more amino acid substitutions include substitutions at the positions corresponding with amino acid residues Phe-607 and Asp-948.

16. The polynucleotide of claim 13, wherein the two or more amino acid substitutions include substitutions at the positions corresponding with amino acid residues Ala-510 and Asp-948.

17. The polynucleotide of claim 1, wherein the non-native glucosyltransferase comprises a catalytic domain that is at least about 95% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

18. The polynucleotide of claim 1, wherein the non-native glucosyltransferase comprises a catalytic domain that is at least about 97% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

19. The polynucleotide of claim 1, wherein the non-native glucosyltransferase comprises an amino acid sequence that is at least about 90% identical to SEQ ID NO:4, SEQ ID NO:65, SEQ ID NO:30, SEQ ID NO:28, or SEQ ID NO: 20.

20. The polynucleotide of claim 1, wherein the non-native glucosyltransferase comprises an amino acid sequence that is at least about 95% identical to SEQ ID NO:4, SEQ ID NO:65, SEQ ID NO:30, SEQ ID NO:28, or SEQ ID NO: 20.

21. The polynucleotide of claim 1, wherein the alpha-glucan is insoluble and comprises at least about 50% alpha-1,3 linkages.

22. The polynucleotide of claim 21, wherein the alpha-glucan comprises at least about 90% alpha-1,3 linkages.

* * * * *